(12) United States Patent
Mueller et al.

(10) Patent No.: US 7,528,129 B2
(45) Date of Patent: May 5, 2009

(54) CGRP-ANTAGONISTS, PROCESS FOR PREPARING THEM AND THEIR USE AS PHARMACEUTICAL COMPOSITIONS

(75) Inventors: Stephan Georg Mueller, Warthausen (DE); Klaus Rudolf, Warthausen (DE); Philipp Lustenberger, Warthausen (DE); Dirk Stenkamp, Biberach (DE); Marco Santagostino, Mittelbiberach (DE); Fabio Paleari, Monza (IT); Gerhard Schaenzle, Biberach-Mettenberg (DE); Kirsten Arndt, Biberach (DE); Henri Doods, Warthausen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 130 days.

(21) Appl. No.: 11/277,177

(22) Filed: Mar. 22, 2006

(65) Prior Publication Data

US 2006/0252931 A1    Nov. 9, 2006

(30) Foreign Application Priority Data

| Mar. 23, 2005 | (AR) | P050101139 |
| Mar. 23, 2005 | (PE) | 000336-2005/OIN |
| Mar. 23, 2005 | (WO) | PCT/EP2005/003094 |
| Apr. 18, 2005 | (WO) | PCT/EP2005/004104 |
| Sep. 29, 2005 | (EP) | 05021283 |

(51) Int. Cl.
  *C07D 401/14* (2006.01)
  *C07D 413/04* (2006.01)
  *A61K 31/551* (2006.01)
  *A61P 25/06* (2006.01)

(52) U.S. Cl. .................... 514/221; 540/500
(58) Field of Classification Search ........... 540/500; 514/221
   See application file for complete search history.

(56) References Cited

U.S. PATENT DOCUMENTS

| 6,344,449 | B1 | 2/2002 | Rudolf et al. |
| 6,521,609 | B1 | 2/2003 | Doods et al. |
| 2003/0069231 | A1 | 4/2003 | Rudolf et al. |
| 2004/0132716 | A1 | 7/2004 | Rudolf et al. |
| 2006/0079504 | A1 | 4/2006 | Rudolf et al. |

FOREIGN PATENT DOCUMENTS

| DE | 10250080 | 5/2004 |
| WO | WO9811128 | 3/1998 |
| WO | WO0018764 | 4/2000 |
| WO | WO0110425 | 2/2001 |
| WO | WO2004037810 | 5/2004 |
| WO | WO2004037811 | 5/2004 |
| WO | WO2004063171 | 7/2004 |
| WO | WO2005092880 | 10/2005 |
| WO | WO2005095383 | 10/2005 |
| WO | WO2005103037 | 11/2005 |

OTHER PUBLICATIONS

Pasternack, A., et al; Potent, Orally Bioavailable Somatostatin Agonists: Good Absorption Achieved by Urea Backbone Cyclization; Bioorganic & Medicinal Chemistry Letters, Bd. 9, Nr. 3; Feb. 8, 1999; Seiten 491-496.

Mallee, J., et al; Receptor Activity-modifying Protein 1 Determines the Species Selectivity of Non-peptide CGRP Receptor Antagonists; The Journal of Biological Chemistry (Apr. 19, 2002); vol. 277, No. 16, pp. 14294-14928; The American Society for Biochemistry and Molecular Biology, Inc.

*Primary Examiner*—Bruck Kifle
(74) *Attorney, Agent, or Firm*—Michael P. Morris; Mary-Ellen M. Devlin; Alan R. Stempel

(57) ABSTRACT

The present invention relates to the CGRP-antagonists of general formula I

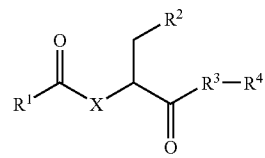

wherein $R^1$, $R^2$, $R^3$, $R^4$ and X are defined as in claim 1, the tautomers, the isomers, the diastereomers, the enantiomers, the hydrates, mixtures and salts thereof and the hydrates of the salts, particularly the physiologically acceptable salts thereof with inorganic or organic acids or bases, as well as those compounds of general formula I in which one or more hydrogen atoms are replaced by deuterium, pharmaceutical compositions containing these compounds, the use thereof and processes for the preparation thereof.

20 Claims, No Drawings

CGRP-ANTAGONISTS, PROCESS FOR PREPARING THEM AND THEIR USE AS PHARMACEUTICAL COMPOSITIONS

FIELD OF THE INVENTION

The present invention relates to the CGRP-antagonists of general formula I

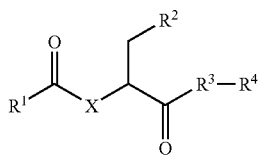

wherein $R^1$, $R^2$, $R^3$, $R^4$ and X are as defined hereinbelow, the tautomers, the isomers, the diastereomers, the enantiomers, the hydrates, mixtures and salts thereof and the hydrates of the salts, particularly the physiologically acceptable salts thereof with inorganic or organic acids or bases, as well as those compounds of general formula I in which one or more hydrogen atoms are replaced by deuterium, pharmaceutical compositions containing these compounds, the use thereof and processes for the preparation thereof.

PRIOR ART

International Patent Applications PCT/EP97/04862 and PCT/EP03/11762 have already described CGRP-antagonists for the treatment of migraine.

DETAILED DESCRIPTION OF THE INVENTION

In the above general formula I in a first embodiment
X denotes $CH_2$, NH, $C_{1-3}$-alkyl-N, O or S,
$R^1$ denotes a group selected from

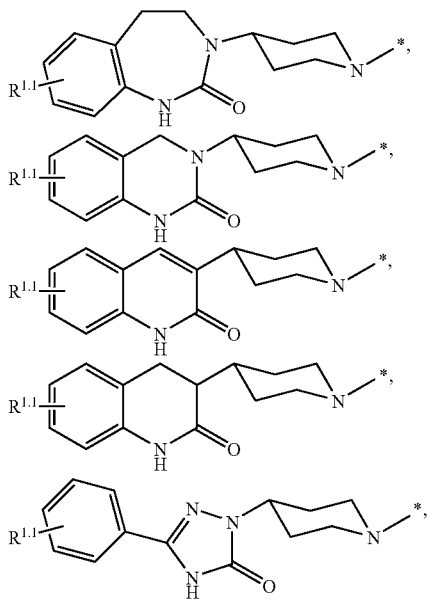

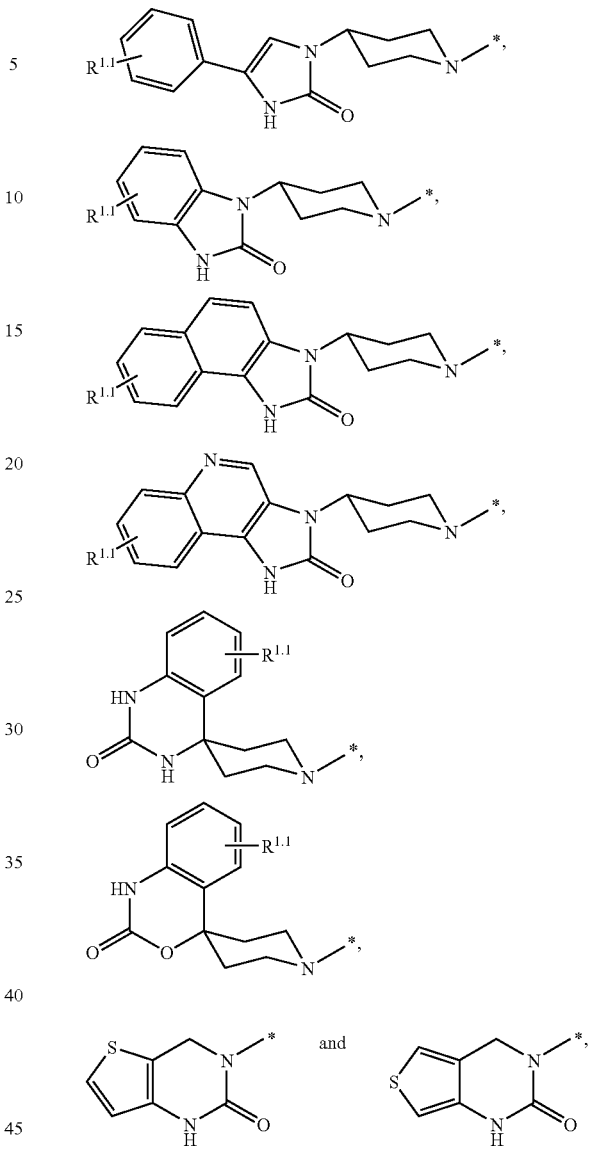

wherein
$R^{1.1}$ denotes H, halogen, HO, $F_3C$ or $C_{1-6}$-alkyl-O,
$R^2$ denotes a group of general formulae II

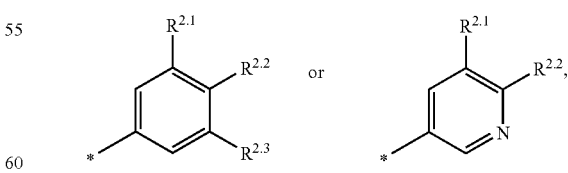

wherein
$R^{2.1}$ denotes H, halogen, $C_{1-3}$-alkyl-O, $C_{1-3}$-alkyl or $F_3C$,
$R^{2.2}$ denotes H, $H_2N$, HO, $H_3C$—O, H—C(O)—O or $C_{1-3}$-alkyl-C(O)—O, $R^{2.3}$ denotes H, halogen, $C_{1-3}$-alkyl or $F_3C$, or
$R^2$ denotes a group selected from

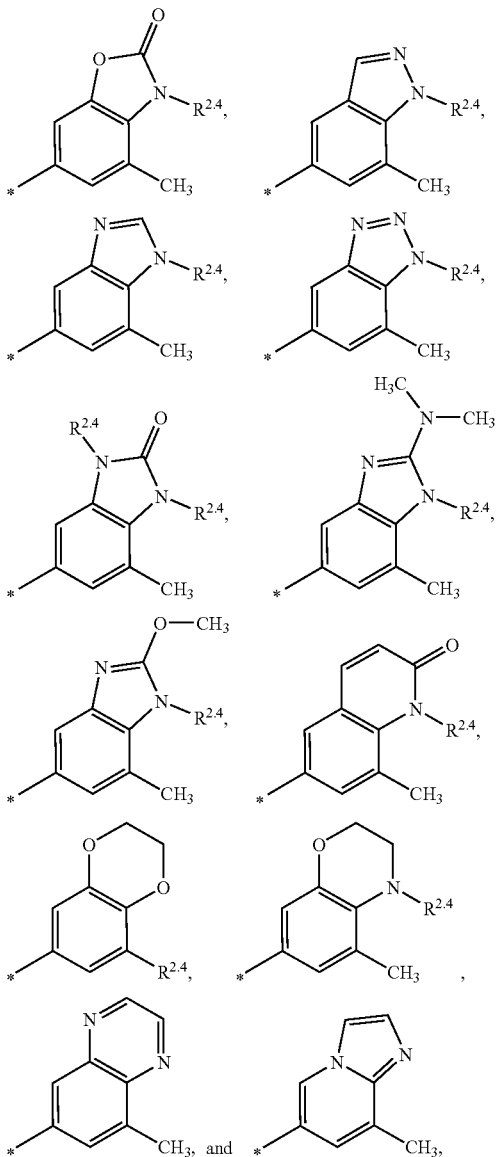

wherein
$R^{2.4}$ denotes H or $H_3C$,
$R^3$ denotes a group of general formulae III

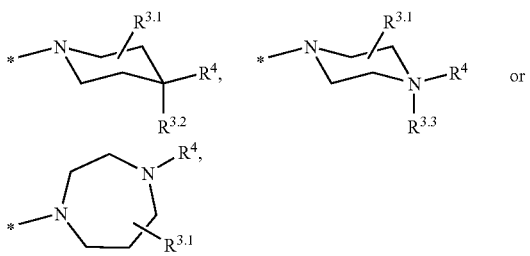

wherein
$R^{3.1}$ denotes H, $C_{1-3}$-alkyl or $R^{3.1.1}$—(O)C,
$R^{3.1.1}$ denotes HO or $C_{1-6}$-alkyl-O,
$R^{3.2}$ denotes H or $C_{1-3}$-alkyl and
$R^{3.3}$ denotes a free pair of electrons or the oxygen atom,
$R^4$ denotes a 4- to 7-membered oxycycloalkyl group optionally substituted by $R^{4.1}$ and
$R^{4.1}$ denotes NC, HO, $C_{1-3}$-alkyl or $C_{1-3}$-alkyl-O, the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A preferred first embodiment of the present invention comprises the compounds of the above general formula I, wherein $R^1$, $R^2$, $R^3$ and $R^4$ are defined as hereinbefore under the first embodiment and X denotes $CH_2$, NH or O, the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A second embodiment of the present invention comprises the compounds of the above general formula I, wherein X, $R^1$, $R^3$ and $R^4$ are defined as hereinbefore under the first embodiment and $R^2$ denotes a group of general formula II

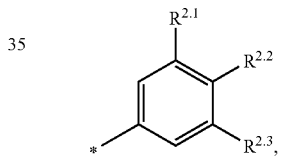

wherein
$R^{2.1}$ denotes H, halogen, $C_{1-3}$-alkyl-O, $C_{1-3}$-alkyl or $F_3C$,
$R^{2.2}$ denotes H, $H_2N$, HO, $H_3C$—O, H—C(O)—O or $C_{1-3}$-alkyl-C(O)—O,
$R^{2.3}$ denotes H, halogen, $C_{1-3}$-alkyl or $F_3C$, the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A preferred second embodiment of the present invention comprises the compounds of the above general formula I, wherein
$R^1$, $R^2$, $R^3$ and $R^4$ are defined as hereinbefore under the second embodiment and
X denotes $CH_2$, NH or O, the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A third embodiment of the present invention comprises the compounds of the above general formula I, wherein X denotes CH₂, NH or O,
R¹ denotes a group selected from
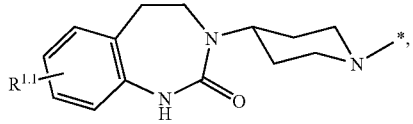
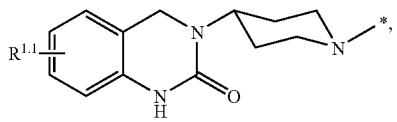
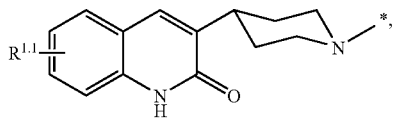
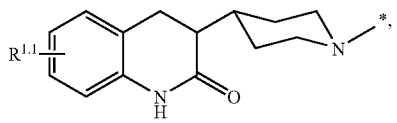
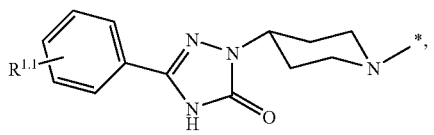
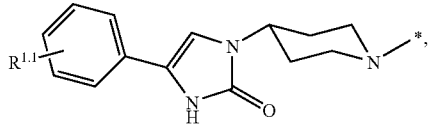
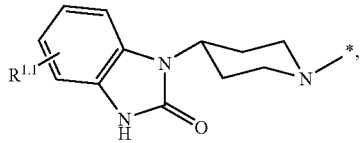
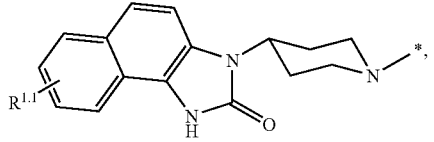
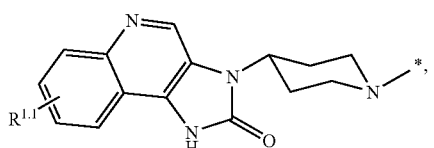
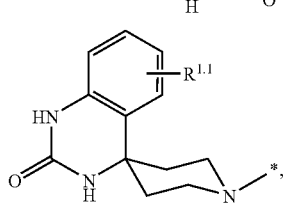
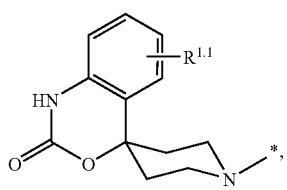
-continued
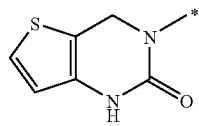 and 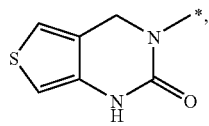
wherein
R$^{1.1}$ denotes H, Cl, Br, HO, F₃C or H₃C—O,
R² denotes a group of general formulae II
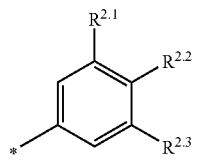 or 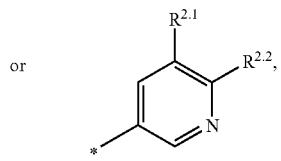,
wherein
R$^{2.1}$ denotes H, Cl, Br, H₃C—O, H₃C, F₃C or H₃C—H₂C,
R$^{2.2}$ denotes H₂N, HO, H₃C—O, H—C(O)—O or H₃C—C(O)—O,
R$^{2.3}$ denotes H, Cl, Br, H₃C or F₃C, or
R² denotes a group selected from
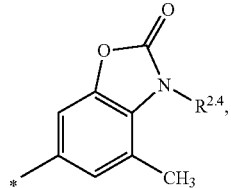 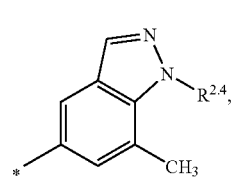
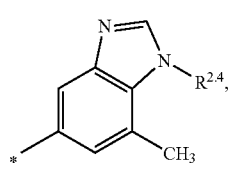 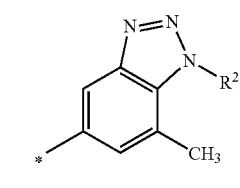
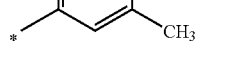 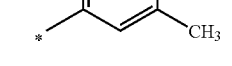
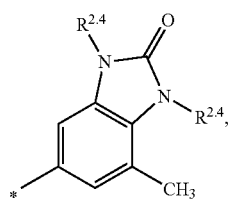 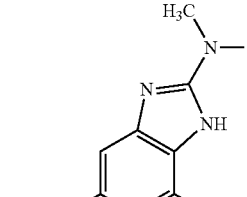
 

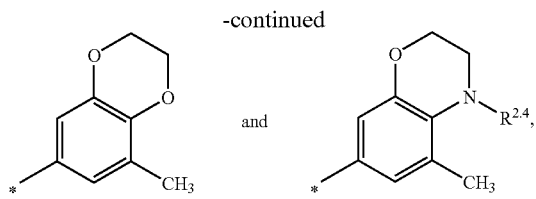

wherein $R^{2.4}$ denotes H or $H_3C$, $R^3$ denotes a group of general formulae III

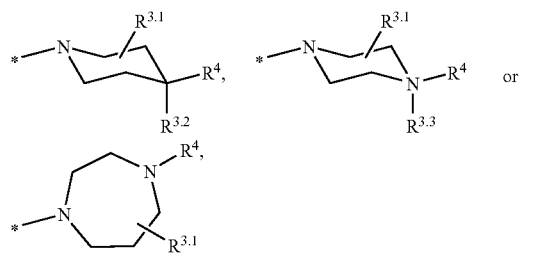

wherein $R^{3.1}$ denotes H or $H_3C$, $R^{3.2}$ denotes H or $H_3C$ and $R^{3.3}$ denotes a free pair of electrons or the oxygen atom, $R^4$ denotes a 4- to 7-membered oxycycloalkyl group optionally substituted by $R^{4.1}$ and $R^{4.1}$ denotes HO or $C_{1-3}$-alkyl, the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A preferred third embodiment of the present invention comprises the compounds of the above general formula I, wherein X, $R^1$, $R^2$ and $R^3$ are defined as hereinbefore under the second embodiment and $R^4$ denotes a group selected from

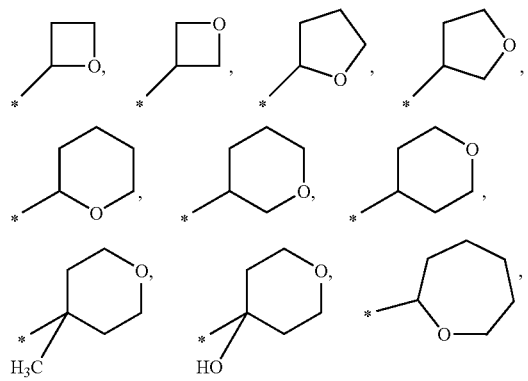

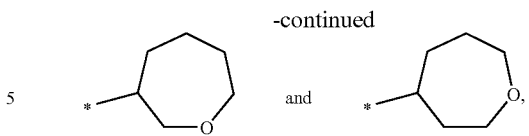

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A fourth embodiment of the present invention comprises the compounds of the above general formula I, wherein X, $R^1$, $R^3$ and $R^4$ are defined as hereinbefore under the third embodiment and $R^2$ denotes a group of general formula II

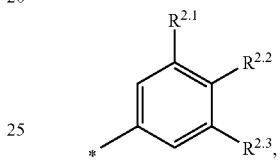

wherein $R^{2.1}$ denotes H, Cl, Br, $H_3C$—O, $H_3C$, $F_3C$ or $H_3C$—$H_2C$, $R^{2.2}$ denotes $H_2N$, HO, $H_3C$—O, H—C(O)—O or $H_3C$—C(O)—O, $R^{2.3}$ denotes H, Cl, Br, $H_3C$ or $F_3C$, the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A preferred fourth embodiment of the present invention comprises the compounds of the above general formula I, wherein X, $R^1$, $R^2$ and $R^3$ are defined as hereinbefore under the fourth embodiment and $R^4$ denotes a group selected from

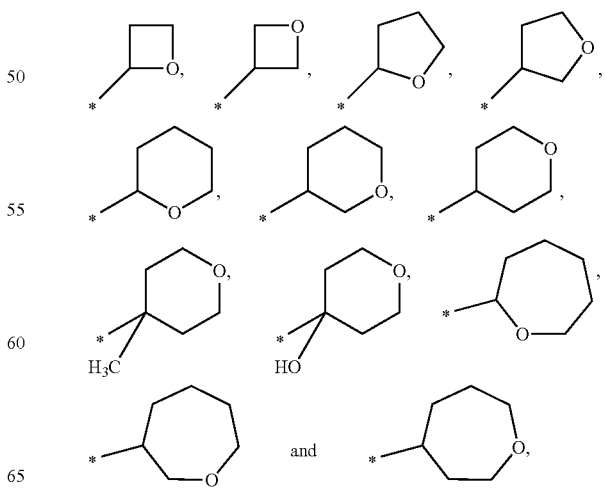

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A fifth embodiment of the present invention comprises the compounds of the above general formula I, wherein X denotes $CH_2$, NH or O, $R^1$ denotes a group selected from

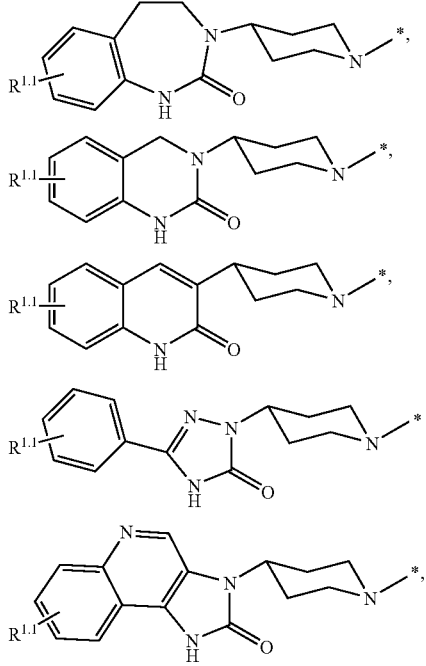

wherein $R^{1.1}$ denotes H or $H_3C$—O, $R^2$ denotes a group selected from

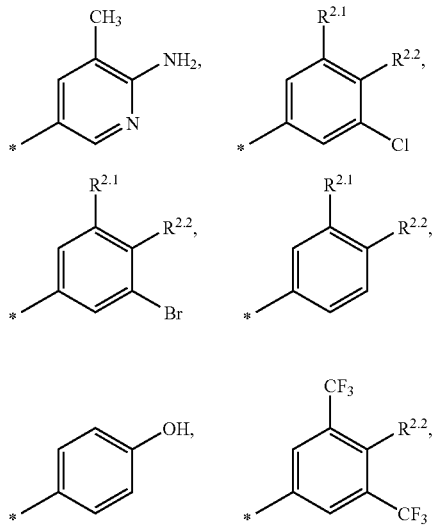

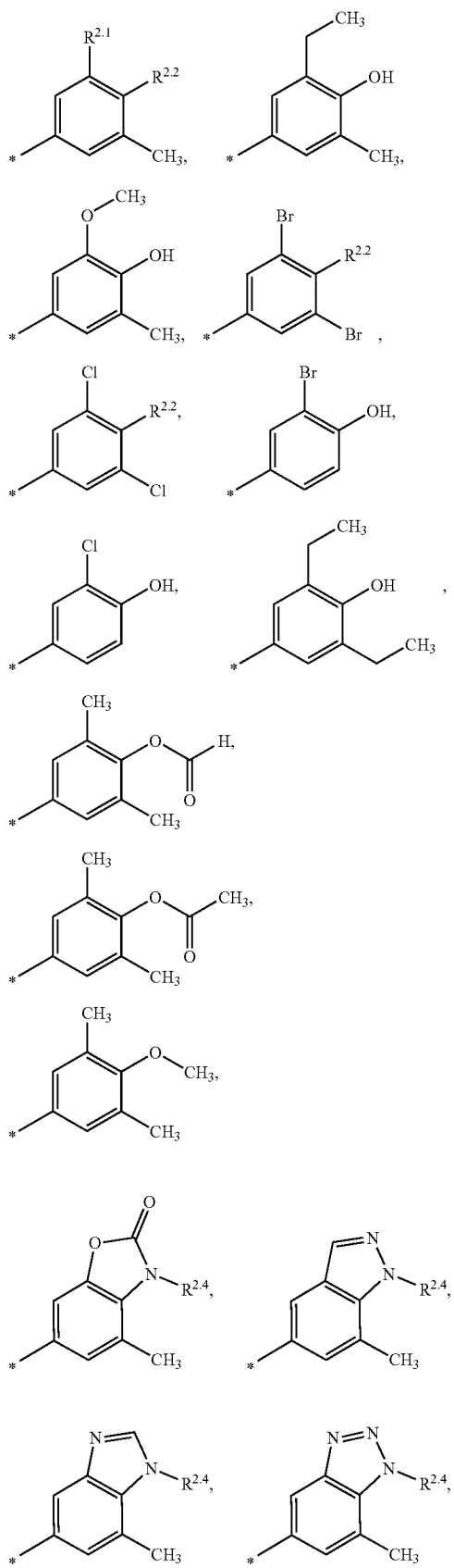

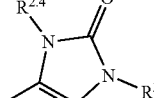

wherein
R<sup>2.1</sup> denotes H₃C or F₃C,
R<sup>2.2</sup> denotes H₂N or HO,
R<sup>2.4</sup> denotes H or H₃C,
R³ denotes a group selected from

and
R⁴ denotes a group selected from

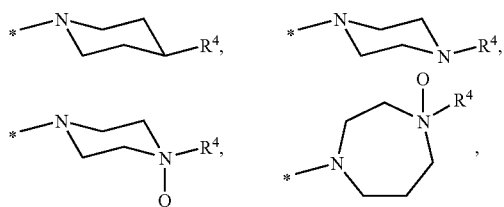

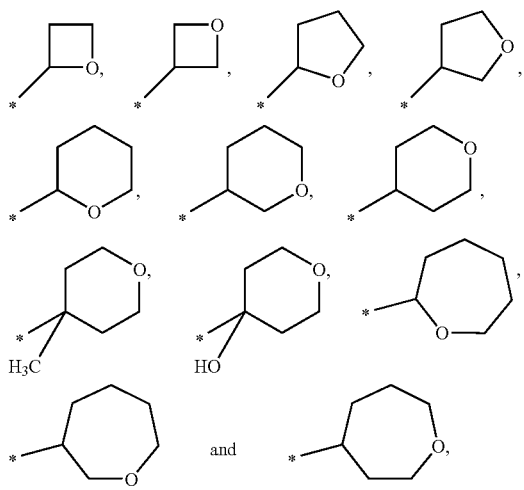

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A preferred fifth embodiment of the present invention comprises the compounds of the above general formula I, wherein R¹, R² and X are defined as hereinbefore under the fifth embodiment and —R³-R⁴ together denote a group selected from

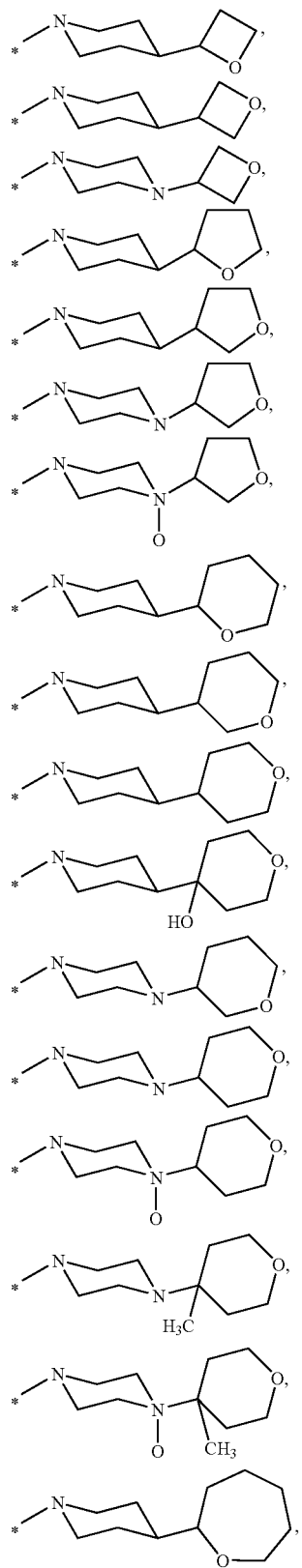

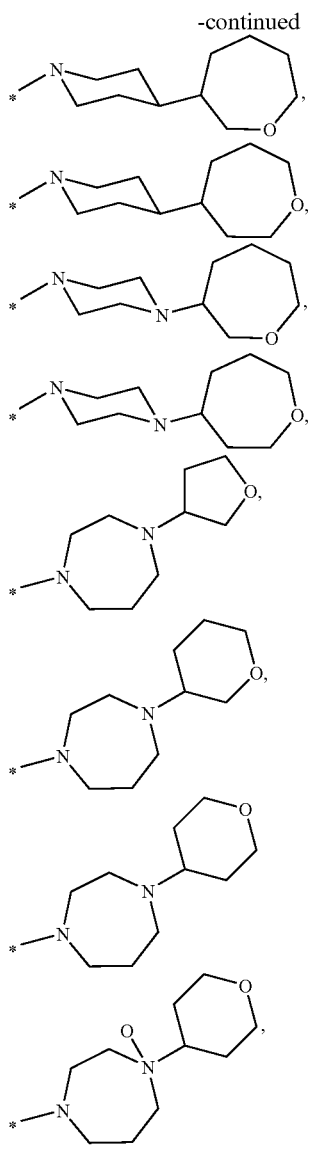

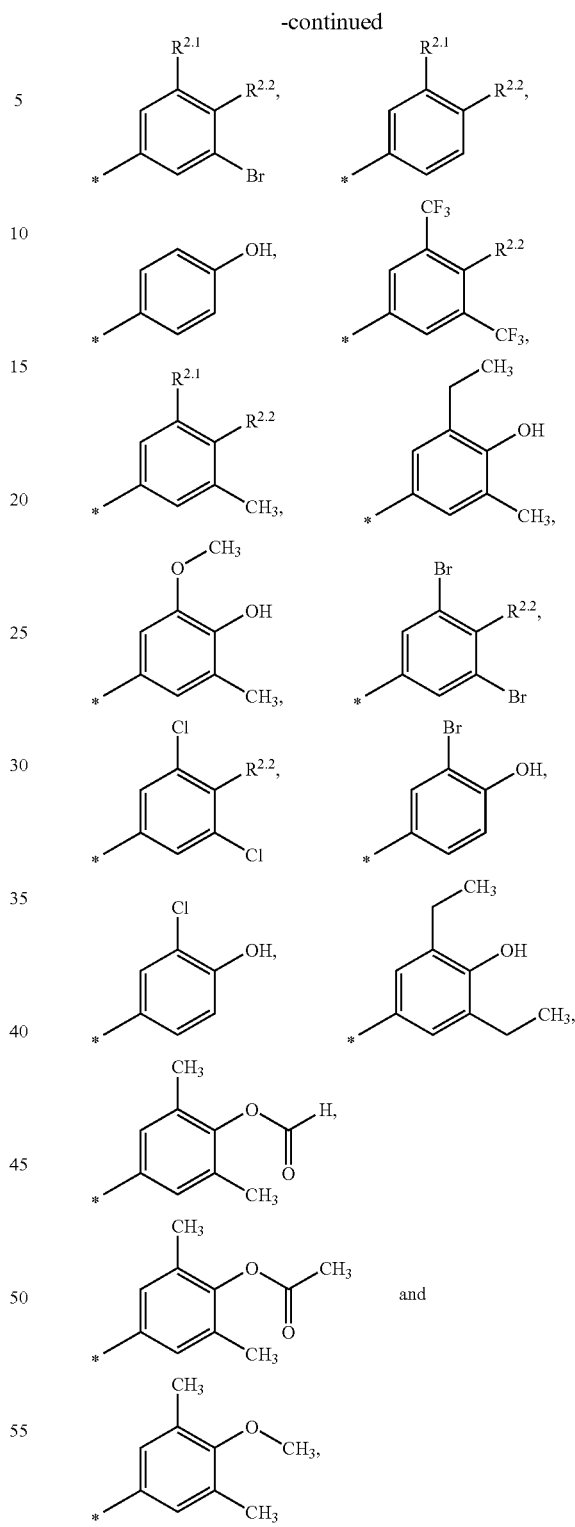

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A sixth embodiment of the present invention comprises the compounds of the above general formula I, wherein X, $R^1$, $R^3$ and $R^4$ are defined as hereinbefore under the fifth embodiment and $R^2$ denotes a group selected from

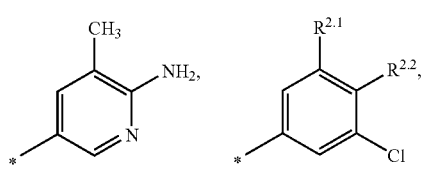

wherein $R^{2.1}$ denotes $H_3C$ or $F_3C$, $R^{2.2}$ denotes $H_2N$ or $HO$, the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A preferred sixth embodiment of the present invention comprises the compounds of the above general formula I, wherein $R^1$, $R^2$ and X are defined as hereinbefore under the sixth embodiment and —$R^3$-$R^4$ together denote a group selected from

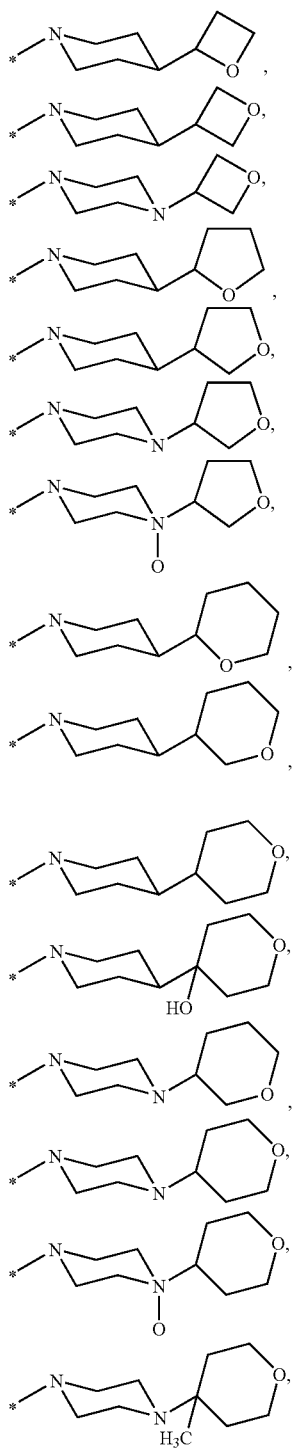

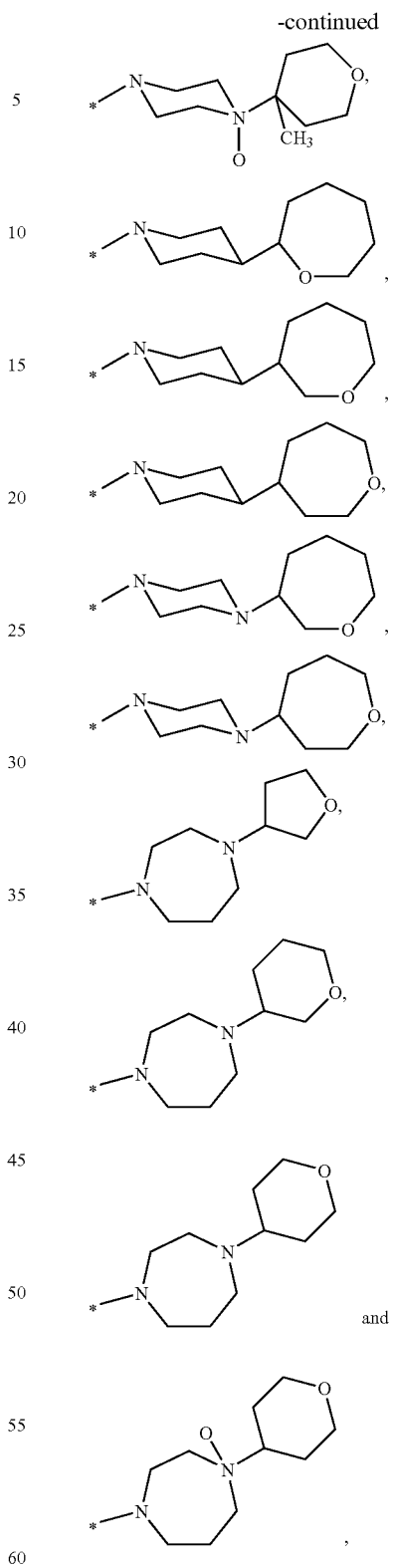

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A seventh embodiment of the present invention comprises the compounds of the above general formula I, wherein $R^1$ denotes a group selected from
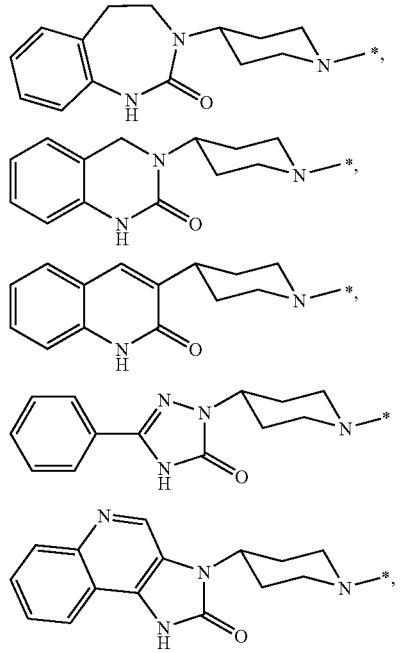
and
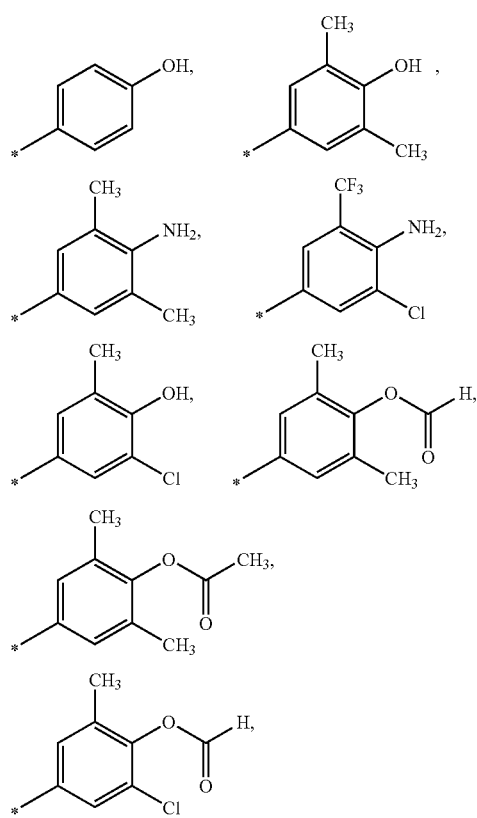
$R^2$ denotes a group selected from
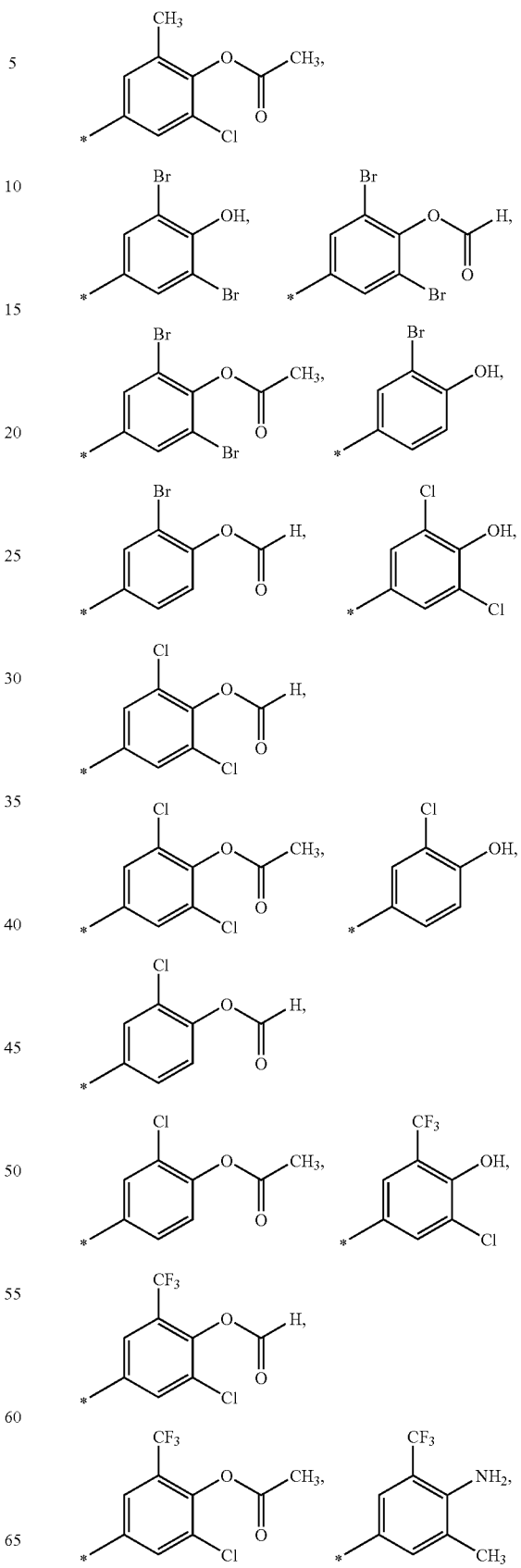

-continued

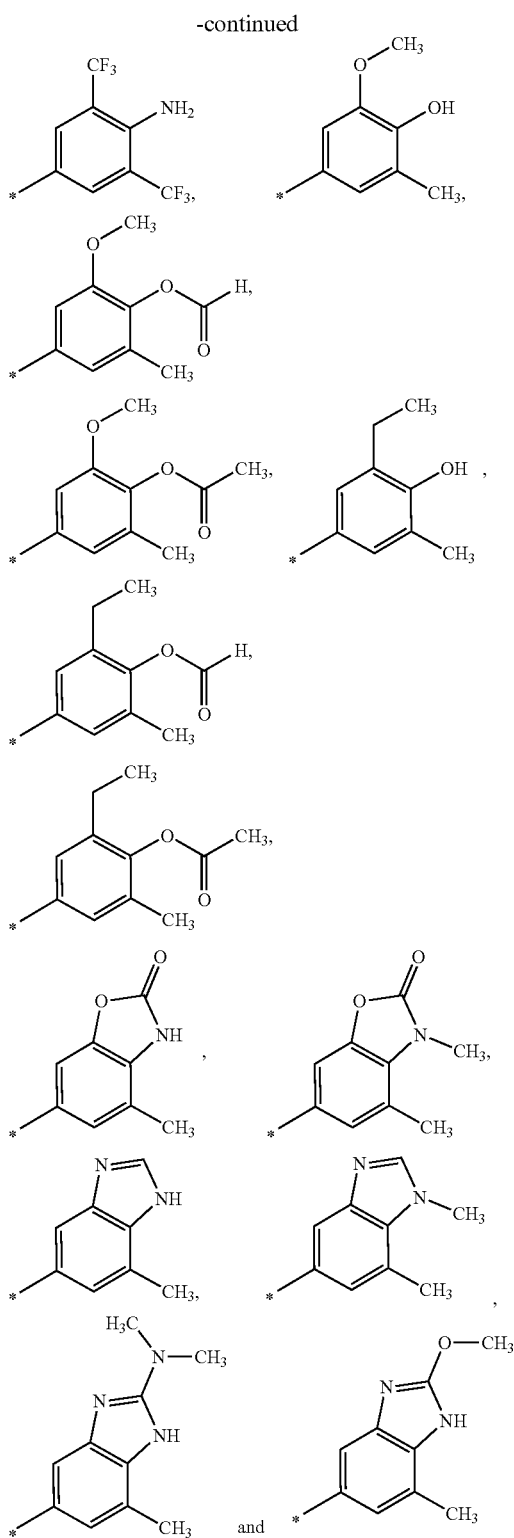

$R^3$ denotes a group selected from

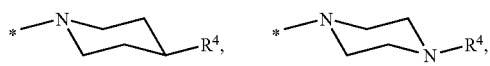

-continued

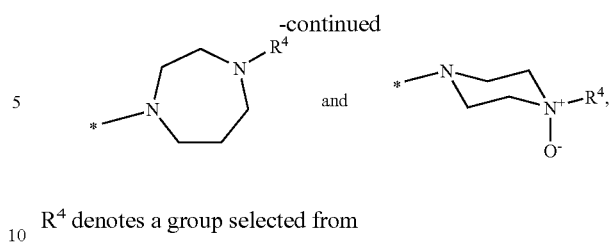

$R^4$ denotes a group selected from

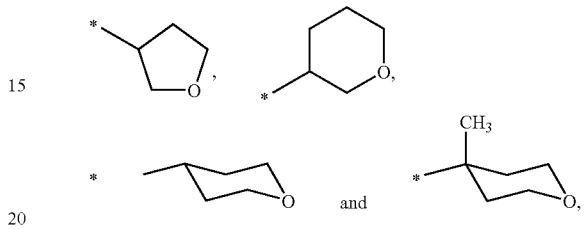

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A preferred seventh embodiment of the present invention comprises the compounds of the above general formula I, wherein X, $R^1$, $R^3$ and $R^4$ are defined as hereinbefore under the seventh embodiment and $R^2$ denotes a group selected from

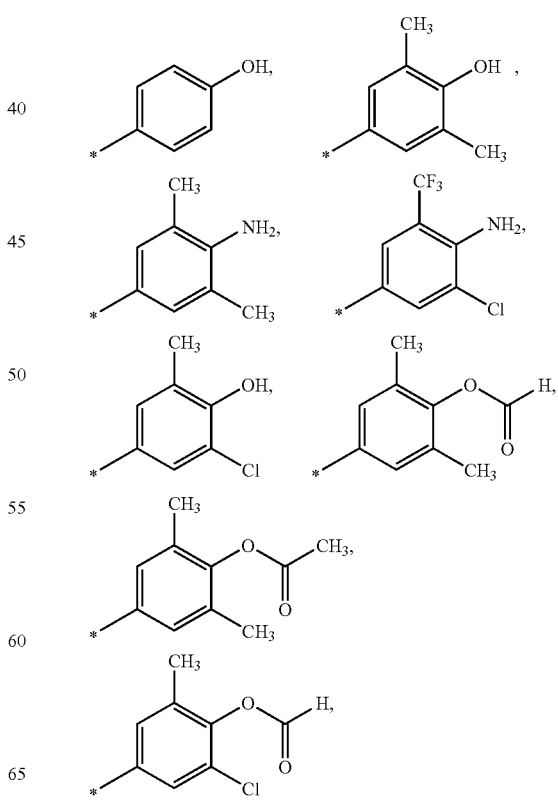

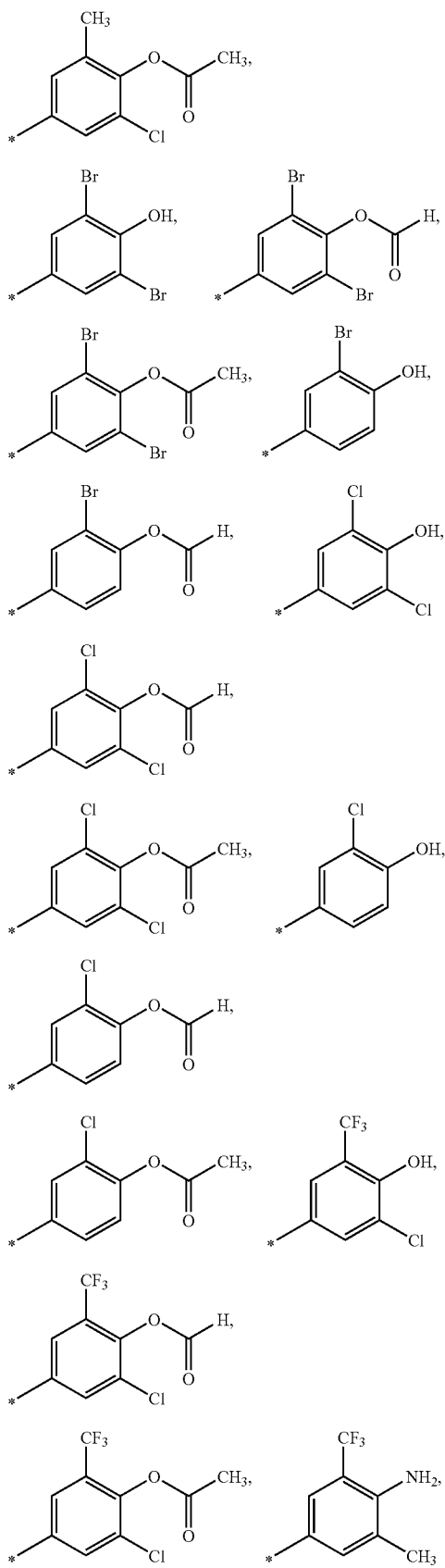
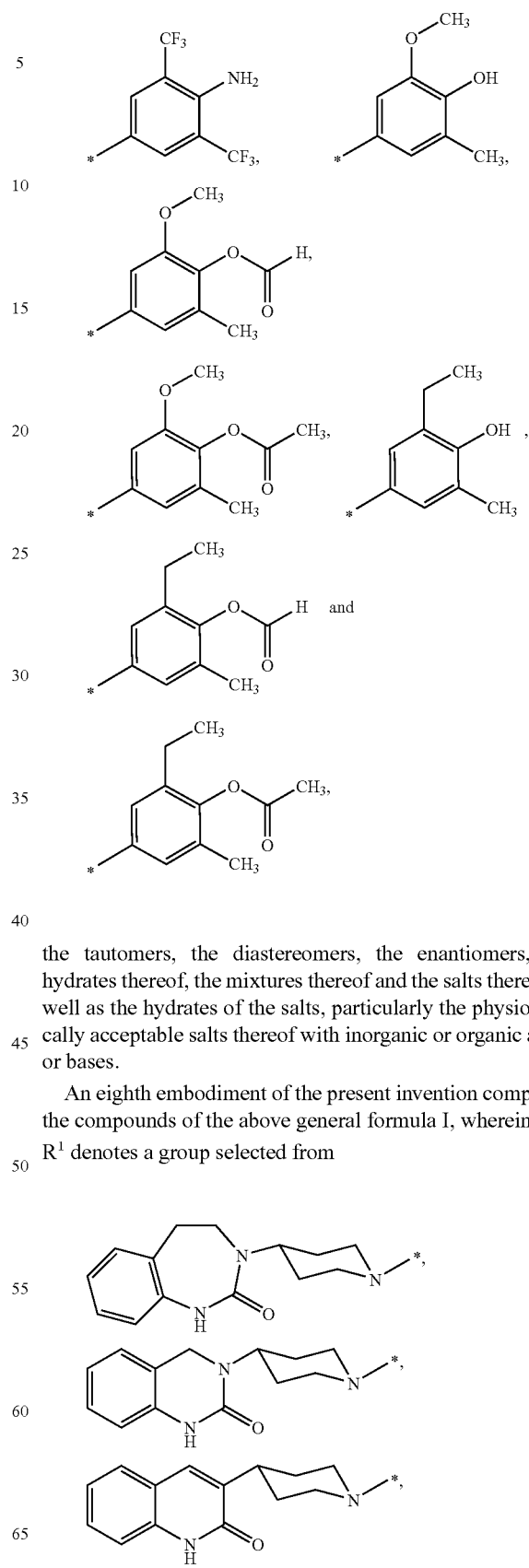

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

An eighth embodiment of the present invention comprises the compounds of the above general formula I, wherein $R^1$ denotes a group selected from

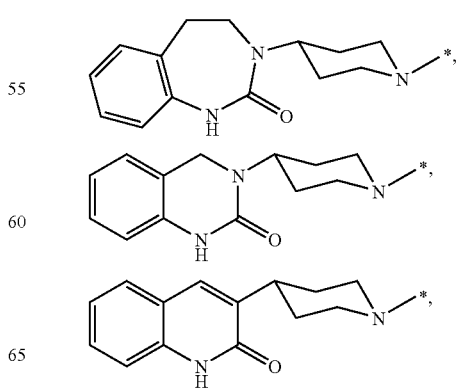

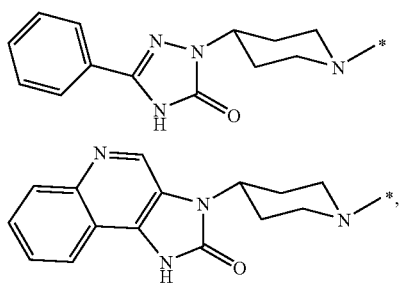
and

R² denotes a group selected from

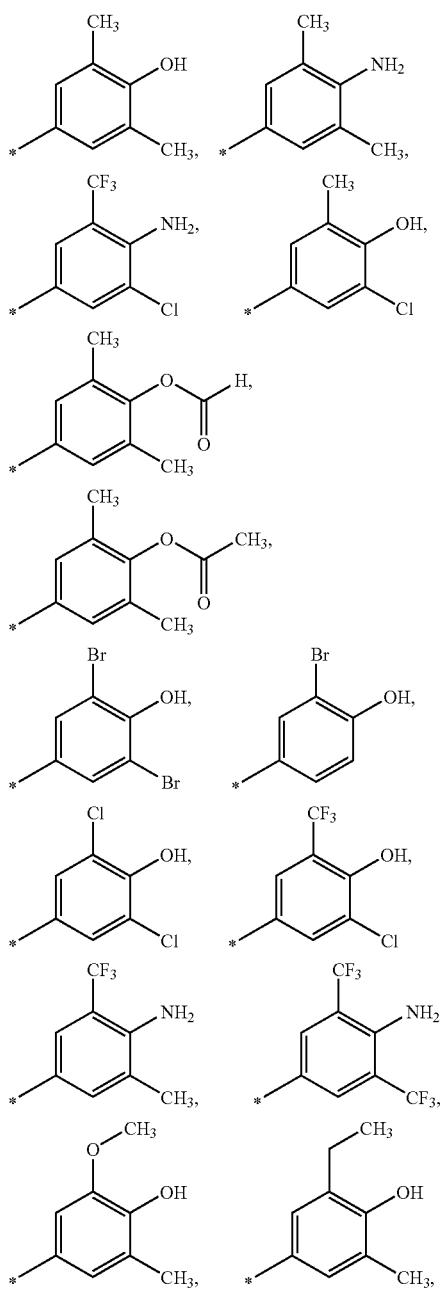

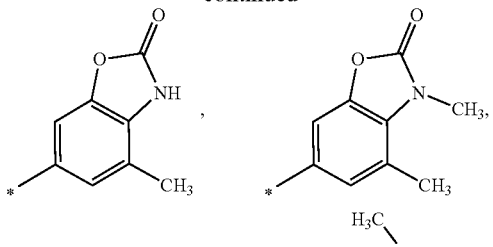

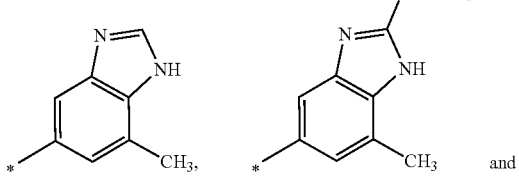

and

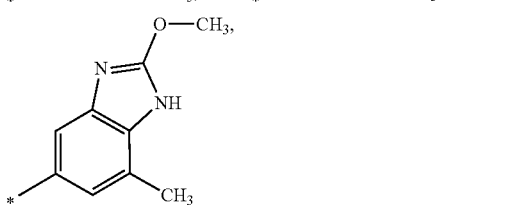

R³-R⁴ together denote a group selected from

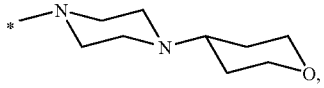

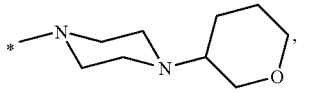

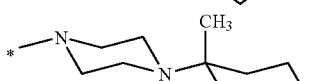

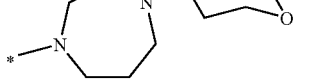

and

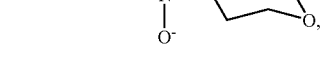

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

A preferred eighth embodiment of the present invention comprises the compounds of the above general formula I, wherein X, R¹, R³ and R⁴ are defined as hereinbefore under the eighth embodiment and
R² denotes a group selected from

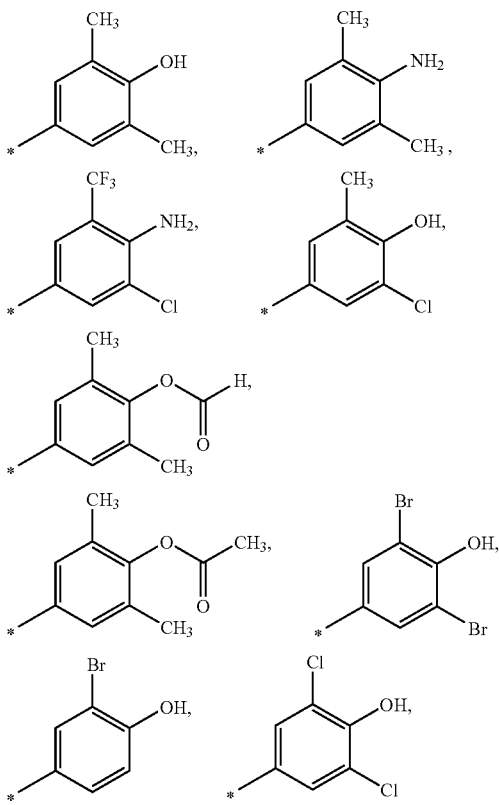
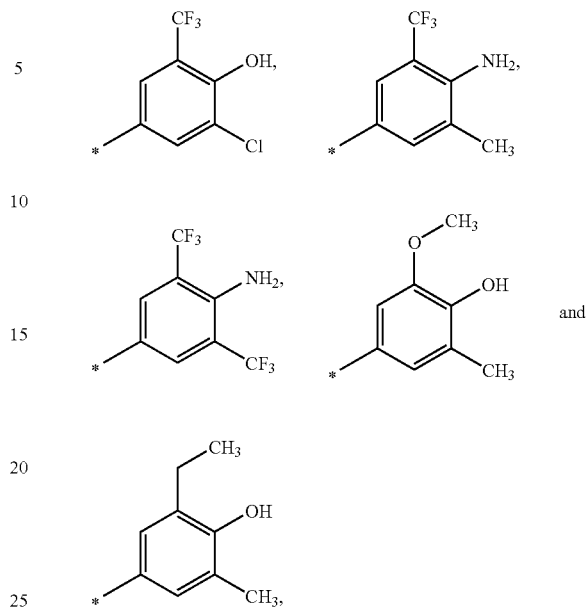

the tautomers, the diastereomers, the enantiomers, the hydrates thereof, the mixtures thereof and the salts thereof as well as the hydrates of the salts, particularly the physiologically acceptable salts thereof with inorganic or organic acids or bases.

The following compounds may also be mentioned as examples of most particularly preferred compounds of the above general formula I:

| No. | Structure |
|---|---|
| (1) | 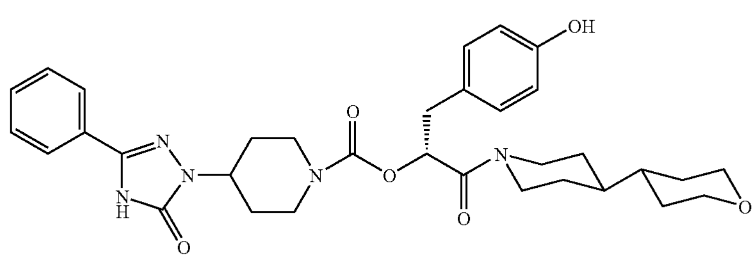 |
| (2) | 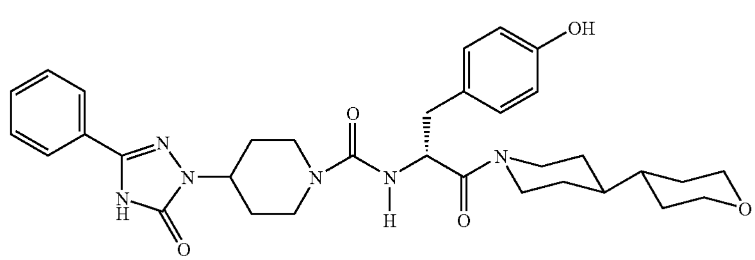 |

-continued
| No. | Structure |
|---|---|
| (3) | 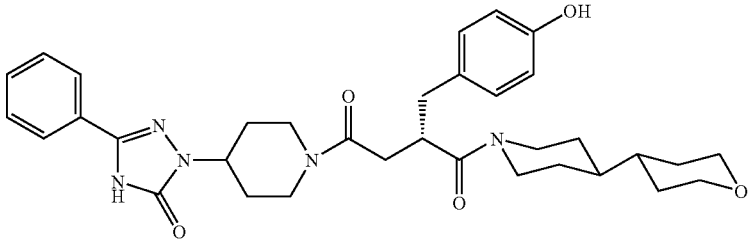 |
| (4) | 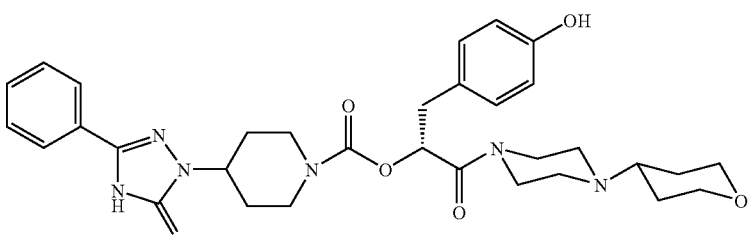 |
| (5) | 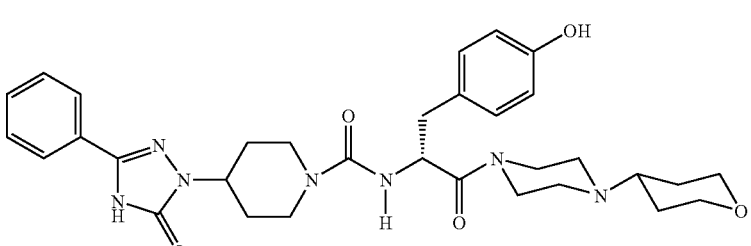 |
| (6) | 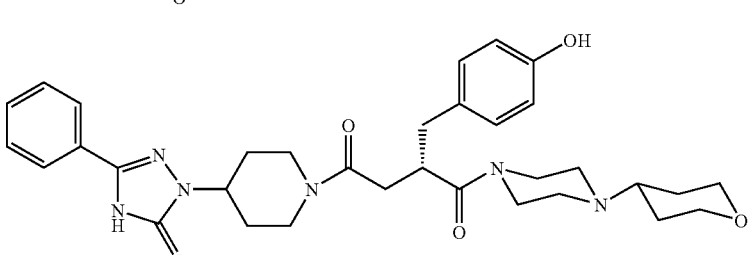 |
| (7) | 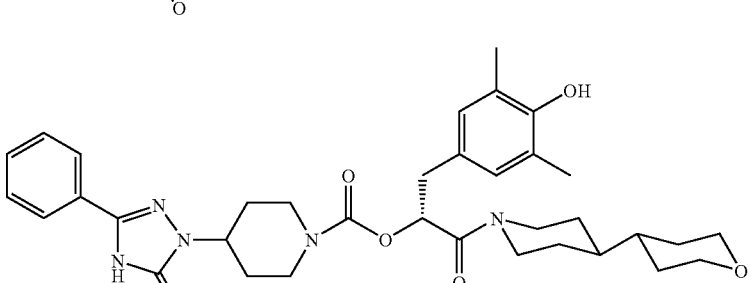 |
| (8) | 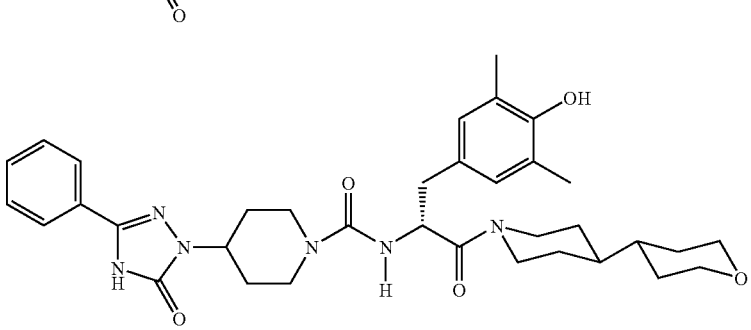 |

| No. | Structure |
|---|---|
| (9) | 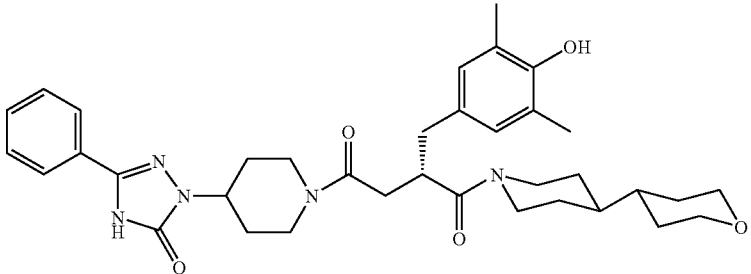 |
| (10) | 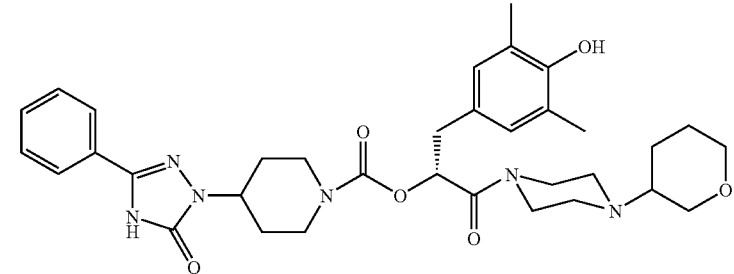 |
| (11) | 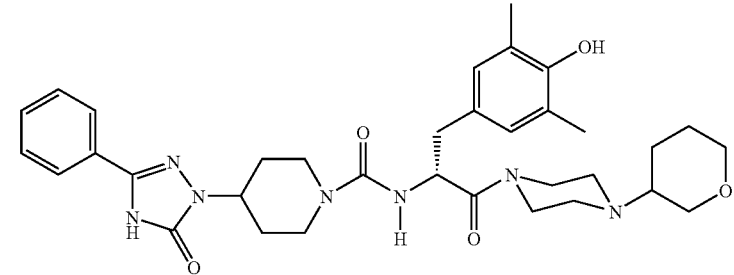 |
| (12) | 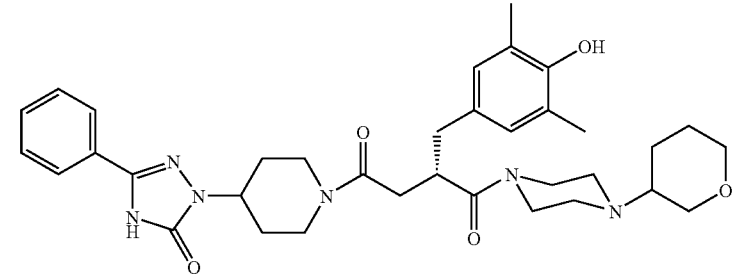 |
| (13) | 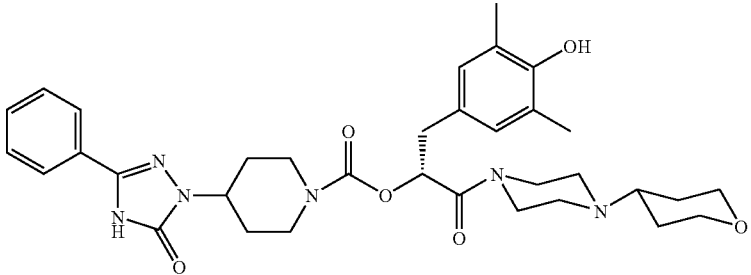 |

-continued
| No. | Structure |
|---|---|
| (14) | 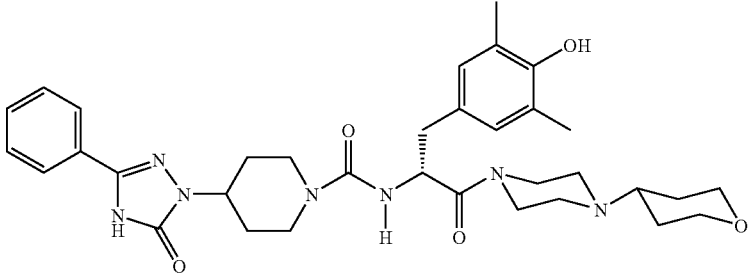 |
| (15) | 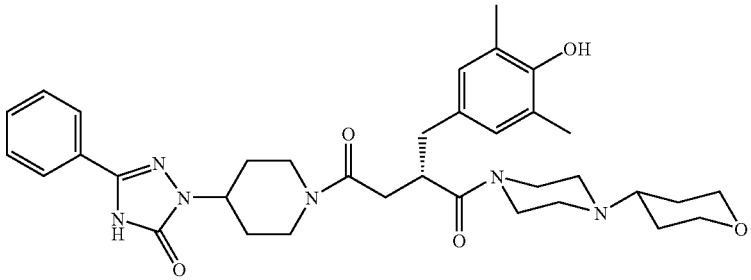 |
| (16) | 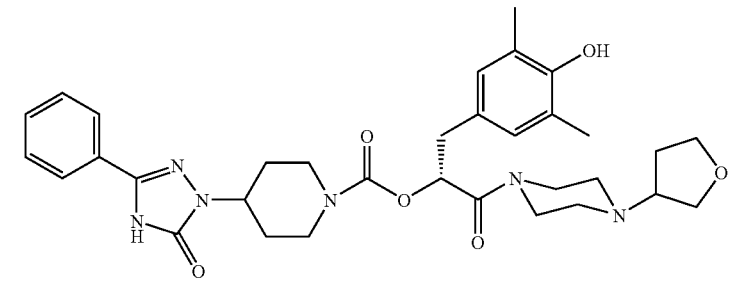 |
| (17) | 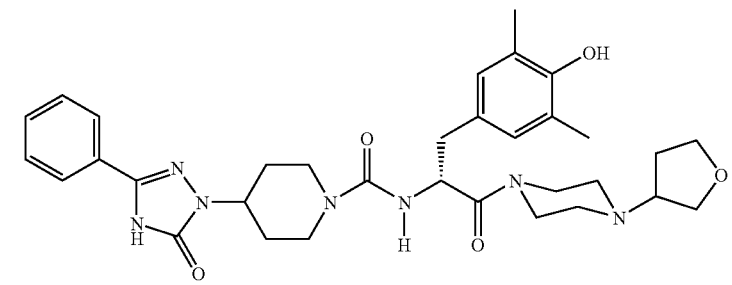 |
| (18) | 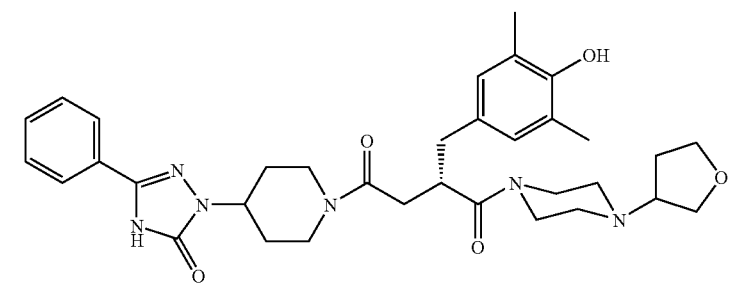 |

-continued

| No. | Structure |
|---|---|
| (19) | 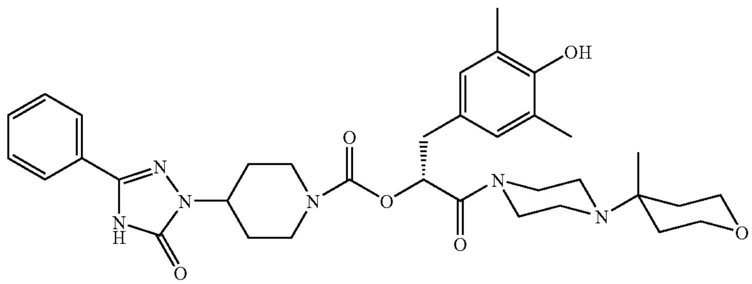 |
| (20) | 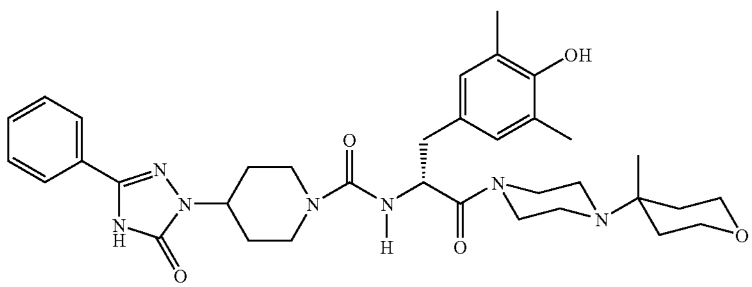 |
| (21) | 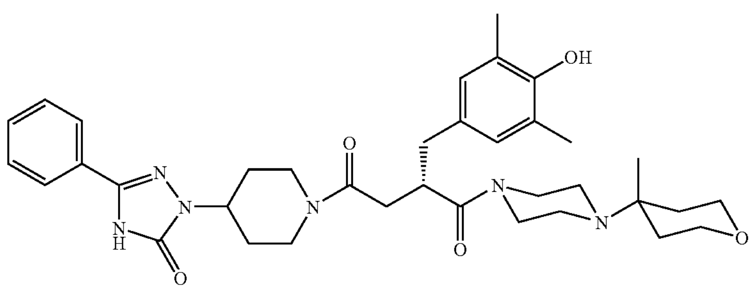 |
| (22) | 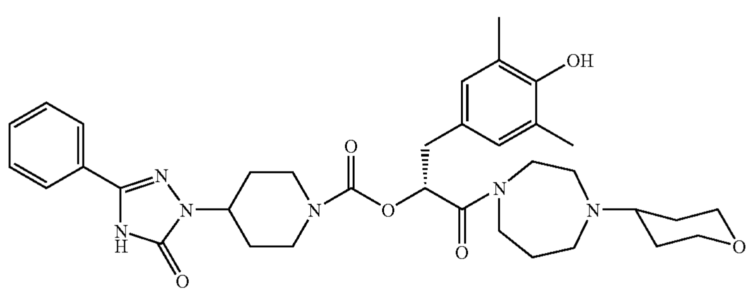 |
| (23) | 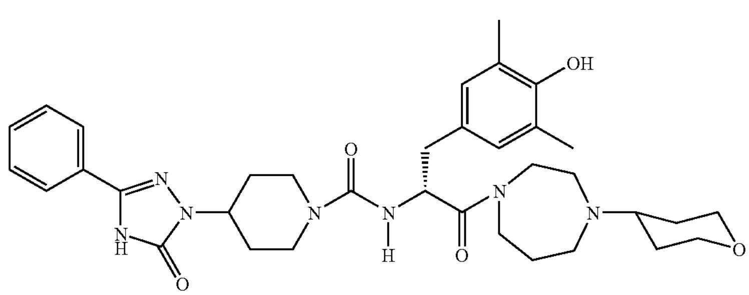 |

-continued
| No. | Structure |
|---|---|
| (24) | 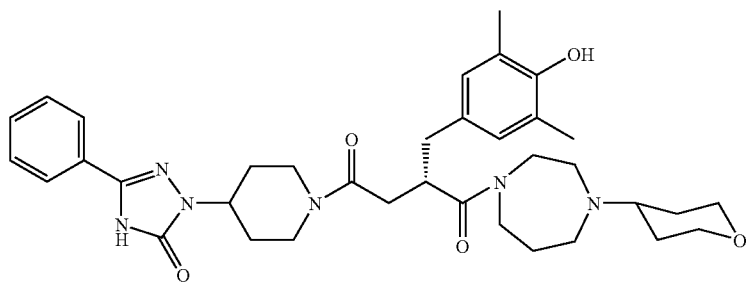 |
| (25) | 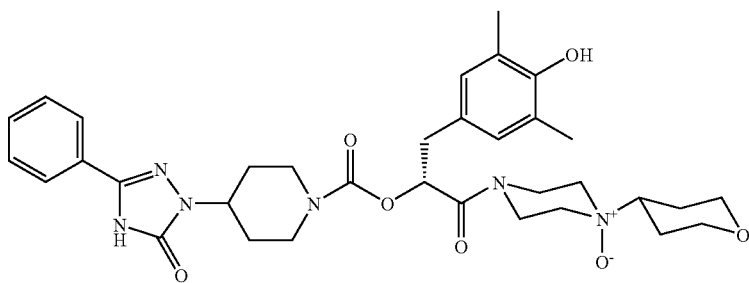 |
| (26) | 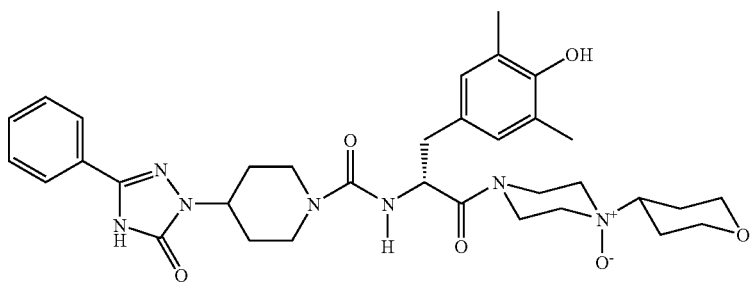 |
| (27) | 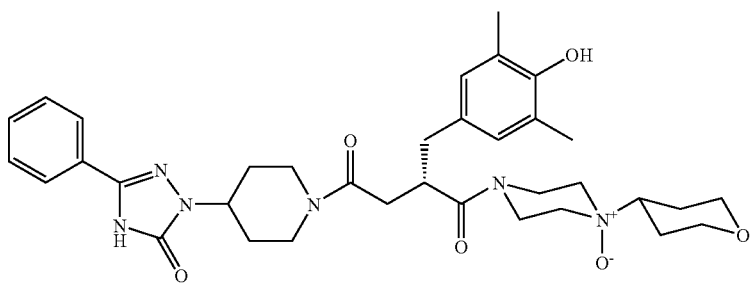 |
| (28) | 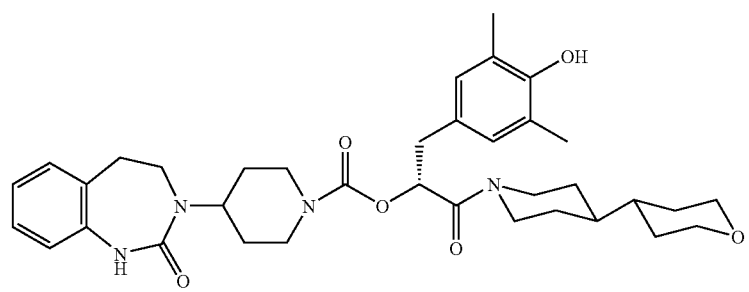 |

-continued

| No. | Structure |
|---|---|
| (29) | 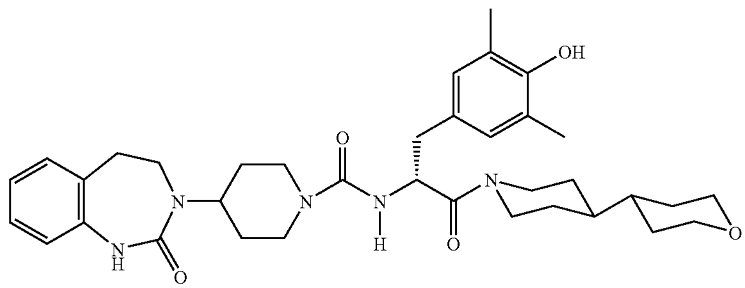 |
| (30) | 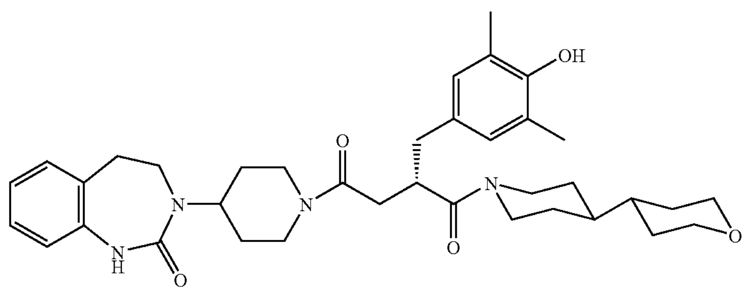 |
| (31) | 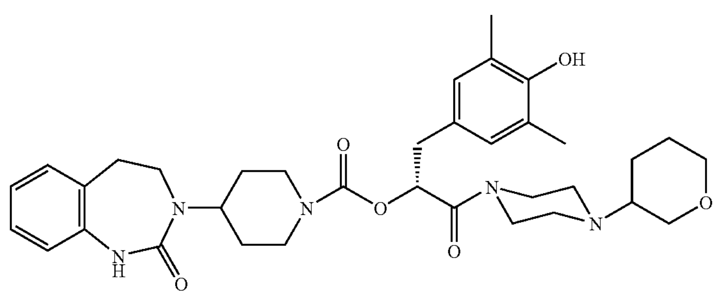 |
| (32) | 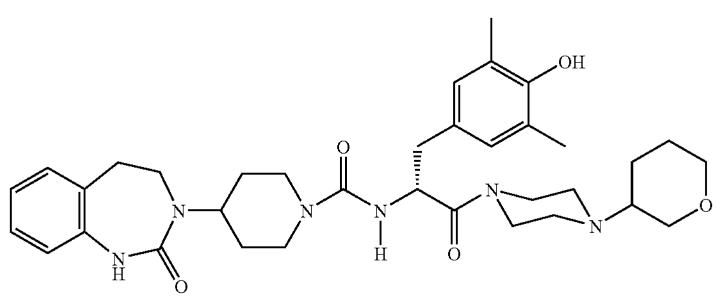 |
| (33) | 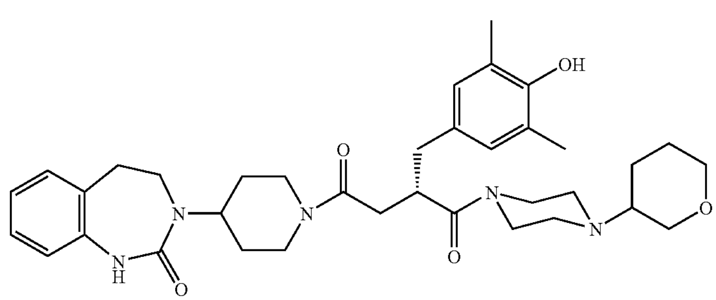 |

-continued
| No. | Structure |
|---|---|
| (34) | 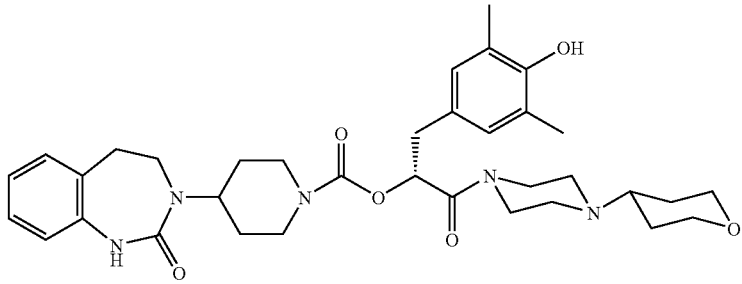 |
| (35) | 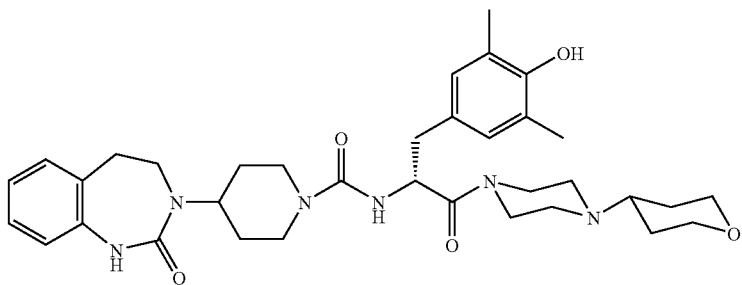 |
| (36) | 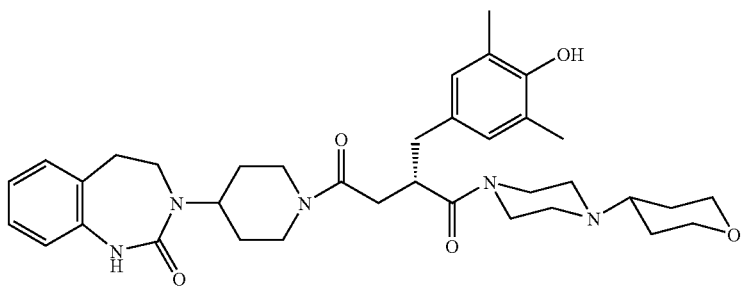 |
| (37) | 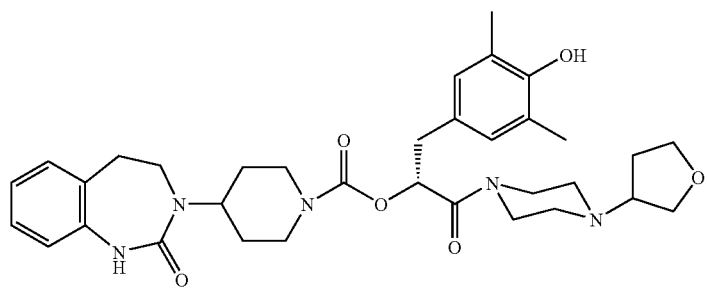 |
| (38) | 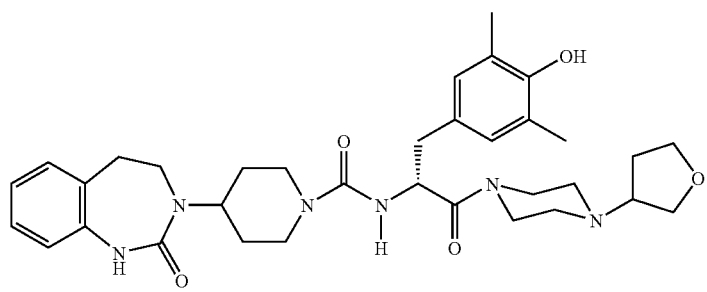 |

| No. | Structure |
|---|---|
| (39) | 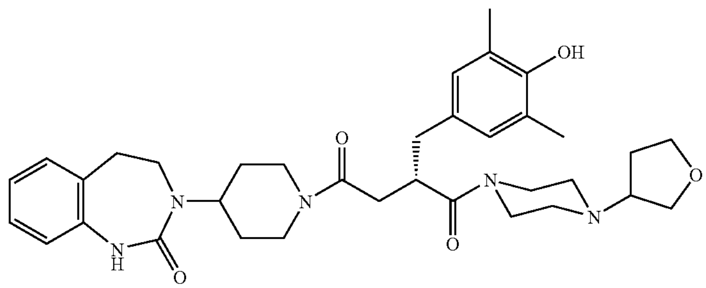 |
| (40) | 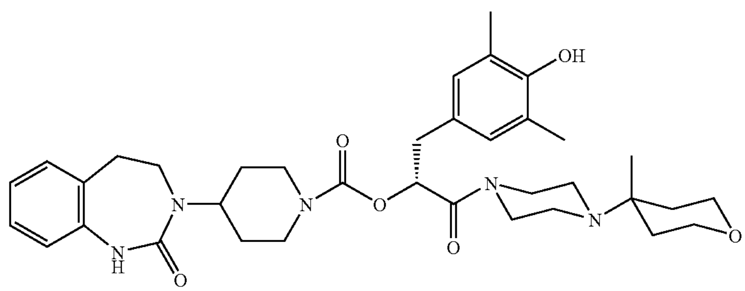 |
| (41) | 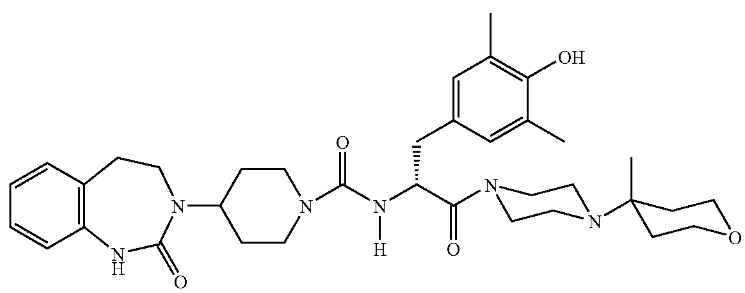 |
| (42) | 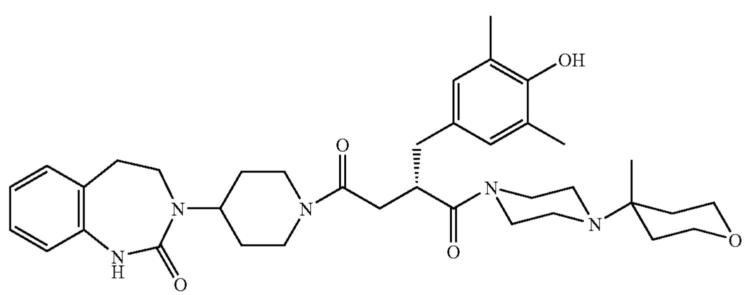 |
| (43) | 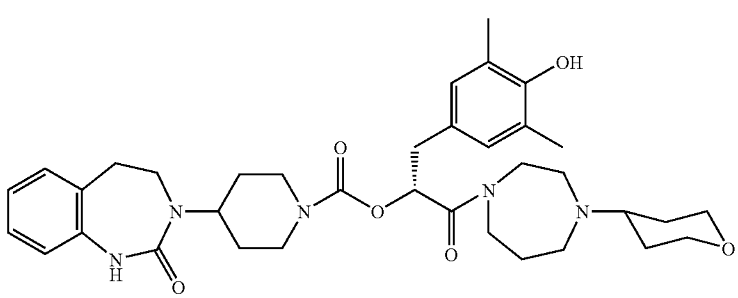 |

-continued

| No. | Structure |
|---|---|
| (44) | 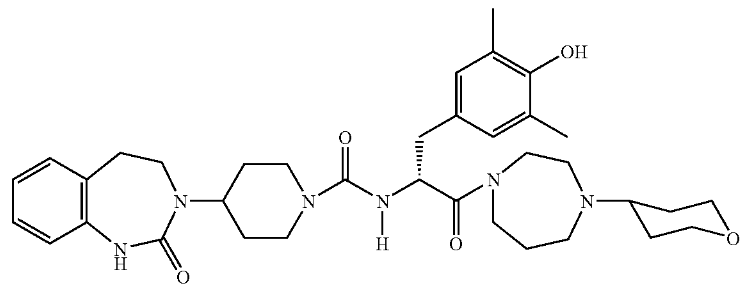 |
| (45) | 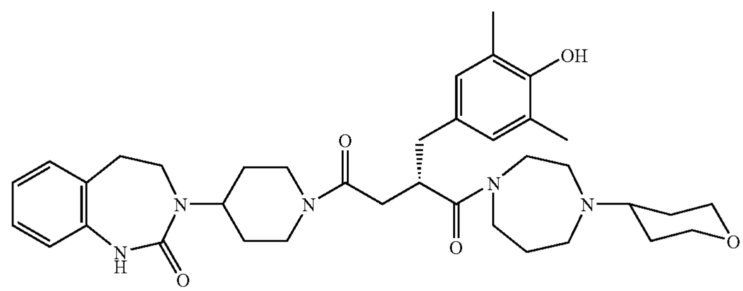 |
| (46) | 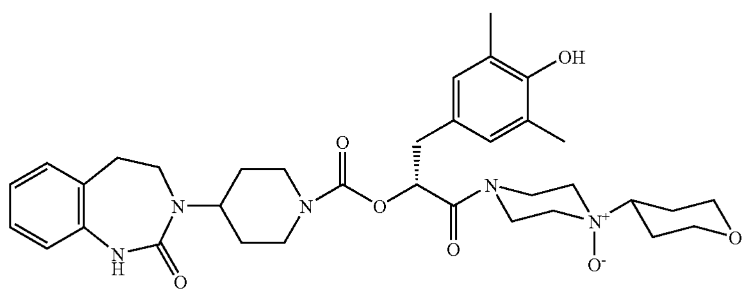 |
| (47) | 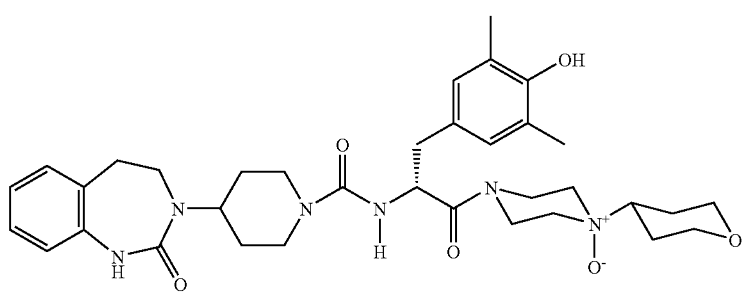 |
| (48) | 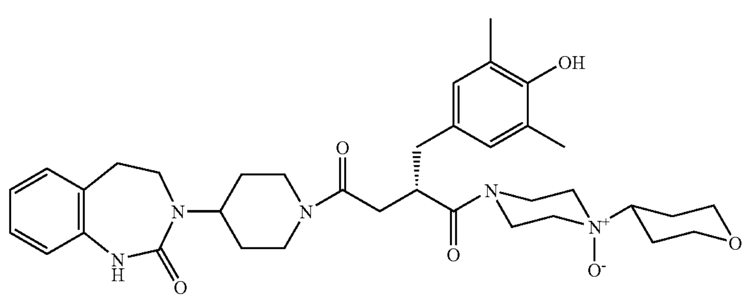 |

-continued
| No. | Structure |
|---|---|
| (49) | 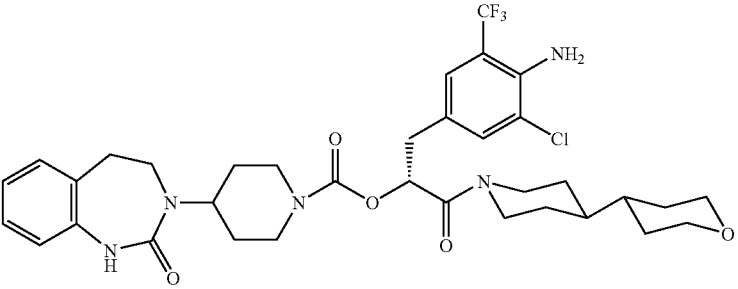 |
| (50) | 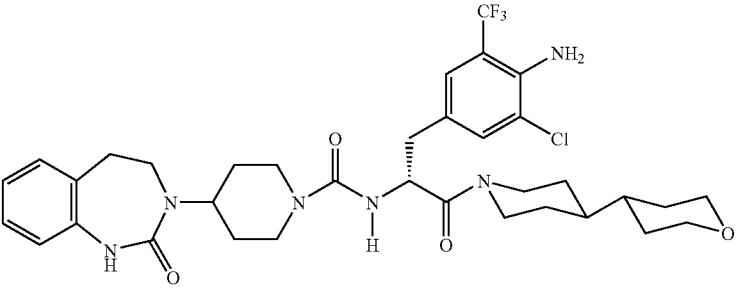 |
| (51) | 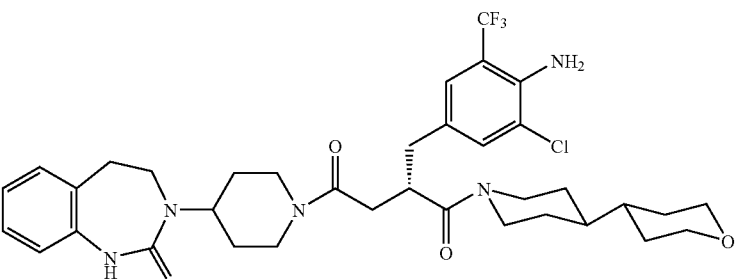 |
| (52) | 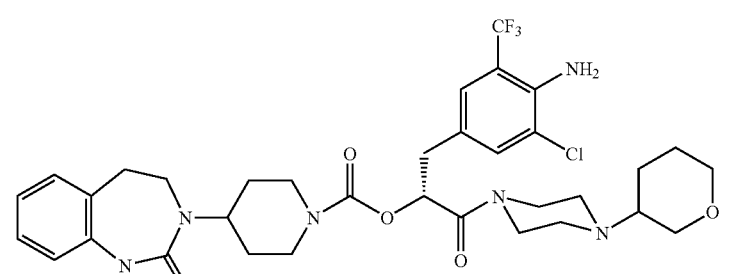 |
| (53) | 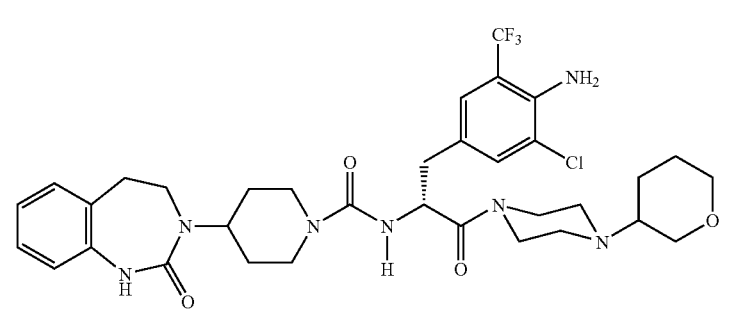 |

-continued

| No. | Structure |
|---|---|
| (54) | 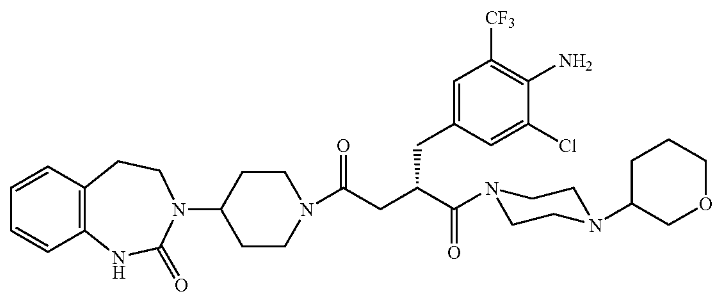 |
| (55) | 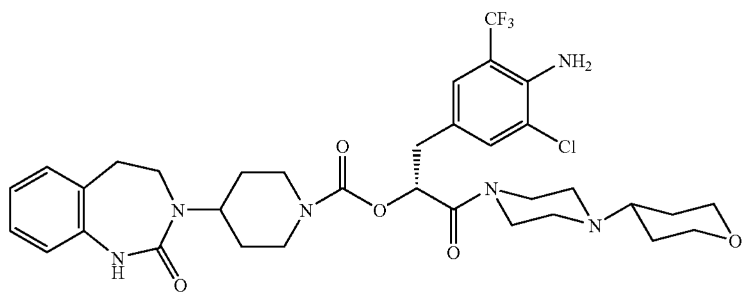 |
| (56) | 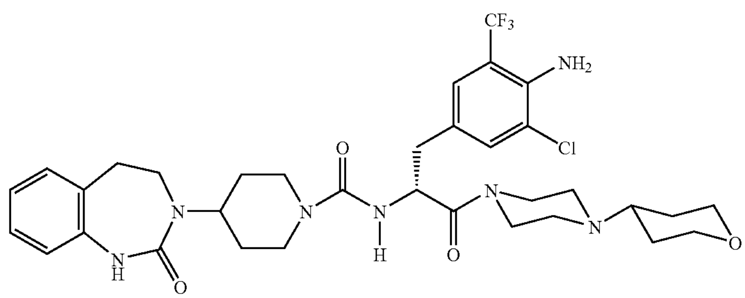 |
| (57) | 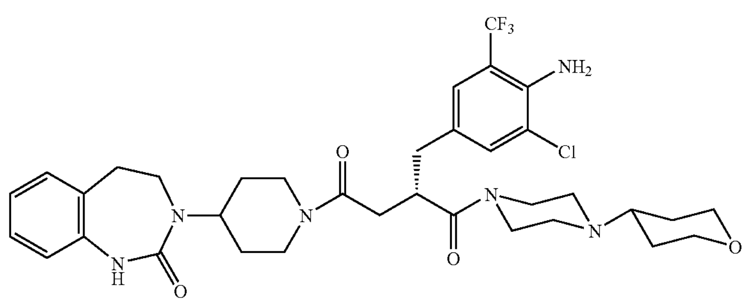 |
| (58) | 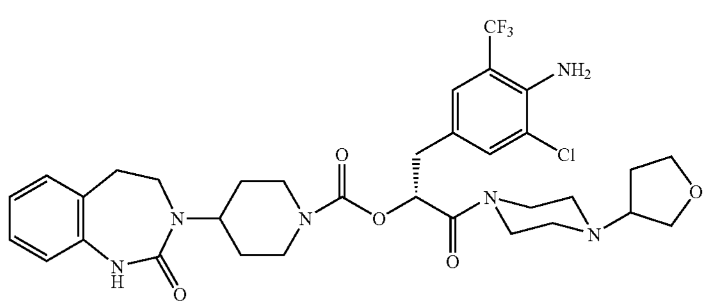 |

-continued
| No. | Structure |
|---|---|
| (59) | 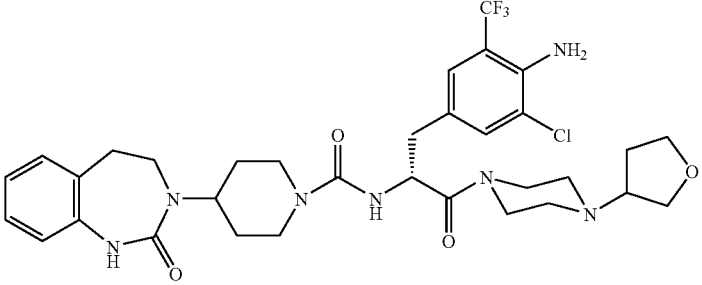 |
| (60) | 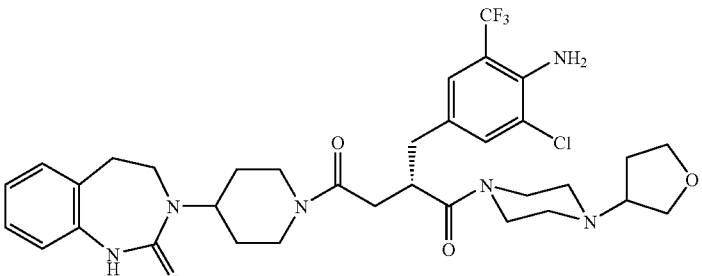 |
| (61) | 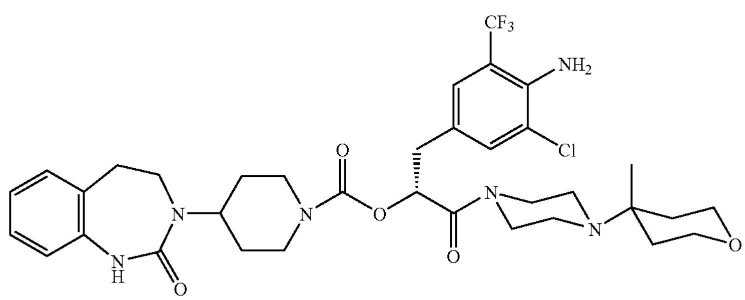 |
| (62) | 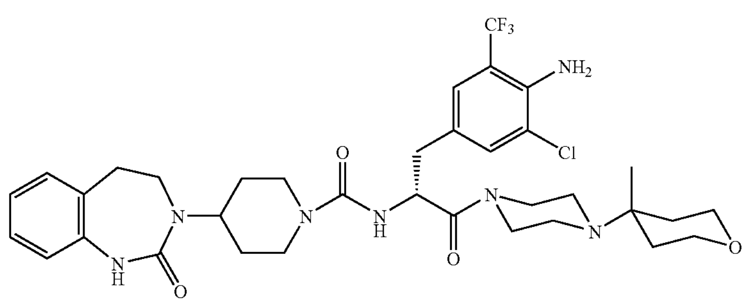 |
| (63) | 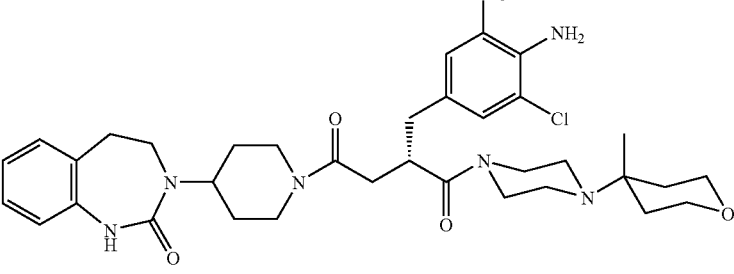 |

-continued

| No. | Structure |
|---|---|
| (64) | 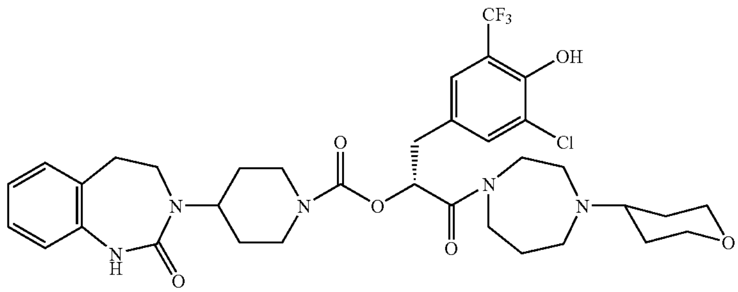 |
| (65) | 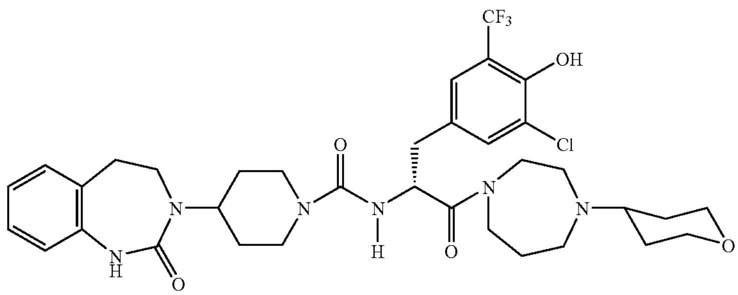 |
| (66) | 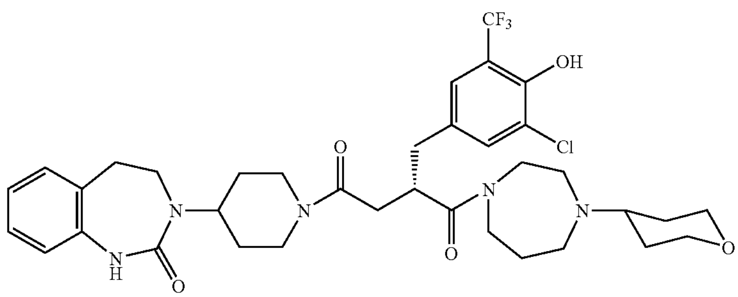 |
| (67) | 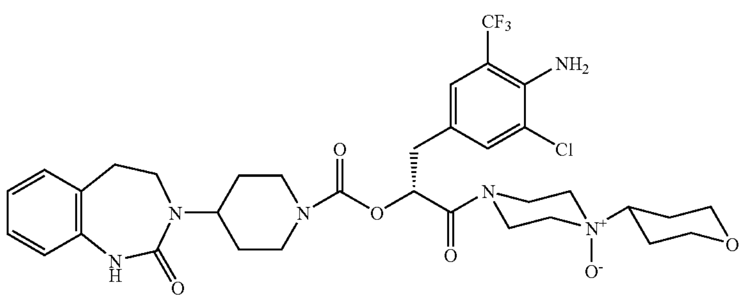 |
| (68) | 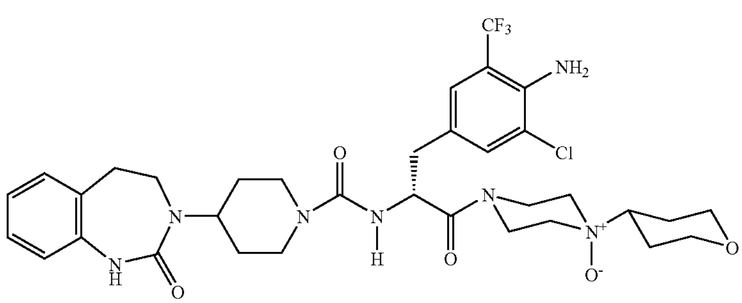 |

| No. | Structure |
|---|---|
| (69) | 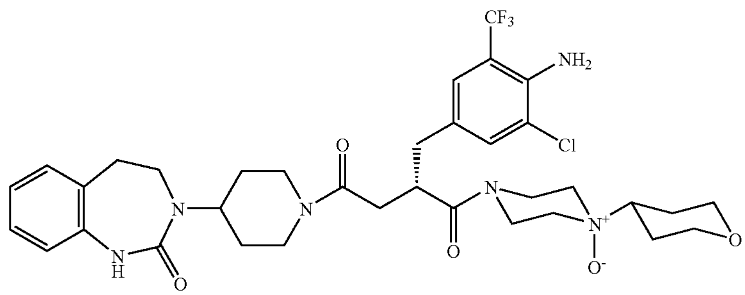 |
| (70) | 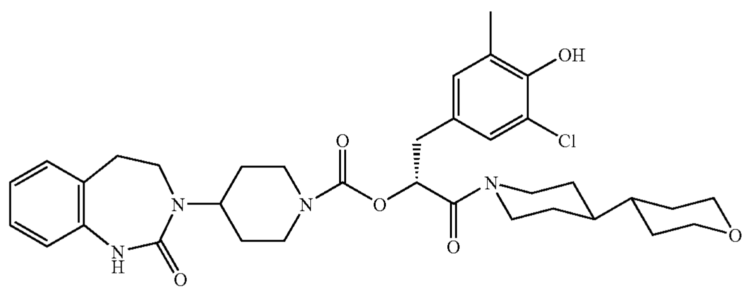 |
| (71) | 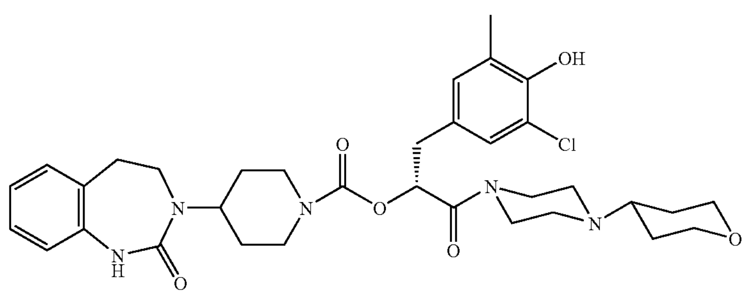 |
| (72) | 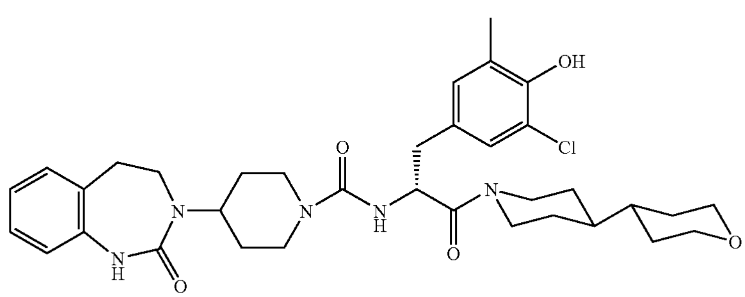 |
| (73) | 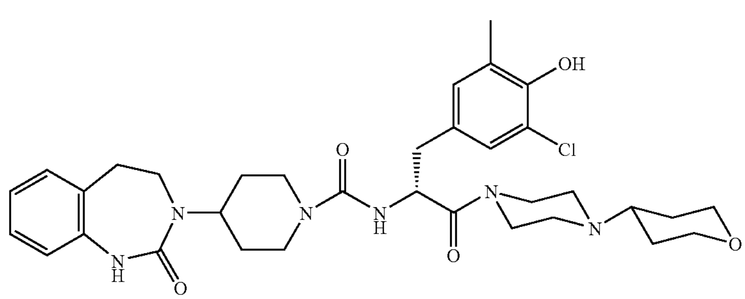 |

-continued

| No. | Structure |
|---|---|
| (74) | 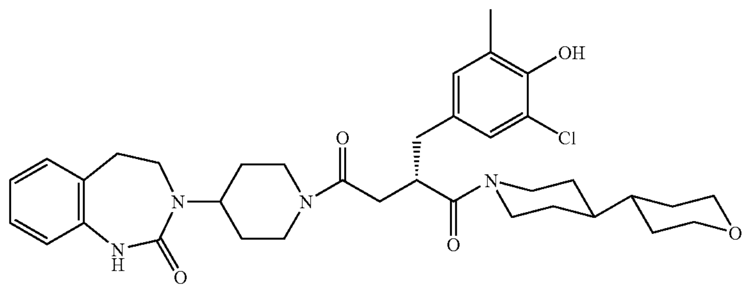 |
| (75) | 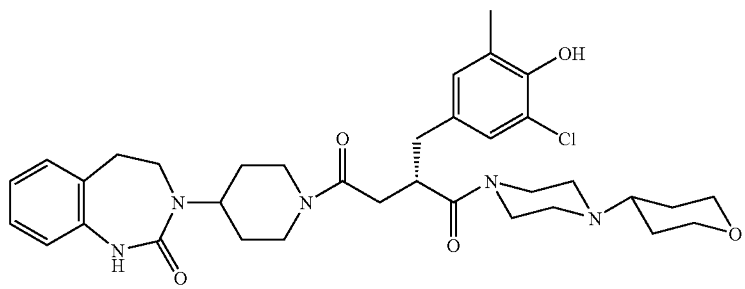 |
| (76) | 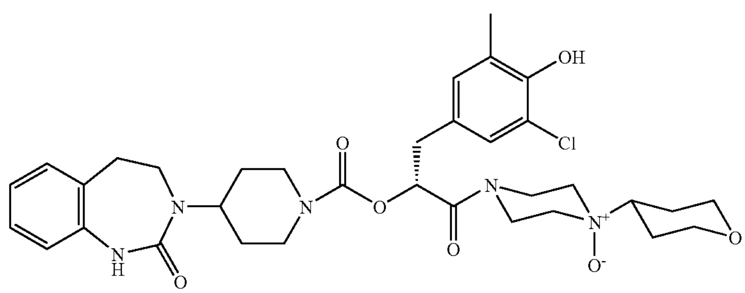 |
| (77) | 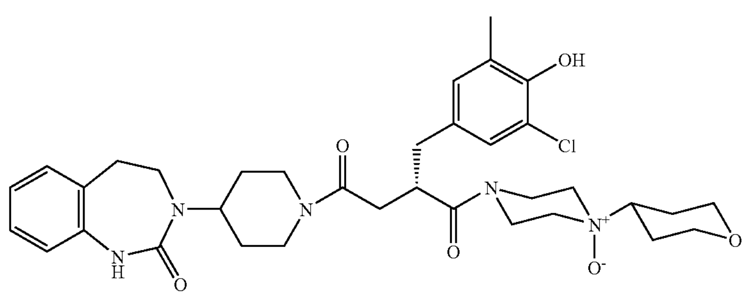 |
| (78) | 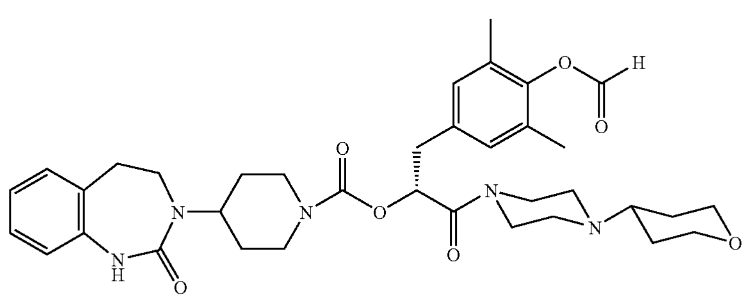 |

-continued
| No. | Structure |
|---|---|
| (79) | 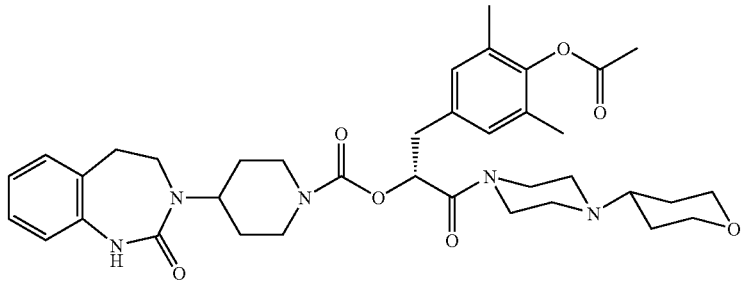 |
| (80) | 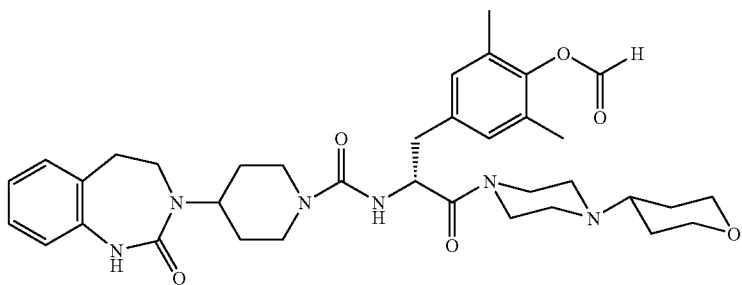 |
| (81) | 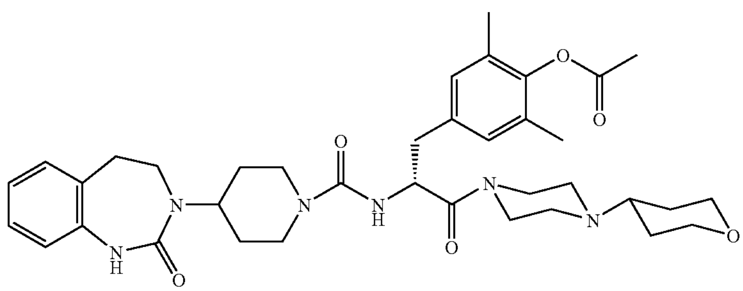 |
| (82) | 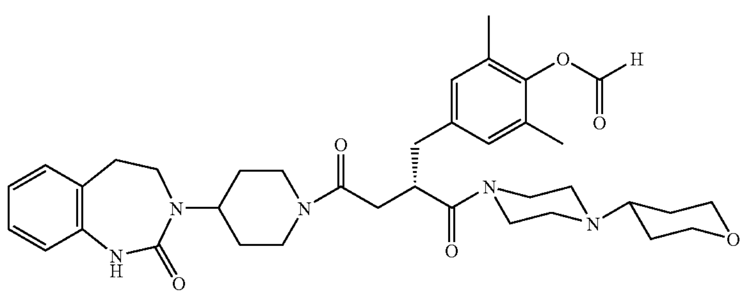 |
| (83) | 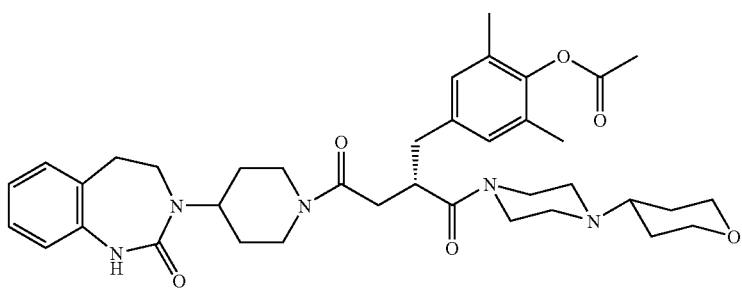 |

| No. | Structure |
|---|---|
| (84) | 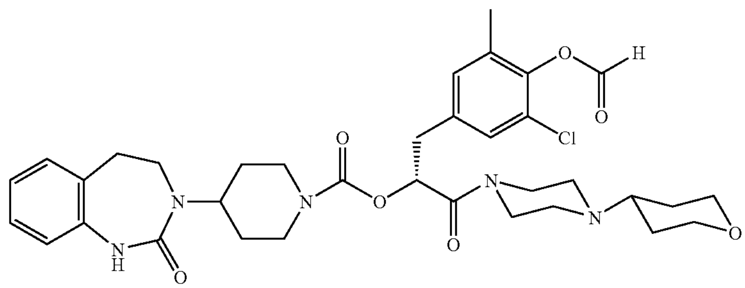 |
| (85) | 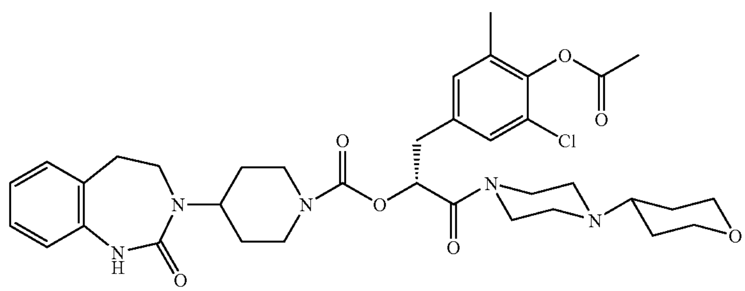 |
| (84a) | 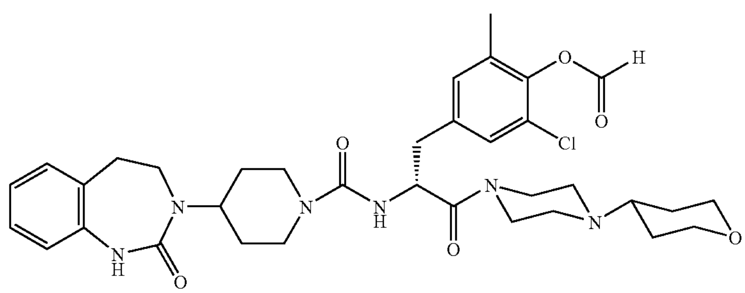 |
| (85a) | 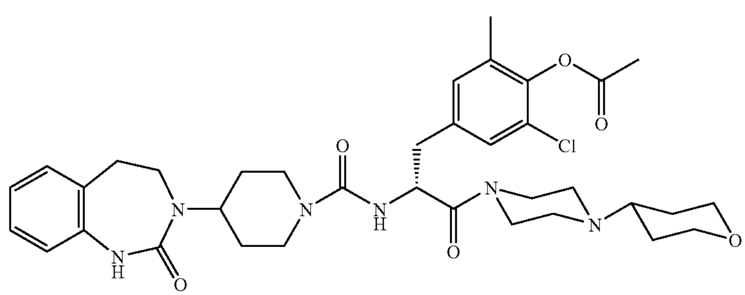 |
| (86) | 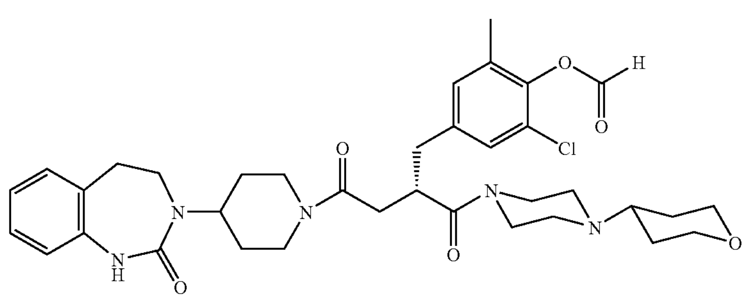 |

-continued
| No. | Structure |
|---|---|
| (87) | 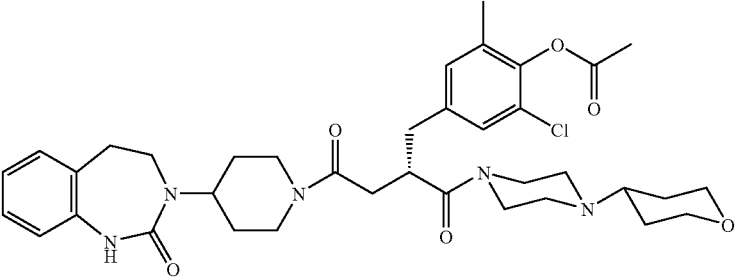 |
| (88) | 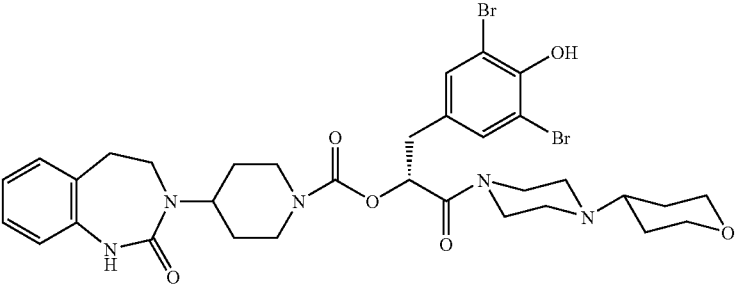 |
| (89) | 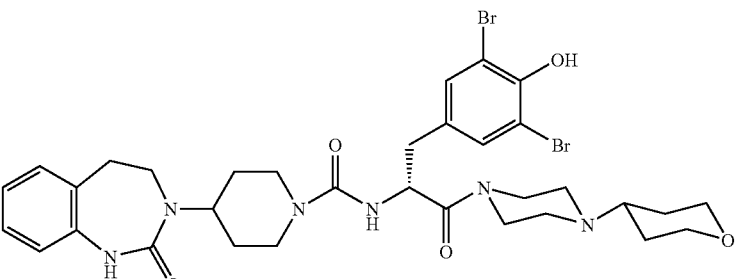 |
| (90) | 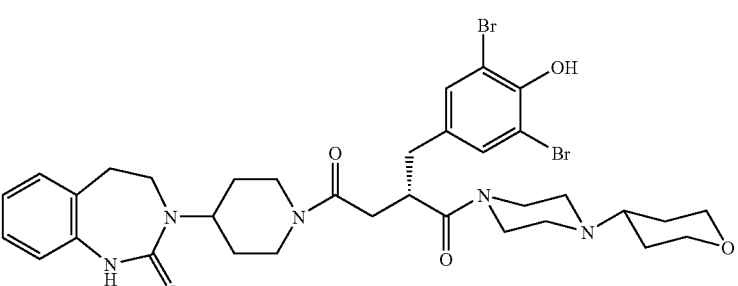 |
| (91) | 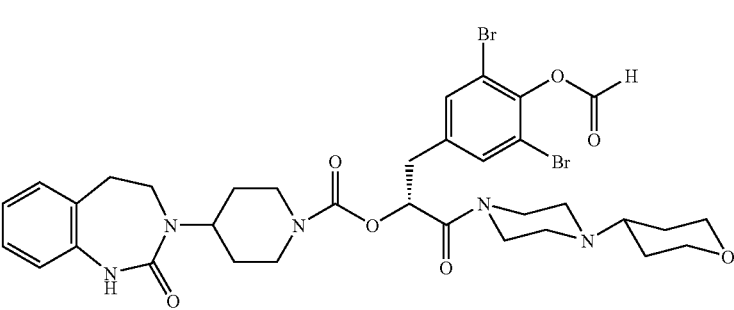 |

-continued
| No. | Structure |
|---|---|
| (92) | 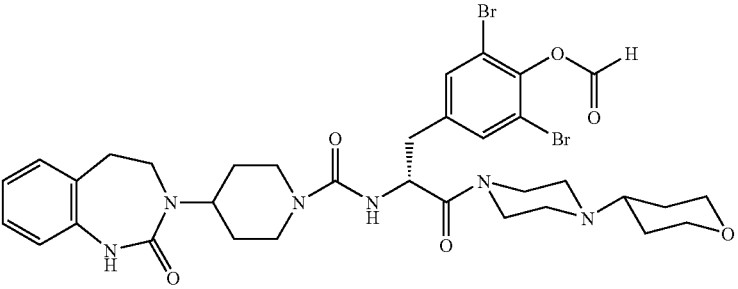 |
| (93) | 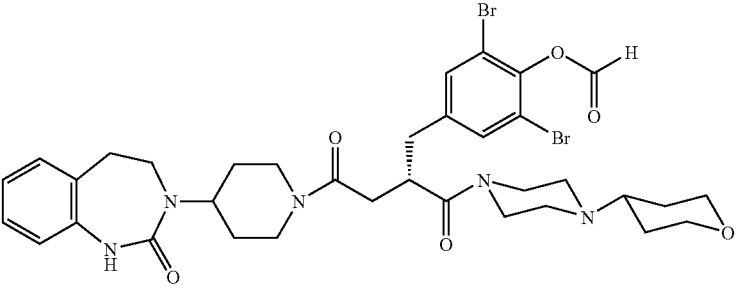 |
| (94) | 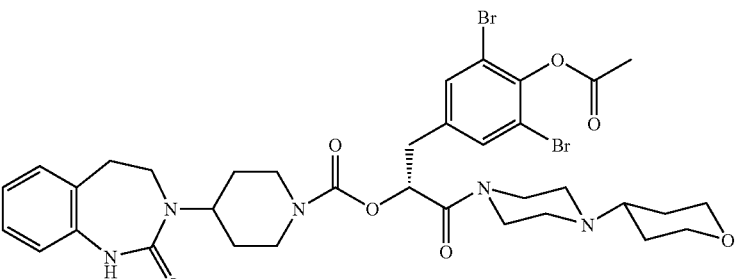 |
| (95) | 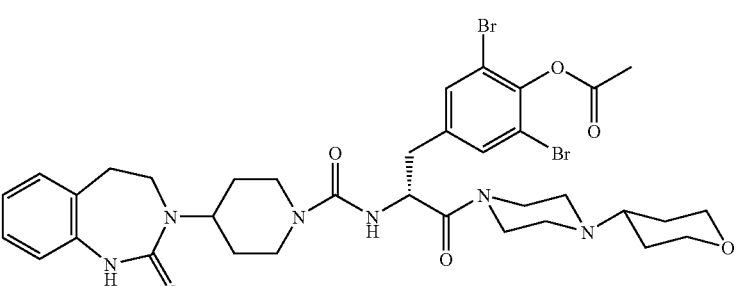 |
| (96) | 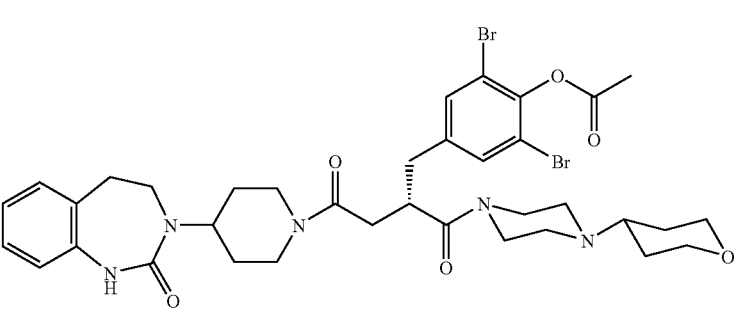 |

-continued
| No. | Structure |
|---|---|
| (97) | 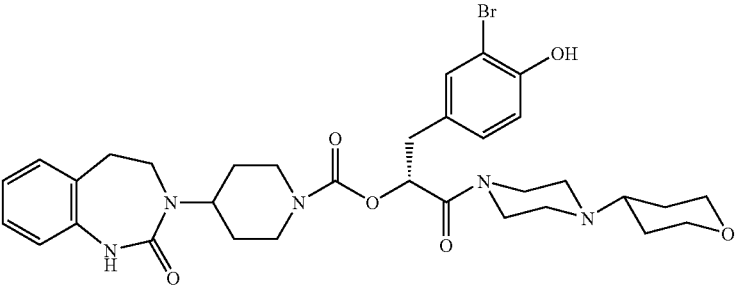 |
| (98) | 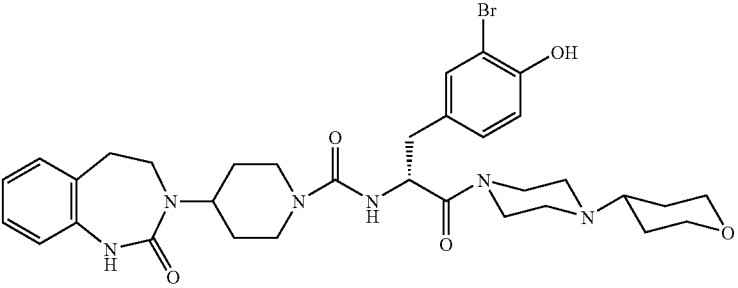 |
| (99) | 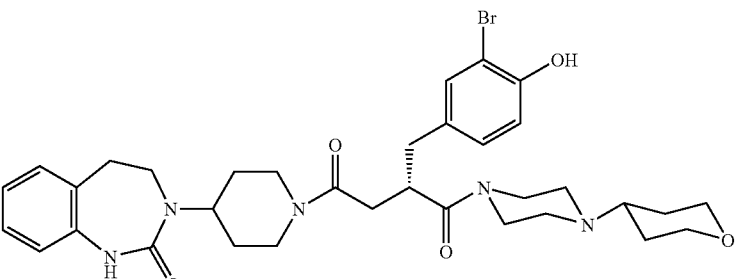 |
| (100) | 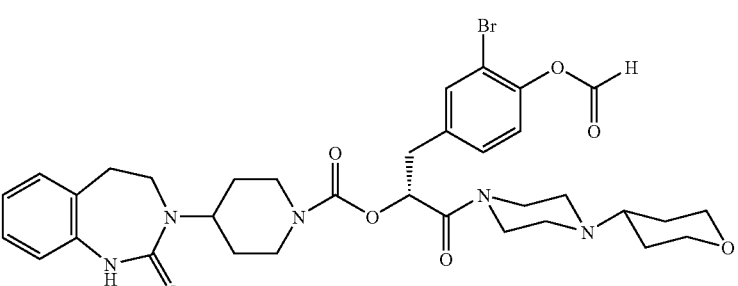 |
| (101) | 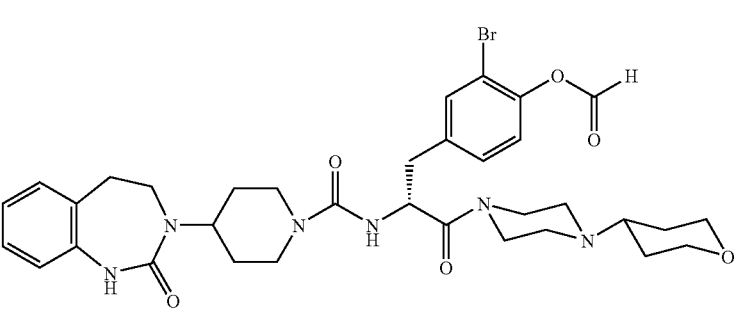 |

-continued

| No. | Structure |
|---|---|
| (102) | 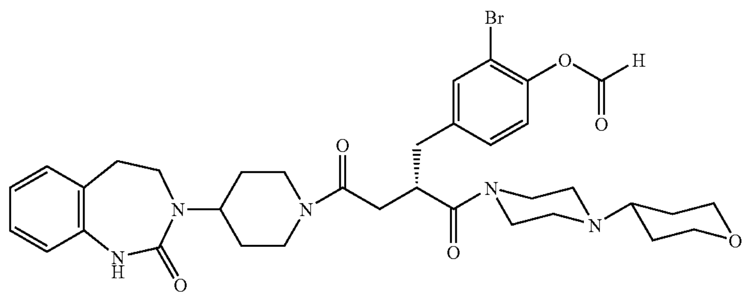 |
| (103) | 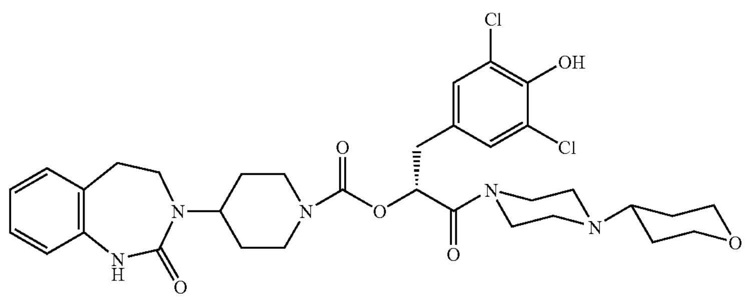 |
| (104) | 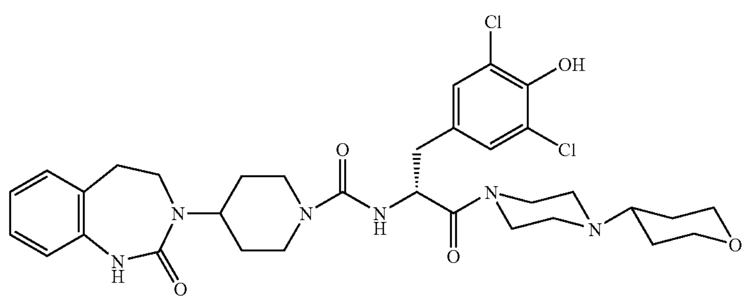 |
| (105) | 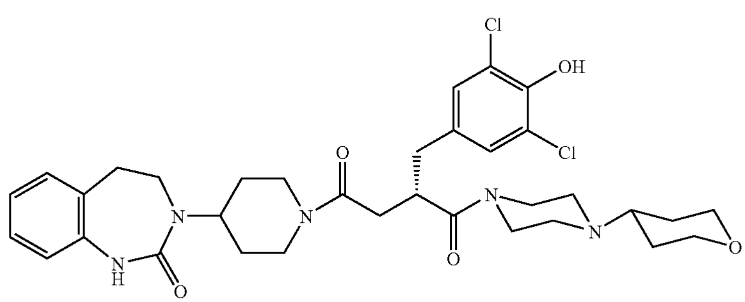 |
| (106) | 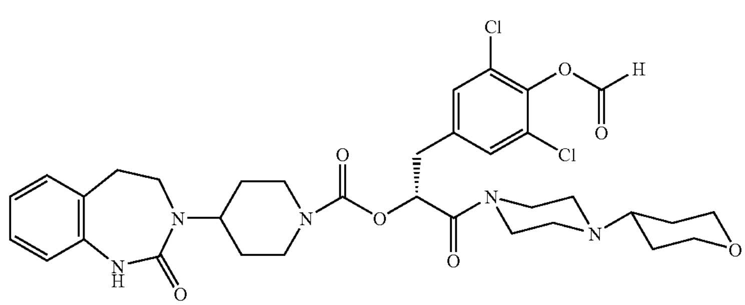 |

-continued
| No. | Structure |
|---|---|
| (107) | 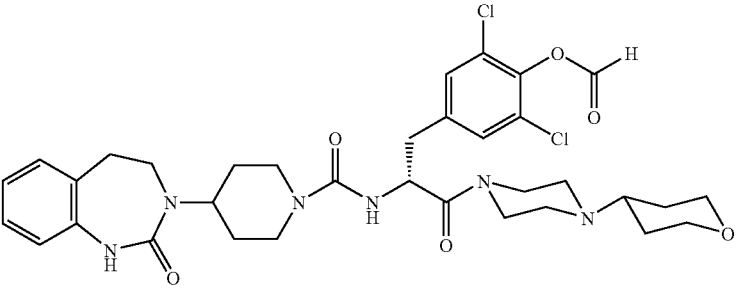 |
| (108) | 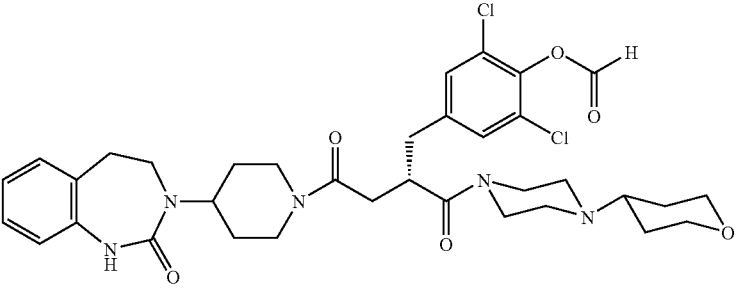 |
| (109) | 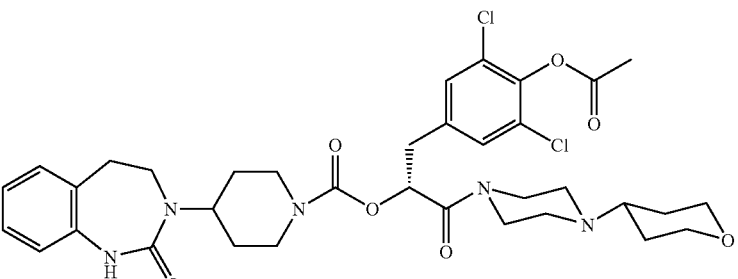 |
| (110) | 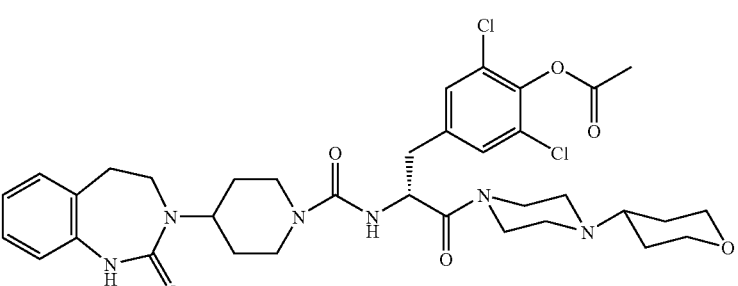 |
| (111) | 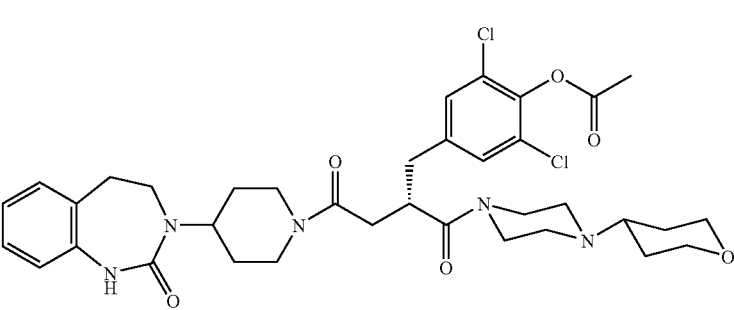 |

-continued

| No. | Structure |
|---|---|
| (112) | 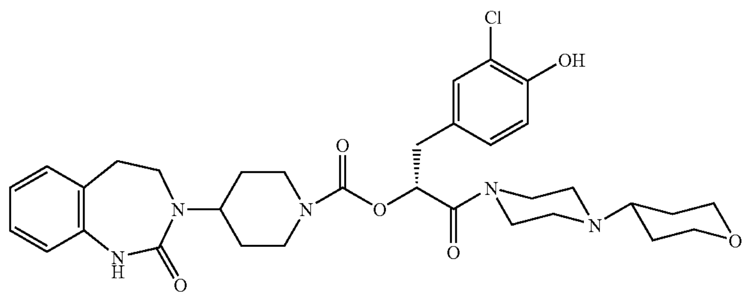 |
| (113) | 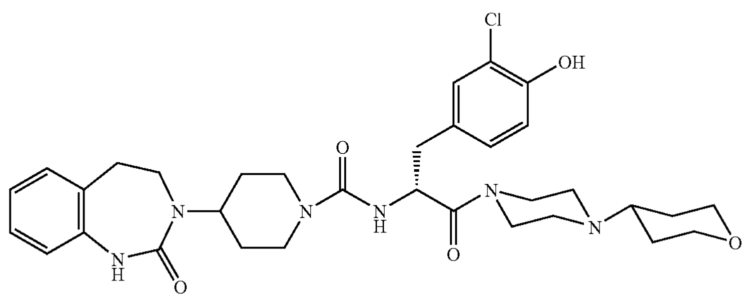 |
| (114) | 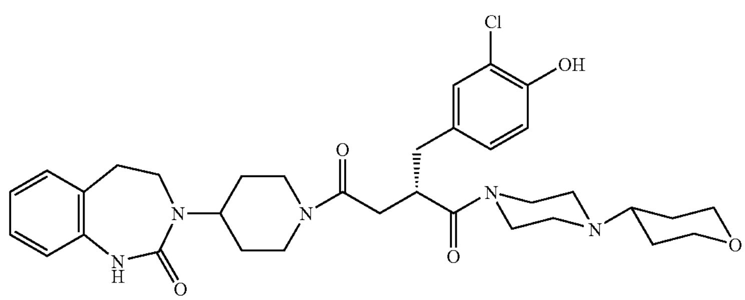 |
| (115) | 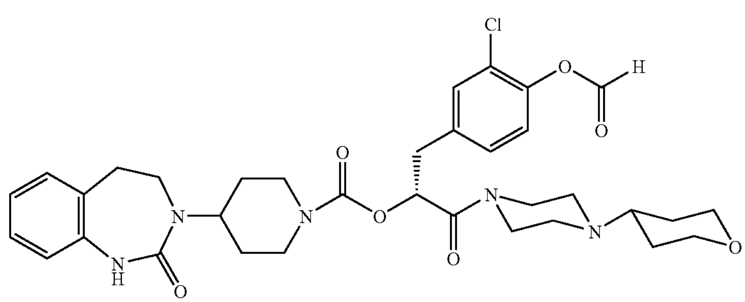 |
| (116) | 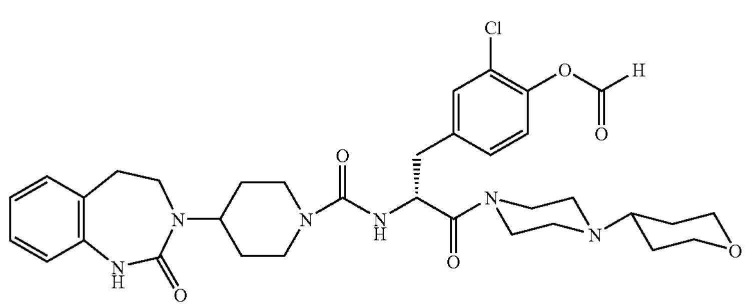 |

-continued

| No. | Structure |
|---|---|
| (117) | 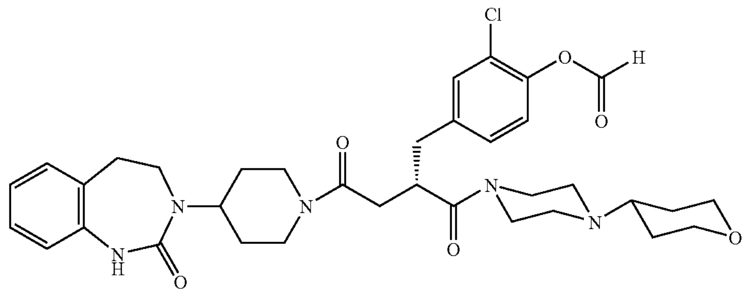 |
| (118) | 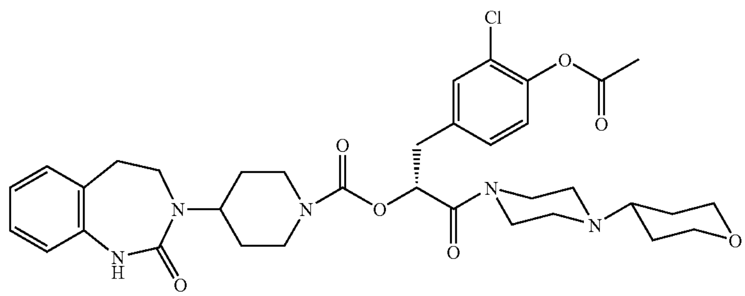 |
| (119) | 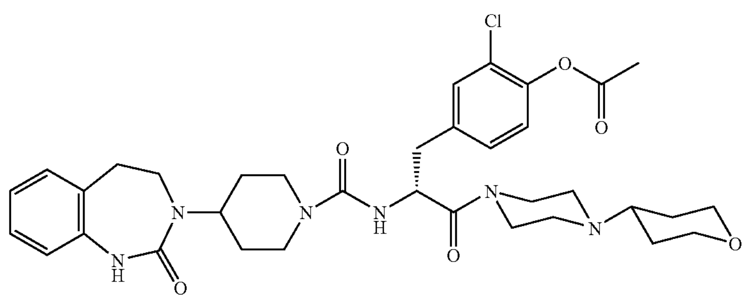 |
| (120) | 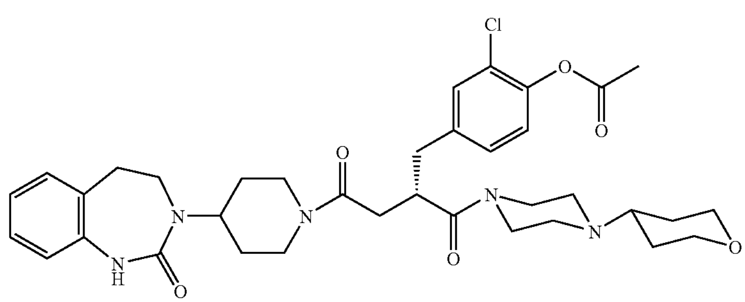 |
| (121) | 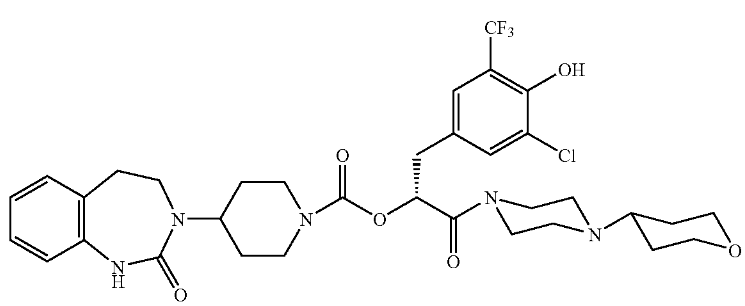 |

-continued
| No. | Structure |
|---|---|
| (122) | 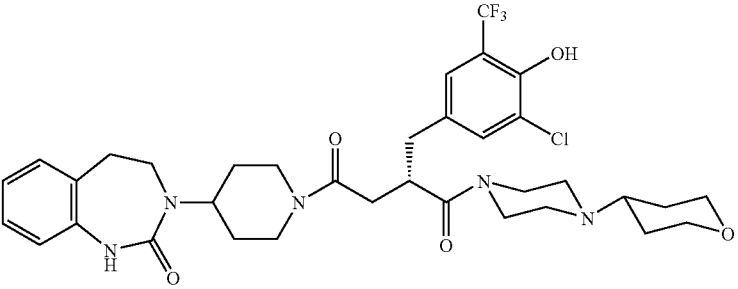 |
| (123) | 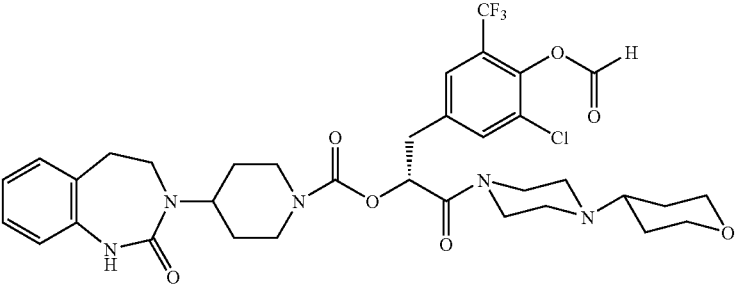 |
| (124) | 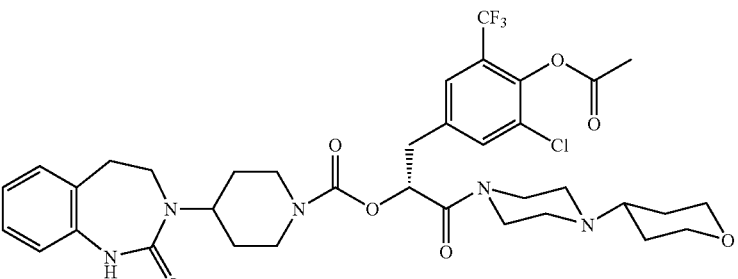 |
| (125) | 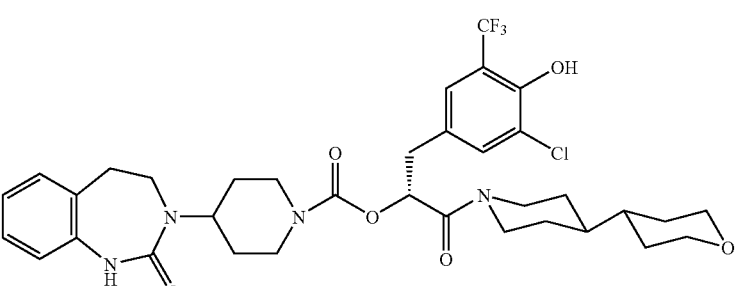 |
| (126) | 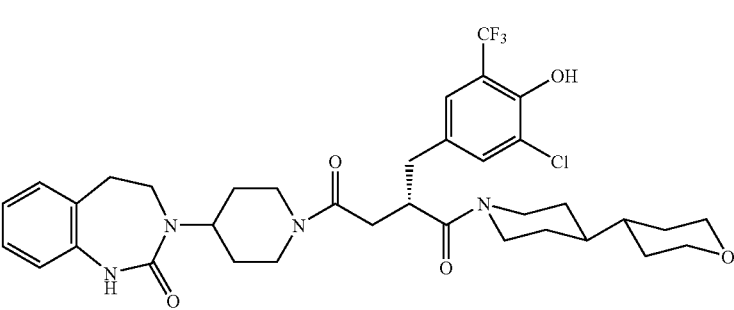 |

-continued
| No. | Structure |
|---|---|
| (127) | 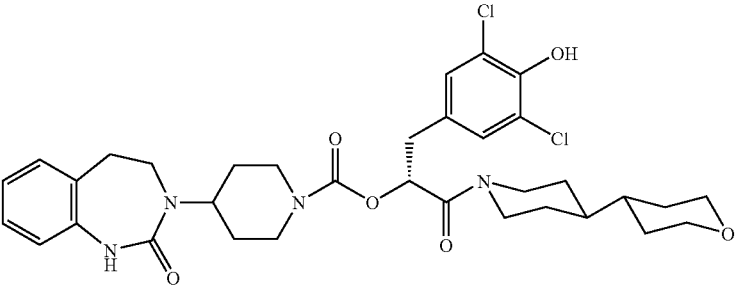 |
| (128) | 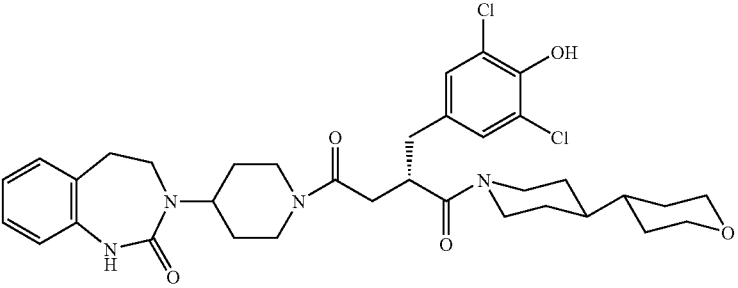 |
| (139) | 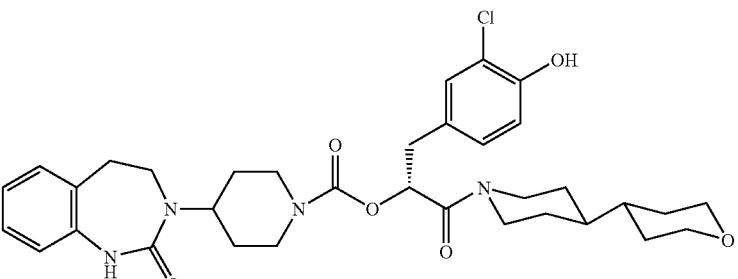 |
| (130) | 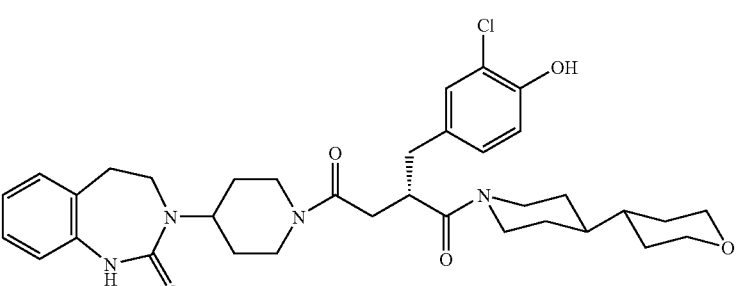 |
| (131) | 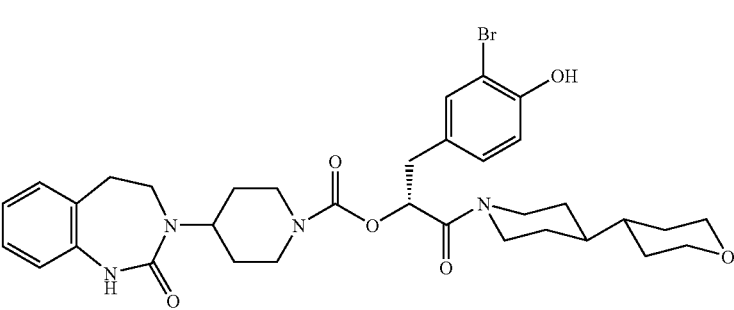 |

-continued
| No. | Structure |
|---|---|
| (132) | 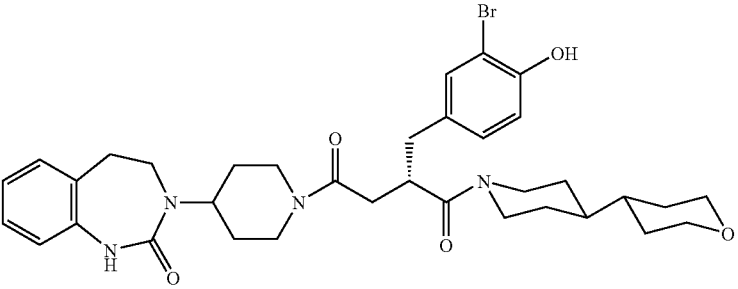 |
| (133) | 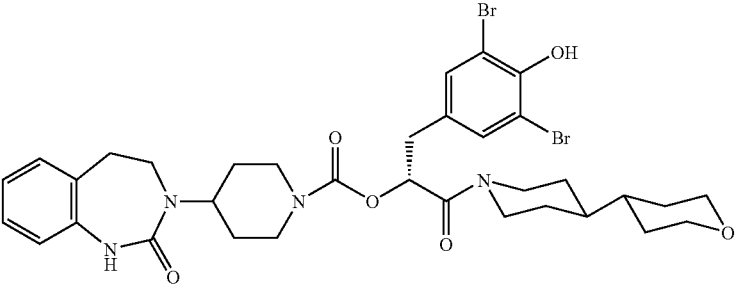 |
| (134) | 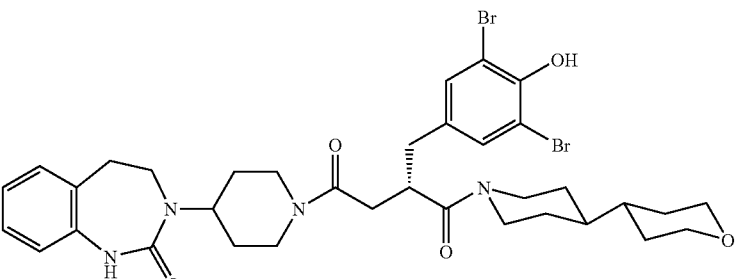 |
| (135) | 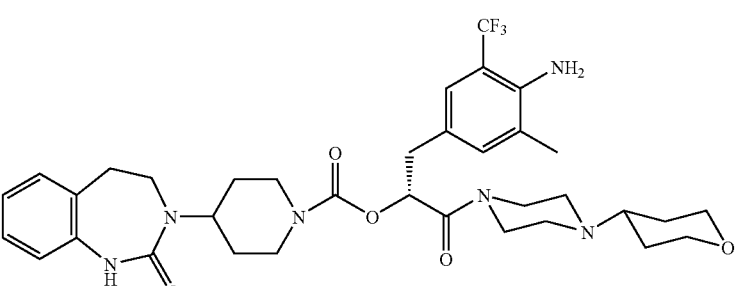 |
| (136) | 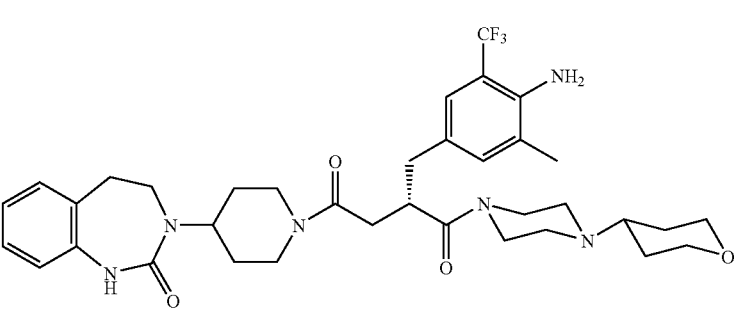 |

-continued
| No. | Structure |
|---|---|
| (137) | 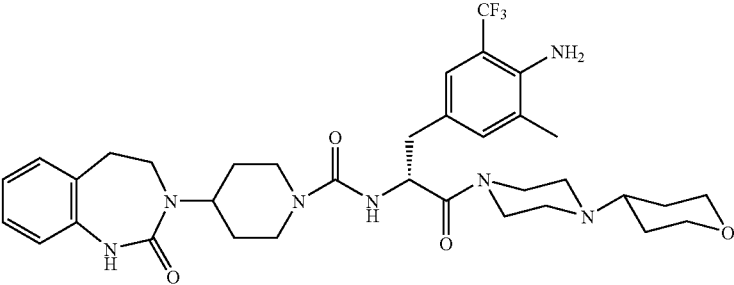 |
| (138) | 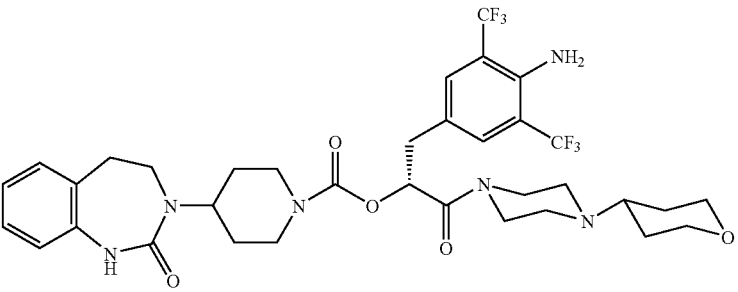 |
| (139) | 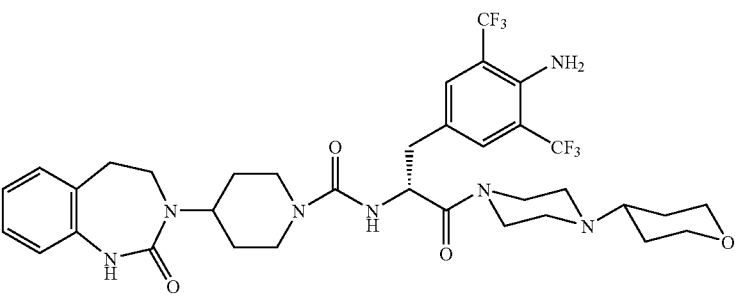 |
| (140) | 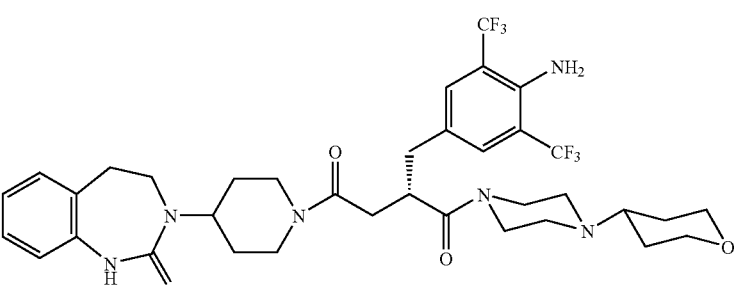 |
| (141) | 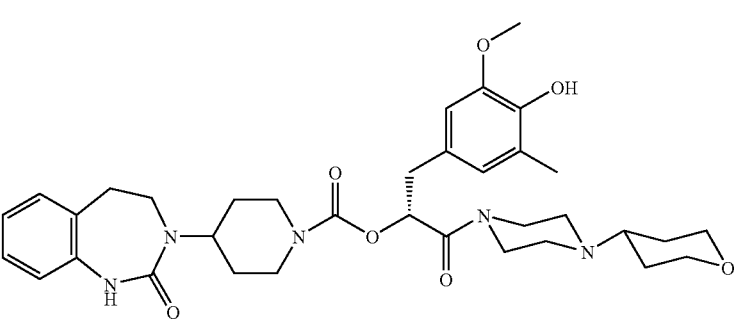 |

-continued
| No. | Structure |
|---|---|
| (142) | 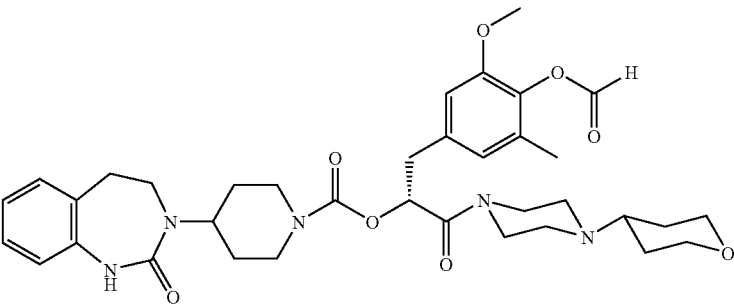 |
| (143) | 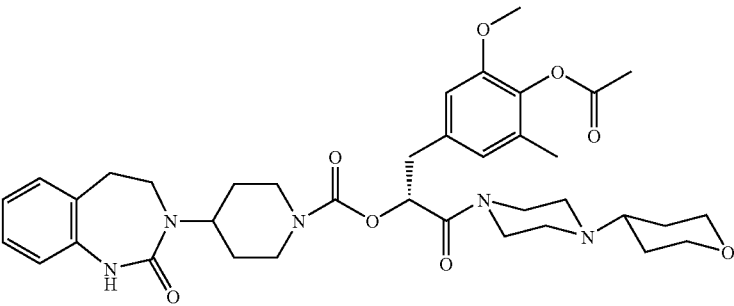 |
| (144) | 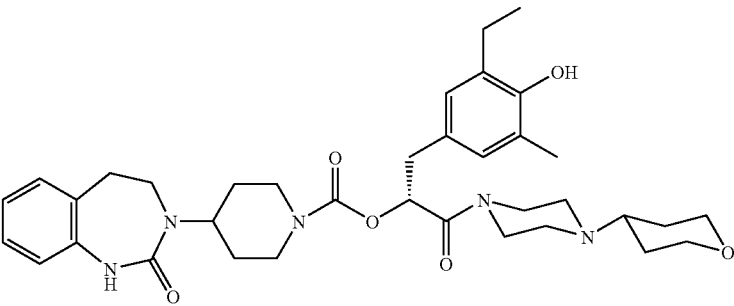 |
| (145) | 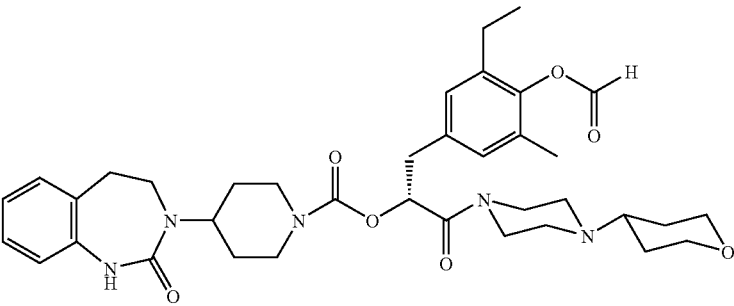 |
| (146) | 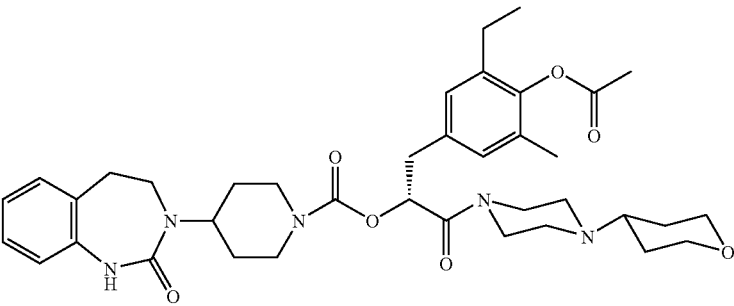 |

-continued
| No. | Structure |
|---|---|
| (147) | 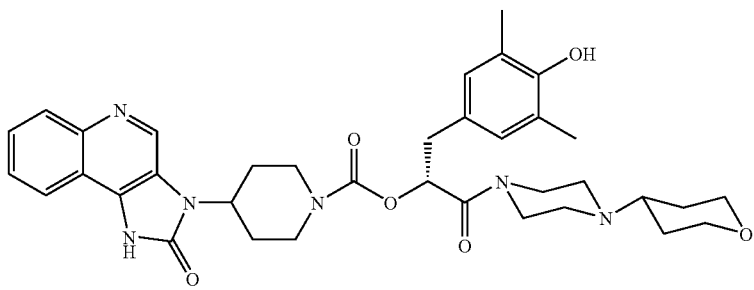 |
| (148) | 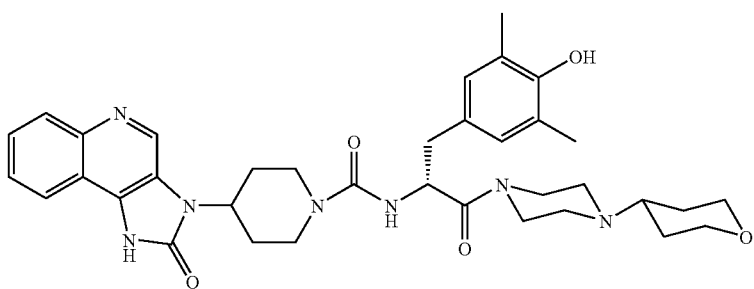 |
| (149) | 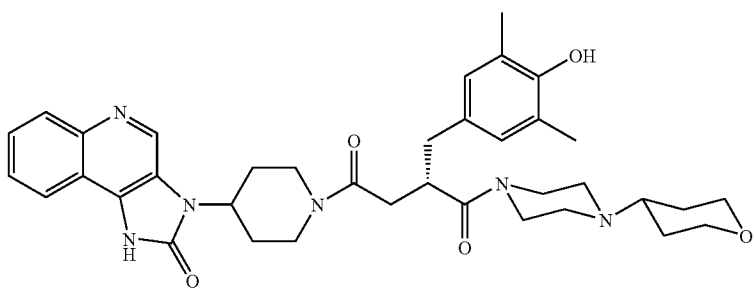 |
| (150) | 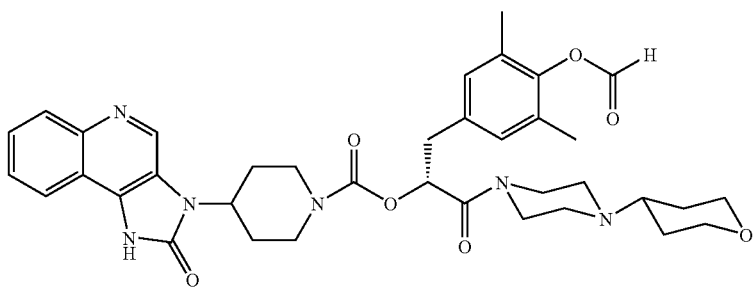 |
| (151) | 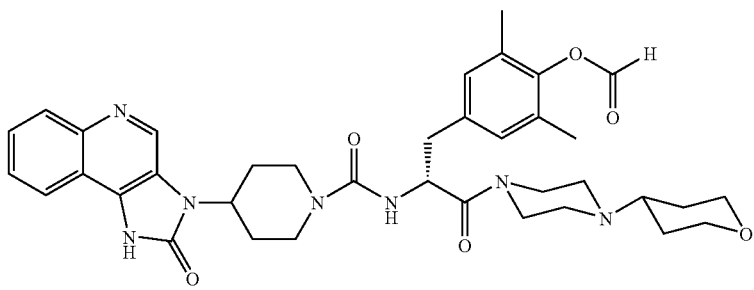 |

-continued
| No. | Structure |
|---|---|
| (152) | 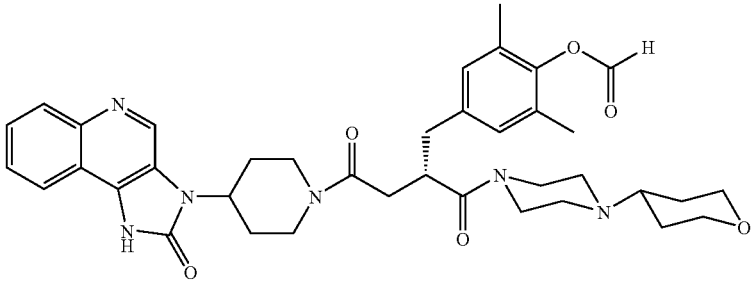 |
| (153) | 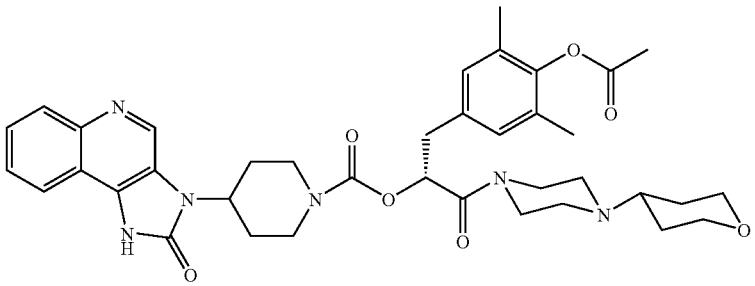 |
| (154) | 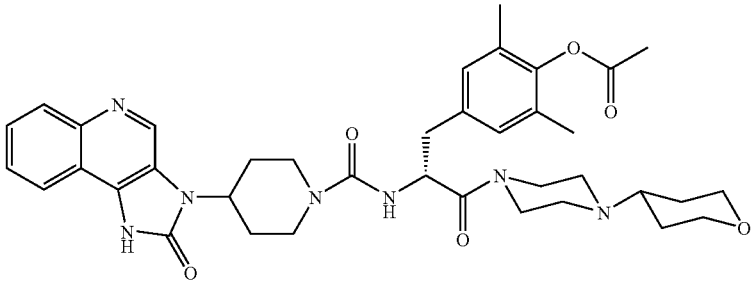 |
| (155) | 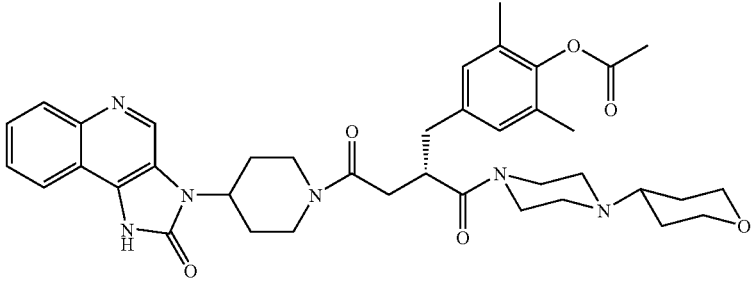 |
| (156) | 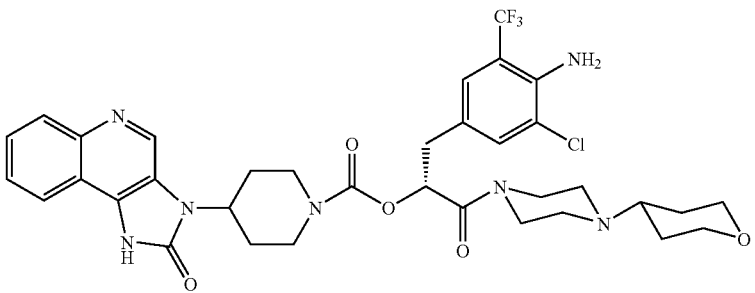 |

-continued

| No. | Structure |
|---|---|
| (157) | 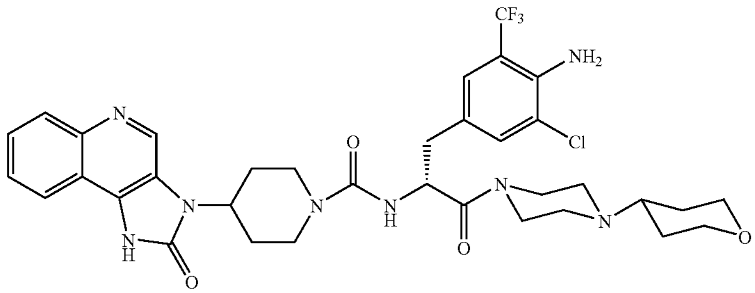 |
| (158) | 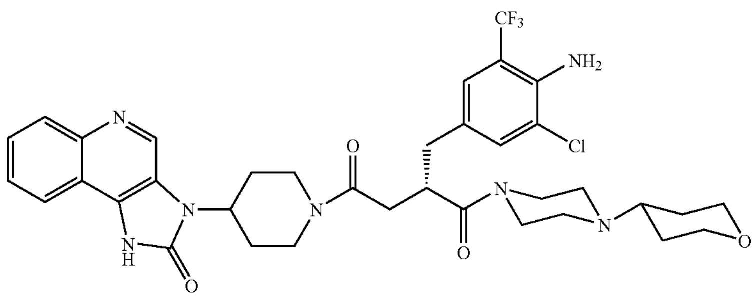 |
| (159) | 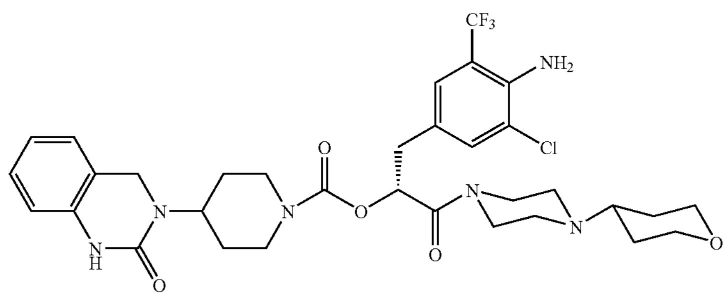 |
| (160) | 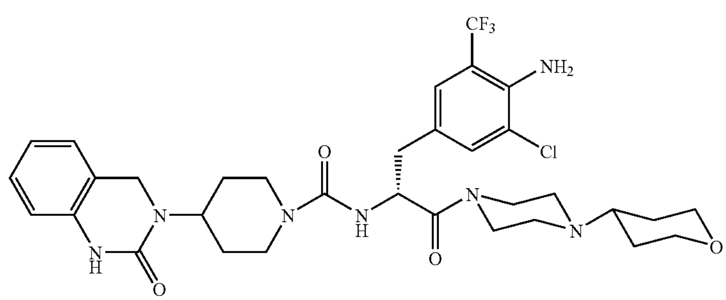 |
| (161) | 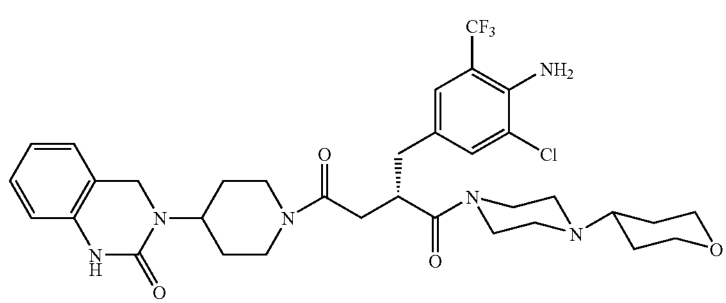 |

| No. | Structure |
|---|---|
| (162) | 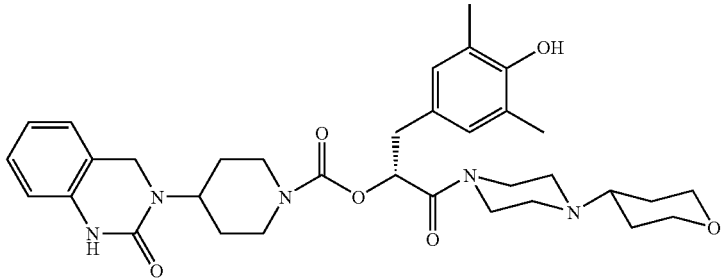 |
| (163) | 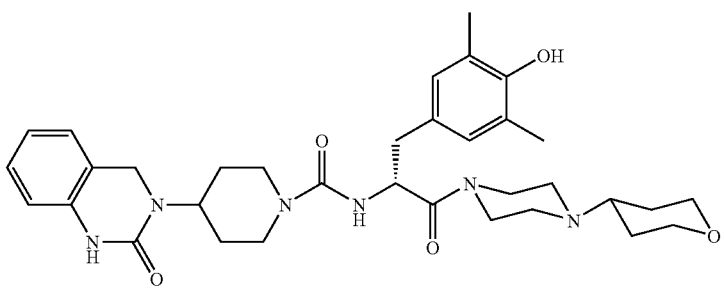 |
| (164) | 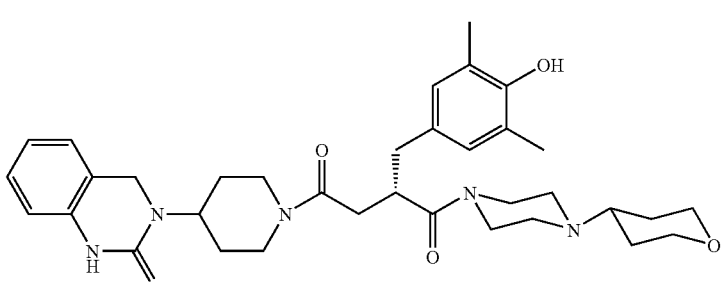 |
| (165) | 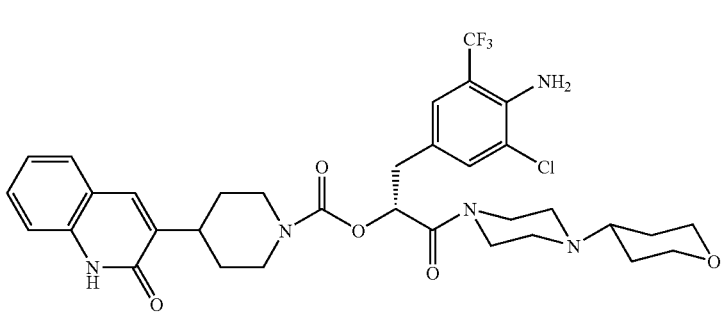 |
| (166) | 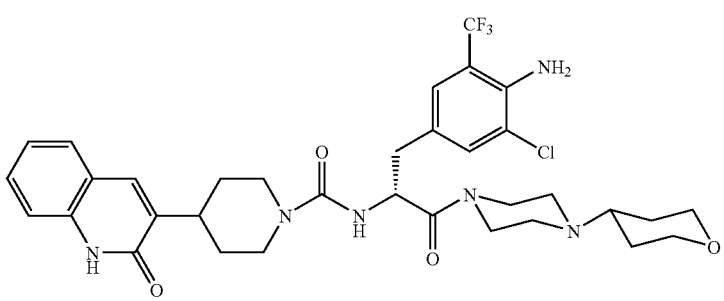 |

-continued
| No. | Structure |
|---|---|
| (167) | 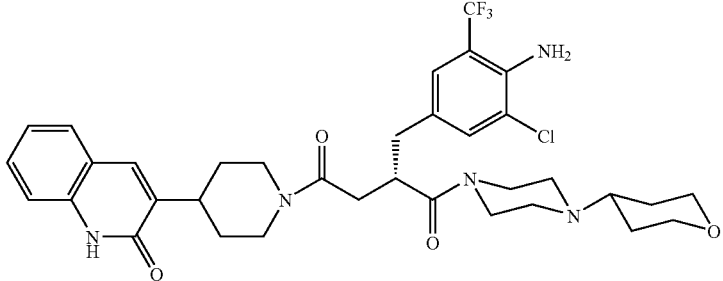 |
| (168) | 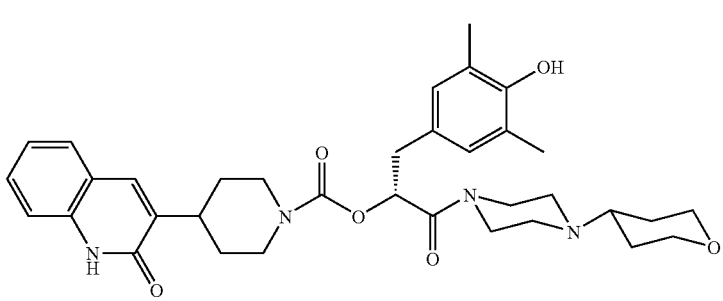 |
| (169) | 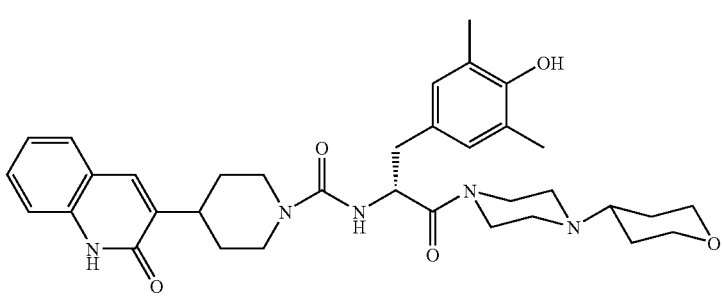 |
| (170) | 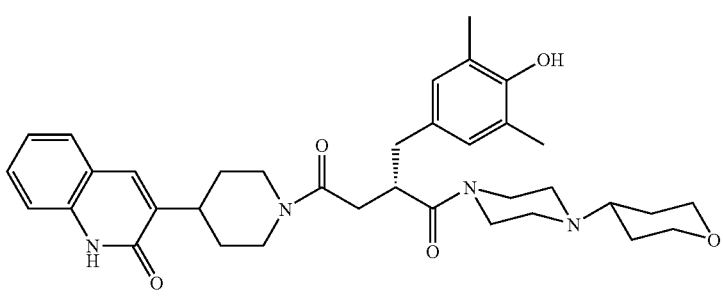 |
| (171) | 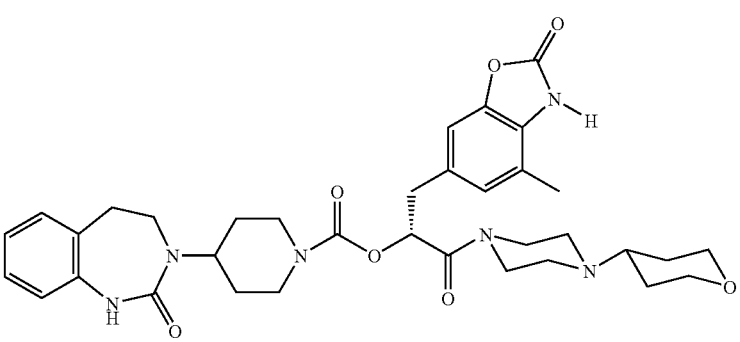 |

| No. | Structure |
|---|---|
| (172) | 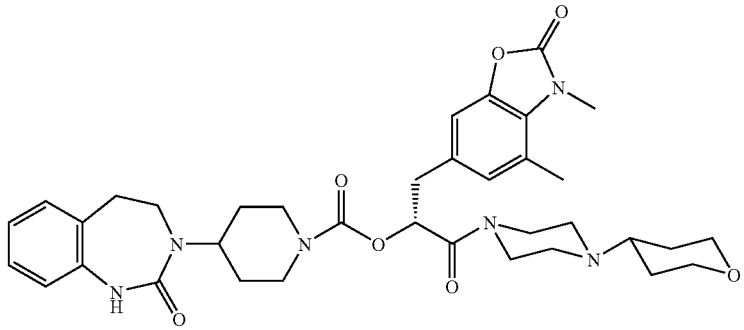 |
| (173) | 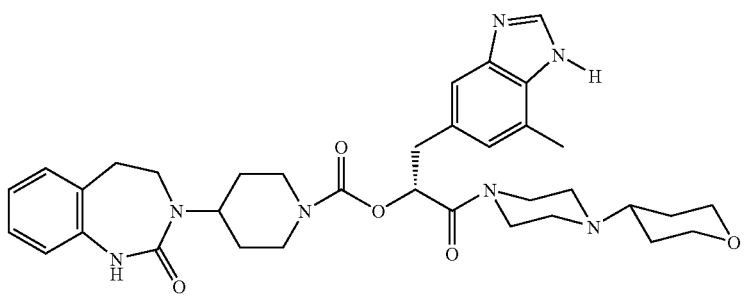 |
| (174) | 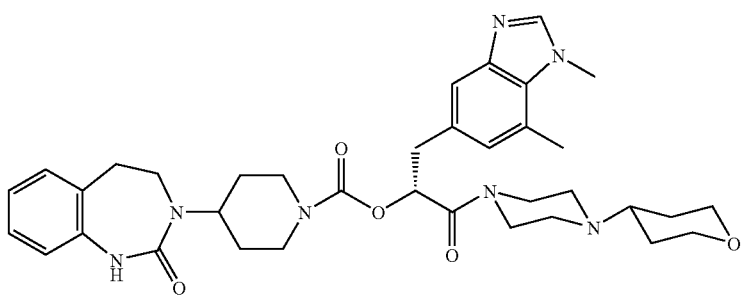 |
| (175) | 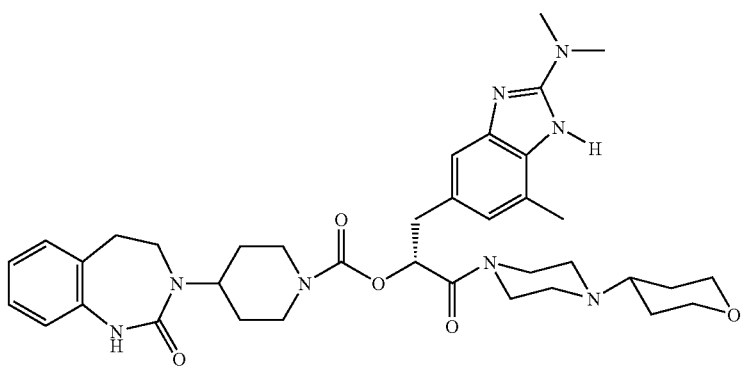 |

-continued

| No. | Structure |
|---|---|
| (176) | 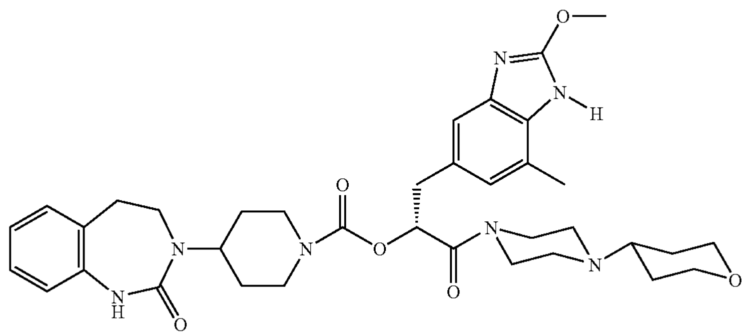 |
| (177) | 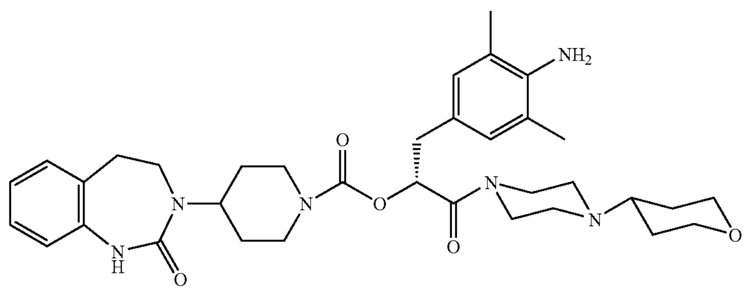 |
| (178) | 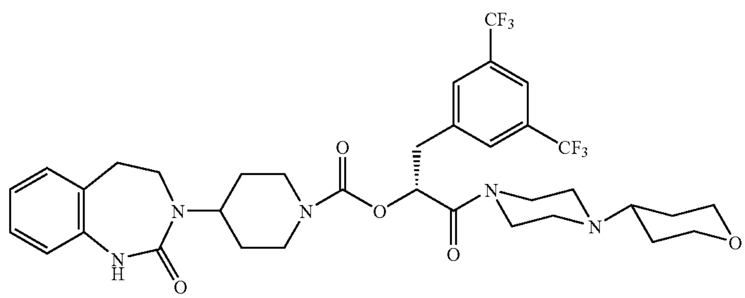 |
| (179) | 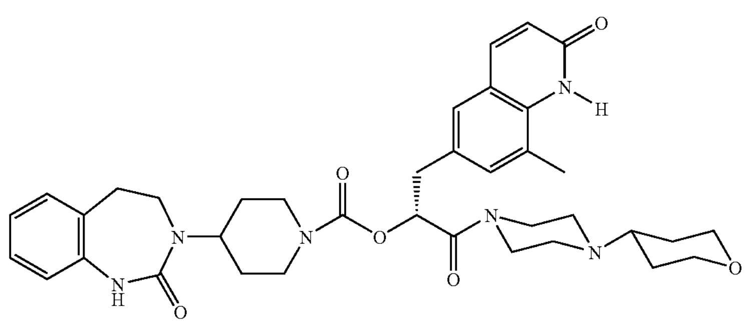 |
| (180) | 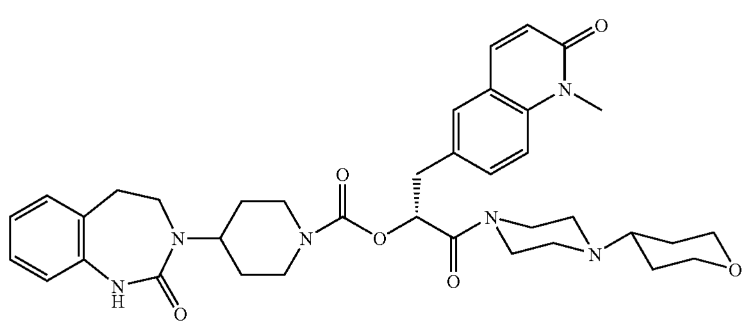 |

-continued
| No. | Structure |
|---|---|
| (181) | 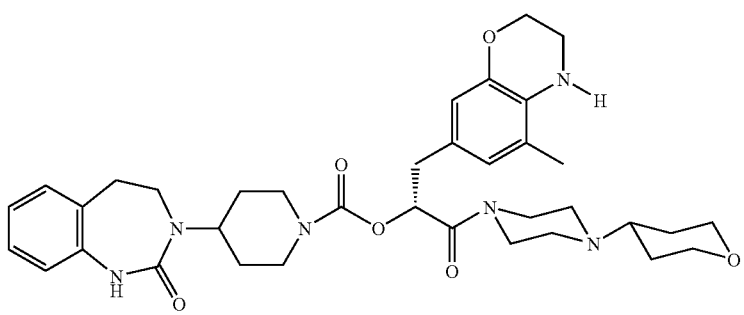 |
| (182) | 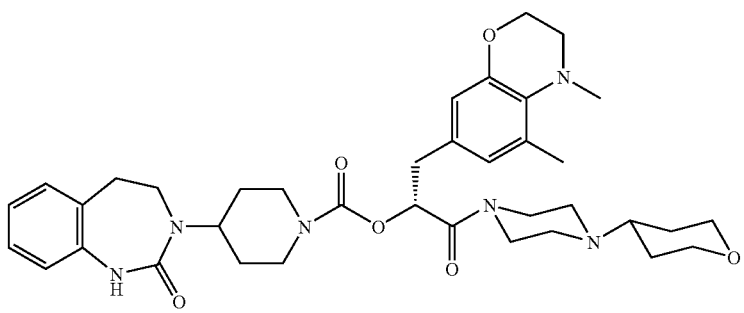 |
| (183) | 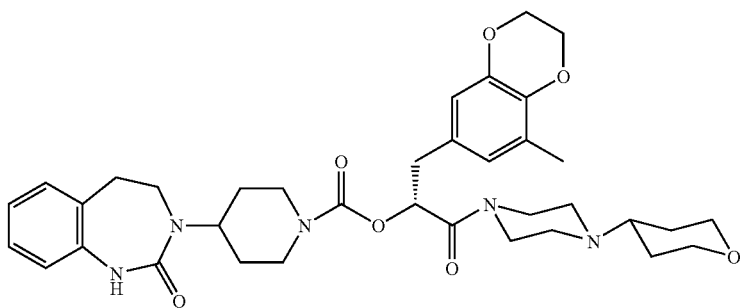 |
| (184) | 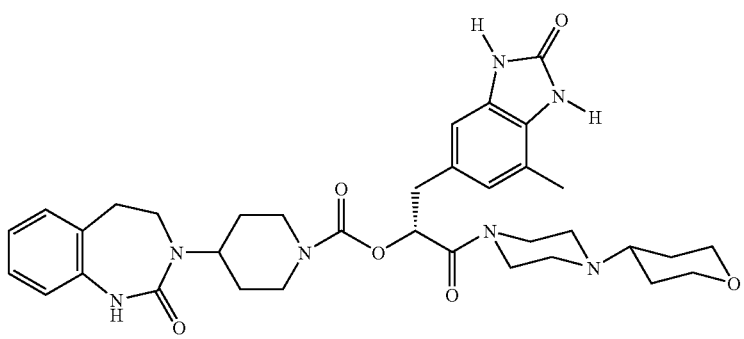 |

-continued

| No. | Structure |
|---|---|
| (185) | 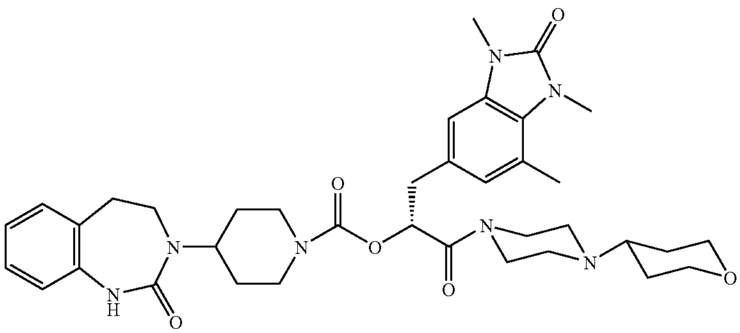 |
| (186) | 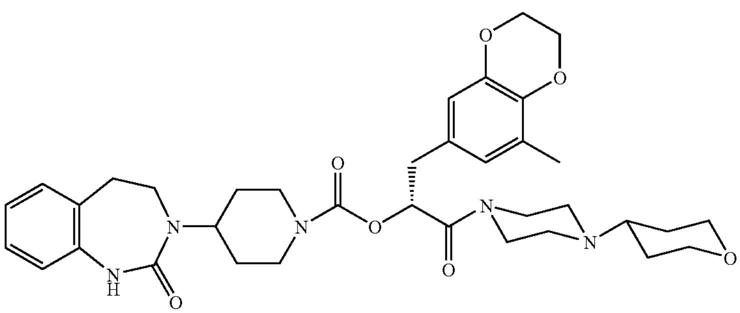 |
| (187) | 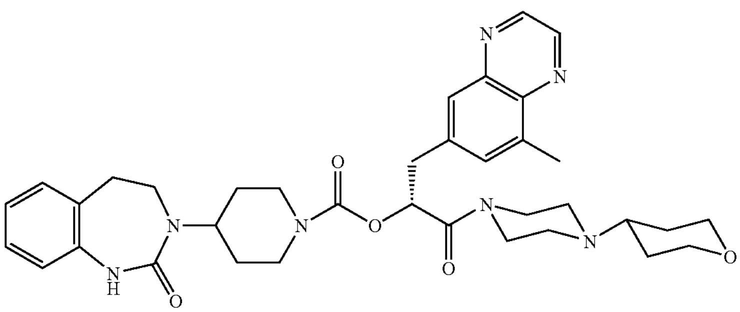 |
| (188) | 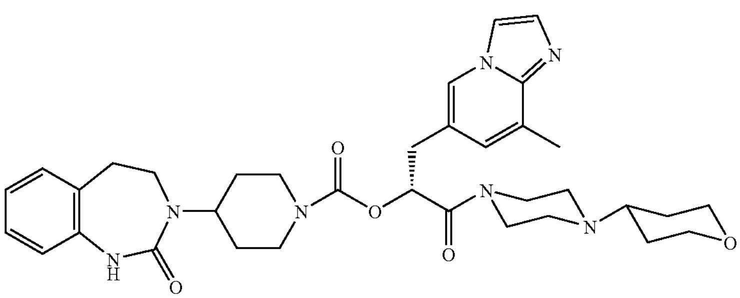 |
| (189) | 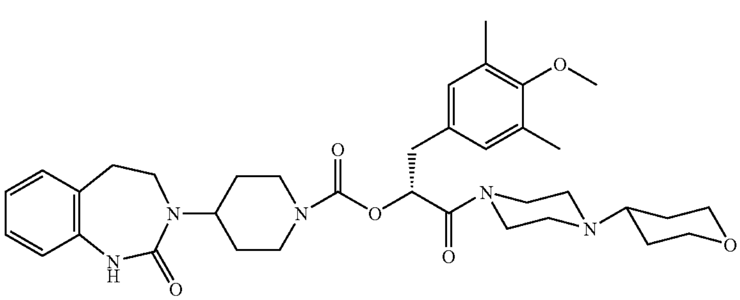 |

| No. | Structure |
|---|---|
| (190) | 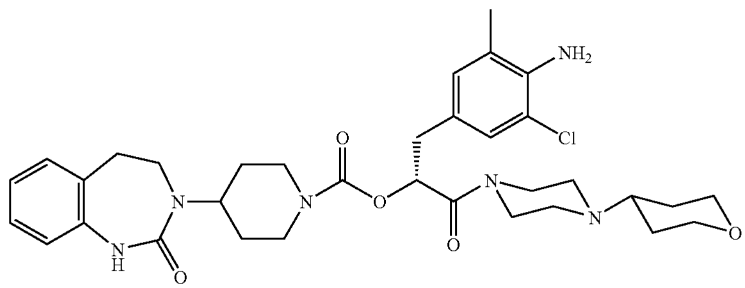 |
| (191) | 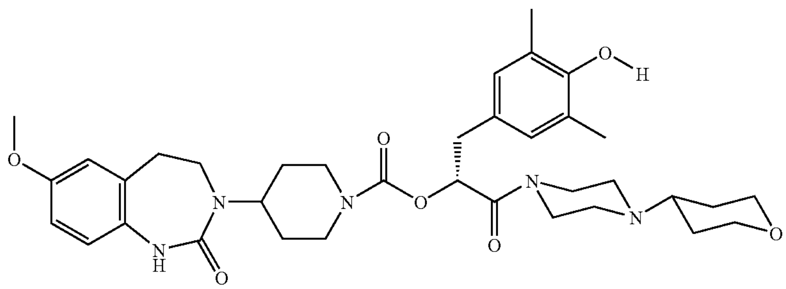 |
| (192) | 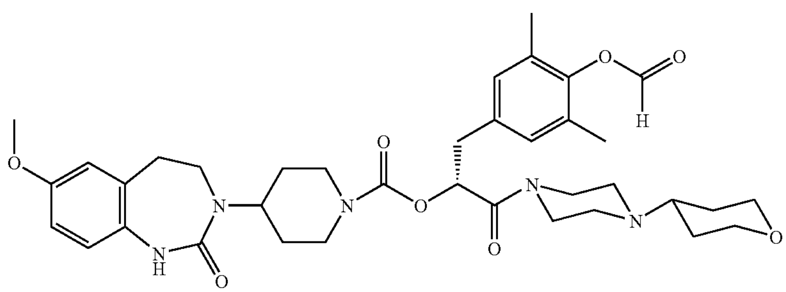 |
| (193) | 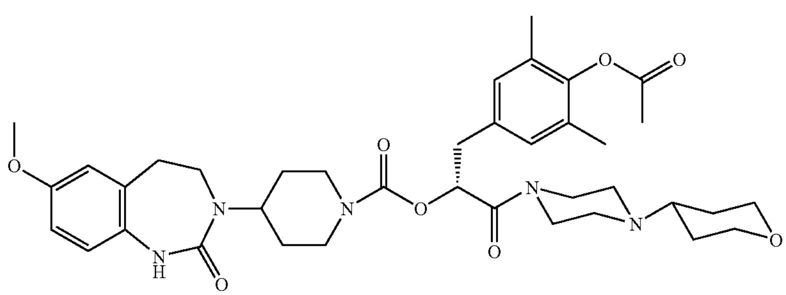 |
| (194) | 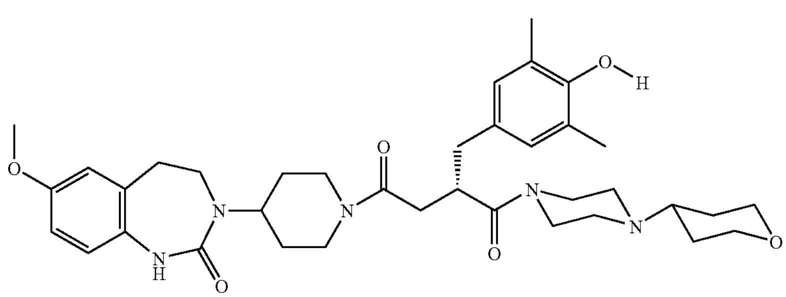 |

| No. | Structure |
|---|---|
| (195) | 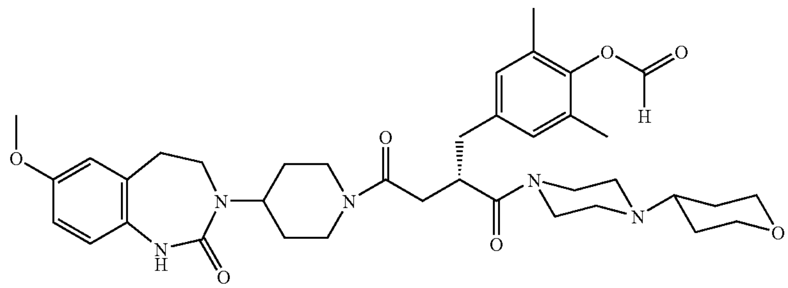 |
| (196) | 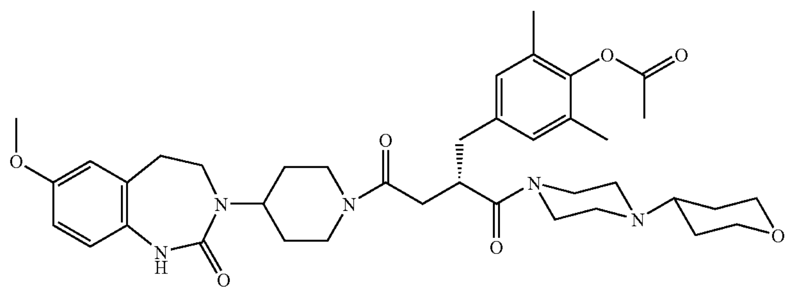 |
| (197) | 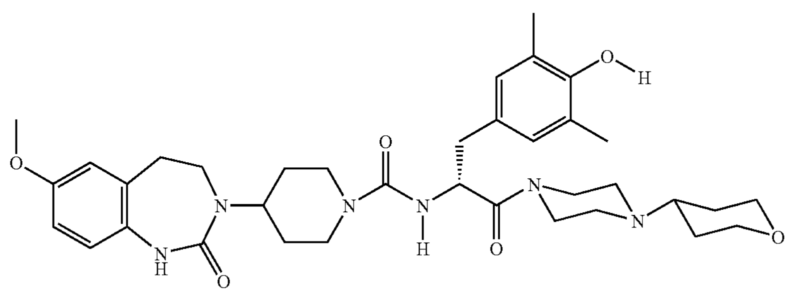 |
| (198) | 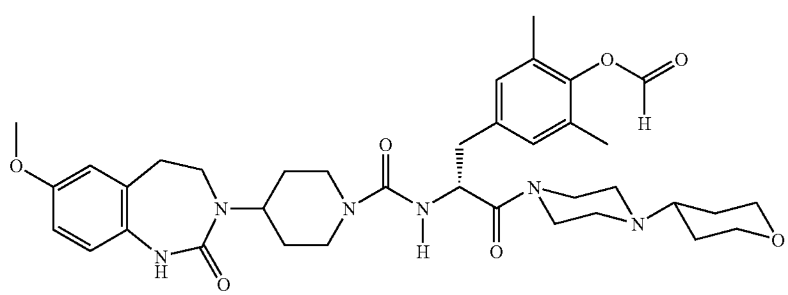 |
| (199) | 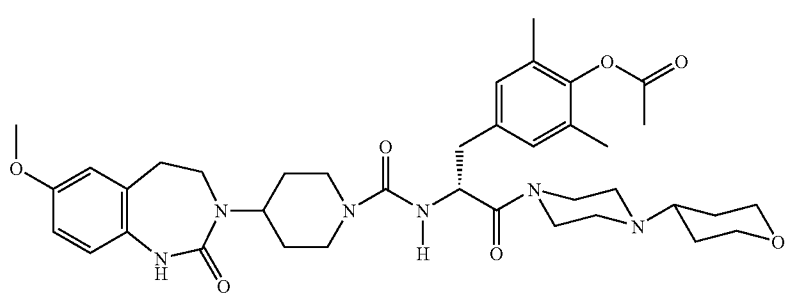 |

-continued

| No. | Structure |
|---|---|
| (200) | 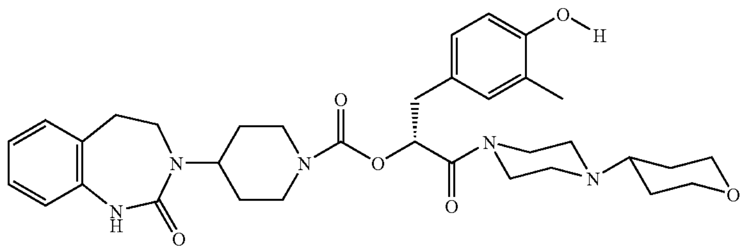 |
| (201) | 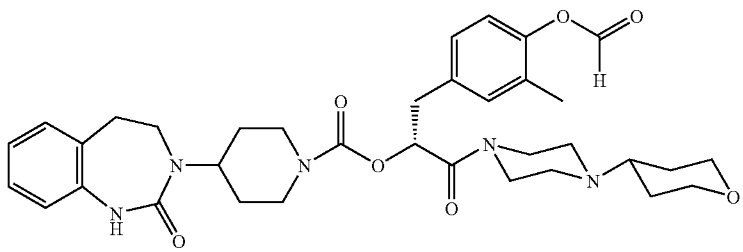 |
| (202) | 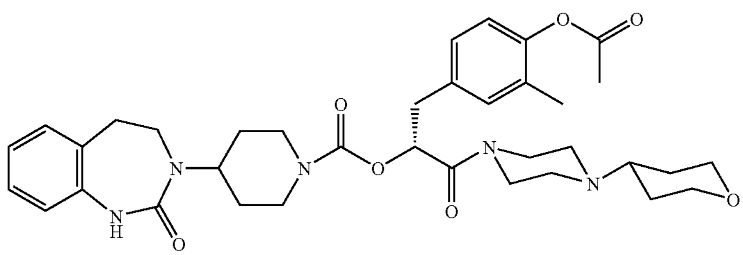 |
| (203) | 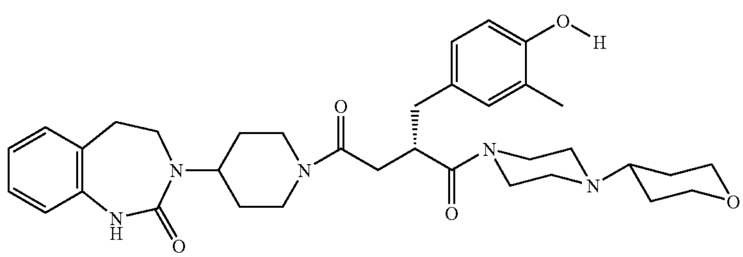 |
| (204) | 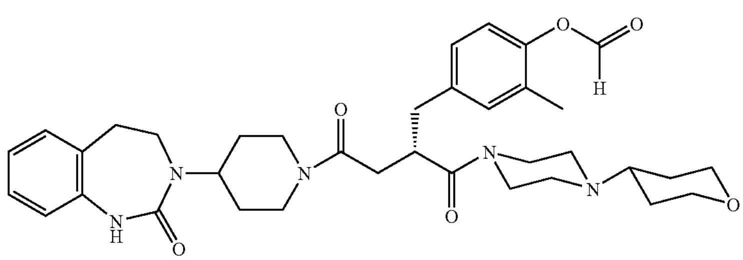 |
| (205) | 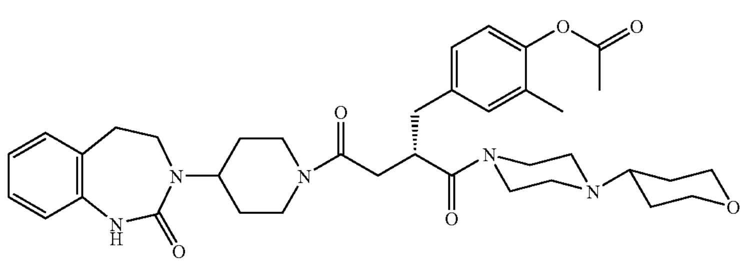 |

-continued

| No. | Structure |
|---|---|
| (206) | 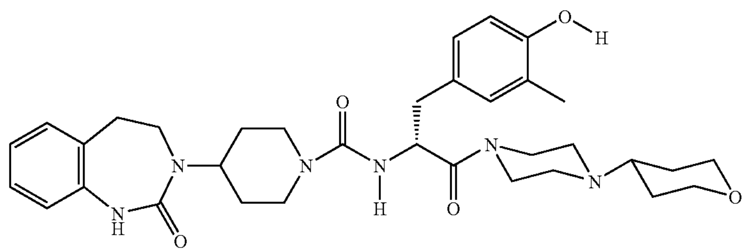 |
| (207) | 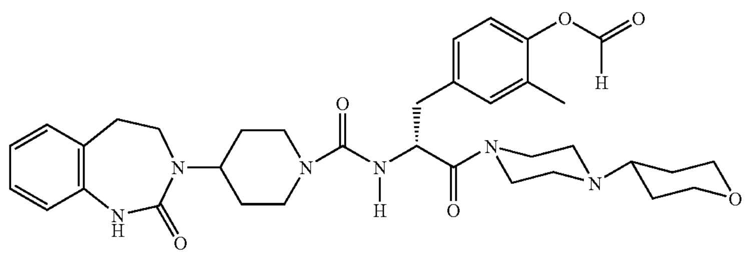 |
| (208) | 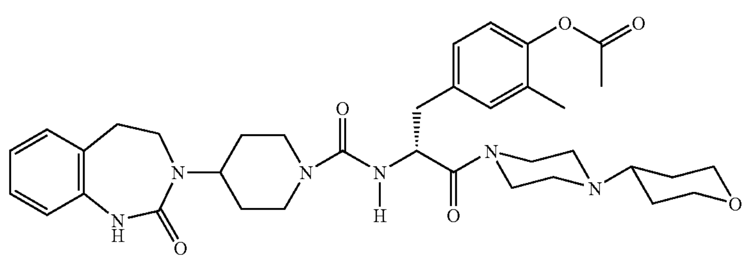 |
| (209) | 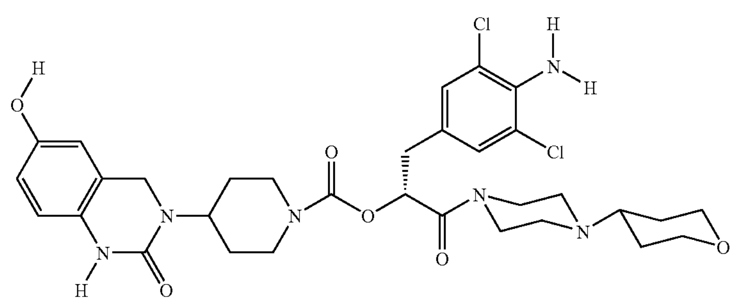 |
| (210) | 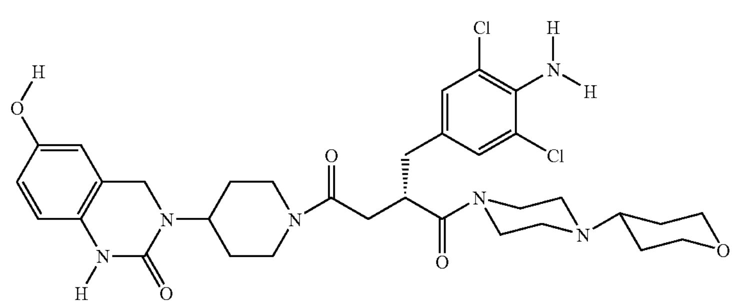 |

| No. | Structure |
|---|---|
| (211) | 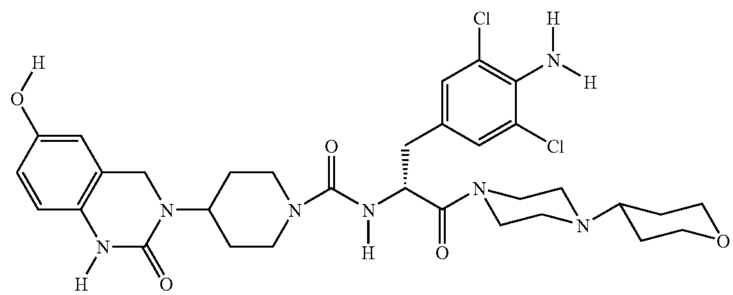 |
| (212) | 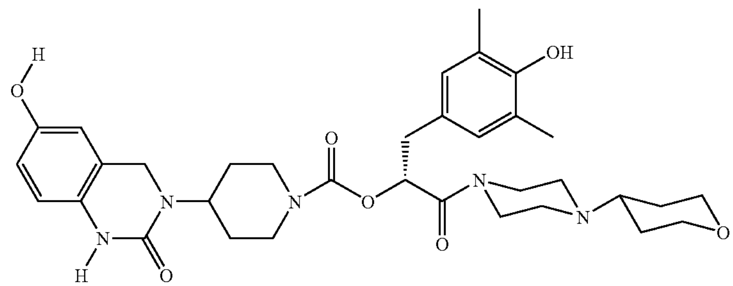 |
| (213) | 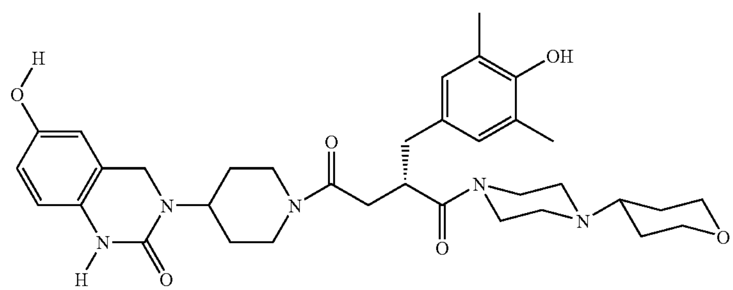 |
| (214) | | the tautomers, the diastereomers, the enantiomers, the hydrates thereof, the mixtures thereof and the salts thereof as well as the hydrates of the salts, particularly the physiologically acceptable salts thereof with inorganic or organic acids or bases.

The following compounds may also be mentioned as more preferred compounds of the above general formula I:

| No. | Structure |
|---|---|
| (34) | 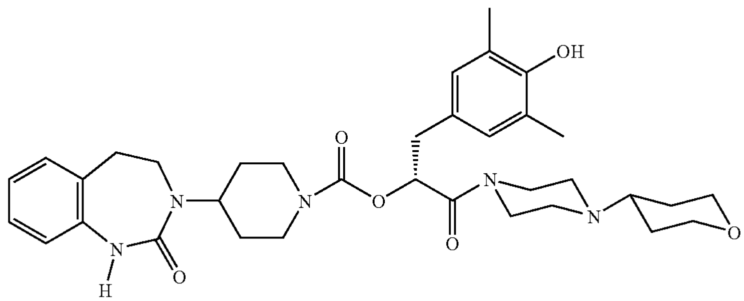 |
| (88) | 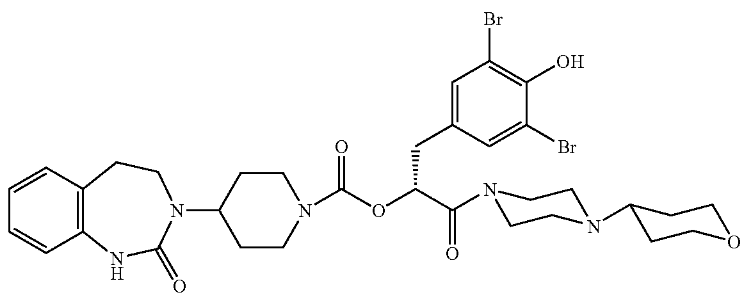 |
| (97) | 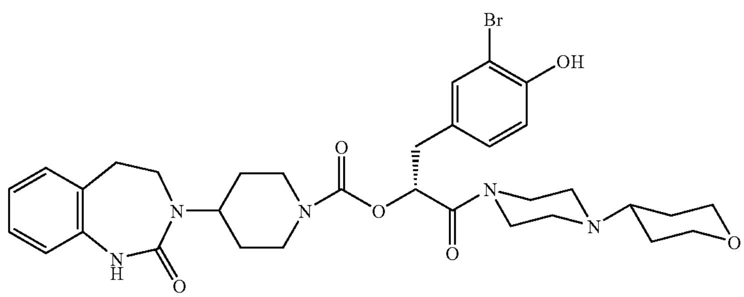 |
| (103) | 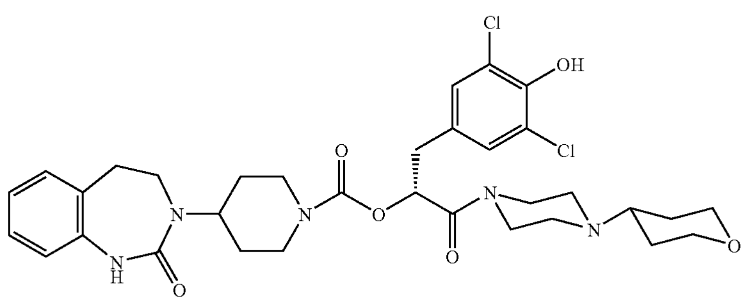 |
| (112) | 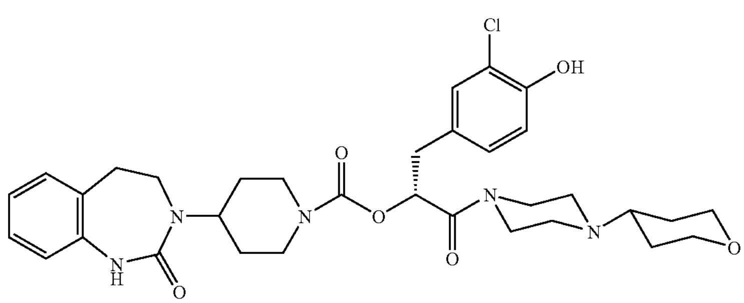 |

-continued

| No. | Structure |
|---|---|
| (171) | 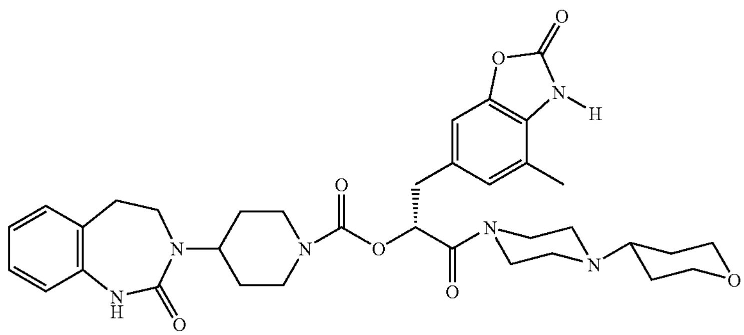 |
| (172) | 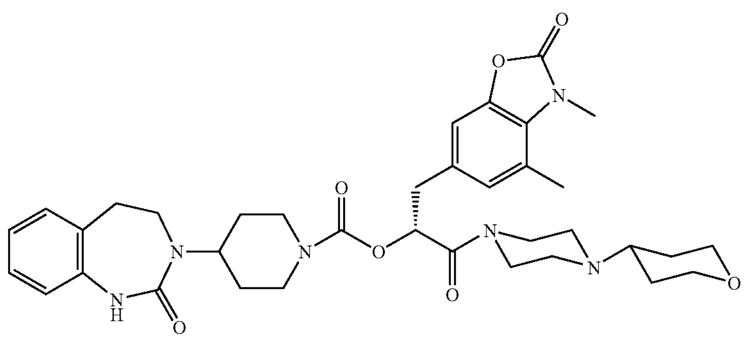 |
| (173) | 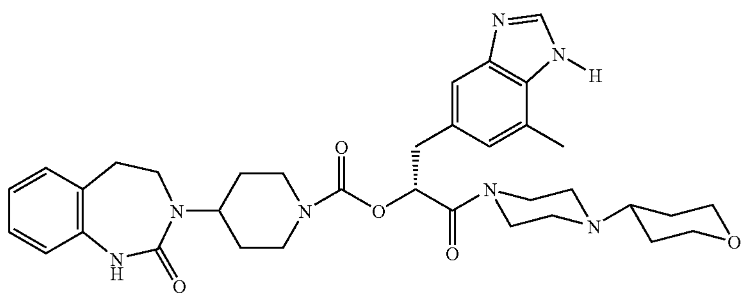 |
| (174) | 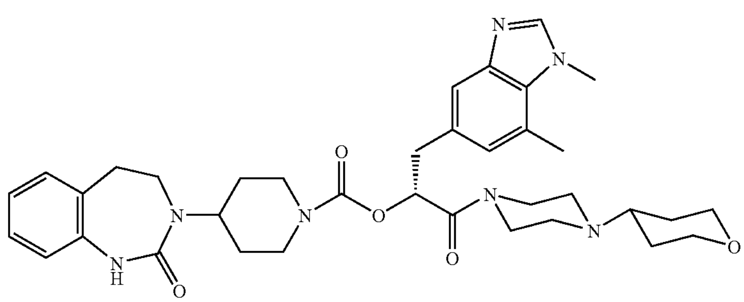 |
| (177) | 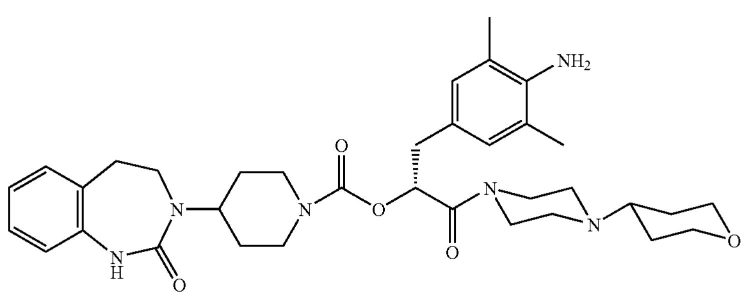 |

-continued

| No. | Structure |
|---|---|
| (178) | 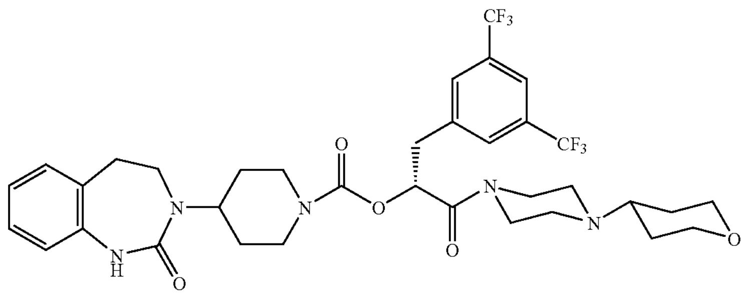 |
| (179) | 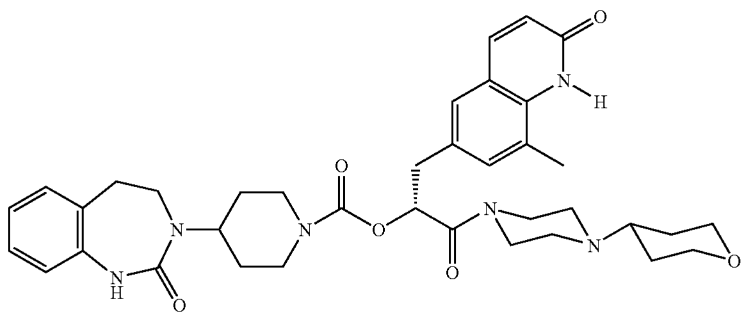 |
| (180) | 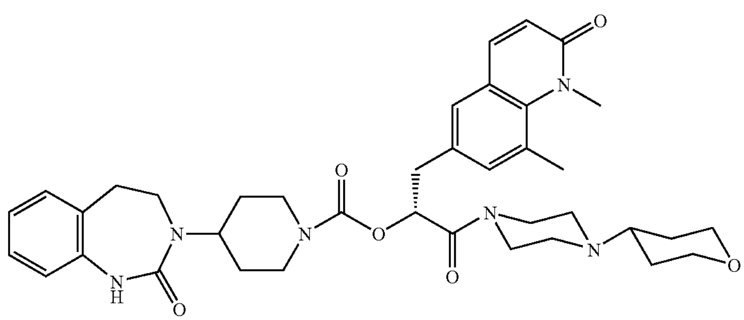 |
| (181) | 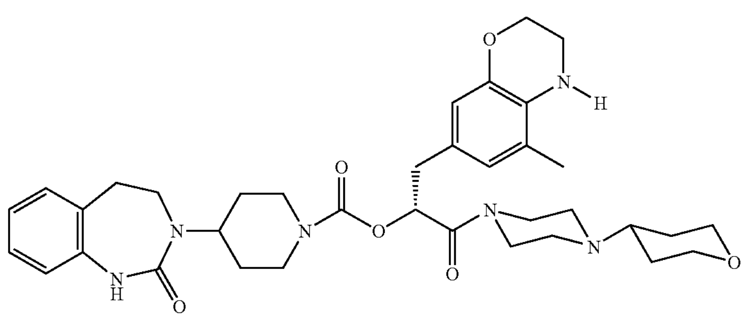 |
| (182) | 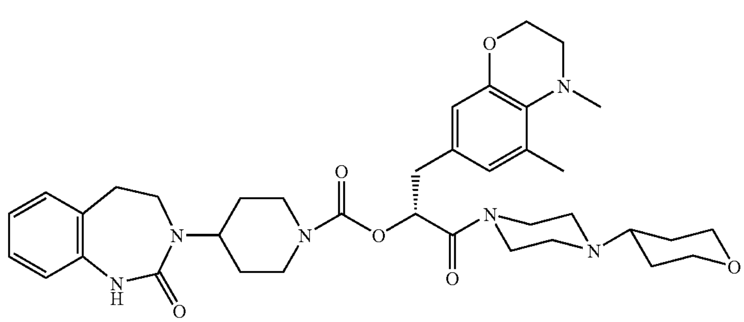 |

-continued
| No. | Structure |
|---|---|
| (183) | 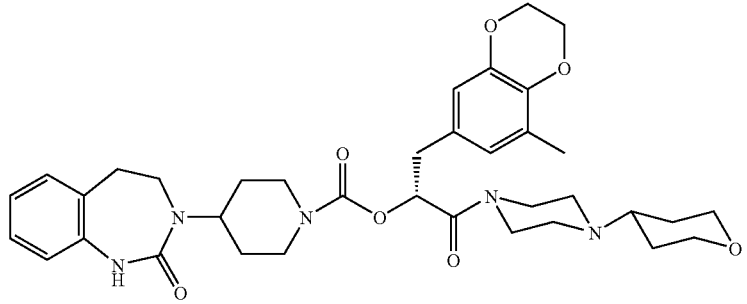 |
| (184) | 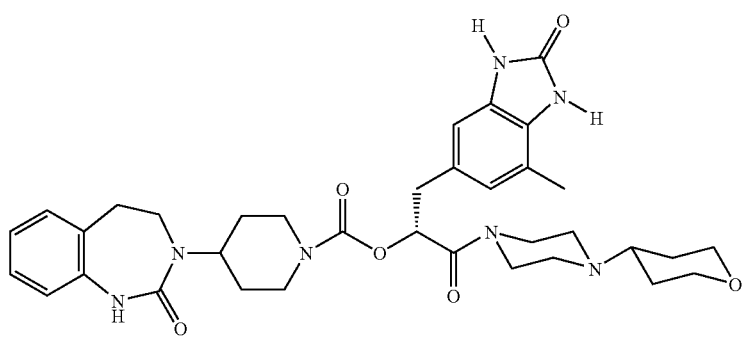 |
| (185) | 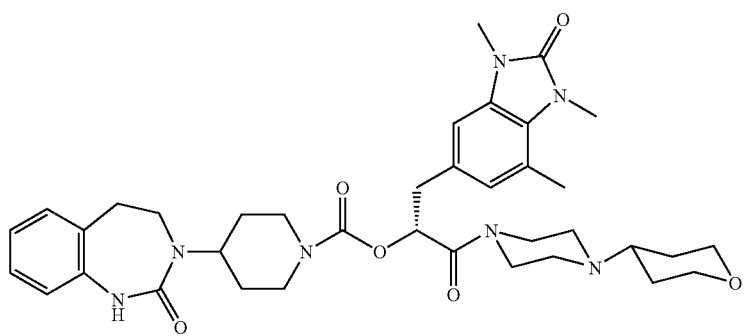 |
| (186) | 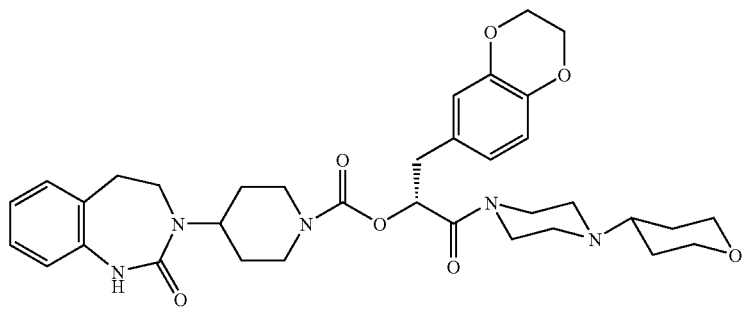 |

| No. | Structure |
|---|---|
| (187) | 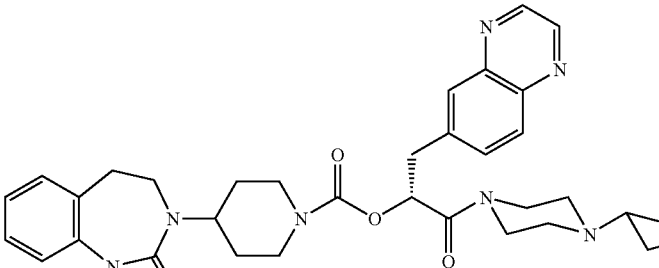 |
| (188) | 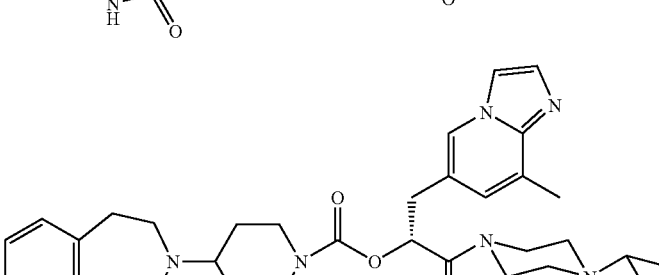 | the tautomers, the diastereomers, the enantiomers, the hydrates thereof, the mixtures thereof and the salts thereof as well as the hydrates of the salts, particularly the physiologically acceptable salts thereof with inorganic or organic acids or bases.

Terms and Definitions Used

Unless stated otherwise, all the substituents are independent of one another. If, for example, one group has a number of $C_{1-6}$-alkyl groups as substituents, in the case of three substituents, independently of one another, one $C_{1-3}$-alkyl may represent methyl, one may represent ethyl and one may represent n-propyl or iso-propyl.

Within the scope of this application, in the definition of possible substituents, these may also be represented in the form of a structural formula. An asterisk (*) in the structural formula of the substituent is to be understood as being the linking point to the rest of the molecule.

Also included in the subject matter of this invention are the compounds according to the invention, including the salts thereof, in which one or more hydrogen atoms, for example one, two, three, four or five hydrogen atoms, are replaced by deuterium.

By the term "$C_{1-3}$-alkyl" (including those which are part of other groups) are meant branched and unbranched alkyl groups with 1 to 3 carbon atoms and by the term "$C_{1-6}$-alkyl" are meant branched and unbranched alkyl groups with 1 to 6 carbon atoms. Examples include: methyl, ethyl, n-propyl, iso-propyl, n-butyl, iso-butyl, sec-butyl, tert-butyl, n-pentyl, iso-pentyl, neo-pentyl or hexyl. The following abbreviations may optionally also be used for the above-mentioned groups: Me, Et, n-Pr, i-Pr, n-Bu, i-Bu, t-Bu, etc. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "4- to 7-membered oxycycloalkyl group" are meant cycloalkyl groups with 4 to 7 carbon atoms, while in each case a $CH_2$ group is replaced by an oxygen atom. Examples include:

The above-mentioned oxycycloalkyl groups may optionally be substituted by hydroxy or methyl groups.

"Halogen" within the scope of the present invention denotes fluorine, chlorine, bromine or iodine. Unless stated to the contrary, fluorine, chlorine and bromine are regarded as preferred halogens.

Compounds of general formula I may have acid groups, mainly carboxyl groups, and/or basic groups such as e.g. amino functions. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, for example sodium hydroxide or potassium hydroxide, or carbonates, ammonia, zinc or ammonium-hydroxides or organic amines such as e.g. diethylamine, triethylamine, ethanolamine, diethanolamine, triethanolamine, cyclohexylamine, dicyclohexylamine, inter alia.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to the invention may occur as racemates if they have only one chiral element, but they may also be obtained as pure enantiomers, i.e. in the (R) or (S) form. Preferred compounds are those which occur as racemates or as the (R) form (for compounds wherein X does not denote the methylene group) or (S) form (for compounds wherein X denotes the methylene group).

However, the application also includes the individual diastereomeric pairs of antipodes or the mixtures thereof which are present when there is more than one chiral element in the compounds of general formula I, as well as the individual optically active enantiomers of which the above-mentioned racemates are made up.

Preparation Methods

The compounds of general formula I are prepared by methods known in principle. Methods of preparing compounds of general formula I wherein $R^1$, $R^2$, $R^3$ and $R^4$ are as hereinbefore defined and wherein X denotes the —CH$_2$, —NH or —C$_{1-3}$-alkylenyl-N group have already been described in International Patent Applications PCT/EP97/04862 and PCT/EP03/11762. Methods of preparing $R^1$ are also described in International Patent Applications PCT/EP97/04862 and PCT/EP03/11762 as well as in EP 1 619 187 A1.

The following methods have proved particularly suitable for preparing the compounds of general formula I according to the invention wherein X denotes the oxygen atom:

(a) In order to prepare compounds of general formula I wherein all the groups are as hereinbefore defined:

coupling a carboxylic acid of general formula IV

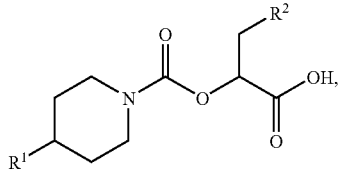

wherein $R^1$ and $R^2$ are as hereinbefore defined, with an amine of general formula V

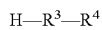

H—$R^3$—$R^4$ wherein $R^3$ and $R^4$ are as hereinbefore defined, the link being made via the nitrogen atom of $R^3$.

Before the reaction is carried out any carboxylic acid functions, primary or secondary amino functions or hydroxy functions present in the groups of the amine of formula H—$R^3$—$R^4$ may be protected by conventional protecting groups and any protecting groups used may be cleaved again after the reaction has been carried out, using methods familiar to the skilled man.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between –30° C. and +30° C., preferably –20° C. and +25° C. If necessary, N-ethyl-diisopropylamine (Hünig base) is preferably used as an additional auxiliary base.

The so-called "anhydride process" is used as a further coupling method for synthesising compounds of general formula I (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the "mixed anhydride process" is preferred (J. R. Vaughan Jr., J. Amer. Chem. Soc. 73, 3547 (1951)), in which the mixed anhydride of the carboxylic acid of general formula IV which is to be coupled and monoisobutyl carbonate is obtained, using isobutyl chlorocarbonate in the presence of bases such as 4-methylmorpholine or 4-ethylmorpholine. The preparation of this mixed anhydride and the coupling with amines of general formula V are carried out in a one-pot process, using the above-mentioned solvents and at temperatures between –20 and +25° C., preferably between 0° C. and +25° C.

(b) In order to prepare compounds of general formula I wherein all the groups are as hereinbefore defined:

coupling a compound of general formula VI

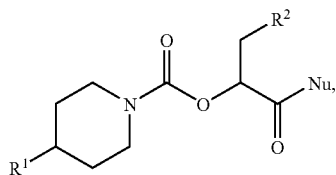

wherein $R^1$ and $R^2$ are as hereinbefore defined and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, wherein the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzotriazol-1-yloxy or azide group, with an amine of general formula V

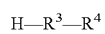

H—$R^3$—$R^4$ wherein all the groups are as hereinbefore defined and the attachment is made via the nitrogen atom of the amine $R^3$.

Before the reaction any carboxylic acid functions, primary or secondary amino functions or hydroxy functions present in the groups of the amine of general formula V may be protected by conventional protecting groups and after the reaction any protecting groups used may be cleaved again using methods familiar to those skilled in the art.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The new compounds of general formula I according to the invention contain one or more chiral centres. If for example there are two chiral centres the compounds may occur in the form of two pairs of diastereomeric antipodes. The invention covers the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+) or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula I is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The carboxylic acids of general formula IV needed as starting compounds are obtained by reacting piperidines of general formula VII

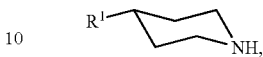

wherein $R^1$ is as hereinbefore defined, with carbonic acid derivatives of general formula VIII

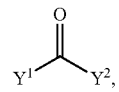

wherein $Y^1$ and $Y^2$ represent nucleofugic groups, which may be identical or different, preferably the chlorine atom, the p-nitrophenoxy or trichloromethoxy group, and with compounds of general formula IX

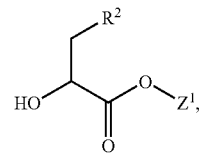

wherein $R^2$ is as hereinbefore defined and $Z^1$ denotes a protective group for a carboxy group, for example a $C_{1-6}$-alkyl or an optionally substituted benzyl group, wherein the alkyl groups may be straight-chained or branched and the benzyl group may be substituted by one or two methoxy groups.

Preferably $Z^1$ denotes the methyl, ethyl, tert-butyl or benzyl group. Before the reaction any hydroxy functions present in the group $R^2$ of a compound of formula V may be protected by conventional protecting groups and any protecting groups used may be cleaved again after the reaction by methods familiar to those skilled in the art.

In a first step the compounds of general formula VII are reacted with the carbonic acid derivatives of general formula VIII in a solvent, for example in dichloromethane, THF, pyridine or mixtures thereof, at a temperature from −20° C. to 50° C. in the presence of a base, for example triethylamine, pyridine or ethyldiisopropylamine. The resulting intermediate may be purified or further reacted without purification.

The reaction of these intermediates with compounds of general formula IX is also carried out in one of the above-mentioned solvents, and at the temperatures specified above, in the presence of a base, such as triethylamine or pyridine, with or without the addition of an activating reagent such as e.g. 4-dimethylaminopyridine. To activate them the compounds of general formula IX may also be deprotonated using a metal hydride, such as e.g. NaH or KH, and in this case it is possible to dispense with the base or the activating reagent.

The starting compounds of formula VII and VIII are either commercially obtainable, known from the literature or may be prepared using methods known from the literature.

Methods of preparing compounds of general formula VII are described for example in International Patent Applications PCT/EP97/04862 and PCT/EP03/11762 and in EP 1 619 187 A1.

One method of obtaining compounds of general formula IX comprises reacting aldehydes of general formula X

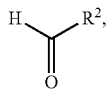

wherein $R^2$ is as hereinbefore defined, with N-acetylglycine in acetic anhydride as solvent in the presence of alkali metal acetate, preferably sodium or potassium acetate, at a suitable temperature, preferably at 80-130° C.

The azlactones obtained as primary product are hydrolysed without being isolated to form the compounds of general formula XI

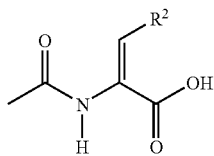

wherein $R^2$ is as hereinbefore defined.

Alternatively enamides of the general structure XII

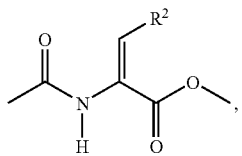

wherein $R^2$ is as hereinbefore defined, may be obtained by a coupling reaction of compounds of general formula XIII Hal-$R^2$, wherein $R^2$ is as hereinbefore defined and Hal denotes the bromine or iodine atom, and methyl 2-acetylaminoacrylate.

The reaction takes place in a suitable solvent such as tetrahydrofuran, dimethylformamide, 1,4-dioxane or acetonitrile, preferably acetonitrile, at temperatures between ambient temperature and 120° C., preferably between 50° C. and 80° C., in the presence of a suitable auxiliary base such as triethylamine or ethyldiisopropylamine, preferably triethylamine, and a suitable catalyst system. Suitable catalyst systems are a combination of a palladium species, such as palladium(II)acetate or bis(acetonitrile)-palladium-dichloride, preferably palladium(II)acetate, and a suitable phosphane ligand, such as triphenyl- or tris-o-tolyl-phosphane, preferably tris-o-tolyl-phosphane.

By further reaction of compounds of general formulae XI and XII in the presence of aqueous inorganic acids, such as for example sulphuric, phosphoric or hydrochloric acid, but preferably hydrochloric acid, compounds of general formula XIV

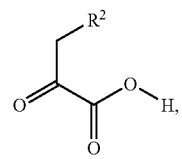

are obtained wherein $R^2$ is as hereinbefore defined.

These are then converted with suitable reducing agents into the compounds of general formula XV

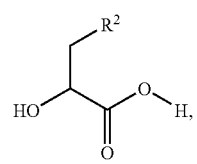

wherein $R^2$ is as hereinbefore defined.

Suitable reducing agents are alkali metal borohydrides, such as sodium or potassium borohydride. Other suitable reducing agents are chlorodialkylboranes, such as chlorodicyclohexylborane. If chiral chlorodialkylboranes, such as e.g. B-chlorodiisopinocampheylborane, are used, the compounds of general formula XIII may be isolated in enantiomerically pure form. The further reaction of compounds of general formula XIII to compounds of general formula IX takes place in an alcoholic medium, preferably in methanol or ethanol, in the presence of a suitable acid, such as hydrochloric acid. The reaction may alternatively be carried out by reaction in alcoholic solvents, preferably methanol, with thionyl chloride.

All the compounds of general formula I which contain primary or secondary amino, hydroxy or hydroxycarbonyl functions are preferably obtained from precursors provided with protective groups. Examples of protective groups for amino functions include for example a benzyloxycarbonyl, 2-nitrobenzyloxycarbonyl, 4-nitro-benzyloxycarbonyl, 4-methoxy-benzyloxycarbonyl, 2-chloro-benzyloxycarbonyl, 3-chloro-benzyloxycarbonyl, 4-chloro-benzyloxycarbonyl, 4-biphenylyl-α,α-dimethyl-benzyloxycarbonyl or 3,5-dimethoxy-α,α-dimethyl-benzyloxycarbonyl group, an alkoxycarbonyl group with a total of 1 to 5 carbon atoms in the alkyl moiety, for example the methoxycarbonyl, ethoxycarbonyl, n-propoxycarbonyl, isopropoxycarbonyl, n-butoxycarbonyl, 1-methyl propoxycarbonyl, 2-methyl propoxy-carbonyl or tert-butyloxycarbonyl group, the allyloxycarbonyl, 2,2,2-trichloro-(1,1-dimethylethoxy)carbonyl or 9-fluorenylmethoxycarbonyl group or a formyl, acetyl or trifluoroacetyl group.

Examples of protective groups for hydroxy functions include a trimethylsilyl, triethylsilyl, triisopropyl, tert-butyldimethylsilyl or tert-butyldiphenylsilyl group, a tert-butyl, benzyl, 4-methoxybenzyl or 3,4-dimethoxybenzyl group.

A protective group for hydroxycarbonyl functions might be, for example, an alkyl group with a total of 1 to 5 carbon atoms, for example the methyl, ethyl, n-propyl, isopropyl, n-butyl, tert-butyl, allyl, 2,2,2-trichloroethyl, benzyl or 4-methoxybenzyl group.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B glass fibre filters treated with polyethyleneimine (0.1%) using a cell harvester. The protein-bound radioactivity is measured using a gamma counter. Non-specific binding is defined as the bound radioactivity in the presence of 1 µM human CGRP-alpha during incubation.

The concentration binding curves are analysed using computer-aided non-linear curve matching.

The compounds mentioned hereinbefore show IC$_{50}$ values $\geq$10000 nM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{-11}$ to $10^{-6}$M), or additionally the substance in 3 to 4 different concentrations, the mixture is incubated for another 15 minutes.

Intracellular cAMP is then extracted by the addition of 20 µl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the pA$_2$ values of antagonistically acting substances are determined graphically.

The compounds according to the invention exhibit CGRP-antagonistic properties in the in vitro test model described, in a dosage range between $10^{-12}$ and $10^{-5}$ M.

Types of Indications

In view of their pharmacological properties the compounds according to the invention and the salts thereof with physiologically acceptable acids are thus suitable for the acute and prophylactic treatment of headaches, particularly migraine, cluster headaches and tension headaches. Moreover, the compounds according to the invention also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, lichen, prurigo, pruriginous toxidermies and severe itching, inflammatory diseases, e.g. inflammatory diseases of the joints (osteoarthritis, rheumatoid arthritis, neurogenic arthritis), generalised soft tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, such as e.g. diabetic neuropathies, neuropathies induced by chemotherapy, HIV-induced neuropathies, post-herpetic neuropathies, neuropathies induced by tissue trauma, trigeminal neuralgias, temporomandibular dysfunctions, CRPS (complex regional pain syndrome), back pain and visceral diseases such as for example irritable bowel syndrome (IBS), inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

Preferably, the compounds according to the invention are suitable for the acute and preventive treatment of migraine and cluster headaches, for treating irritable bowel syndrome (IBS) and for the preventive and acute therapeutic treatment of hot flushes in oestrogen-deficient women.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3×a day in each case.

If the treatment with CGRP antagonists and/or CGRP release inhibitors is given as a supplement to conventional hormone replacement, it is advisable to reduce the doses specified above, in which case the dosage may be from ⅕ of the lower limits mentioned above up to ⅕ of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in the combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiinflammatories, corticosteroids, calcium antagonists, $5\text{-HT}_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective $COX_2$-inhibitors, such as for example rofecoxib, valdecoxib, parecoxib, etoricoxib and celecoxib, as well as substances which inhibit earlier or later stages in prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabaline, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other $5\text{-HT}_{1B/1D}$-agonists such as, for example, almotriptan, avitriptan, eletriptan, frovatriptan, naratriptan, rizatriptan, sumatriptan and zolmitriptan.

In addition, CGRP-antagonists may be combined with vanilloid receptor antagonists, such as e.g. VR-1 antagonists, glutamate receptor antagonists, such as e.g. mGlu5-receptor antagonists, mGlu1-receptor antagonists, iGlu5-receptor antagonists, AMPA-receptor antagonists, purine receptor blockers, such as e.g. P2X3 antagonists, NO-synthase inhibitors, such as e.g. iNOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA-receptor antagonists, acid-sensing ion channel antagonists, such as e.g. ASIC3 antagonists, bradykinin receptor antagonists such as e.g. B1-receptor antagonists, cannabinoid receptor agonists, such as e.g. CB2 agonists, CB1 agonists, somatostatin receptor agonists, such as e.g. sst2 receptor agonists.

The dosage for these active substances is conveniently ⅕ of the normally recommended dose to ⅓ of the normally recommended dose, i.e. for example 20 to 100 mg sumatriptan.

Formulations

The compounds prepared according to the invention may be administered either on their own or optionally in combination with other active substances for the treatment of migraine by intravenous, subcutaneous, intramuscular, intra-articular, intrarectal or intranasal route, by inhalation, topically, transdermally or orally, while aerosol formulations are particularly suitable for inhalation. The combinations may be administered either simultaneously or sequentially.

Suitable forms for administration include for example tablets, capsules, solutions, syrups, emulsions or inhalable powders or aerosols. The proportion of pharmaceutically active compound or compounds should be in the range from 0.1 to 90% by weight, preferably 0.5 to 50% by weight of the total composition, i.e. in amounts which are sufficient to achieve the dosage range mentioned herein before.

The preparations may be given orally in the form of tablets, powders, powders in capsules (e.g. hard gelatine capsules), or as solutions or suspensions. When taken by inhalation the active substance combination may be administered as a powder, an aqueous or aqueous-ethanolic solution or by means of a propellant gas formulation.

Preferably, therefore, pharmaceutical formulations are characterised in that they contain one or more compounds of formula I according to the preferred embodiments described hereinbefore.

It is particularly preferable if the compounds of formula I are administered orally, and it is most preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium lauryl sulphate and talc may also be used to produce the tablets. In the case of aqueous suspensions the active substances may be combined with various flavour enhancers or colourings in addition to the abovementioned excipients.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions which are optionally in admixture with conventional physiologically acceptable excipients.

Within the scope of the present invention, the term propellant-free inhalable solutions also includes concentrates or sterile inhalable solutions ready for use. The formulations which may be used within the scope of the present invention are described in more detail in the next part of the specification.

Inhalable Powders

If the compounds of formula I are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Processes for producing the inhalable powders according to the invention by grinding and micronising and by finally mixing the ingredients together are known from the prior art.

Propellant-Containing Aerosols for Inhalation

The inhalation aerosols containing propellant gas which may be used according to the invention may contain I dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols which may be used for the purpose according to the invention may also contain other ingredients such as co-solvents, stabilisers, surfactants, antioxidants, lubricants and pH adjusters. All these ingredients are known in the art.

Propellant-Free Inhalable Solutions

The compounds of formula I are preferably used to prepare propellant-free inhalable solutions and inhalable suspensions. The solvent used may be an aqueous or alcoholic, preferably an ethanolic solution. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc . . . Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters.

The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically unobjectionable salts such as sodium chloride as isotonic agents. The preferred excipients include antioxidants such as ascorbic acid, for example, provided that it has not already been used to adjust the pH, vitamin A, vitamin E, tocopherols and similar vitamins and provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

EXPERIMENTAL SECTION

As a rule, IR, $^1$H-NMR and/or mass spectra have been obtained for the compounds prepared. Unless otherwise stated, $R_f$ values are obtained using ready-made silica gel TLC plates 60 F254 (E. Merck, Darmstadt, Item no. 1.05714) without chamber saturation. The $R_f$ values determined under the heading Polygram-Alox are obtained using ready-made Polygram Alox N/UV$_{254}$ TLC films (coated with 0.2 mm aluminium oxide) made by Macherey-Nagel (Düren, Item No. 802 021). The ratios given for the eluants relate to units by volume of the solvents in question. The units by volume specified for NH$_3$ refer to a concentrated solution of NH$_3$ in water.

Unless otherwise stated, the acid, base and salt solutions used for working up the reaction solutions are aqueous systems of the specified concentrations. For chromatographic purification, silica gel made by Millipore (MATREX™, 35-70 µm) is used. For chromatographic purification, aluminium oxide (Alox) made by ICN Biomedicals (Eschwege, Item number 02090) is used. According to the manufacturer's instructions the required activity stage is produced before use.

The HPLC data given are measured using the parameters shown below:

Method A:

| time (min) | percent by volume of water (with 0.1% formic acid) | percent by volume of acetonitrile (with 0.1% formic acid) |
| --- | --- | --- |
| 0 | 95 | 5 |
| 4.5 | 10 | 90 |
| 5 | 10 | 90 |
| 5.5 | 90 | 10 |

Analytical column: Zorbax column (Agilent Technologies), SB (Stable Bond) C18; 3.5 µm; 4.6×75 mm; column temperature: 30° C.; flow: 1.6 mL/min; injection volume: 5 µL; detection at 254 nm Method B:

| time (min) | percent by volume of water (with 0.1% formic acid) | percent by volume of acetonitrile (with 0.1% formic acid) |
| --- | --- | --- |
| 0 | 95 | 5 |
| 9 | 10 | 90 |
| 10 | 10 | 90 |
| 11 | 95 | 5 |

Analytical column: Zorbax column (Agilent Technologies), SB (Stable Bond) C18; 3.5 µm; 4.6×75 mm; column temperature: 30° C.; flow: 0.8 mL/min; injection volume: 5 µL; detection at 254 nm Method C:

| time (min) | percent by volume of water (with 0.1% formic acid) | percent by volume of acetonitrile (with 0.1% formic acid) |
| --- | --- | --- |
| 0 | 95 | 5 |
| 4 | 50 | 50 |
| 4.5 | 10 | 90 |
| 5 | 10 | 90 |
| 5.5 | 90 | 10 |

Analytical column: Zorbax column (Agilent Technologies), SB (Stable Bond) C18; 3.5 µm; 4.6×75 mm; column temperature: 30° C.; flow: 1.6 mL/min; injection volume: 5 µL; detection at 254 nm Method D:

| time (min) | percent by volume of water (with 0.04% TFA) | percent by volume of acetonitrile (with 0.04% TFA) |
| --- | --- | --- |
| 0 | 80 | 20 |
| 15 | 20 | 80 |
| 17 | 20 | 80 |

Analytical column: Symmetry C8 Waters—4.6×150 mm; 5 micron, flow: 1.3 ml/min, column temperature: 25° C., detection at 254 nm.

Method E:

| time (min) | percent by volume of water (with 0.1% formic acid) | percent by volume of acetonitrile (with 0.1% formic acid) |
| --- | --- | --- |
| 0 | 95 | 5 |
| 8 | 50 | 50 |
| 9 | 10 | 90 |
| 10 | 10 | 90 |
| 11 | 90 | 10 |

Analytical column: Zorbax column (Agilent Technologies), SB (Stable Bond) C18; 3.5 µm; 4.6×75 mm; column temperature: 30° C.; flow: 0.8 mL/min; injection volume: 5 µL; detection at 254 nm Method F:

| time (min) | percent by volume of water (with 0.1% formic acid) | percent by volume of acetonitrile (with 0.1% formic acid) |
| --- | --- | --- |
| 0 | 95 | 5 |
| 2 | 10 | 90 |
| 5 | 10 | 90 |
| 5.5 | 90 | 10 |

Analytical column: Zorbax column (Agilent Technologies), SB (Stable Bond) C18; 3.5 µm; 4.6×75 mm; column temperature: 30° C.; flow: 1.6 mL/min; injection volume: 5 µL; detection at 254 nm Method G:

| time (min) | percent by volume of water (with 0.04% TFA) | percent by volume of acetonitrile (with 0.04% TFA) |
|---|---|---|
| 0 | 80 | 20 |
| 30 | 20 | 80 |

Analytical column: Waters Symmetry C8, 5 µm, 4.6×150 mm; column temperature: 25° C., flow: 1.3 mL/min, injection volume: 5 µL, detection at 254 nm.

In preparative HPLC purifications as a rule the same gradients are used as were used to collect the analytical HPLC data.

The products are collected under mass control and the fractions containing the product are combined and freeze-dried.

If no detailed information is given as to the configuration, it is not clear whether it is a pure enantiomer or whether partial or even complete racemisation has occurred.

The following abbreviations are used in the description of the experiments:
CDT 1,1'-carbonyl-di-(1,2,4-triazole)
Cyc cyclohexane
DCM dichloromethane
DIPE diisopropylether
DMF N,N-dimethylformamide
EtOAc ethyl acetate
EtOH ethanol
HATU O-(7-azabenzotriazol-1-yl)-N,N,N',N'-tetramethyluronium-hexafluoro-phosphate
ACOH acetic acid
i.vac. in vacuo (under vacuum)
MCPBA m-chloroperbenzoic acid
MeOH methanol
NaOAc sodium acetate
PE petroleum ether
RT ambient temperature
TBME tert-butylmethylether
TBTU O-(benzotriazol-1-yl)-N,N,N',N'-tetramethyluronium-tetrafluoroborate
TFA trifluoroacetic acid
THF tetrahydrofuran Amine A1

1-(4-methyl-tetrahydropyran-4-yl)-piperazine

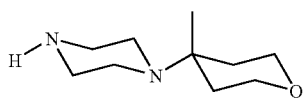

A1a) 4-(4-benzyl-piperazin-1-yl)-tetrahydropyran-4-carbonitrile 6.5 g (99.8 mmol) potassium cyanide were added to a solution of 10.0 g (96.9 mmol) tetrahydropyran-4-one and 17.1 g (97.0 mmol) 1-benzyl-piperazine in 25 mL 4 M HCl and 50 mL water while cooling with ice and the reaction mixture was stirred for 40 h at RT. The precipitate formed was suction filtered, washed with water and dried.
Yield: 22.0 g (76% of theory)
ESI-MS: (M+H)$^+$=286

A1b) 1-benzyl-4-(4-methyl-tetrahydropyran-4-yl)-piperazine

Under a nitrogen atmosphere 6.00 g (21.02 mmol) 4-(4-benzyl-piperazin-1-yl)-tetrahydropyran-4-carbonitrile in 200 mL dry THF were prepared and 30 mL ethylmagnesium chloride solution (90.0 mmol, 3 M in diethyl ether) was added dropwise and the reaction solution was stirred for 3 h at RT. Saturated NH$_4$Cl solution was added, the mixture was stirred for 10 min, extracted exhaustively with diethyl ether and the combined organic phases were dried over Na$_2$SO$_4$. After the desiccant and solvent had been eliminated the residue was purified by chromatography (Alox, activity stage II-III, gradient DCM/MeOH 100:1 towards 50:1).
Yield: 4.85 g (84% of theory)
ESI-MS: (M+H)$^+$=275

A1c) 1-(4-methyl-tetrahydropyran-4-yl)-piperazine

A suspension of 4.84 g (17.6 mmol) 1-benzyl-4-(4-methyl-tetrahydropyran-4-yl)-piperazine and 400 mg 10% Pd/C in 100 mL MeOH was hydrogenated at 50° C. and 3447 hPa hydrogen pressure for 4 h. To complete the reaction 1 mL concentrated HCl was added and the mixture was hydrogenated for a further 18 h at 50° C. and 3447 hPa hydrogen pressure. The catalyst was suction filtered and the filtrate was evaporated to dryness. The product, which was obtained as the hydrochloride salt, was further reacted without purification.
Yield: 4.00 g (100% of theory)
ESI-MS: (M+H)$^+$=185

EXAMPLE 1

(R)-1-(4-methyl-2-oxo-2,3-dihydro-benzoxazol-6-yl methyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

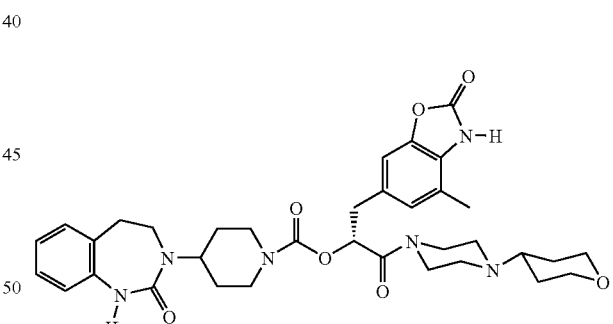

1a) 4-methyl-3H-benzoxazol-2-one 76.0 g (0.45 mol) CDI in 1 L DCM were added dropwise at 0° C. to a solution of 50.0 g (0.39 mol) 5-amino-m-cresol and 210 mL ethyldiisopropylamine (1.2 mol) in 1 L DCM. After the end of the reaction the reaction mixture was combined with 250 mL water, the organic phase was separated off and washed twice with 250 mL 1 M KHSO$_4$ solution and 250 mL water and dried over MgSO$_4$. After the desiccant and solvent had been eliminated the residue obtained was dissolved in 200 mL EtOAc, refluxed, combined with 100 mL PE, slowly cooled to RT, the precipitate formed was suction filtered and dried.

Yield: 39.2 g (67% of theory)
ESI-MS: $(M+H)^+=150$
$R_f=0.65$ (silica gel, DCM/Cyc/MeOH/NH$_3$ 70:15:15:2)

1b) 6-bromo-4-methyl-3H-benzoxazol-2-one 35.8 g (199.1 mmol) N-bromosuccinimide were added to a solution of 29.5 g (197.8 mmol) 4-methyl-3H-benzoxazol-2-one in 200 mL AcOH and the mixture was stirred overnight at RT. The reaction solution was combined with 800 mL water, stirred for 15 min at RT, the precipitate was suction filtered, washed with water and dried in the vacuum drying cupboard at 60° C.
Yield: 43.0 g (95% of theory)
ESI-MS: $(M+H)^+=226/228$ (Br)
$R_f=0.35$ (silica gel, DCM/Cyc/MeOH/NH$_3$ 70:15:15:2)

1c) methyl(Z,E)-2-acetylamino-3-(4-methyl-2-oxo-2,3-dihydro-benzoxazol-6-yl)-acrylate Under a nitrogen atmosphere 5.4 g (23.9 mmol) Pd(OAc)$_2$ and 7.5 g (24.0 mmol) tri-o-tolyl-phosphane were added to a solution of 38.3 g (168.0 mmol) 6-bromo-4-methyl-3H-benzoxazol-2-one and 28.0 g (191.7 mmol) methyl 2-acetylamino-acrylate in 800 mL acetonitrile and 480 mL triethylamine, the reaction mixture was stirred for 18 h at 80° C. and then evaporated down i.vac. The residue was combined with 100 mL water and 50 mL EtOAc and the precipitate was filtered off. The crystals were dissolved by refluxing in MeOH/DCM 1:1, combined with activated charcoal, filtered off and the filtrate was evaporated to dryness.
Yield: 31.2 g (64% of theory)
ESI-MS: $(M+H)^+=291$
$R_f=0.38$ (silica gel, DCM/Cyc/MeOH/NH$_3$ 70:15:15:2)

1d) 3-(4-methyl-2-oxo-2,3-dihydro-benzoxazol-6-yl)-2-oxo-propionic acid 160 mL 4 M HCl were added to a solution of 31.2 g (107.5 mmol) methyl(Z,E)-2-acetylamino-3-(4-methyl-2-oxo-2,3-dihydro-benzoxazol-6-yl)-acrylate in 320 mL 1,4-dioxane and the reaction solution was refluxed for 5 h. The mixture was evaporated down i.vac., the precipitate was filtered off, washed with water and dried at 60° C. in the vacuum drying cupboard.
Yield: 24.9 g (98% of theory)
ESI-MS: $(M+H)^+=236$
$R_f=0.38$ (silica gel, DCM/Cyc/MeOH/NH$_3$ 70:15:15:2)

1e) (R)-2-hydroxy-3-(4-methyl-2-oxo-2,3-dihydro-benzoxazol-6-yl)-propionic acid Under a nitrogen atmosphere a solution of 60.0 g (187.1 mmol) (1R)-B-chloro-diisopinocampheylborane in 200 mL THF was added dropwise to a solution of 24.9 g (105.9 mmol) 3-(4-methyl-2-oxo-2,3-dihydro-benzoxazol-6-yl)-2-oxo-propionic acid and 20.0 mL (143.9 mmol) triethylamine in 400 mL THF, cooled to −35° C., within 15 min and the reaction solution was stirred overnight at RT. Then the reaction solution was carefully made alkaline with 1 M NaOH at 5° C., combined with 400 mL EtOAc and stirred for 15 min. The organic phase was separated off, extracted twice with 100 mL of 1 M NaOH and with 100 mL water. The combined aqueous phases were acidified with semiconc. HCl and extracted twice with 150 mL EtOAc in each case. The combined organic phases were dried over MgSO$_4$ and evaporated down i.vac.
Yield: 20.8 g (83% of theory)
ESI-MS: $(M+H)^+=238$
$R_f=0.10$ (silica gel, DCM/Cyc/MeOH/NH$_3$ 70:15:15:2)

1f) methyl(R)-2-hydroxy-3-(4-methyl-2-oxo-2,3-dihydro-benzoxazol-6-yl)-propionate 23.0 g (97.0 mmol) (R)-2-hydroxy-3-(4-methyl-2-oxo-2,3-dihydro-benzoxazol-6-yl)-propionic acid were dissolved in 200 mL methanolic HCl (1.3 M), stirred overnight at RT and then evaporated down i.vac. The residue was combined with 200 mL EtOAc, washed with 15% K$_2$CO$_3$ solution and the organic phase was dried over Na$_2$SO$_4$. After the desiccant and solvent had been eliminated the residue was combined with DIPE, the crystals were filtered off and dried at 50° C. in the vacuum drying cupboard.
Yield: 14.6 g (60% of theory)
ESI-MS: $(M+H)^+=252$
$R_f=0.44$ (silica gel, DCM/Cyc/MeOH/NH$_3$ 70:15:15:2)

1g) (R)-1-carboxy-2-(4-methyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate Under a nitrogen atmosphere 4.1 g (20.1 mmol) 4-nitrophenyl chloroformate in 20 mL THF were metered into 40 mL pyridine at a bath temperature of 60° C. within 10 min, the mixture was stirred for 5 min, then 5.0 g (19.9 mmol) methyl (R)-2hydroxy-3-(4-methyl-2-oxo-2,3-dihydro-benzoxazol-6-yl)-propionate and 20 mL pyridine were added and the reaction mixture was stirred for 1.5 h at 60° C. The reaction solution was combined with 4.9 g (20.0 mmol) 3-piperidin-4-yl-1,3,4,5-tetrahydro-1,3-benzodiazepin-2-one and stirred for 2 h at 100° C. After the end of the reaction the mixture was combined with 150 mL EtOAc, washed three times with 70 mL 1 M KHSO$_4$ solution and 12 times with 50 mL 15% K$_2$CO$_3$ solution and the organic phase was dried over MgSO$_4$. After the desiccant and solvent had been eliminated the residue was dissolved in 60 mL THF, combined with 250 mg LiOH in 10 mL water and the reaction mixture was stirred for 3 h at RT. The THF was eliminated i.vac., the aqueous residue was combined with 60 mL TBME, insoluble ingredients were filtered off, the organic phase was separated off and the aqueous phase was acidified with 1 M HCl. After 1 h at RT the precipitate formed was suction filtered, washed with water and dried at 60° C. in the vacuum drying cupboard.
Yield: 2.5 g (25% of theory)
ESI-MS: $(M-H)^-=507$
$R_f=0.10$ (silica gel, DCM/Cyc/MeOH/NH$_3$ 70:15:15:2)

1h (R)-1-(4-methyl-2-oxo-2,3-dihydro-benzoxazol-6-ylmethyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate 30 mg (0.18 mmol) 1-(tetrahydropyran-4-yl)-piperazine were added at RT to a solution of 70 mg (0.14 mmol) (R)-1-carboxy-2-(4-methyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate, 50 mg (1.12 mmol) TBTU and 25 µL (0.18 mmol) triethylamine in 1 mL DMF and the reaction solution was stirred overnight. It was purified by HPLC without any further working up; the fractions containing the product were combined and lyophilised.
Yield: 69 mg (68% of theory)
ESI-MS: $(M-H)^-=659$
retention time (HPLC): 2.7 min (method A)

EXAMPLE 2

(R)-1-(3,4-dimethyl-2-oxo-2,3-dihydro-benzoxazol-6-yl methyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

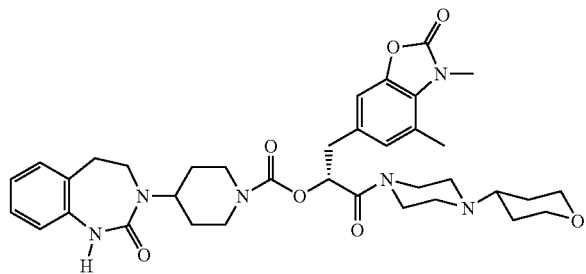

2a) 3,4-dimethyl-3H-benzoxazol-2-one

A solution of 10.0 g (67.0 mmol) 4-methyl-3H-benzoxazol-2-one in 200 mL THF was combined with 8.0 g (70.6 mmol) potassium-tert.-butoxide, stirred for 30 min at RT, then combined with 7.0 mL (110.3 mmol) iodomethane and stirred overnight at RT. The reaction mixture was combined with 100 mL EtOAc, washed twice with 50 mL saturated NaCl solution, the organic phase was dried over MgSO$_4$ dried, filtered and evaporated to dryness i.vac. The residue was combined with PE/EtOAc 2:1, the precipitate was suction filtered and dried at 60° C. in the vacuum drying cupboard.

Yield: 9.0 g (82% of theory)
ESI-MS: (M+H)$^+$=164
R$_f$=0.56 (silica gel, PE/EtOAc 2:1)

2b) 6-bromo-3,4-dimethyl-3H-benzoxazol-2-one 11.0 g (60.0 mmol) N-bromosuccinimide were added to a solution of 9.0 g (55.2 mmol) 3,4-dimethyl-3H-benzoxazol-2-one in 50 mL AcOH and the reaction mixture was stirred overnight at RT. The reaction solution was combined with 300 mL water, stirred for 15 min at RT, the precipitate was suction filtered, washed with water and dried at 60° C. in the vacuum drying cupboard.

Yield: 12.7 g (95% of theory)
ESI-MS: (M+H)$^+$=242/244 (Br)
R$_f$=0.52 (silica gel, PE/EtOAc 2:1)

2c) methyl(Z,E)-2-acetylamino-3-(3,4-dimethyl-2-oxo-2,3-dihydro-benzoxazol-6-yl)-acrylate Under a nitrogen atmosphere 1.8 g (8.0 mmol) Pd(OAc)$_2$ and 2.5 g (8.0 mmol) tri-o-tolyl-phosphane was added to a solution of 13.2 g (54.5 mmol) 6-bromo-3,4-dimethyl-3H-benzoxazol-2-one and 9.0 g (61.6 mmol) methyl 2-acetylamino-acrylate in 250 mL acetonitrile and 160 mL triethylamine and the reaction mixture was stirred for 18 h at 80° C. The reaction solution was evaporated down i.vac., the residue was combined with 100 mL water and 50 mL EtOAc and the precipitate was filtered off. This was dissolved in MeOH/DCM (1:1), combined with activated charcoal, filtered off and the filtrate was evaporated to dryness.

Yield: 8.7 g (52% of theory)
ESI-MS: (M+H)$^+$=305
R$_f$=0.47 (silica gel, DCM/Cyc/MeOH/NH$_3$ 70:15:15:2)

2d) 3-(3,4-dimethyl-2-oxo-2,3-dihydro-benzoxazol-6-yl)-2-oxo-propionic acid 40 mL of 4 M HCl were added to a solution of 8.7 g (28.6 mmol) methyl(Z,E)-2-acetylamino-3-(3,4-dimethyl-2-oxo-2,3-dihydro-benzoxazol-6-yl)-acrylate in 80 mL of 1,4-dioxane and the reaction solution was refluxed for 5 h and then left overnight at RT. The mixture was evaporated down i.vac., the precipitated product was filtered off, this was washed with water and dried at 60° C. in the vacuum drying cupboard.

Yield: 6.6 g (93% of theory)
ESI-MS: (M+H)$^+$=250
R$_f$=0.13 (silica gel, DCM/Cyc/MeOH/NH$_3$ 70:15:15:2)

2e) (R)-3-(3,4-dimethyl-2-oxo-2,3-dihydro-benzoxazol-6-yl)-2-hydroxy-propionic acid Under a nitrogen atmosphere a solution of 15.0 g (46.8 mmol) (1R)-B-chlorodiisopinocampheylborane in 50 mL THF was added dropwise within 15 min to a solution of 6.6 g (26.5 mmol) 3-(3,4-dimethyl-2-oxo-2,3-dihydro-benzoxazol-6-yl)-2-oxo-propionic acid and 5.0 mL (36.0 mmol) triethylamine in 100 mL THF, cooled to −35° C., and the reaction solution was stirred overnight at RT. Then at 5° C. the mixture was combined with 60 mL 1 M NaOH and 100 mL EtOAc, stirred for 15 min, the organic phase was separated off and extracted twice with 30 mL 1 M NaOH and 40 mL water. The combined aqueous phases were acidified with semiconc. HCl and extracted twice with 100 mL EtOAc. The combined organic phases were dried over MgSO$_4$ and evaporated down i.vac.

Yield: 3.4 g (51% of theory)
ESI-MS: (M+H)$^+$=252
R$_f$=0.13 (silica gel, DCM/Cyc/MeOH/NH$_3$ 70:15:15:2)

2f) methyl(R)-3-(3,4-dimethyl-2-oxo-2,3-dihydro-benzoxazol-6-yl)-2-hydroxy-propionate 3.4 g (13.5 mmol) (R)-3-(3,4-dimethyl-2-oxo-2,3-dihydro-benzoxazol-6-yl)-2-hydroxy-propionic acid were dissolved in 40 mL methanolic HCl (1.3 M) and the reaction mixture was stirred overnight at RT. The mixture was evaporated down i.vac., the residue was taken up in 200 mL EtOAc, washed with 15% K$_2$CO$_3$ solution and the organic phase was dried over Na$_2$SO$_4$. After the desiccant and solvent had been eliminated the residue was further reacted without purification.

Yield: 2.5 g (70% of theory)
ESI-MS: (M+H)$^+$=266
R$_f$=0.54 (silica gel, DCM/Cyc/MeOH/NH$_3$ 70:15:15:2)

2g) (R)-1-carboxy-2-(3,4-dimethyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate Under a nitrogen atmosphere at 60° C., a solution of 2.0 g (10.0 mmol) 4-nitrophenyl chloroformate in 10 mL THF was added within 10 min to 20 mL pyridine and stirred for 10 min. Then a solution of 2.5 g (9.4 mmol) methyl(R)-3(3,4-dimethyl-2-oxo-2,3-dihydro-benzoxazol-6-yl)-2-hydroxy-propionate in 10 mL pyridine was added, the mixture was stirred for a further 2.5 h at 60° C. and then combined with 2.5 g (10.0 mmol) 3-piperidin-4-yl-1,3,4,5-tetrahydro-1,3-benzodiazepin-2-one. The reaction solution was stirred for 3 h at 100° C. After the reaction had ended the reaction mixture was evaporated down i.vac., combined 150 mL EtOAc, the organic phase was washed three times with 40 mL 1 M KHSO$_4$ solution and 12 times with 30 mL 15% K$_2$CO$_3$ solution and dried over MgSO$_4$. After the desiccant and solvent had been eliminated the residue was dissolved in 60 mL THF, combined with 250 mg LiOH in 10 mL water and the reaction mixture was stirred for 3 h at RT. The THF was eliminated i.vac., the aqueous phase was diluted with 60 mL EtOAc, filtered to remove any insoluble constituents and the organic phase was separated off. The aqueous phase was acidified with 15 mL 1 M HCl, extracted three times with 50 mL EtOAc and the combined organic phases were dried over MgSO$_4$. After the desiccant and solvent had been eliminated the residue was dissolved in 30 mL isopropanol at 80° C. The solution was left to cool slowly overnight, the precipitate suction filtered, washed with isopropanol and dried at 60° C. in the vacuum drying cupboard.

Yield: 1.1 g (22% of theory)
ESI-MS: (M+H)$^+$=523
R$_f$=0.31 (silica gel, DCM/Cyc/MeOH/NH$_3$ 70:15:15:2)

2h) (R)-1-(3,4-dimethyl-2-oxo-2,3-dihydro-benzoxazol-6-ylmethyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate Prepared analogously to Example 1h from 70 mg (0.13 mmol) (R)-1-carboxy-2-(3,4-dimethyl-2-oxo-2,3-dihydro-benzoxazol-6-yl)-ethyl 4-(2-oxo-1,2,4,5,-tetrahydro-1,3-benzodiazepin-3-yl)-piperidine-1-carboxylate and 25 mg (0.15 mmol) 1-(tetrahydropyran-4-yl)-piperazine.

Yield: 70 mg (66% of theory)
ESI-MS: (M+H)$^+$=675
R$_f$=0.63 (silica gel, DCM/Cyc/MeOH/NH$_3$ 70:15:15:2)

EXAMPLE 3

(R)-1-(7-methyl-1H-benzimidazol-5-ylmethyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

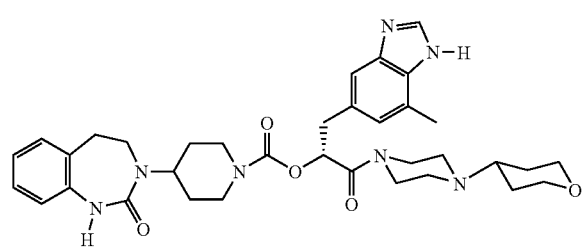

3a) methyl(Z,E)-2-acetylamino-3-(4-amino-methyl-5-nitro-phenyl)-acrylate

Under an argon atmosphere 0.7 g (2.9 mmol) Pd(OAc)$_2$ and 0.9 g (2.9 mmol) tri-o-tolyl-phosphane were added to a solution of 9.0 g (39.0 mmol) 4-bromo-2-methyl-6-nitro-phenylamine and 10.0 g (69.9 mmol) methyl 2-acetylamino-acrylate in 100 mL acetonitrile and 100 mL triethylamine. The reaction mixture was stirred for 24 h at 90° C. bath temperature, evaporated down i.vac., the residue was combined with 200 mL water and 200 mL EtOAc and the precipitate was filtered off. The crystals were dissolved in 500 mL MeOH by refluxing, filtered off while hot and the filtrate was evaporated to dryness i.vac.

Yield: 8.0 g (70% of theory)
ESI-MS: (M+H)$^+$=294

3b) 3-(4-amino-3-methyl-5-nitro-phenyl)-2-oxo-propionic acid 60 mL of a 4 M HCl were metered into a solution of 8.0 g (53.1 mmol) methyl(Z,E)-2-acetylamino-3-(4-amino-methyl-5-nitro-phenyl)-acrylate in 60 mL 1,4-dioxane, refluxed for 3 h with stirring, the reaction solution was evaporated down i.vac. and the residue was combined with ice. The precipitate was filtered off, washed with ice water and dried.

Yield: 6.5 g (95% of theory)
EI-MS: (M)$^+$=238

3c) (R)-3-(4-amino-3-methyl-5-nitro-phenyl)-2-hydroxy-propionic acid

Under a nitrogen atmosphere a solution of 12.0 g (37.4 mmol) (1R)-B-chlorodiisopinocampheylborane in 40 mL THF was added dropwise within 15 min to a solution of 6.5 g (26.0 mmol) 3-(4-amino-3-methyl-5-nitro-phenyl)-2-oxo-propionic acid and 4.5 mL (32.4 mmol) triethylamine in 100 mL THF cooled to −35° C. and the reaction solution was stirred overnight at RT. Then the reaction solution was carefully combined with 60 mL 1 M NaOH and 150 mL diethyl ether at 5° C. and stirred for 15 min. The organic phase was separated off, extracted three times with 40 mL 1 M NaOH and once with 40 mL water. The combined aqueous phases were acidified with semiconc. HCl while cooling with an ice bath and extracted twice with 120 mL EtOAc in each case. The combined organic phases were dried over Na$_2$SO$_4$ and evaporated down i.vac. The crude product was obtained, which was further reacted without purification.

Yield: 6.0 g (67% of theory)

3d) methyl(R)-3-(4-amino-3-methyl-5-nitro-phenyl)-2-hydroxy-propionate 4.0 mL (54.8 mmol) SOCl$_2$ were slowly added dropwise to 90 mL MeOH while cooling with ice/acetone and at 0° C. 6.0 g (17.5 mmol) (R)-3-(4-amino-3-methyl-5-nitro-phenyl)-2-hydroxy-propionic acid in 10 mL MeOH were also added dropwise. The reaction solution was stirred for 1 h at 0° C. and for 1 h at RT and then evaporated down i.vac. The residue was combined with EtOAc, washed with saturated NaHSO$_4$ solution and dried over Na$_2$SO$_4$. After the desiccant and solvent had been eliminated the residue was purified by chromatography (silica gel, gradient DCM/MeOH 100:1 to 50:1).

Yield: 3.4 g (76% of theory)
ESI-MS: (M+H)$^+$=255
R$_f$=0.43 (Polygram, DCM/MeOH 50:1)

3e) (R)-2-(4-amino-3-methyl-5-nitro-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere 1.8 g (14.7 mmol) 4-dimethylaminopyridine in 25 mL pyridine were first combined with 2.7 g (13.4 mmol) 4-nitrophenyl chloroformate while cooling with an ice bath, stirred for 30 min at RT, then combined with 3.4 g (13.2 mmol) methyl(R)-3-(4-amino-3-methyl-5-nitro-phenyl)-2-hydroxy-propionate in 15 mL pyridine, stirred again for 2 h at RT, and then combined with 3.5 g (14.3 mmol) 3-piperidin-4-yl-1,3,4,5-tetrahydro-1,3-benzodiazepin-2-one and stirred for 5 h at RT. After the end of the reaction the reaction mixture was evaporated down i.vac., the residue was combined with EtOAc, the organic phase was washed with 10% KHSO$_4$ solution and saturated NaHSO$_4$ solution and dried over Na$_2$SO$_4$. After the desiccant and solvent had been eliminated the residue was purified by chromatography (silica gel, DCM/MeOH 25:1).

Yield: 3.7 g (50% of theory)
ESI-MS: (M+H)$^+$=526
R$_f$=0.42 (Polygram, DCM/MeOH 25:1)

3f) (R)-1-methoxycarbonyl-2-(7-methyl-1H-benzimidazol-5-yl)-ethyl 4-(2-oxo-1,2,4,5-tetrahydro-1,3-benzodiazepin-3-yl)-piperidine-1-carboxylate 1.2 g (2.3 mmol) (R)-2-(4-amino-3-methyl-5-nitro-phenyl)-1-methoxycarbonyl-ethyl 4-(2-oxo-1,2,4,5-tetrahydro-1,3-benzodiazepin-3-yl)-piperidine-1-carboxylate were dissolved in 50 mL formic acid and combined with 300 mg 10% Pd/C. The mixture was hydrogenated for 2 h in a Parr apparatus at 60° C. under a hydrogen pressure of 3447 hPa. Then the catalyst was filtered off, the filtrate was evaporated down i.vac. and the residue was purified by chromatography (Alox, gradient DCM/MeOH 40:1 to 30:1).

Yield: 880 mg (76% of theory)
ESI-MS: (M+H)$^+$=506
R$_f$=0.40 (Polygram-Alox, DCM/MeOH 25:1)

3g) (R)-1-carboxy-2-(7-methyl-1H-benzimidazol-5-yl)-ethyl 4-(2-oxo-1,2,4,5-tetrahydro-1,3-benzodiazepin-3-yl)-piperidine-1-carboxylate A solution of 96 mg (4.0 mmol) LiOH in 5 mL water was added dropwise to a solution of 910 mg (1.8 mmol) (R)-1-methoxycarbonyl-2-(7-methyl-1H-benzimidazol-5-yl)-ethyl 4-(2-oxo-1,2,4,5-tetrahydro-1,3-benzodiazepin-3-yl)-piperidine-1-carboxylate in 12 mL THF and the reaction solution was stirred overnight at RT. The residue was combined with 1 mL 4 M HCl and evaporated to dryness i.vac.

Yield: 980 mg (100% of theory)
ESI-MS: (M+H)$^+$=492

3h) (R)-1-(7-methyl-1H-benzimidazol-5-ylmethyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate Prepared analogously to Example 1h from 120 mg (0.22 mmol) (R)-1-carboxy-2-(7-methyl-1H-benzimidazol-5-yl)-ethyl 4-(2-oxo-1,2,4,5-tetrahydro-1,3-benzodiazepin-3-yl)-piperidine-1-carboxylate and 50 mg (0.29 mmol) 1-(tetrahydropyran-4-yl)-piperazine.

Yield: 70 mg (45% of theory)
ESI-MS: (M+H)$^+$=644
retention time (HPLC): 2.0 min (method A)

EXAMPLE 4

(R)-1-(2-dimethylamino-7-methyl-1H-benzimidazol-5-ylmethyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

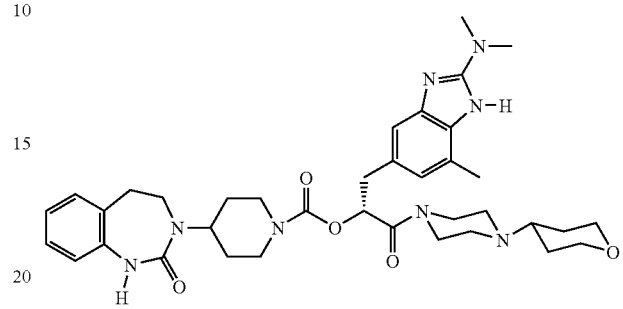

4a) (R)-2-(3,4-diamino-5-methyl-phenyl)-1-methoxycarbonyl-ethyl 4-(2-oxo-1,2,4,5-tetrahydro-1,3-benzodiazepin-3-yl)-piperidine-1-carboxylate A solution of 2.00 g (3.24 mmol) (R)-2-(4-amino-3-methyl-5-nitro-phenyl)-1-methoxy-carbonyl-ethyl 4-(2-oxo-1,2,4,5-tetrahydro-1,3-benzodiazepin-3-yl)-piperidine-1-carboxylate (Example 3e, purity 85%) in 100 mL MeOH was hydrogenated for 3.5 h at 50° C. and 3447 hPa hydrogen pressure. The catalyst was filtered off and the filtrate was evaporated down i.vac. The residue was purified by chromatography (Alox, activity stage II-III, gradient DCM/MeOH 30:1 to 15:1).

Yield: 1.35 g (84% of theory)
ESI-MS: (M+H)$^+$=496

4b) (R)-2-(2-dimethylamino-7-methyl-1H-benzimidazol-5-yl)-1-methoxycarbonyl-ethyl 4-(2-oxo-1,2,4,5-tetrahydro-1,3-benzodiazepin-3-yl)-piperidine-1-carboxylate Under a nitrogen atmosphere 230 mg (0.72 mmol) TBTU was added to a solution of 310 mg (0.63 mmol) (R)-2-(3,4-diamino-5-methyl-phenyl)-1-methoxycarbonyl-ethyl 4-(2-oxo-1,2,4,5-tetrahydro-1,3-benzodiazepin-3-yl)-piperidine-1-carboxylate and 140 μL (1.00 mmol) triethylamine in 30 mL 1,4-dioxane and the reaction mixture was refluxed for 12 h. The mixture was evaporated down i.vac., the residue was taken up in EtOAc, the organic phase was washed with saturated NaHCO$_3$ solution and dried over Na$_2$SO$_4$. After the desiccant and solvent had been eliminated the residue was purified by chromatography (Alox, activity stage II-III, DCM/MeOH 30:1). Further purification was carried out by silica gel chromatography (gradient DCM/MeOH 12:1 to 6:1).

Yield: 85 mg (25% of theory)
ESI-MS: (M+H)$^+$=549
R$_f$=0.50 (Polygram-Alox, DCM/MeOH 25:1)

4c) (R)-1-carboxy-2-(2-dimethylamino-7-methyl-1H-benzimidazol-5-yl)-ethyl 4-(2-oxo-1,2,4,5-tetrahydro-1,3-benzodiazepin-3-yl)-piperidine-1-carboxylate A solution of 9.0 mg (0.38 mmol) LiOH in 0.5 mL water was added to a solution of 80 mg (0.15 mmol) (R)-2-(2-dimethylamino-7-methyl-1H-benzimidazol-5-yl)-1-methoxycarbonyl-ethyl 4-(2-oxo-1,2,4,5-tetrahydro-1,3-benzodiazepin-3-yl)-piperidine-1-carboxylate in 4 mL THF and the reaction mixture was stirred for 4 h at RT. 100 μL of 4 M HCl was added, the mixture was evaporated down i.vac. and the crude product was dried and then further reacted without purification.

ESI-MS: (M+H)$^+$=535
retention time (HPLC): 2.8 min (method A)

4d) (R)-1-(2-dimethylamino-7-methyl-1H-benzimidazol-5-ylmethyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate Prepared analogously to Example 1h from 90 mg (0.14 mmol, purity 85%) (R)-1-carboxy-2-(2-dimethylamino-7-methyl-1H-benzimidazol-5-yl)-ethyl 4-(2-oxo-1,2,4,5-tetrahydro-1,3-benzodiazepin-3-yl)-piperidine-1-carboxylate and 35 mg (0.21 mmol) 1-(tetrahydropyran-4-yl)-piperazine.

Yield: 25 mg (25% of theory)
ESI-MS: (M+H)$^+$=687
retention time (HPLC): 2.5 min (method A)

EXAMPLE 5

(R)-1-(2-methoxy-7-methyl-1H-benzimidazol-5-yl methyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

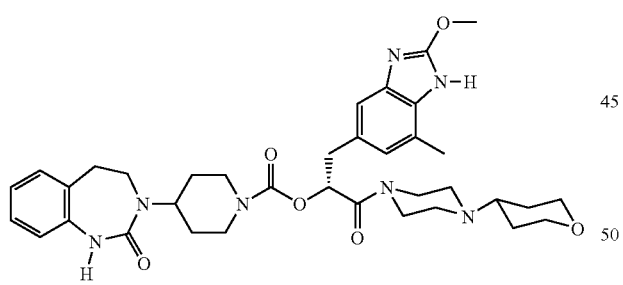

5a) (R)-1-methoxycarbonyl-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate A solution of 1.00 g (2.02 mmol) (R)-2-(3,4-diamino-5-methyl-phenyl)-1-methoxycarbonyl-ethyl 4-(2-oxo-1,2,4,5-tetrahydro-1,3-benzodiazepin-3-yl)-piperidine-1-carboxylate (Example 4a), 2.0 mL (15.0 mmol) tetramethoxymethane and 40 mg p-toluenesulphonic acid-monohydrate in 20 mL MeOH was refluxed for 1 h. The mixture was evaporated down i.vac. and the residue was purified by chromatography (Alox, activity stage II-III, DCM/MeOH 20:1).

Yield: 0.99 g (92% of theory)
ESI-MS: (M+H)$^+$=536

5b) (R)-1-carboxy-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate A solution of 100 mg (4.18 mmol) LiOH in 6 mL water was added to a solution of 980 mg (1.83 mmol) (R)-1-methoxycarbonyl-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate in 18 mL THF and the reaction mixture was stirred overnight at RT. 1.05 mL of 4 M HCl was added, the THF was evaporated down i.vac., whereby the crude product was produced in the form of an oil. The water was decanted off, the residue was dissolved in DCM/MeOH and dried over Na$_2$SO$_4$. After the desiccant and solvent had been eliminated the residue was further reacted without purification.

Yield: 0.80 g (80% of theory)
ESI-MS: (M–H)$^-$=520

5c) (R)-1-(2-methoxy-7-methyl-1H-benzimidazol-5-ylmethyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate Prepared analogously to Example 1h from 90 mg (0.16 mmol) (R)-1-carboxy-2-(2-methoxy-7-methyl-1H-benzimidazol-5-yl)-ethyl 4-(2-oxo-1,2,4,5-tetrahydro-1,3-benzodiazepin-3-yl)-piperidine-1-carboxylate and 40 mg (0.24 mmol) 1-(tetrahydropyran-4-yl)-piperazine.

Yield: 33 mg (30% of theory)
ESI-MS: (M+H)$^+$=674
retention time (HPLC): 2.8 min (method A)

EXAMPLE 6

(S)-2-(4-amino-3-chloro-5-trifluoromethyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione

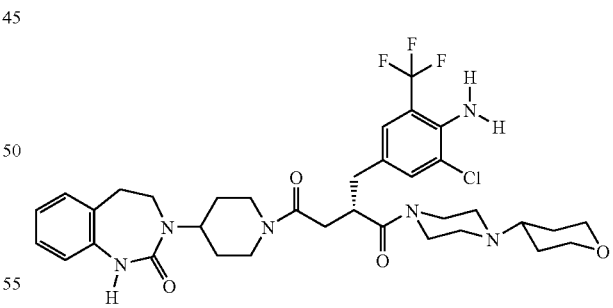

A solution of 100 mg (0.18 mmol) (S)-2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butanoic acid, 65 mg (0.20 mmol) TBTU and 35 μL (0.18 mmol) triethylamine in 10 mL THF was stirred for 1 h at RT. Then 40 mg (0.24 mmol) 1-(tetrahydropyran-4-yl)-piperazine was added and the reaction solution was stirred overnight. 20 mL semisaturated NaHCO$_3$ solution was added, extracted twice with 40 mL EtOAc and the combined organic phases were dried over Na$_2$SO$_4$. After the desiccant and solvent had been eliminated the residue was purified by HPLC; the fractions containing the product were combined and lyophilised.

Yield: 84 mg (66% of theory)
ESI-MS: (M+H)⁺=705/707 (Cl)
retention time (HPLC): 6.3 min (method B)

EXAMPLE 7

(R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

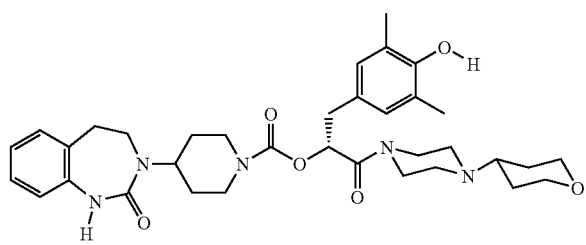

7a) 2-benzyloxy-5-bromo-1,3-dimethylbenzene 39.9 g (286 mmol) $K_2CO_3$ were added to a solution of 50.0 g (249 mmol) 2,6-dimethyl-4-bromophenol in 500 mL DMF and stirred for 20 min. Then 34.0 mL (286 mmol) benzyl chloride were slowly added dropwise and the reaction mixture was stirred for 3 h at a bath temperature of 100° C. After the end of the reaction the mixture was poured onto 500 mL water and exhaustively extracted with EtOAc. The organic phases were combined, dried over $Na_2SO_4$ and evaporated down i.vac.

Yield: quantitative
GC-MS: (M⁺)=290/292 (Br)
$R_f$=0.87 (silica gel, Cyc/EtOAc 3:1)

7b) methyl 2-acetylamino-3-(4-benzyloxy-3,5-dimethyl-phenyl)-acrylate

Under a nitrogen atmosphere a mixture of 40.0 g (137 mmol) 2-benzyloxy-5-bromo-1,3-dimethylbenzene and 24.1 g (165 mmol) methyl 2-acetylamino-acrylate in 420 mL triethylamine and 200 mL acetonitrile was combined with 3.5 g (11.2 mmol) tri-o-tolyl-phosphane and 2.5 g (11.1 mmol) Pd(OAc)₂ and stirred for 18 h at 80° C. The precipitate was suction filtered, the filtrate was evaporated down i.vac. and combined with 800 mL DCM and 800 mL water. The organic phase was separated off, suction filtered through $Na_2SO_4$, the solvent was eliminated i.vac., the residue was stirred with EtOAc, suction filtered and dried i.vac.

Yield: 31.1 g (64% of theory)
ESI-MS: (M+H)⁺=354
retention time (HPLC-MS): 8.6 min (method B)

7c) 3-(4-benzyloxy-3,5-dimethyl-phenyl)-2-oxo-propionic acid 31.1 g (88.1 mmol) methyl 2-acetylamino-3-(4-benzyloxy-3,5-dimethyl-phenyl)-acrylate in 150 mL 1,4-dioxane were combined with 125 mL 4 M HCl, refluxed for 7 h and stirred overnight at RT. The precipitate was suction filtered, washed with water and dried at 45° C. in the vacuum drying cupboard.

Yield: 14.3 g (54% of theory)
EI-MS: (M)⁺=298
retention time (HPLC-MS): 9.0 min (method B)

7d) (R)-3-(4-benzoyl-3,5-dimethyl-phenyl)-2-hydroxy-propionic acid

Under a nitrogen atmosphere a solution of 14.3 g (47.8 mmol) 3-(4-benzyloxy-3,5-dimethyl-phenyl)-2-oxo-propionic acid and 8.3 mL (59.8 mmol) triethylamine in 170 mL THF at −35° C. was combined with a solution of 22.1 (69.0 mmol) (1R)-B-chlorodiisopinocampheylborane in 70 mL THF within 30 min. After the addition had ended the cooling bath was removed and the reaction solution was stirred overnight at RT. The reaction mixture was made alkaline with 70 mL 1 M NaOH at 0° C., combined with 100 mL TBME, stirred for 15 min and the phases were separated. The organic phase was washed with 50 mL water and three times with 50 mL 1 M NaOH. The combined aqueous phases were acidified with semiconc. HCl, exhaustively extracted with EtOAc and the combined organic phases were dried over $Na_2SO_4$. After the desiccant and solvent had been eliminated the residue was further reacted without purification.

Yield: 14.0 g (98% of theory)
ESI-MS: (M−H)⁻=299
retention time (HPLC-MS): 7.9 min (method B)

7e) methyl(R)-3-(4-benzyloxy-3,5-dimethyl-phenyl)-2-hydroxy-propionate 2.0 mL (27.4 mmol) SOCl₂ were added dropwise to a solution, cooled to 0° C., of 14.0 g (23.3 mmol) (R)-3-(4-benzoyl-3,5-dimethyl-phenyl)-2-hydroxy-propionic acid in 150 mL MeOH and the reaction mixture was stirred for 1 h at RT. The reaction solution was evaporated down i.vac. and the residue was purified by chromatography (silica gel, Cyc/EtOAc 3:1).

Yield: 5.7 g (78% of theory)
ESI-MS: (M+NH₄)⁺=332
retention time (HPLC-MS): 9.1 min (method B)

7f) (R)-2-(4-benzyloxy-3,5-dimethyl-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere 1.93 g (9.58 mmol) 4-nitrophenyl chloroformate was added to a solution of 1.17 g (9.58 mmol) 4-dimethylaminopyridine in 50 mL pyridine, stirred for 1.5 h at RT, combined with 3.0 g (9.58 mmol) methyl(R)-3-(4-benzyloxy-3,5-dimethyl-phenyl)-2-hydroxy-propionate and stirred for 20 min at RT. Then 2.35 g (9.58 mmol) 3-piperidin-4-yl-1,3,4,5-tetrahydro-1,3-benzodiazepin-2-one were added and the mixture was stirred for 20 h at RT. The reaction mixture was evaporated down i.vac., the residue was taken up in EtOAc, the organic phase was washed with 10% KHSO₄ and saturated NaHCO₃ solution and dried over $Na_2SO_4$. After the desiccant and solvent had been eliminated the residue was purified by chromatography (silica gel, gradient Cyc/EtOAc 1:1 to 1:2).

Yield: 3.21 g (57% of theory)
ESI-MS: (M+H)$^+$=586
retention time (HPLC-MS): 10.4 min (method B)

7g) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate A solution of 3.21 g (5.48 mmol) (R)-2-(4-benzyloxy-3,5-dimethyl-phenyl)-1-methoxy-carbonyl-ethyl 4-(2-oxo-1,2,4,5-tetrahydro-1,3-benzodiazepin-3-yl)-piperidine-1-carboxylate in 80 mL THF was combined with a solution of 200 mg (8.35 mmol) LiOH in 40 mL water and stirred for 1 h at RT. The reaction mixture was evaporated down i.vac., the residue was taken up in 100 mL water, acidified with 2 M HCl, the precipitate was suction filtered and dried in the vacuum drying cupboard at 40° C.

Yield: quantitative
ESI-MS: (M+H)$^+$=572
retention time (HPLC-MS): 9.2 min (method B)

7h) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate 3.72 g (6.51 mmol) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate in 50 mL DCM were combined with 300 mg 10% Pd/C and shaken at RT and 3000 hPa hydrogen until the reaction came to an end. The catalyst was suction filtered and the solvent evaporated down i.vac. The residue was triturated with DIPE and suction filtered.

Yield: 2.41 g (77% of theory)
ESI-MS: (M+H)$^+$=482
retention time (HPLC-MS): 7.0 min (method B)

7i) (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate A solution of 70 mg (0.15 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate, 51 mg (0.16 mmol) TBTU and 25 μL (0.18 mmol) triethylamine in 1 mL DMF was stirred for 1 h at RT. Then 25 mg (0.15 mmol) 1-(tetrahydropyran-4-yl)-piperazine was added and the reaction solution was stirred for 16 h. The reaction solution was purified by HPLC without any further working up; the fractions containing the product were combined and lyophilised.

Yield: 36 mg (39% of theory)
ESI-MS: (M+H)$^+$=634
retention time (HPLC-MS): 5.7 min (method B)

EXAMPLE 7.1

(R)-1-(4-hydroxy-3,5-dimethyl-benzyl)-2-oxo-2-[4-oxy-4-(tetrahydropyran-4-yl)-piperazin-1-yl]-ethyl 4-(2-oxo-1,2,4,5-tetrahydro-1,3-benzodiazepin-3-yl)-piperidine-1-carboxylate

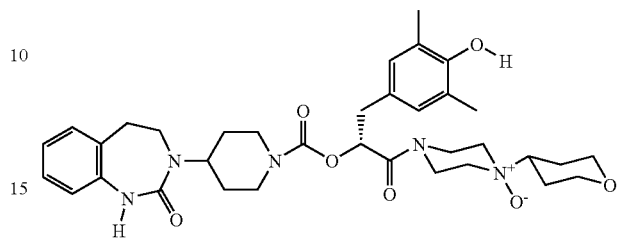

30 mg (0.17 mmol) MCPBA were added to a solution, cooled to 0° C., of 100 mg (0.16 mmol) (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate in 3 mL chloroform and the reaction solution was stirred for 2 h. After the solvent had been eliminated the residue was taken up in 1 mL DMF and purified by HPLC; the fractions containing the product were combined and lyophilised.

Yield: 70 mg (69% of theory)
ESI-MS: (M+H)$^+$=650
retention time (HPLC-MS): 4.1 min (method C)

EXAMPLE 7.2

(R)-1-(4-hydroxy-3,5-dimethyl-benzyl)-2-[4-(4-methyl-tetrahydropyran-4-yl)-piperazin-1-yl]-2-oxo-ethyl 4-(2-oxo-1,2,4,5-tetrahydro-1,3-benzodiazepin-3-yl)-piperidine-1-carboxylate

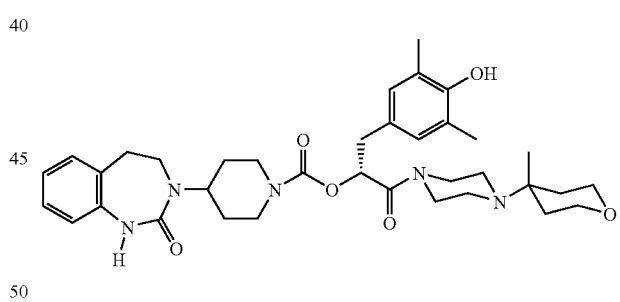

50 mg (0.23 mmol) 1-(4-methyl-tetrahydropyran-4-yl)-piperazine (amine A1, used as the hydrochloride salt) were added to a solution of 90 mg (0.19 mmol) (R)-2-(4-hydroxy-3,5-dimethyl-phenyl)-1-carboxy-ethyl 4-(2-oxo-1,2,4,5-tetrahydro-1,3-benzodiazepin-3-yl)-piperidine-1-carboxylate (Example 7h), 70 mg (0.22 mmol) TBTU and 70 μL (0.50 mmol) triethylamine in 1 mL DMF and the reaction mixture was stirred for 20 h at RT. Semisaturated NaHCO$_3$ solution was added, the precipitate was filtered off and dried. The purification was carried out by chromatography (Alox, activity stage II-III, DCM/MeOH 30:1). After the solvent had been eliminated the residue was triturated with diethyl ether, suction filtered and dried.

Yield: 56 mg (44% of theory)
ESI-MS: (M+H)$^+$=648
retention time (HPLC-MS): 3.1 min (method A)

EXAMPLE 7.3

(R)-1-(4-acetoxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

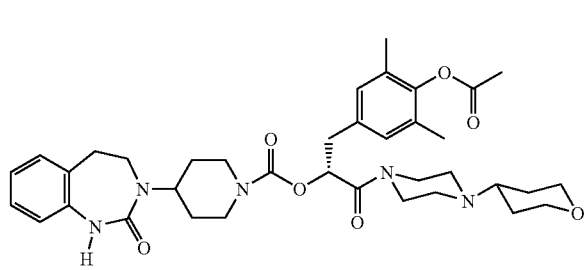

A solution of 42 mg (0.07 mmol) (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate (Example 7i) in 5 mL acetic anhydride was heated to 50° C. for 2 h. The mixture was evaporated down i.vac. and the residue was purified by HPLC. The fractions containing the product were combined and lyophilised.

Yield: 16 mg (37% of theory)
ESI-MS: (M+H)$^+$=676
retention time (HPLC-MS): 2.8 min (method A)

EXAMPLE 7.4

(R)-1-(4-formyloxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

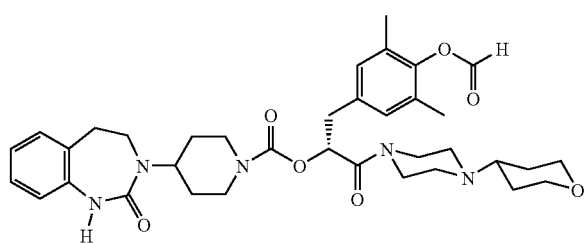

A solution of 25 µL acetic anhydride and 0.5 mL formic acid in 1 mL DCM was stirred for 2 h at RT (formation of the mixed anhydride). Then 38 mg (0.06 mmol) (R)-1-(4-hydroxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate was added (Example 7i) and the reaction mixture was stirred overnight at RT. The reaction solution was evaporated down and the residue was again added to a solution of the mixed anhydride and stirred overnight at RT. The mixture was evaporated down i.vac. and the residue was purified by HPLC. The fractions containing the product were combined and lyophilised.

Yield: 19 mg (45% of theory)
ESI-MS: (M+H)$^+$=662
retention time (HPLC-MS): 7.2 min (method E)

EXAMPLE 7.5

(R)-1-(4-methoxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

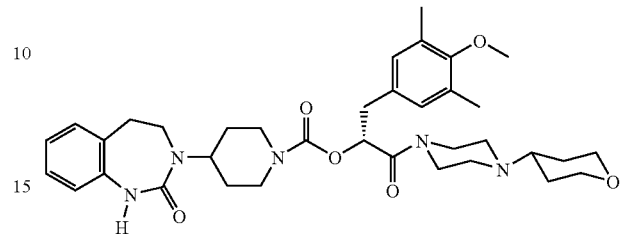

7.5a) (R)-2-(4-hydroxy-3,5-dimethyl-phenyl)-1-methoxycarbonyl-ethyl 4-(2-oxo-1,2,4,5-tetrahydro-1,3-benzodiazepin-3-yl)-piperidine-1-carboxylate A suspension of 1.00 g (1.75 mmol) (R)-2-(4-benzyloxy-3,5-dimethyl-phenyl)-1-carboxy-ethyl 4-(2-oxo-1,2,4,5-tetrahydro-1,3-benzodiazepin-3-yl)-piperidine-1-carboxylate (Example 7g) and 150 mg 10% Pd/C in 30 mL MeOH was hydrogenated at RT and 3000 hPa hydrogen pressure until the reaction stopped. The catalyst was suction filtered and the residue was purified by chromatography (silica gel, EtOAc).

Yield: 370 mg (43% of theory)
ESI-MS: (M–H)$^-$=494
retention time (HPLC-MS): 4.1 min (method A)

7.5b) (R)-2-(4-methoxy-3,5-dimethyl-phenyl)-1-methoxycarbonyl-ethyl 4-(2-oxo-1,2,4,5-tetrahydro-1,3-benzodiazepin-3-yl)-piperidine-1-carboxylate 19 µL (0.30 mmol) iodomethane were added to a solution of 100 mg (0.20 mmol) (R)-2-(4-hydroxy-3,5-dimethyl-phenyl)-1-methoxycarbonyl-ethyl 4-(2-oxo-1,2,4,5-tetrahydro-1,3-benzodiazepin-3-yl)-piperidine-1-carboxylate in 2 mL DMF and the mixture was stirred for 15 min at RT. Then 131 mg (0.40 mmol) Cs$_2$CO$_3$ was added and the reaction solution was heated to 50° C. for 3 h. The precipitate was filtered, the filtrate was evaporated down to 1 mL down and combined with 3 mL water. The precipitate was suction filtered, dried and further reacted without purification.

Yield: 84 mg (82% of theory)
ESI-MS: (M+H)$^+$=510
retention time (HPLC-MS): 4.6 min (method A)

7.5c) (R)-2-(4-methoxy-3,5-dimethyl-phenyl)-1-carboxy-ethyl 4-(2-oxo-1,2,4,5-tetrahydro-1,3-benzodiazepin-3-yl)-piperidine-1-carboxylate A solution of 11.3 mg (0.47 mmol) LiOH*H$_2$O in 8 mL water was added to a solution of 160 mg (0.31 mmol) (R)-2-(4-methoxy-3,5-dimethyl-phenyl)-1-methoxycarbonyl-ethyl 4-(2-oxo-1,2,4,5-tetrahydro-1,3-benzodiazepin-3-yl)-piperidine-1-carboxylate in 15 mL THF and the reaction mixture was stirred for 1 h at RT. The mixture was evaporated down i.vac., the residue was taken up in 150 mL water and acidified with 2 M HCl. The precipitate formed was separated off and dried.

Yield: 138 mg (89% of theory)
ESI-MS: (M–H)$^-$=494
retention time (HPLC-MS): 4.0 min (method A)

7.5d) (R)-1-(4-methoxy-3,5-dimethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate A solution of 40 mg (0.08 mmol) (R)-2-(4-methoxy-3,5-dimethyl-phenyl)-1-carboxy-ethyl 4-(2-oxo-1,2,4,5-tetrahydro-1,3-benzodiazepin-3-yl)-piperidine-1-carboxylate, 29 mg (0.09 mmol) TBTU and 14 µL (0.10 mmol) triethylamine in 1 mL DMF was stirred for 1 h at RT. Then 15 mg (0.09 mmol) 1-(tetrahydropyran-4-yl)-piperazine was added and the mixture was stirred for a further 16 h at RT. The reaction solution was purified by HPLC without any further working up; the fractions containing the product were combined and lyophilised.

Yield: 19 mg (37% of theory)
ESI-MS: (M+H)$^+$=648
retention time (HPLC-MS): 3.3 min (method A)

EXAMPLE 8

(R)-1-(3-ethyl-4-hydroxy-5-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

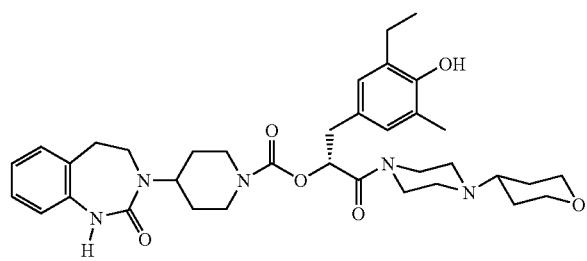

8a) 2-ethyl-6-methyl-phenol 19.4 mL (0.23 mmol) concentrated HCl and a solution of 16.1 g (0.23 mmol) sodium nitrite in water (approx. 70 mL) were added to a solution of 30 g (222 mmol) 2-ethyl-6-methyl-aniline in 135 mL EtOH at 0° C. and the mixture was stirred for 15 min. This mixture was added at 45° C. to a solution of 10.5 mL concentrated $H_2SO_4$ in 300 mL water and at the end of the addition heated to 70° C. The aqueous phase was cooled to RT and exhaustively extracted with EtOAc. The combined organic phases were extracted with 1 M NaOH solution. The aqueous phase was washed with DCM, acidified to pH 1 with 4 N HCl solution and extracted with DCM. The organic phase was washed with saturated NaCl solution, dried over $Na_2SO_4$ and evaporated down i.vac. The crude product was used in the next reaction step without any further purification.

Yield: 12.0 g (40% of theoretical)

8b) 4-bromo-2-ethyl-6-methyl-phenol

At RT a solution of 12.7 mL (247 mmol) bromine in 10 mL chloroform was added dropwise to a solution of 33.6 g (247 mmol) 2-ethyl-6-methyl-phenol in 350 mL chloroform and the mixture was stirred for 2 h. The reaction mixture was combined with an aqueous $NaHSO_3$ solution and stirred for 20 min. The phases were separated and the organic phase was washed with saturated NaCl solution, dried over $Na_2SO_4$ and evaporated down i.vac. Column chromatography (silica gel, Cyc/EtOAc 9:1) yielded the product.

Yield: 39.8 g (75% of theoretical)
ESI-MS: (M+H)$^+$=214/216 (Br)
retention time (HPLC-MS): 6.3 min (method D)

8c) 2-benzyloxy-5-bromo-1-ethyl-3-methyl-benzene

A suspension of 39.8 g (185 mmol) 4-bromo-2-ethyl-6-methyl-phenol, 63.9 g (0.46 mmol) $K_2CO_3$ and 22.0 mL (185 mmol) benzylbromide in 450 mL acetonitrile was refluxed for 3 h, cooled to RT and evaporated down i.vac. The residue was combined with EtOAc, the organic phase was washed with water and saturated NaCl solution, dried over $Na_2SO_4$ and evaporated down i.vac.

Yield: 54.5 g (96% of theoretical)
ESI-MS: (M+H)$^+$=304/306 (Br)
retention time (HPLC-MS): 9.4 min (method D)

8d) methyl(Z,E)-2-acetylamino-3-(4-benzyloxy-3-ethyl-5-methyl-phenyl)-acrylate Prepared analogously to Example 7b from 50.4 g (165.1 mmol) 2-benzyloxy-5-bromo-1-ethyl-3-methyl-benzene and 28.9 g (198.2 mmol) methyl 2-acetylamino-acrylate.

Yield: 41.0 g (68% of theoretical)
ESI-MS: (M+H)$^+$=368
retention time (HPLC-MS): 4.5 min (method A)

8e) 3-(4-benzyloxy-3-ethyl-5-methyl-phenyl)-2-oxo-propionic acid 200 mL 4 M HCl were added to a solution of 41.0 g (111.6 mmol) methyl(Z,E)-2-acetylamino-3-(4-benzyloxy-3-ethyl-5-methyl-phenyl)-acrylate in 300 mL 1,4-dioxane and the reaction solution was heated to 130° C. (bath temperature) for 7 h. The organic phase was separated off while hot, evaporated down i.vac. and the residue obtained was recrystallised from toluene.

Yield: 9.6 g (28% of theoretical)
ESI-MS: (M+H)$^+$=312
retention time (HPLC-MS): 4.1 min (method A)

8f) (R)-3-(4-benzyloxy-3-ethyl-5-methyl-phenyl)-2-hydroxy-propionic acid

Under an argon atmosphere a solution of 9.59 g (30.7 mmol) 3-(4-benzyloxy-3-ethyl-5-methyl-phenyl)-2-oxo-propionic acid in 25 mL THF was combined with 4.26 mL (31.0 mmol) triethylamine, stirred for 5 min and cooled to −30° C. (internal temperature). A solution of 19.7 g (61.0 mmol) (1R)-B-chlorodiisopinocampheylborane in 35 mL THF was added dropwise and after the end of the addition the reaction solution was stirred for 30 min without cooling. 15 mL 4 N NaOH was added (temperature rose to 20° C.), the mixture was stirred for 5 min, cooled to 0° C., combined with 50 mL MTBE and stirred for 20 min. The organic phase was separated off and dried over $Na_2SO_4$. After the desiccant and solvent had been eliminated the residue was further reacted without purification.

Yield: 10.3 g (100% of theoretical)
ESI-MS: (M−H)$^-$=313
retention time (HPLC-MS): 4.2 min (method A)

8g) methyl(R)-3-(4-benzyloxy-3-ethyl-5-methyl-phenyl)-2-hydroxy-propionate

Prepared analogously to Example 7e from 10.3 g (30.7 mmol) (R)-3-(4-benzyloxy-3-ethyl-5-methyl-phenyl)-2-hydroxy-propionic acid and 4.71 mL (64.5 mmol) thionyl chloride. The crude product obtained was further reacted without purification.

8h) (R)-2-(4-benzyloxy-3-ethyl-5-methyl-phenyl)-1-methoxycarbonyl-ethyl 4-(2-oxo-1,2,4,5-tetrahydro-1,3-benzodiazepin-3-yl)-piperidine-1-carboxylate A solution of 7.12 g (34.3 mmol) 4-nitrophenyl-chloroformate in 30 mL THF was added within 10 min to a solution of 75 mL pyridine heated to 60° C. (bath temperature), the mixture was stirred for 10 min and then a solution of 10.0 g of the crude product from Example 8g in 50 mL pyridine was added dropwise. The mixture was stirred for 1 h, combined with 6.72 g (27.4 mmol) 3-piperidin-4-yl-1,3,4,5-tetrahydro-1,3-benzodiazepin-2-one and the bath temperature was increased to 100° C. (2 h). The precipitate formed was filtered, the filtrate was evaporated down i.vac., the residue was combined with 150 mL EtOAc, the organic phase was washed twice with 50 mL 1 M KHSO$_4$ solution and ten times with 50 mL 15% K$_2$CO$_3$ solution and dried over Na$_2$SO$_4$. After the desiccant and solvent had been eliminated the residue was purified by chromatography (silica gel, EtOAc/Cyc 2:1).

Yield: 2.28 g (14% of theoretical)
ESI-MS: (M+H)$^+$=600
retention time (HPLC-MS): 5.4 min (method A)

8i) (R)-2-(4-benzyloxy-3-ethyl-5-methyl-phenyl)-1-carboxy-ethyl 4-(2-oxo-1,2,4,5-tetrahydro-1,3-benzodiazepin-3-yl)-piperidine-1-carboxylate A solution of 50 mg (2.09 mmol) LiOH in 5 mL water was added to a solution of 800 mg (1.33 mmol) (R)-2-(4-benzyloxy-3-ethyl-5-methyl-phenyl)-1-methoxy-carbonyl-ethyl 4-(2-oxo-1,2,4,5-tetrahydro-1,3-benzodiazepin-3-yl)-piperidine-1-carboxylate in 15 mL THF and the reaction mixture was stirred for 1 h at RT. The mixture was evaporated down i.vac., the residue was taken up in 50 mL water and 2 M HCl was added until an acidic reaction was obtained. The precipitate formed was filtered off, washed with water and dried. Further purification was carried out by decocting with 150 mL water, filtration and drying again.

Yield: quantitative
ESI-MS: (M+H)$^+$=586
retention time (HPLC-MS): 4.8 min (method A)

8k (R)-1-carboxy-2-(3-ethyl-4-hydroxy-5-methyl-phenyl)-ethyl 4-(2-oxo-1,2,4,5-tetrahydro-1,3-benzodiazepin-3-yl)-piperidine-1-carboxylate 810 mg (1.38 mmol) (R)-2-(4-benzyloxy-3-ethyl-5-methyl-phenyl)-1-carboxy-ethyl 4-(2-oxo-1,2,4,5-tetrahydro-1,3-benzodiazepin-3-yl)-piperidine-1-carboxylate in 25 mL MeOH were combined with 80 mg 10% Pd/C and hydrogenated at RT and 3000 hPa hydrogen until the reaction stopped. The catalyst was suction filtered and the solvent was evaporated down i.vac. The residue was triturated with DIPE, suction filtered and dried.

Yield: 639 mg (93% of theory)
ESI-MS: (M+H)$^+$=496
retention time (HPLC-MS): 3.7 min (method A)

8l) (R)-1-(3-ethyl-4-hydroxy-5-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate 30 mg (0.18 mmol) 1-(tetrahydropyran-4-yl)-piperazine were added at RT to a solution of 80 mg (0.16 mmol) (R)-1-carboxy-2-(3-ethyl-4-hydroxy-5-methyl-phenyl)-ethyl 4-(2-oxo-1,2,4,5-tetrahydro-1,3-benzodiazepin-3-yl)-piperidine-1-carboxylate, 57 mg (0.18 mmol) TBTU and 28 μL (0.20 mmol) triethylamine in 1 mL DMF and the reaction mixture was stirred for 2 h. The reaction solution was purified by HPLC without any further working up, the fractions containing the product were combined and lyophilised.

Yield: 75 mg (72% of theory)
ESI-MS: (M+H)$^+$=648
retention time (HPLC-MS): 3.2 min (method A)

EXAMPLE 9

(R)-1-(4-hydroxy-3-methoxy-5-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

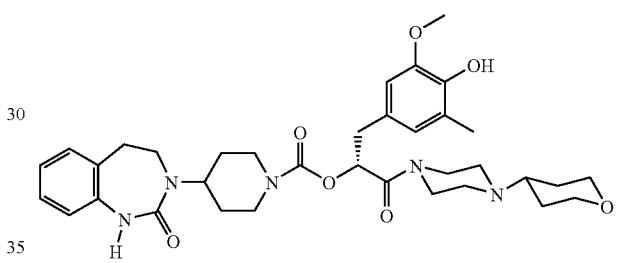

9a) 4-bromo-2-methoxy-6-methyl-phenol

A solution of 56.2 g (0.32 mol) N-bromosuccinimide in 1700 mL ACOH was added dropwise within 5.5 h to a solution of 42.3 g (0.31 mol) 2-methoxy-6-methyl-phenol in 450 mL ACOH and the mixture was stirred for 16 h at RT. The reaction mixture was evaporated down i.vac. and the residue was taken up in DCM. The organic phase was washed with 5% NaHCO$_3$ and saturated NaCl solution, dried over Na$_2$SO$_4$ and evaporated down i.vac. The red oil was used in the next reaction step without any further purification.

Yield: 65.9 g (66% of theoretical)
R$_f$=0.32 (silica gel, hexane/EtOAc 4:1)
retention time (HPLC-MS): 11.1 min (method D)

9b) 2-benzyloxy-5-bromo-1-methoxy-3-methyl-benzene 45.7 g (0.33 mol) K$_2$CO$_3$ and a solution of 40.3 mL (0.33 mol) benzylbromide were added at RT to a solution of 65.9 g (0.26 mol) 4-bromo-2-methoxy-6-methyl-phenol in 330 mL DMF and the mixture was stirred for 18 h at RT. The mixture was filtered, evaporated down i.vac. and the residue was taken up in diethyl ether. The organic phase was washed with water, 5% Na$_2$CO$_3$ and NaCl solution, dried over Na$_2$SO$_4$ and evaporated down i.vac. The crude product was used in the next reaction step without any further purification.

Yield: 92.2 g (81% of theoretical)
R$_f$=0.56 (silica gel, hexane/EtOAc 4:1)
retention time (HPLC-MS): 16.3 min (method D)

9c) 4-benzyloxy-3-methoxy-5-methyl-benzaldehyde 96 mL (240 mmol) n-butyllithium (2.5 M in hexane) were added dropwise at −75° C. to a solution of 61.2 g (119.5 mmol) 2-benzyloxy-5-bromo-1-methoxy-3-methyl-benzene in 240 mL THF and the mixture was stirred for 15 min at −75° C. A solution of 31 mL (402 mmol) DMF in 30 mL THF was added dropwise, the mixture was heated to 0° C. and stirred for a further 2 h. The reaction was combined with saturated NH$_4$Cl solution, diluted with 150 mL water and the phases were separated. The aqueous phase was exhaustively extracted with diethyl ether. The combined organic phases were washed with saturated NaCl solution, dried over Na$_2$SO$_4$ and evaporated down i.vac. Column chromatography (silica gel, hexane/EtOAc 85:15) yielded the product as a yellow oil.

Yield: 27.1 g (88% of theoretical)
R$_f$=0.32 (silica gel, hexane/EtOAc 4:1)
retention time (HPLC-MS): 13.3 min (method D)

9d) 2-acetylamino-3-(4-benzyloxy-3-methoxy-5-methyl-phenyl)-acrylic acid

A suspension of 27.0 g (105.4 mmol) 4-benzyloxy-3-methoxy-5-methyl-benzaldehyde, 18.5 g (158.0 mmol) N-acetylglycine and 12.96 g (158.0 mmol) NaOAc in 120 mL acetic anhydride was heated to 115° C. under nitrogen for 3.5 h. At 100° C. 60 mL water were slowly added dropwise and the mixture was stirred for 1 h. The reaction mixture was cooled to RT, poured into water and the aqueous phase was exhaustively extracted with EtOAc. The combined organic phases were washed with saturated NaCl solution, dried over Na$_2$SO$_4$ and evaporated down i.vac. The residue was triturated with isopropanol, the solid obtained was washed with isopropanol, diethyl ether and a little acetone and dried i.vac. at 45° C.

Yield: 21.2 g (57% of theoretical)
R$_f$=0.24 (silica gel, hexane/EtOAc 4:1)
retention time (HPLC-MS): 9.4 min (method D)

9e) 3-(4-benzyloxy-3-methoxy-5-methyl-phenyl)-2-oxo-propionic acid

The product was obtained analogously to Example 7c starting from 20.0 g (56.3 mmol) 2-acetylamino-3-(4-benzyloxy-3-methoxy-5-methyl-phenyl)-acrylic acid. The crude product was used in the next reaction step without any further purification.

Yield: 15.6 g (53% of theoretical)
retention time (HPLC-MS): 11.9 min (method D)

9f) (R)-3-(4-benzyloxy-3-methoxy-5-methyl-phenyl)-2-hydroxy-propionic acid

The product was prepared analogously to Example 7d starting from 16.0 g (50.90 mmol) 3-(4-benzyloxy-3-methoxy-5-methyl-phenyl)-2-oxo-propionic acid.

Yield: 7.63 g (47% of theoretical)
retention time (HPLC-MS): 9.8 min (method D)

9g) methyl(R)-3-(4-benzyloxy-3-methoxy-5-methyl-Phenyl)-2-hydroxy-propionate The product was prepared analogously to Example 7e starting from 7.6 g (24.02 mmol) (R)-3-(4-benzyloxy-3-methoxy-5-methyl-phenyl)-2-hydroxy-propionic acid.

Yield: 6.84 g (86% of theoretical)
retention time (HPLC-MS): 11.7 min (method D)

9h) (R)-2-(4-benzyloxy-3-methoxy-5-methyl-phenyl)-1-methoxycarbonyl-ethyl 4-(2-oxo-1,2,4,5-tetrahydro-1,3-benzodiazepin-3-yl)-piperidine-1-carboxylate The product was prepared analogously to Example 7f starting from 6.8 g (20.6 mmol) methyl(R)-3-(4-benzyloxy-3-methoxy-5-methyl-phenyl)-2-hydroxy-propionate in acetonitrile.

Yield: 8.16 g (66% of theoretical)
ESI-MS: (M+H)$^+$=602
retention time (HPLC-MS): 14.1 min (method D)

9i) (R)-2-(4-benzyloxy-3-methoxy-5-methyl-phenyl)-1-carboxy-ethyl 4-(2-oxo-1,2,4,5-tetrahydro-1,3-benzodiazepin-3-yl)-piperidine-1-carboxylate The product was prepared analogously to Example 7g starting from 8.16 g (13.65 mmol) (R)-2-(4-benzyloxy-3-methoxy-5-methyl-phenyl)-1-methoxycarbonyl-ethyl 4-(2-oxo-1,2,4,5-tetrahydro-1,3-benzodiazepin-3-yl)-piperidine-1-carboxylate.

Yield: 7.83 g (98% of theoretical)
ESI-MS: (M+H)$^+$=588
retention time (HPLC-MS): 12.2 min (method D)

9k) (R)-1-carboxy-2-(4-hydroxy-3-methoxy-5-methyl-phenyl)-ethyl 4-(2-oxo-1,2,4,5-tetrahydro-1,3-benzodiazepin-3-yl)-piperidine-1-carboxylate The product was prepared analogously to Example 7h starting from 7.80 g (13.27 mmol) (R)-2-(4-benzyloxy-3-methoxy-5-methyl-phenyl)-1-carboxy-ethyl 4-(2-oxo-1,2,4,5-tetrahydro-1,3-benzodiazepin-3-yl)-piperidine-1-carboxylate.

Yield: 5.33 g (80% of theoretical)
ESI-MS: (M+H)$^+$=498
retention time (HPLC-MS): 8.4 min (method D)

9l) (R)-1-(4-hydroxy-3-methoxy-5-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate 84 mg (0.22 mmol) HATU was added at RT under nitrogen to a solution of 100 mg (0.20 m mol) (R)-1-carboxy-2-(4-hydroxy-3-methoxy-5-methyl-phenyl)-ethyl 4-(2-oxo-1,2,4,5-tetrahydro-1,3-benzodiazepin-3-yl)-piperidine-1-carboxylate, 110 μL (0.64 mmol) ethyldiisopropylamine and 59 mg (0.24 mmol) 1-(tetrahydropyran-4-yl)-piperazine (used as the bis-hydrochloride salt) in 5 mL DMF and the mixture was stirred for 3 h. The reaction mixture was evaporated down i.vac. at 50° C. and the crude product was purified by HPLC-MS; the fractions containing the product were combined and lyophilised.

Yield: 112 mg (73% of theoretical)
ESI-MS: (M+H)$^+$=650
retention time (HPLC-MS): 3.6 min (method D)

EXAMPLE 10

{(R)-1-(3-chloro-4-hydroxy-5-methyl-benzyl)-2-oxo-2-[4-(tetrahydropyran-4-yl)-piperazin-1-yl]-ethyl}-amide 4-(2-oxo-1,2,4,5-tetrahydro-1,3-benzo-diazepin-3-yl)-piperidine-1-carboxylate

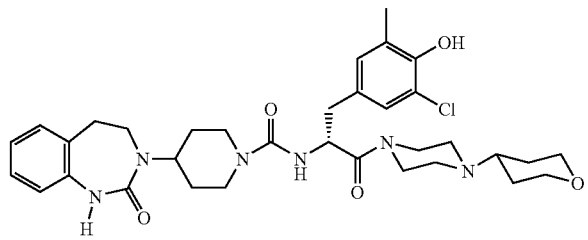

10a) 2-benzyloxy-5-bromo-1-chloro-3-methyl-benzene

A mixture of 10.2 g (46.0 mmol) 4-bromo-2-chloro-6-methyl-phenol, 7.0 mL (57.6 mmol) benzylbromide, 30.0 g (217.1 mmol) $K_2CO_3$ and 130 mL DMF was stirred overnight at RT. After the reaction had ended the insoluble matter was filtered off, the filtrate was evaporated down i.vac., combined with water and exhaustively extracted with EtOAc. The organic phases were combined, dried over $Na_2SO_4$ and evaporated down i.vac.

Yield: 14.0 g (98% of theory)
$R_f$=0.91 (silica gel, DCM/Cyc/MeOH/$NH_3$ 70:15:15:2)

10b) methyl 2-acetylamino-3-(4-benzyloxy-3-chloro-5-methyl-phenyl)-acrylate

Prepared analogously to Example 7b from 28.0 g (89.8 mmol) 2-benzyloxy-5-bromo-1-chloro-3-methyl-benzene, 15.0 g (102.7 mmol) methyl 2-acetylamino-acrylate, 260 mL triethylamine, 400 mL acetonitrile, 4.4 g (14.0 mmol) tri-o-tolyl-phosphane and 3.2 g (14.2 mmol) Pd(OAc)$_2$.

Yield: 12.5 g (37% of theory)
ESI-MS: (M+H)$^+$=374/376 (Cl)
$R_f$=0.67 (silica gel, DCM/Cyc/MeOH/$NH_3$ 70:15:15:2)

10c) methyl 2-acetylamino-3-(3-chloro-4-hydroxy-5-methyl-phenyl)-propionate

A mixture of 7.40 g (19.8 mmol) methyl 2-acetylamino-3-(4-benzyloxy-3-chloro-5-methyl-phenyl)-acrylate, 300 mL MeOH and 800 mg Raney nickel was shaken at RT and 3000 hPa hydrogen pressure for 7 h. After the reaction had ended the catalyst was filtered off and the remainder was evaporated down i.vac.

Yield: 5.6 g (99% of theory)
ESI-MS: (M+H)$^+$=286/288 (Cl)
retention time (HPLC-MS): 3.0 min (method A)

10d) methyl(R)-2-acetylamino-3-(3-chloro-4-hydroxy-5-methyl-phenyl)-propionate 6.0 mL Alcalase 2.4 L FG (Novozymes A/S; DK 2880 Bagsvaerd) was added to a warm solution (37° C.) of 7.2 g (40.4 mmol) Na$_2$HPO$_4$ dihydrate in 100 mL water and by the addition of NaH$_2$PO$_4$ dihydrate the pH was adjusted to 7.5. Then a solution of 5.5 g (19.2 mmol) methyl 2-acetylamino-3-(3-chloro-4-hydroxy-5-methyl-phenyl)-propionate in 50 mL acetone was added dropwise with stirring at 37° C. The pH value of the reaction mixture was kept constantly in the range from pH 7.4-7.6 by the addition of 1 M NaOH. After the addition had ended the mixture was stirred for 4 h at 37° C. After cooling to RT the reaction mixture was exhaustively extracted with MTBE, the combined organic extracts were washed with 15% K$_2$CO$_3$ solution and dried over Na$_2$SO$_4$. After the desiccant and solvent had been eliminated the crude product (1.6 g) was further reacted without purification.

ESI-MS: (M+H)$^+$=286/288 (Cl)

10e) methyl(R)-2-amino-3-(3-chloro-4-hydroxy-5-methyl-phenyl)-propionate

A mixture of 1.5 g of the above crude product and 8.75 mL of 4 M HCl was refluxed for 5 h. The mixture was evaporated down i.vac., the residue was taken up in water and made alkaline by the addition of K$_2$CO$_3$ solution. The aqueous phase was acidified by the addition of 4 M HCl, exhaustively extracted with EtOAc, the combined organic extracts were dried and evaporated down i.vac. The residue was combined with methanolic HCl and stirred overnight at RT. The reaction mixture was evaporated down i.vac., the residue was taken up in 15% K$_2$CO$_3$ solution and exhaustively extracted with EtOAc. The combined organic phases were dried and evaporated down i.vac.

Yield: 0.50 g (39% of theory)
ESI-MS: (M+H)$^+$=244/246 (Cl)
$R_f$=0.59 (silica gel, DCM/Cyc/MeOH/$NH_3$ 70:15:15:2)

10f) methyl(R)-3-(3-chloro-4-hydroxy-5-methyl-phenyl)-2-{[4-(2-oxo-1,2,4,5-tetrahydro-1,3-benzo-diazepin-3-yl)-piperidine-1-carbonyl]-amino}-propionate 0.39 g (2.4 mmol) CDT were added to a solution of 0.5 g (2.1 mmol) methyl(R)-2-amino-3-(3-chloro-4-hydroxy-5-methyl-phenyl)-propionate in 20 mL THF cooled in the ice bath and the reaction mixture was stirred for 1 h while cooling with ice and for 1 h at RT. Then 0.54 g (2.2 mmol) 3-piperidin-4-yl-1,3,4,5-tetrahydro-1,3-benzodiazepin-2-one were added and the reaction mixture was refluxed for 3 h. The mixture was evaporated down i.vac., the residue was combined with 1 M KHSO$_4$ solution, the precipitate formed was suction filtered and dried.

Yield: 1.0 g (95% of theory)
ESI-MS: (M+H)$^+$=513/515 (Cl)
$R_f$=0.55 (silica gel, DCM/Cyc/MeOH/$NH_3$ 70:15:15:2)

10g) (R)-3-(3-chloro-4-hydroxy-5-methyl-phenyl)-2-{[4-(2-oxo-1,2,4,5-tetrahydro-1,3-benzodiazepin-3-yl)-piperidine-1-carbonyl]-amino}-propionic acid A solution of 0.07 g (3.0 mmol) LiOH in 3 mL water was added to a solution of 1.0 g (1.94 mmol) methyl(R)-3-(3-chloro-4-hydroxy-5-methyl-phenyl)-2-{[4-(2-oxo-1,2,4,5-tetrahydro-1,3-benzodiazepin-3-yl)-piperidine-1-carbonyl]-amino}-propionate in 15 mL THF and the reaction mixture was stirred overnight at RT. The THF was eliminated i.vac., 100 mL of water were added and the mixture was acidified with 2 M HCl. The precipitated product was suction filtered, washed with 50 mL water and dried at 60° C. in the drying cupboard.

Yield: 0.9 g (93% of theory)
ESI-MS: (M+H)$^+$=501/503 (Cl)
$R_f$=0.08 (silica gel, DCM/Cyc/MeOH/$NH_3$ 70:15:15:2)

10h) {(R)-1-(3-chloro-4-hydroxy-5-methyl-benzyl)-2-oxo-2-[4-(tetrahydropyran-4-yl)-piperazin-1-yl]-ethyl}-amide 4-(2-oxo-1,2,4,5-tetrahydro-1,3-benzodiazepin-3-yl)-piperidine-1-carboxylate Prepared analogously to Example 7i from 70 mg (0.14 mmol) (R)-3-(3-chloro-4-hydroxy-5-methyl-phenyl)-2-{[4-(2-oxo-1,2,4,5-tetrahydro-1,3-benzodiazepin-3-yl)-piperidine-1-carbonyl]-amino}-propionic acid and 27.4 mg (0.16 mmol) 1-(tetrahydropyran-4-yl)-piperazine.

Yield: 52 mg (57% of theory)
ESI-MS: $(M+H)^+$=653/655 (Cl)
retention time (HPLC-MS): 2.5 min (method A)

EXAMPLE 11

(R)-1-(3-chloro-4-hydroxy-5-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

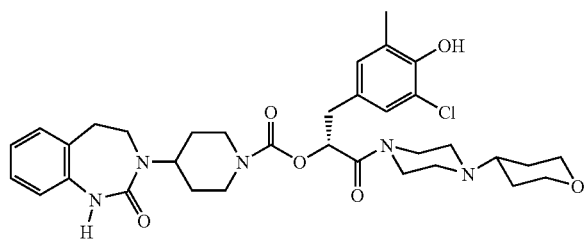

11a) 3-(4-benzyloxy-3-chloro-5-methyl-phenyl)-2-oxo-propionic acid

Prepared analogously to Example 7c from 18.4 g (49.2 mmol) methyl 2-acetylamino-3-(4-benzyloxy-3-chloro-5-methyl-phenyl)-acrylate (Example 10b) and 75 mL 4 M HCl.

Yield: 15.5 g (99% of theory)
ESI-MS: $(M+H)^+$=317/319 (Cl)
$R_f$=0.20 (silica gel, DCM/Cyc/MeOH/NH$_3$ 70:15:15:2)

11b) methyl(R)-3-(4-benzyloxy-3-chloro-5-methyl-phenyl)-2-hydroxy-propionate (R)-3-(4-benzyloxy-3-chloro-5-methyl-phenyl)-2-hydroxy-propionic acid was prepared analogously to Example 7d from 15.5 g (48.6 mmol) 3-(4-benzyloxy-3-chloro-5-methyl-phenyl)-2-oxo-propionic acid and 27.6 g (86.1 mmol) (1R)-B-chlorodiisopinocampheylborane. The crude product was combined with 150 mL methanolic HCl (1.25 M) and stirred overnight at RT. The reaction solution was evaporated down i.vac., the residue was combined with 70 mL 15% K$_2$CO$_3$ solution and extracted twice with 50 mL EtOAc. The combined organic extracts were dried, filtered and evaporated down i.vac.

Yield: 7.0 g (43% of theory)
ESI-MS: $(M+NH_4)^+$=352/354 (Cl)
$R_f$=0.87 (silica gel, DCM/Cyc/MeOH/NH$_3$ 70:15:15:2)

11c) (R)-2-(4-benzyloxy-3-chloro-5-methyl-phenyl)-1-carboxy-ethyl 4-(2-oxo-1,2,4,5-tetrahydro-1,3-benzodiazepin-3-yl)-piperidine-1-carboxylate (R)-2-(4-benzyloxy-3-chloro-5-methyl-phenyl)-1-methoxycarbonyl-ethyl 4-(2-oxo-1,2,4,5-tetrahydro-1,3-benzodiazepin-3-yl)-piperidine-1-carboxylate was prepared analogously to Example 7f from 7.0 g (20.9 mmol) methyl(R)-3-(4-benzyloxy-3-chloro-5-methyl-phenyl)-2-hydroxy-propionate and 5.2 g (21.2 mmol) 3-piperidin-4-yl-1,3,4,5-tetrahydro-1,3-benzodiazepin-2-one. The crude product was dissolved in 150 mL THF and combined with a solution of 0.50 g (20.6 mmol) LiOH in 50 mL water. The reaction mixture was stirred overnight at RT, combined with water and the organic solvent was eliminated i.vac. The aqueous phase was washed twice with EtOAc and acidified with 21 mL 1 M HCl. The resulting oil was exhaustively extracted with EtOAc. The combined organic extracts were dried, filtered and evaporated down i.vac.

Yield: 3.3 g (26% of theory)
ESI-MS: $(M+H)^+$=592/594 (Cl)
$R_f$=0.35 (silica gel, DCM/Cyc/MeOH/NH$_3$ 70:15:15:2)

11d) (R)-1-carboxy-2-(3-chloro-4-hydroxy-5-methyl-phenyl)-ethyl 4-(2-oxo-1,2,4,5-tetrahydro-1,3-benzodiazepin-3-yl)-piperidine-1-carboxylate 200 mg 5% Rh on aluminium oxide were added to a solution of 800 mg (1.35 m mol) (R)-2-(4-benzyloxy-3-chloro-5-methyl-phenyl)-1-carboxy-ethyl 4-(2-oxo-1,2,4,5-tetrahydro-1,3-benzodiazepin-3-yl)-piperidine-1-carboxylate in 20 mL THF and the suspension was hydrogenated for 12 h at 40° C. and 3000 hPa hydrogen pressure. To complete the reaction the mixture was combined with 5 mL DCM/MeOH (1:1) and hydrogenated for a further 20 h at 40° C. and 3000 hPa. The catalyst was filtered off, the filtrate was evaporated down, the residue was triturated with DIPE, suction filtered and dried.

Yield: 639 mg (94% of theory)
ESI-MS: $(M+H)^+$=502/504 (Cl)
retention time (HPLC-MS): 3.6 min (method A)

11e) (R)-1-(3-chloro-4-hydroxy-5-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate Prepared analogously to Example 7i from 80 mg (0.16 mmol) (R)-1-carboxy-2-(3-chloro-4-hydroxy-5-methyl-phenyl)-ethyl 4-(2-oxo-1,2,4,5-tetrahydro-1,3-benzodiazepin-3-yl)-piperidine-1-carboxylate and 29.8 mg (0.18 mmol) 1-(tetrahydropyran-4-yl)-piperazine.

Yield: 13 mg (12% of theory)
ESI-MS: $(M+H)^+$=654/656 (Cl)
retention time (HPLC-MS): 3.2 min (method A)

EXAMPLE 11.1

(R)-1-(4-hydroxy-3-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

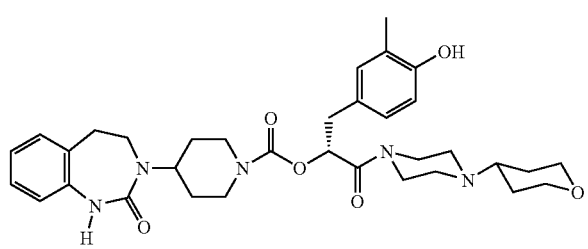

11.1a) (R)-1-(4-benzyloxy-3-chloro-5-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-Piperidine-1-carboxylate A solution of 150 mg (0.25 mmol) (R)-2-(4-benzyloxy-3-chloro-5-methyl-phenyl)-1-carboxy-ethyl 4-(2-oxo-1,2,4,5-tetrahydro-1,3-benzodiazepin-3-yl)-piperidine-1-carboxylate, 89 mg (0.28 mmol) TBTU and 44 µL (0.32 mmol) triethylamine in 1.5 mL DMF was stirred for 1 h at RT. Then 47 mg (0.28 mmol) 1-(tetrahydropyran-4-yl)-piperazine were added and the reaction solution was stirred for 2 h. The reaction solution was purified by HPLC without any further working up; the fractions containing the product were combined and lyophilised.

Yield: 108 mg (57% of theory)
ESI-MS: (M+H)$^+$=744/746 (Cl)
retention time (HPLC-MS): 4.1 min (method A)

11.1b) (R)-1-(4-hydroxy-3-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate A suspension of 108 mg (0.15 mmol) (R)-1-(4-benzyloxy-3-chloro-5-methyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate and 30 mg 10% Pd/C in 10 mL MeOH and 0.5 mL triethylamine was hydrogenated at RT and 3000 hPa hydrogen pressure until the theoretical amount of hydrogen had been taken up. The catalyst was filtered off, the residue was dissolved in 1 mL DMF and purified by HPLC. The fractions containing the product were combined and lyophilised.

Yield: 39 mg (43% of theory)
ESI-MS: (M+H)$^+$=620
retention time (HPLC-MS): 3.0 min (method A)

EXAMPLE 12

(S)-2-(3-chloro-4-hydroxy-5-methyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione

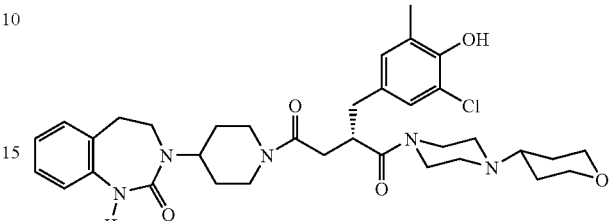

12a) 3-chloro-4-hydroxy-5-methyl-benzaldehyde 79.2 mL of a 2.5 M solution of n-butyllithium in n-hexane was added dropwise within 30 min to a mixture, cooled to −70° C., of 20.0 g (90.3 mmol) 4-bromo-2-chloro-6-methyl-phenol and 250 mL of THF. The reaction mixture was stirred for 2 h and then combined dropwise with 28.47 mL (370 mmol) DMF and heated to RT overnight. Then 150 mL 2 M HCl was added dropwise to the reaction solution while cooling with an ice bath, the mixture was stirred for 15 min and the pH was adjusted to 9-10 by the addition of saturated NaHCO$_3$ solution. The organic phase was separated off and discarded and the aqueous phase was extracted twice with EtOAc. The combined organic phases were dried, filtered and evaporated down i.vac.

Yield: 15.1 g (98% of theory)
ESI-MS: (M−H)$^-$=169/171 (Cl)
R$_f$=0.93 (silica gel, EtOAc)

12b) 1-methyl 2-[1-(3-chloro-4-hydroxy-5-methyl-phenyl)-meth-(Z)-ylidene]-succinate 69.5 g (177.0 mmol) 1-methyl 2-(triphenyl-λ$^5$-phosphanylidene)-succinate were added to a solution of 15.0 g (87.9 mmol) 3-chloro-4-hydroxy-5-methyl-benzaldehyde in 250 mL THF and the reaction mixture was heated to 40° C. for 120 h. The mixture was evaporated down i.vac., water and EtOAc were combined with the residue, the organic phase was separated off, washed with water and extracted three times with 200 mL 5% K$_2$CO$_3$ solution each time. The combined aqueous phases were acidified with semiconcentrated HCl and the oily precipitate was extracted twice with 250 mL EtOAc each time. The combined organic phases were dried, filtered and evaporated down i.vac.

Yield: 11.1 g (44% of theory)
EI: (M−H)$^-$=283/285 (Cl)
R$_f$=0.70 (silica gel, EtOAc)

12c) 1-methyl(S)-2-(3-chloro-4-hydroxy-5-methyl-benzyl)-succinate

Under an argon atmosphere 450 mg (−)-1,2-bis((2R,5R)-2,5-diethyl-phospholano)benzene(cyclooctadiene)rhodium (1)tetrafluoroborate were added to a solution of 11.0 g (38.6 mmol) 1-methyl 2-[1-(3-chloro-4-hydroxy-5-methyl-phenyl)-meth-(Z)-ylidene]-succinate in 150 mL degassed MeOH and 11.0 mL triethylamine and the reaction mixture was hydrogenated at 3447 hPa hydrogen pressure for 8 h. Then the reaction solution was evaporated down i.vac., the residue was dissolved in 100 mL EtOAc, washed twice with 2 M HCl and exhaustively extracted with 15% $K_2CO_3$ solution. The aqueous phase was acidified with concentrated HCl, exhaustively extracted with EtOAc and the organic phase was dried over $Na_2SO_4$. After the desiccant and solvent had been eliminated the desired product was obtained.

Yield: 11.0 g (99% of theory)
ESI-MS: (M−H)⁻=285/287 (Cl)
retention time (HPLC-MS): 3.3 min (method A)

12d) methyl(S)-2-(3-chloro-4-hydroxy-5-methyl-benzyl)-4-oxo-4-[4-(2-oxo-1,2,4,5-tetrahydro-1,3-benzodiazepin-3-yl)-piperidin-1-yl]-butanoate 6.6 g (27.0 mmol) 3-piperidin-4-yl-1,3,4,5-tetrahydro-1,3-benzodiazepin-2-one was added to a mixture of 7.0 g (24.4 mmol) 1-methyl(S)-2-(3-chloro-4-hydroxy-5methyl-benzyl)-succinate, 8.7 g (27.0 mmol) TBTU, 4.65 mL (27 mmol) ethyldiisopropylamine, 100 mL THF and 10 mL DMF and the reaction mixture was stirred overnight at RT. The reaction solution was evaporated down i.vac., the residue was taken up in DCM, the organic phase was washed with 15% $Na_2CO_3$ solution and dried over $Na_2SO_4$. After the desiccant and solvent had been eliminated the desired product was obtained.

Yield: 12.1 g (96% of theory)
ESI-MS: (M+H)⁺=514/516 (Cl)
$R_f$=0.49 (silica gel, DCM/Cyc/MeOH/NH₃ 70:15:15:2)

12e) (S)-2-(3-chloro-4-hydroxy-5-methyl-benzyl)-4-oxo-4-[4-(2-oxo-1,2,4,5-tetrahydro-1,3-benzodiazepin-3-yl)-piperidin-1-yl]-butanoic acid Prepared analogously to Example 7g from 12.1 g (23.5 mmol) methyl(S)-2-(3-chloro-4-hydroxy-5-methyl-benzyl)-4-oxo-4-[4-(2-oxo-1,2,4,5-tetrahydro-1,3-benzodiazepin-3-yl)-piperidin-1-yl]-butanoate and 848 mg (34.4 mmol) LiOH.

Yield: 9.7 g (82% of theory)
ESI-MS: (M+H)⁺=500/502 (Cl)
$R_f$=0.31 (silica gel, DCM/Cyc/MeOH/NH₃ 70:15:15:2)

12f) (S)-2-(3-chloro-4-hydroxy-5-methyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione Prepared analogously to Example 7i from 100 mg (0.20 mmol) (S)-2-(3-chloro-4-hydroxy-5-methyl-benzyl)-4-oxo-4-[4-(2-oxo-1,2,4,5-tetrahydro-1,3-benzodiazepin-3-yl)-piperidin-1-yl]-butanoic acid and 37.5 mg (0.22 mmol) 1-(tetrahydropyran-4-yl)-piperazine.

Yield: 33 mg (25% of theory)
ESI-MS: (M+H)⁺=652/654 (Cl)
retention time (HPLC-MS): 3.3 min (method B)

EXAMPLE 13

(R)-1-(4-hydroxy-3,5-dimethyl-benzyl)-2-oxo-2-[4-(tetrahydropyran-4-yl)-piperazin-1-yl]-ethyl 4-(5-oxo-3-phenyl-4,5-dihydro-1,2,4-triazol-1-yl)-piperidine-1-carboxylate

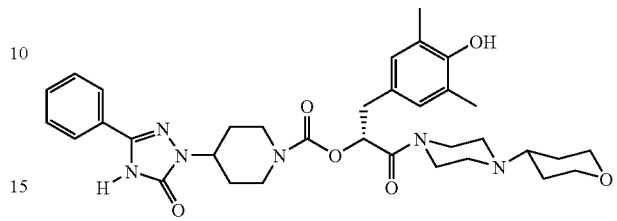

13a) (R)-2-(4-benzyloxy-3,5-dimethyl-phenyl)-1-methoxycarbonyl-ethyl 4-(5-oxo-3-phenyl-4,5-dihydro-1,2,4-triazol-1-yl)-piperidine-1-carboxylate Prepared analogously to Example 7f from 5.0 g (15.9 mmol) methyl(R)-3-(4-benzyloxy-3,5-dimethyl-phenyl)-2-hydroxy-propionate (Example 7e) and 5.98 g (15.9 mmol) 5-phenyl-2-piperidin-4-yl-2,4-dihydro-1,2,4-triazol-3-one (purity 65%).

Yield: 4.96 g (53% of theory)
ESI-MS: (M+H)⁺=585
retention time (HPLC-MS): 5.0 min (method A)

13b) (R)-2-(4-benzyloxy-3,5-dimethyl-phenyl)-1-carboxy-ethyl 4-(5-oxo-3-phenyl-4,5-dihydro-1,2,4-triazol-1-yl)-Piperidine-1-carboxylate A solution of 310 mg (12.93 mmol) LiOH in 30 mL water was added to a solution of 4.96 g (8.48 mmol) (R)-2-(4-benzyloxy-3,5-dimethyl-phenyl)-1-methoxy-carbonyl-ethyl 4-(5-oxo-3-phenyl-4,5-dihydro-1,2,4-triazol-1-yl)-piperidine-1-carboxylate in 50 mL THF and the reaction mixture was stirred for 7 h at RT. The solution was stored overnight at −18° C. and after heating to RT a further 310 mg LiOH were added thereto to complete the reaction. After 1 h the reaction solution was evaporated down i.vac., the residue was taken up in 150 mL water and acidified with 1 M HCl. The precipitate was filtered off and dried at 40° C.

Yield: 4.75 g (98% of theory)
ESI-MS: (M+H)⁺=571
retention time (HPLC-MS): 4.3 min (method A)

13c) (R)-1-carboxy-2-(4-hydroxy-3,5-dimethyl-phenyl)-ethyl 4-(5-oxo-3-phenyl-4,5-dihydro-1,2,4-triazol-1-yl)-piperidine-1-carboxylate A solution of 2.50 g (4.38 mmol) (R)-2-(4-benzyloxy-3,5-dimethyl-phenyl)-1-carboxy-ethyl 4-(5-oxo-3-phenyl-4,5-dihydro-1,2,4-triazol-1-yl)-piperidine-1-carboxylate in 50 mL DCM was combined with 250 mg 10% Pd/C and hydrogenated at RT under a hydrogen pressure of 3000 hP for 4.5 h. To complete the reaction a further 250 mg catalyst were added, the mixture was hydrogenated for 12 h at 40° C., combined with 25 mL THF and 250 mg catalyst and hydrogenated for a further 12 h at 40° C. The catalyst was suction filtered and the filtrate was evaporated down i.vac. The residue was stirred with DIPE, suction filtered and dried.

Yield: 1.87 g (89% of theory)
ESI-MS: (M−H)⁻=479
retention time (HPLC-MS): 3.5 min (method A)

13d) (R)-1-(4-hydroxy-3,5-dimethyl-benzyl)-2-oxo-2-[4-(tetrahydropyran-4-yl)-piperazin-1-yl]-ethyl 4-(5-oxo-3-phenyl-4,5-dihydro-1,2,4-triazol-1-yl)-piperidine-1-carboxylate A solution of 100 mg (0.21 mmol) (R)-1-carboxy-2-(4-hydroxy-3,5-dimethyl-phenyl)-ethyl 4-(5-oxo-3-phenyl-4,5-dihydro-1,2,4-triazol-1-yl)-piperidine-1-carboxylate, 74 mg (0.23 mmol) TBTU and 35 µL (0.26 mmol) triethylamine in 1 mL DMF was stirred for 1 h at RT. Then 35 mg (0.21 mmol) 1-(tetrahydropyran-4-yl)-piperazine was added and the reaction mixture was stirred for a further 5 h at RT. The reaction solution was purified by HPLC without any further working up. The fractions containing the product were combined and lyophilised.

Yield: 39 mg (30% of theory)
ESI-MS: (M+H)$^+$=633
retention time (HPLC-MS): 2.9 min (method A)

EXAMPLE 14

(R)-1-(4-amino-3-methyl-5-trifluoromethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

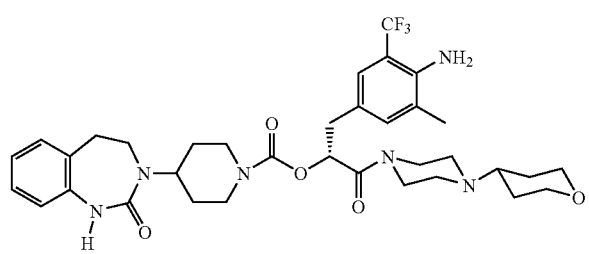

14a) 2-methyl-6-trifluoromethyl-phenylamine

A suspension of 50 g (0.24 mol) 1-methyl-2-nitro-3-trifluoromethyl-benzene and 4.4 g 10% Pd/C in 300 mL MeOH was hydrogenated at RT and 3000 hPa hydrogen pressure until the theoretical amount of hydrogen had been taken up. The catalyst was filtered off, washed with MeOH and the filtrate was evaporated down. The crude product was further reacted without purification.

Yield: quantitative
ESI-MS: (M+H)$^+$=176

14b) 4-bromo-2-methyl-6-trifluoromethyl-phenylamine

Under a nitrogen atmosphere a solution of 11.0 mL (214 mmol) bromine in 100 mL chloroform was added dropwise to a solution of 35.8 g (204 mmol) 2-methyl-6-trifluoromethyl-phenylamine in 350 mL chloroform and after the end of the addition the reaction mixture was stirred for 3 h at RT. Saturated NaHCO$_3$ solution was added with stirring, the mixture was stirred for a further 20 min at RT, the organic phase was separated off and dried over Na$_2$SO$_4$. After the desiccant and solvent had been eliminated the product was obtained as an oil, which was further reacted without purification.

Yield: 47.0 g (52% of theory)
EI-MS: (M)$^+$=253/255 (Br)

14c) methyl(Z,E)-2-acetylamino-3-(4-amino-3-methyl-5-trifluoromethyl-phenyl)-acrylate Under a nitrogen atmosphere 5.2 g (23.2 mmol) Pd(OAc)$_2$ and 7.2 g (22.9 mmol) tri-o-tolyl-phosphane were added to a solution of 37.2 g (146 mmol) 4-bromo-2-methyl-6-trifluoromethyl-phenylamine and 24.5 g (168 mmol) methyl 2-acetylamino-acrylate in 700 mL acetonitrile and 440 mL triethylamine and the reaction mixture was stirred for 18 h at a bath temperature of 80° C. After cooling the precipitate formed was suction filtered, the filtrate was evaporated to dryness and the residue was combined with 100 mL water and 50 mL EtOAc. The precipitate was suction filtered and dried at 50° C.

Yield: 21.6 g (47% of theory)
ESI-MS: (M+H)$^+$=317
R$_f$=0.41 (silica gel, DCM/Cyc/MeOH/NH$_3$ 70:15:15:2)

14d) 3-(4-amino-3-methyl-5-trifluoromethyl-phenyl)-2-oxo-propionic acid

A solution of 21.6 g (68.3 mmol) methyl(Z,E)-2-acetylamino-3-(4-amino-3-methyl-5-trifluoromethyl-phenyl)-acrylate in 200 mL 1,4-dioxane and 100 mL 4 M HCl was refluxed for 5 h. The 1,4-dioxane was eliminated i.vac., the precipitate was filtered off, washed with water and dried at 50° C.

Yield: 11.6 g (65% of theory)
ESI-MS: (M−H)$^−$=260
R$_f$=0.11 (silica gel, DCM/Cyc/MeOH/NH$_3$ 70:15:15:2)

14e) (R)-3-(4-amino-3-methyl-5-trifluoromethyl-phenyl)-2-hydroxy-propionic acid Under a nitrogen atmosphere a solution of 24.5 g (76.3 mmol) (1R)-B-chlorodiisopinocampheylborane in 100 mL THF was added dropwise within 15 min to a solution, cooled to −35° C., of 11.6 g (44.4 mmol) 3-(4-amino-3-methyl-5-trifluoromethyl-phenyl)-2-oxo-propionic acid and 8.1 mL (58.3 mmol) triethylamine in 200 mL THF and the reaction solution was stirred overnight at RT. Then at RT the reaction solution was carefully made alkaline with 23 mL 4 M NaOH, combined with 200 mL MTBE and 150 mL water and stirred for 1 h. The aqueous phase was separated off, the organic phase was extracted twice with 50 mL water and the combined aqueous extracts were acidified with 4 M HCl. The mixture was extracted three times with 100 mL EtOAc and the combined organic phases were dried over MgSO$_4$. After the desiccant and solvent had been eliminated the residue was further reacted without purification.

Yield: 8.4 g (72% of theory)
ESI-MS: (M+H)$^+$=264
R$_f$=0.11 (silica gel, DCM/Cyc/MeOH/NH$_3$ 70:15:15:2)

14f) methyl(R)-3-(4-amino-3-methyl-5-trifluoromethyl-phenyl)-2-hydroxy-propionate A solution of 8.4 g (31.9 mmol) (R)-3-(4-amino-3-methyl-5-trifluoromethyl-phenyl)-2-hydroxy-propionic acid in 100 mL methanolic HCl (1.3 M) was stirred for 3 h at RT. The mixture was evaporated down i.vac., the residue was combined with 150 mL of 15% K$_2$CO$_3$ solution, extracted three times with 100 mL EtOAc and the combined organic phases were dried over MgSO$_4$. After the desiccant and solvent had been eliminated the residue was further reacted without purification.

Yield: 6.1 g (69% of theory)
ESI-MS: (M+H)⁺=278
$R_f$=0.77 (silica gel, DCM/Cyc/MeOH/NH₃ 70:15:15:2)

14g) (R)-2-(4-amino-3-methyl-5-trifluoromethyl-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere 4.7 g (23.3 mmol) 4-nitrophenyl chloroformate in 30 mL THF were metered into 60 mL pyridine at a bath temperature of 60° C. within 10 min, the mixture was stirred for 5 min, then 6.1 g (22.0 mmol) methyl (R)-3-(4-amino-3-methyl-5-trifluoromethyl-phenyl)-2-hydroxy-propionate in 40 mL pyridine were added and the reaction mixture was stirred for 2.5 h at 60° C. The reaction solution was combined with 5.7 g (23.3 mmol) 3-piperidin-4-yl-1,3,4,5-tetrahydro-1,3-benzodiazepin-2-one and stirred for 3 h at 100° C. The reaction mixture was evaporated down i.vac., the residue was combined with 200 mL EtOAc, the organic phase was washed three times with 100 mL of 1 M KHSO₄ solution and 12 times with 50 mL 15% K₂CO₃ solution and dried over MgSO₄. After the desiccant and solvent had been eliminated the residue was further reacted without purification.
Yield: 9.0 g (75% of theory)
ESI-MS: (M+H)⁺=549
$R_f$=0.64 (silica gel, DCM/Cyc/MeOH/NH₃ 70:15:15:2)

14h) (R)-2-(4-amino-3-methyl-5-trifluoromethyl-phenyl)-1-carboxy-ethyl 4-(2-oxo-1,2,4,5-tetrahydro-1,3-benzodiazepin-3-yl)-piperidine-1-carboxylate A solution of 0.85 g (34.7 mmol) LiOH in 40 mL water was added to a solution of 9.0 g (16.4 mmol) (R)-2-(4-amino-3-methyl-5-trifluoromethyl-phenyl)-1-methoxy-carbonyl-ethyl 4-(2-oxo-1,2,4,5-tetrahydro-1,3-benzodiazepin-3-yl)-piperidine-1-carboxylate in 100 mL THF and the reaction mixture was stirred for 2 h at RT. The THF was eliminated i.vac., the residue was diluted with water, extracted twice with 50 mL MTBE and the aqueous phase was acidified with 9 mL of 4 M HCl. The precipitate was separated off, washed with water and dried. Further purification was carried out by trituration with 50 mL MTBE and further suction filtering of the product.
Yield: 7.5 g (86% of theory)
ESI-MS: (M+H)⁺=535
$R_f$=0.25 (silica gel, DCM/Cyc/MeOH/NH₃ 70:15:15:2)

14i) (R)-1-(4-amino-3-methyl-5-trifluoromethyl-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate A solution of 100 mg (0.19 mmol) (R)-2-(4-amino-3-methyl-5-trifluoromethyl-phenyl)-1-carboxy-ethyl 4-(2-oxo-1,2,4,5-tetrahydro-1,3-benzodiazepin-3-yl)-piperidine-1-carboxylate, 67 mg (0.21 mmol) TBTU and 50 µL (0.36 mmol) triethylamine in 1 mL DMF was stirred for 10 min at RT. Then 40 mg (0.24 mmol) 1-(tetrahydropyran-4-yl)-piperazine were added and the reaction mixture was stirred for a further 20 h at RT. The reaction solution was purified by HPLC without any further working up. The fractions containing the product were combined and lyophilised.
Yield: 83 mg (65% of theory)
ESI-MS: (M+H)⁺=687
retention time (HPLC-MS): 3.3 min (method A)

EXAMPLE 15

(S)-2-(4-amino-3-chloro-5-methyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione

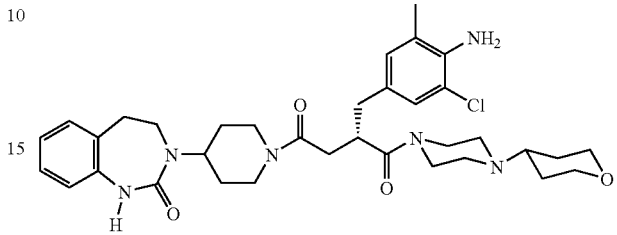

15a) ethyl 4-amino-3-bromo-5-chloro-benzoate

A solution of 20.0 g (81.9 mmol) ethyl 4-amino-3-bromo-benzoate in 150 mL AcOH was heated to 40° C. Then 11.0 mL (133 mmol) sulphuryl chloride were added dropwise in such a way that the internal temperature did not exceed 45° C. After the addition had ended the mixture was stirred for a further 2 h at 45° C. The reaction mixture was evaporated down to about 50 mL i.vac., poured onto ice water, the mixture was stirred for 10 min, the precipitate formed was filtered off and dried at 40° C.
Yield: 21.8 g (96% of theory)
$R_f$=0.62 (silica gel, PE/EtOAc 1:1)

15b) 4-amino-3-bromo-5-chloro-benzoic acid

A solution of 21.0 g (75.4 mmol) ethyl 4-amino-3-bromo-5-chloro-benzoate in 200 mL 4 M HCl and 100 mL EtOH was refluxed overnight. After cooling the precipitate formed was suction filtered and dried.
Yield: 14.5 g (77% of theory)
ESI-MS: (M–H)⁻=248/250/252 (Br/Cl)

15c) (4-amino-3-bromo-5-chloro-phenyl)-methanol 10.3 g (63.8 mmol) CDI were added to a solution of 14.5 g (57.9 mmol) 4-amino-3-bromo-5-chloro-benzoic acid in 200 mL THF and the reaction mixture was stirred for 1 h at 40° C. The reaction mixture was left to cool to RT and then added to a solution of 7.67 g (203 mmol) sodium borohydride in 200 mL water under a nitrogen atmosphere such that the temperature did not exceed 30° C. After the addition had ended the mixture was stirred for 2 h at RT, then diluted with 150 mL water, acidified with 100 mL 4 M HCl and stirred for a further hour at RT. The mixture was extracted twice with EtOAc and the combined organic phases were dried over Na₂SO₄. After the desiccant and solvent had been eliminated the product was further reacted without purification.
Yield: 13.4 g (98% of theory)
ESI-MS: (M–H₂O+H)⁺=218/220/222 (Br/Cl)
$R_f$=0.44 (silica gel, DCM/MeOH/NH₃ 90:10:1)

15d) 4-amino-3-bromo-5-chloro-benzaldehyde

A solution of 13.4 g (56.7 mmol) (4-amino-3-bromo-5-chloro-phenyl)-methanol in 300 mL DCM was combined batchwise with 78.0 g (897 mmol) manganese(IV)oxide while cooling with ice and the resulting mixture was stirred for 4 h at RT. The reaction mixture was filtered and evaporated down i.vac. The product was further reacted without purification.

Yield: 12.9 g (97% of theory)
ESI-MS: (M+H)$^+$=234/236/238 (Br/Cl)
R$_f$=0.92 (silica gel, DCM/MeOH/NH$_3$ 90:10:1)

15e) 1-methyl 2-[1-(4-amino-3-bromo-5-chloro-phenyl)-meth-(Z)-ylidene]-succinate Prepared analogously to Example 12b from 12.9 g (55.0 mmol) 4-amino-3-bromo-5-chloro-benzaldehyde and 43.6 g (111 mmol) 1-methyl 2-(triphenyl-λ$^5$-phosphanylidene)-succinate.

Yield: 12.5 g (65% of theory)
ESI-MS: (M−H)$^−$=346/348/350 (Br/Cl)
R$_f$=0.63 (silica gel, EtOAc)

15f) 1-methyl(S)-2-(4-amino-3-bromo-5-chloro-benzyl)-succinate

Prepared analogously to Example 12c from 12.4 g (35.6 mmol) 1-methyl 2-[1-(4-amino-3-bromo-5-chloro-phenyl)-meth-(Z)-ylidene]-succinate and 450 mg (−)-1,2-bis((2R,5R)-2,5-diethylphospholano)benzene(cyclooctadiene)rhodium(I)tetrafluoroborate, the reaction mixture being hydrogenated for 20 h.

Yield: 11.3 g (91% of theory)
ESI-MS: (M−H)$^−$=348/350/352 (Br/Cl)
retention time (HPLC-MS): 7.1 min (method B)

15g) methyl(S)-2-(4-amino-3-bromo-5-chloro-benzyl)-4-oxo-4-[4-(2-oxo-1,2,4,5-tetrahydro-1,3-benzodiazepin-3-yl)-piperidin-1-yl]-butanoate 5.4 g (22.0 mmol) 3-piperidin-4-yl-1,3,4,5-tetrahydro-1,3-benzodiazepin-2-one were added to a mixture of 7.0 g (20.0 mmol) 1-methyl(S)-2-(4-amino-3-bromo-5-chloro-benzyl)-succinate, 7.1 g (22.0 mmol) TBTU and 3.78 mL (22.0 mmol) ethyldiisopropylamine in 40 mL THF and the reaction mixture was shaken overnight at RT. The reaction solution was evaporated down i.vac., the residue was combined with 15% K$_2$CO$_3$ solution and treated in the ultrasound bath. The precipitate was suction filtered, washed with water, dried, taken up in a little DCM and purified by chromatography (silica gel, gradient DCM to DCM/MeOH/NH$_3$ 70:30:3).

Yield: 8.4 g (73% of theory)
ESI-MS: (M+H)$^+$=577/579/581 (Br/Cl)
R$_f$=0.60 (silica gel, DCM/Cyc/MeOH/NH$_3$ 70:15:15:2)

15h) methyl(S)-2-(4-amino-3-chloro-5-methyl-benzyl)-4-oxo-4-[4-(2-oxo-1,2,4,5-tetrahydro-1,3-benzodiazepin-3-yl)-piperidin-1-yl]-butanoate Under a nitrogen atmosphere 0.99 g (16.0 mmol) methylboric acid, 15.5 mL 2 M Na$_2$CO$_3$ solution and 1.02 g (1.40 mmol) Pd(dppf)Cl$_2$ were added to a solution of 8.40 g (14.5 mmol) methyl(S)-2-(4-amino-3-bromo-5-chloro-benzyl)-4-oxo-4-[4-(2-oxo-1,2,4,5-tetrahydro-1,3-benzodiazepin-3-yl)-piperidin-1-yl]-butanoate in 50 mL 1,4-dioxane and 3 mL MeOH and the reaction mixture was refluxed overnight. The reaction solution was filtered while hot and the filtrate was combined with EtOAc. The organic phase was washed several times with semisaturated NaHCO$_3$ solution and dried over Na$_2$SO$_4$. It was filtered through activated charcoal and evaporated down i.vac. The residue was taken up in a little DCM and purified by chromatography (silica gel, gradient DCM to DCM/MeOH/NH$_3$ 90:10:1). The fractions containing the product were combined, evaporated down i.vac., triturated with DIPE, suction filtered and dried.

Yield: 2.2 g (30% of theory)
ESI-MS: (M+H)$^+$=513/515 (Cl)
retention time (HPLC-MS): 4.0 min (method A)

15i) (S)-2-(4-amino-3-chloro-5-methyl-benzyl)-4-oxo-4-[4-(2-oxo-1,2,4,5-tetrahydro-1,3-benzodiazepin-3-yl)-piperidin-1-yl]-butanoic acid A solution of 2.20 g (4.29 mmol) methyl(S)-2-(4-amino-3-chloro-5-methyl-benzyl)-4-oxo-4-[4-(2-oxo-1,2,4,5-tetrahydro-1,3-benzodiazepin-3-yl)-piperidin-1-yl]-butanoate in 20 mL THF was combined with a solution of 156 mg (6.50 mmol) LiOH in 5 mL water and stirred overnight at RT. The reaction mixture was evaporated down i.vac., the residue was taken up in water, acidified with 2 M HCl, the precipitate was suction filtered and dried in the vacuum drying cupboard at 40° C. This was taken up in a little DCM and purified by chromatography (silica gel, gradient DCM/MeOH/NH$_3$ 90:10:1 to DCM/MeOH/NH$_3$ 70:30:3).

Yield: 1.3 g (61% of theory)
ESI-MS: (M+H)$^+$=499/501 (Cl)
R$_f$=0.18 (silica gel, DCM/Cyc/MeOH/NH$_3$ 70:15:15:2)

15k) (S)-2-(4-amino-3-chloro-5-methyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione Prepared analogously to Example 7i from 70 mg (0.14 mmol) (S)-2-(4-amino-3-chloro-5-methyl-benzyl)-4-oxo-4-[4-(2-oxo-1,2,4,5-tetrahydro-1,3-benzodiazepin-3-yl)-piperidin-1-yl]-butanoic acid and 27 mg (0.16 mmol) 1-(tetrahydropyran-4-yl)-piperazine.

Yield: 40 mg (44% of theory)
ESI-MS: (M+H)$^+$=651/653 (Cl)
retention time (HPLC-MS): 2.6 min (method A)

EXAMPLE 16

(S)-2-(3-chloro-4-hydroxy-5-trifluoromethyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione

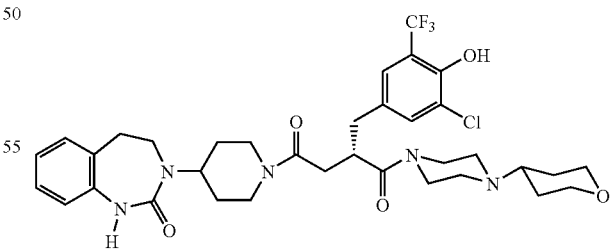

16a) 4-hydroxy-3-trifluoromethyl-benzoic acid 10.0 g (45.4 mmol) 4-methoxy-3-trifluoromethyl-benzoic acid and 75 g pyridinium-hydrochloride were mixed well and then heated to 180° C. under a nitrogen atmosphere for 5 h. The reaction mixture was poured onto 1 L 10% citric acid solution and extracted with 50 mL EtOAc. The organic phase was washed with 1 L water and dried over $Na_2SO_4$. After the desiccant and solvent had been eliminated the product was further reacted without purification.
Yield: 11.7 g
ESI-MS: $(M–H)^-=205$
retention time (HPLC-MS): 6.1 min (method B)

16b) 3-chloro-4-hydroxy-5-trifluoromethyl-benzoic acid 11.7 g of the crude product from Example 16a was dissolved in 40 mL AcOH at 40° C. At this temperature 5.15 mL (63 mmol) sulphuryl chloride were added dropwise and after the end of the addition the reaction mixture was stirred for a further 2 h at this temperature. To complete the reaction another 2.5 mL sulphuryl chloride were added dropwise and the reaction mixture was heated to 60° C. for 4 h. The reaction solution was poured onto 300 mL water, extracted with 200 mL EtOAc, the organic phase was washed twice with water and dried over $Na_2SO_4$. After the desiccant and solvent had been eliminated the residue was stirred out with 80 mL PE, the precipitated substance was suction filtered, washed with 20 mL PE and dried.
Yield: 7.7 g (70% of theory over 2 steps)
ESI-MS: $(M–H)^-=239/241$ (Cl)
retention time (HPLC-MS): 6.5 min (method B)

16c) 2-chloro-4-hydroxymethyl-6-trifluoromethyl-phenol 5.76 g (36.0 mmol) CDI were added to a solution of 7.70 g (32.0 mmol) 3-chloro-4-hydroxy-5-trifluoromethyl-benzoic acid in 100 mL THF and the reaction mixture was stirred for 1 h at 40° C. After cooling to RT this solution was carefully added to a solution of 3.78 g (100 mmol) sodium borohydride in 40 mL water under a nitrogen atmosphere, such that the temperature did not exceed 30° C. during the addition. After the addition had ended the mixture was stirred for a further 2 h at RT, diluted with 200 mL water, acidified with 50 mL semiconcentrated HCl, stirred for 1 h, exhaustively extracted with EtOAc and the combined organic phases were dried over $Na_2SO_4$. After the desiccant and solvent had been eliminated the product was further reacted without purification.
Yield: 5.9 g (81% of theory)
ESI-MS: $(M–H)^-=225/227$ (Cl)
$R_f=0.85$ (silica gel, EtOAc)

16d) 3-chloro-4-hydroxy-5-trifluoromethyl-benzaldehyde 30.0 g (345 mmol) manganese(IV)oxide were added to a solution of 5.90 g (26.0 mmol) 2-chloro-4-hydroxymethyl-6-trifluoromethyl-phenol in 100 mL DCM and the reaction mixture was stirred for 2 h at RT. The precipitate was filtered off, the filtrate was evaporated down i.vac. and further reacted without purification.
Yield: 3.0 g (51% of theory)
ESI-MS: $(M–H)^-=223/225$ (Cl)
$R_f=0.5$ (silica gel, PE/EtOAc 1:1)

16e) 1-methyl 2-[1-(3-chloro-4-hydroxy-5-trifluoromethyl-phenyl)-meth-(Z)-ylidene]-succinate Prepared analogously to Example 12b from 3.0 g (13.4 mmol) 3-chloro-4-hydroxy-5-trifluoromethyl-benzaldehyde and 10.5 g (26.7 mmol) 1-methyl 2-(triphenyl-$\lambda^5$-phospha-nylidene)-succinate. The crude product obtained was purified by chromatography (silica gel, gradient PE/EtOAc 1:1 to EtOAc).
Yield: 2.5 g (55% of theory)
ESI-MS: $(M–H)^-=337/339$ (Cl)
$R_f=0.75$ (silica gel, EtOAc)

16f) 1-methyl(S)-2-(3-chloro-4-hydroxy-5-trifluoromethyl-benzyl)-succinate

Prepared analogously to Example 12c from 2.30 g (6.79 mmol) 1-methyl 2-[1-(3-chloro-4-hydroxy-5-trifluoromethyl-phenyl)-meth-(Z)-ylidene]-succinate and 100 mg (−)-1,2-bis((2R,5R)-2,5-diethylphospholano)benzene(cyclooctadiene)rhodium(I)tetrafluoroborate.
Yield: 1.7 g (74% of theory)
ESI-MS: $(M–H)^-=339/341$ (Cl)
retention time (HPLC-MS): 7.1 min (method B)

16g) methyl(S)-2-(3-chloro-4-hydroxy-5-trifluoromethyl-benzyl)-4-oxo-4-[4-(2-oxo-1,2,4,5-tetrahydro-1,3-benzodiazepin-3-yl)-piperidin-1-yl]-butanoate 1.65 g (4.84 mmol) 3-piperidin-4-yl-1,3,4,5-tetrahydro-1,3-benzodiazepin-2-one were added to a mixture of 1.19 g (4.85 mmol) 1-methyl(S)-2-(3-chloro-4-hydroxy-5-trifluoromethyl-benzyl)-succinate, 1.56 g (4.85 mmol) TBTU, 0.73 mL (5.00 mmol) triethylamine, in 30 mL DMF and the reaction mixture was stirred overnight at RT. The reaction solution was evaporated down i.vac., the residue was taken up in 200 mL EtOAc, the organic phase was washed with 10% citric acid and saturated $Na_2CO_3$ solution and dried over $Na_2SO_4$. After the desiccant and solvent had been eliminated the desired product was obtained.
Yield: 1.8 g (65% of theory)
ESI-MS: $(M+H)^+=568/570$ (Cl)
retention time (HPLC-MS): 8.1 min (method B)

16h) (S)-2-(3-chloro-4-hydroxy-5-trifluoromethyl-benzyl)-4-oxo-4-[4-(2-oxo-1,2,4,5-tetrahydro-1,3-benzodiazepin-3-yl)-piperidin-1-yl]-butanoic acid A solution of 115 mg (4.80 mmol) LiOH in 50 mL water was added to a solution of 1.80 g (3.17 mmol) methyl(S)-2-(3-chloro-4-hydroxy-5-trifluoromethyl-benzyl)-4-oxo-4-[4-(2-oxo-1,2,4,5-tetrahydro-1,3-benzodiazepin-3-yl)-piperidin-1-yl]-butanoate in 50 mL THF and the reaction mixture was stirred overnight at RT. The reaction solution was freed from the THF i.vac., diluted with 150 mL water, the aqueous phase was washed with 150 mL EtOAc, acidified with concentrated HCl, extracted with 150 mL EtOAc, the organic phase was separated off and dried over $Na_2SO_4$. After the desiccant and solvent had been eliminated the product was further reacted without purification.
Yield: 1.5 g (85% of theory)
ESI-MS: $(M+H)^+=554/556$ (Cl)
retention time (HPLC-MS): 8.2 min (method B)

16i) (S)-2-(3-chloro-4-hydroxy-5-trifluoromethyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione Prepared analogously to Example 7i from 70 mg (0.13 mmol) (S)-2-(3-chloro-4-hydroxy-5-trifluoromethyl-benzyl)-4-oxo-4-[4-(2-oxo-1,2,4,5-tetrahydro-1,3-benzodiazepin-3-yl)-piperidin-1-yl]-butanoic acid and 22 mg (0.13 mmol) 1-(tetrahydropyran-4-yl)-piperazine.

Yield: 56 mg (63% of theory)
ESI-MS: $(M+H)^+ = 706/708$ (Cl)
retention time (HPLC-MS): 6.0 min (method B)

EXAMPLE 17

(S)-2-(4-hydroxy-3,5-dimethyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione

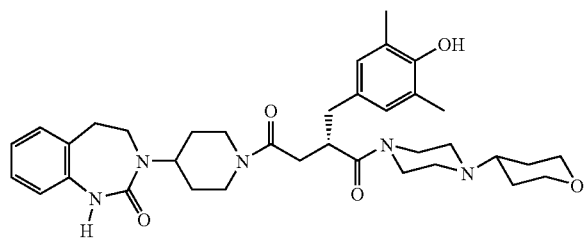

17a) 4-benzyloxy-3,5-dimethyl-benzaldehyde

Under an argon atmosphere 60.8 g (440 mmol) $K_2CO_3$ and 52.3 mL (440 mmol) benzylbromide were added to a solution of 60.1 g (400 mmol) 4-hydroxy-3,5-di-methyl-benzaldehyde in 600 mL acetone and the reaction mixture was heated to 50° C. for 2.5 h. The precipitate was filtered off, washed with acetone and the filtrate was evaporated down i.vac. The residue was purified by chromatography (silica gel, Cyc/EtOAc 9:1).

Yield: 94.8 g (99% of theory)
ESI-MS: $(M+H)^+ = 241$
$R_f = 0.45$ (silica gel, Cyc/EtOAc 4:1)

17b) 1-methyl 2-[1-(4-benzyloxy-3,5-dimethyl-phenyl)-meth-(Z)-ylidene]-succinate Prepared analogously to Example 12b from 29.0 g (96.6 mmol) 4-benzyloxy-3,5-dimethyl-benzaldehyde and 75.8 g (193 mmol) 1-methyl 2-(triphenyl-$\lambda^5$-phosphanylidene)-succinate.

Yield: 5.67 g (17% of theory)
ESI-MS: $(M+H)^+ = 355$

17c) 1-methyl(S)-2-(4-benzyloxy-3,5-dimethyl-benzyl)-succinate

Under an argon atmosphere 100 mg (−)-1,2-bis((2R,5R)-2,5-diethylphospholano)benzene(cyclooctadiene)rhodium (I)tetrafluoroborate were added to a solution of 5.67 g (16.0 mmol) 1-methyl 2-[1-(4-benzyloxy-3,5-dimethyl-phenyl)-meth-(Z)-ylidene]-succinate in 40 mL degassed MeOH and 5.0 mL triethylamine and the reaction mixture was hydrogenated at 3447 hPa hydrogen pressure for 7 h. Then the reaction solution was evaporated down i.vac., the residue was suspended in 80 mL 15% $K_2CO_3$ solution, extracted with 80 mL EtOAc and the organic phase was separated off. The aqueous phase was acidified with 2 M HCl, extracted twice with 40 mL EtOAc, the combined organic phases were washed with saturated NaCl solution and dried over $Na_2SO_4$. After the desiccant and solvent had been eliminated the desired product was obtained.

Yield: 1.69 g (30% of theory)
ESI-MS: $(M-H)^- = 355$
retention time (HPLC-MS): 9.2 min (method B)

17d) methyl(S)-2-(4-benzyloxy-3,5-dimethyl-benzyl)-4-oxo-4-[4-(2-oxo-1,2,4,5-tetrahydro-1,3-benzodiazepin-3-yl)-piperidin-1-yl]-butanoate A mixture of 1.69 g (4.74 mmol) 1-methyl(S)-2-(4-benzyloxy-3,5-dimethyl-benzyl)-succinate, 1.55 g (4.83 mmol) TBTU, 0.69 g (5.10 mmol) HOBt and 1.34 mL (7.71 mmol) ethyldiisopropylamine in 40 mL THF and 5 mL DMF was stirred for 16 h at RT. Then 1.16 g (4.74 mmol) 3-piperidin-4-yl-1,3,4,5-tetrahydro-1,3-benzodiazepin-2-one was added to the reaction mixture, which was then stirred for a further 2.5 h at RT. The reaction solution was combined with 40 mL EtOAc, the organic phase was washed twice with 30 mL semisaturated $NaHCO_3$ and once with 40 mL saturated NaCl solution washed and dried over $Na_2SO_4$. After the desiccant and solvent had been eliminated the residue was purified by chromatography (silica gel, EtOAc/Cyc 3:1).

Yield: 2.43 g (88% of theory)
ESI-MS: $(M+H)^+ = 584$
retention time (HPLC-MS): 10.0 min (method B)

17e) (S)-2-(4-benzyloxy-3,5-dimethyl-benzyl)-4-oxo-4-[4-(2-oxo-1,2,4,5-tetrahydro-1,3-benzodiazepin-3-yl)-piperidin-1-yl]-butanoic acid A solution of 200 mg (8.35 mmol) LiOH in 40 mL water was added to a solution of 2.43 g (4.16 mmol) methyl(S)-2-(4-benzyloxy-3,5-dimethyl-benzyl)-4-oxo-4-[4-(2-oxo-1,2,4,5-tetrahydro-1,3-benzodiazepin-3-yl)-piperidin-1-yl]-butanoate in 80 mL THF and the reaction mixture was stirred for 1 h at RT. The mixture was evaporated down i.vac., the residue was taken up in 100 mL water and acidified with 2 M HCl with stirring. The precipitate formed was separated off and dried at 40° C.

Yield: 2.41 g (100% of theory)
ESI-MS: $(M+H)^+ = 570$
retention time (HPLC-MS): 9.0 min (method B)

17f) (S)-2-(4-hydroxy-3,5-dimethyl-benzyl)-4-oxo-4-[4-(2-oxo-1,2,4,5-tetrahydro-1,3-benzodiazepin-3-yl)-piperidin-1-yl]-butanoic acid A suspension of 2.41 g (4.23 mmol) (S)-2-(4-benzyloxy-3,5-dimethyl-benzyl)-4-oxo-4-[4-(2-oxo-1,2,4,5-tetrahydro-1,3-benzodiazepin-3-yl)-piperidin-1-yl]-butanoic acid and 300 mg 10% Pd/C in 50 mL DCM was hydrogenated at RT and 3447 hPa hydrogen pressure until the theoretical amount of hydrogen had been taken up. The catalyst was filtered off and the filtrate was evaporated down i.vac. The residue was triturated with DIPE, suction filtered and dried.

Yield: 1.88 g (93% of theory)
ESI-MS: $(M+H)^+ = 480$
retention time (HPLC-MS): 6.7 min (method B)

17g) (S)-2-(4-hydroxy-3,5-dimethyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione A mixture of 70 mg (0.15 mmol) (S)-2-(4-hydroxy-3,5-dimethyl-benzyl)-4-oxo-4-[4-(2-oxo-1,2,4,5-tetrahydro-1,3-benzodiazepin-3-yl)-piperidin-1-yl]-butanoic acid, 52 mg (0.15 mmol) TBTU and 25 µL (0.18 mmol) triethylamine in 1 mL DMF was stirred for 1 h at RT. Then 25 mg (0.15 mmol) 1-(tetrahydropyran-4-yl)-piperazine was added to the reaction mixture, which was then stirred for a further 16 h at RT. The reaction mixture was purified by HPLC without any further working up; the fractions containing the product were combined and lyophilised.

Yield: 37 mg (40% of theory)
ESI-MS: (M+H)$^+$=632
retention time (HPLC-MS): 5.6 min (method B)

EXAMPLE 18

(S)-2-(4-amino-3-chloro-5-trifluoromethyl-benzyl)-4-[4-(6-hydroxy-2-oxo-1,4-dihydro-2H-quinazolin-3-yl)-piperidin-1-yl]-1-[4-(tetrahydropyran-4-yl)-piperazin-1-yl]-butane-1,4-dione

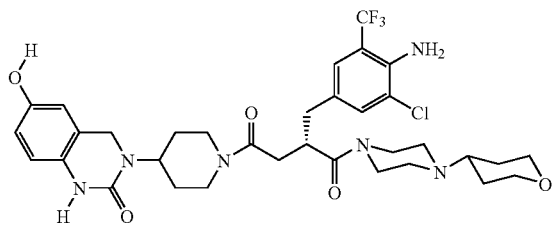

18a) methyl(S)-2-(4-amino-3-chloro-5-trifluoromethyl-benzyl)-4-[4-(6-hydroxy-2-oxo-1,4-dihydro-2H-quinazolin-3-yl)-piperidin-1-yl]-4-oxo-butanoate A solution of 1.37 g (4.04 mmol) 1-methyl(S)-2-(4-amino-3-chloro-5-trifluoromethyl-benzyl)-succinate, 1.42 g (4.40 mmol) TBTU, 0.63 mL (4.50 mmol) triethylamine and 1.00 g (4.04 mmol) 6-hydroxy-3-piperidin-4-yl-3,4-dihydro-1H-quinazolin-2-one in 10 mL DMF was stirred for 3 h at RT. The reaction mixture was poured onto 300 mL saturated NaHCO$_3$ solution, the precipitated substance was suction filtered, washed with 50 mL water and dried at 60° C. in the circulating air dryer.

Yield: 2.30 g (100% of theory)
ESI-MS: (M+H)$^+$=569/571 (Cl)
retention time (HPLC): 3.6 min (method A)

18b) (S)-2-(4-amino-3-chloro-5-trifluoromethyl-benzyl)-4-[4-(6-hydroxy-2-oxo-1,4-dihydro-2H-quinazolin-3-yl)-piperidin-1-yl]-4-oxo-butanoic acid A solution of 144 mg (6.00 mmol) LiOH in 15 mL water was added to a solution of 2.30 g (4.04 mmol) methyl(S)-2-(4-amino-3-chloro-5-trifluoromethyl-benzyl)-4-[4-(6-hydroxy-2-oxo-1,4-dihydro-2H-quinazolin-3-yl)-piperidin-1-yl]-4-oxo-butanoate in 30 mL THF and the reaction mixture was stirred for 1 h at RT. The organic solvent was eliminated i.vac., the residue was diluted with 50 mL water and acidified with 1 M HCl. The precipitate formed was filtered, washed with 10 mL water and dried at 50° C.

Yield: 2.20 g (98% of theory)
ESI-MS: (M+H)$^+$=555/557 (Cl)
retention time (HPLC): 3.2 min (method A)

18c) (S)-2-(4-amino-3-chloro-5-trifluoromethyl-benzyl)-4-[4-(6-hydroxy-2-oxo-1,4-dihydro-2H-quinazolin-3-yl)-piperidin-1-yl]-1-[4-(tetrahydropyran-4-yl)-piperazin-1-yl]-butane-1,4-dione Prepared analogously to Example 81 from 80.0 mg (0.14 mmol) (S)-2-(4-amino-3-chloro-5-trifluoromethyl-benzyl)-4-[4-(6-hydroxy-2-oxo-1,4-dihydro-2H-quinazolin-3-yl)-piperidin-1-yl]-4-oxo-butanoic acid and 24.5 mg (0.14 mmol) 1-(tetrahydropyran-4-yl)-piperazine.

Yield: 56 mg (55% of theory)
ESI-MS: (M+H)$^+$=707/709 (Cl)
retention time (HPLC-MS): 2.8 min (method A)

EXAMPLE 19

(S)-2-(4-amino-3-chloro-5-trifluoromethyl-benzyl)-4-[4-(2-oxo-1,2-dihydro-imidazo[4,5-c]quinolin-3-yl)-piperidin-1-yl]-1-[4-(tetrahydropyran-4-yl)-piperazin-1-yl]-butane-1,4-dione

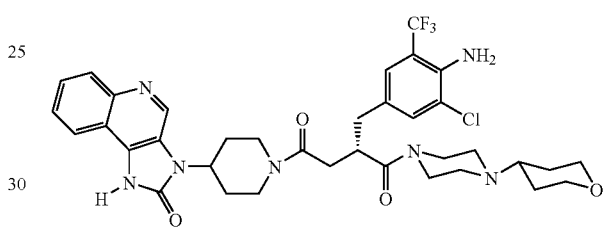

19a) methyl(S)-2-(4-amino-3-chloro-5-trifluoromethyl-benzyl)-4-oxo-4-[4-(2-oxo-1,2-dihydro-imidazo[4,5-c]quinolin-3-yl)-piperidin-1-yl]-butanoate A mixture of 3.00 g (8.83 mmol) 1-methyl(S)-2-(4-amino-3-chloro-5-trifluoromethyl-benzyl)-succinate, 3.05 g (9.50 mmol) TBTU and 1.7 mL (9.76 mmol) ethyldiisopropylamine in 100 mL DMF was stirred for 1 h at RT. Then 2.55 g (9.50 mmol) 3-piperidin-4-yl-1,3-dihydro-imidazo[4,5-c]quinoline-2-one was added to the reaction mixture, which was then stirred overnight at RT. The reaction mixture was evaporated down i.vac., the residue was taken up in DCM, the organic phase was washed with 10% citric acid and 15% K$_2$CO$_3$ solution and dried over Na$_2$SO$_4$. After filtration through activated charcoal and elimination of the solvent the product was further reacted without purification.

Yield: 5.20 g (100% of theory)
ESI-MS: (M+H)$^+$=590/592 (Cl)
R$_f$=0.66 (silica gel, DCM/Cyc/MeOH/NH$_3$ 70:15:15:2)

19b) (S)-2-(4-amino-3-chloro-5-trifluoromethyl-benzyl)-4-oxo-4-[4-(2-oxo-1,2-dihydro-imidazo[4,5-c]quinolin-3-yl)-piperidin-1-yl]-butanoic acid A solution of 566 mg (13.22 mmol) LiOH*H$_2$O in 12 mL water was added to a solution of 5.20 g (8.81 mmol) methyl (S)-2-(4-amino-3-chloro-5-trifluoromethyl-benzyl)-4-oxo-4-[4-(2-oxo-1,2-dihydro-imidazo[4,5-c]quinolin-3-yl)-piperidin-1-yl]-butanoate in 29 mL THF and the reaction mixture was stirred for 7 h at RT. This was evaporated down i.vac., the residue was combined with 100 mL water and acidified with 1 M HCl. The precipitate was suction filtered, dissolved again in EtOAc, extracted with 15% K$_2$CO$_3$ solution and the aqueous phase was acidified with 1 M HCl. The precipitate was suction filtered and dried.
Yield: 2.75 g (54% of theory)
ESI-MS: (M+H)$^+$=576/578 (Cl)
$R_f$=0.09 (silica gel, DCM/Cyc/MeOH/NH$_3$ 70:15:15:2)

19c) (S)-2-(4-amino-3-chloro-5-trifluoromethyl-benzyl)-4-[4-(2-oxo-1,2-dihydro-imidazo[4,5-c]quinolin-3-yl)-piperidin-1-yl]-1-[4-(tetrahydropyran-4-yl)-piperazin-1-yl]-butane-1,4-dione Prepared analogously to Example 7i from 80 mg (0.14 mmol) (S)-2-(4-amino-3-chloro-5-trifluoromethyl-benzyl)-4-oxo-4-[4-(2-oxo-1,2-dihydro-imidazo[4,5-c]quinolin-3-yl)-piperidin-1-yl]-butanoic acid and 26.0 mg (0.15 mmol) 1-(tetrahydropyran-4-yl)-piperazine.
Yield: 38 mg (38% of theory)
ESI-MS: (M+H)$^+$=728/730 (Cl)
retention time (HPLC-MS): 2.3 min (method H)

EXAMPLE 20

(R)-1-(4-hydroxy-3,5-dimethyl-benzyl)-2-oxo-2-[4-(tetrahydropyran-4-yl)-piperazin-1-yl]-ethyl 4-(2-oxo-1,2-dihydro-imidazo[4,5-c]quinolin-3-yl)-piperidine-1-carboxylate

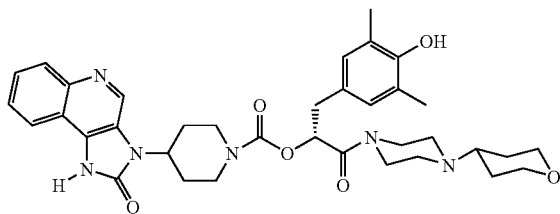

20a) (R)-2-(4-benzyloxy-3,5-dimethyl-phenyl)-1-methoxycarbonyl-ethyl 4-(2-oxo-1,2-dihydro-imidazo[4,5-c]quinolin-3-yl)-piperidine-1-carboxylate Under a nitrogen atmosphere 1.28 g (6.36 mmol) 4-nitrophenyl chloroformate were added at RT to a solution of 0.78 g (6.36 mmol) 4-dimethylaminopyridine in 100 mL pyridine and the mixture was stirred for 1 h at RT. Then a solution of 2.00 g (6.36 mmol) methyl(R)-3-(4-benzyloxy-3,5-dimethyl-phenyl)-2-hydroxy-propionate in 20 mL pyridine was added dropwise at RT and the reaction mixture was stirred for 2 h after the end of the addition. Then 1.71 g (6.36 mmol) 3-piperidin-4-yl-1,3-dihydro-imidazo[4,5-c]quinoline-2-one was added to the reaction mixture, which was then heated to 100° C. for 4 h. The precipitate formed was filtered off, the filtrate was evaporated down i.vac., the residue was mixed with 200 mL EtOAc and 200 mL semisaturated KHSO$_4$ solution, the product being obtained as a precipitate. This was suction filtered and dried.
Yield: 2.50 g (65% of theory)
ESI-MS: (M+H)$^+$=609
retention time (HPLC-MS): 3.9 min (method A)

20b) (R)-1-carboxy-2-(4-benzyloxy-3,5-dimethyl-phenyl)-ethyl 4-(2-oxo-1,2-dihydro-imidazo[4,5-c]quinolin-3-yl)-piperidine-1-carboxylate A solution of 250 mg (10.42 mmol) LiOH in 10 mL water was added to a solution of 2.50 g (4.11 mmol) (R)-2-(4-benzyloxy-3,5-dimethyl-phenyl)-1-methoxycarbonyl-ethyl 4-(2-oxo-1,2-dihydro-imidazo[4,5-c]quinolin-3-yl)-piperidine-1-carboxylate in 20 mL THF and the reaction mixture was stirred for 2 h at RT. The organic solvent was removed i.vac., the aqueous residue was acidified with 2 M HCL and combined with EtOAc/DCM (2:1). The precipitate formed was filtered off and dried.
Yield: 1.84 g (75% of theory)
ESI-MS: (M+H)$^+$=595
retention time (HPLC-MS): 3.6 min (method A)

20c) (R)-1-carboxy-2-(4-hydroxy-3,5-dimethyl-phenyl)-ethyl 4-(2-oxo-1,2-dihydro-imidazo[4,5-c]quinolin-3-yl)-piperidine-1-carboxylate A suspension of 1.80 g (3.03 mmol) (R)-1-carboxy-2-(4-benzyloxy-3,5-dimethyl-phenyl)-ethyl 4-(2-oxo-1,2-dihydro-imidazo[4,5-c]quinolin-3-yl)-piperidine-1-carboxylate and 300 mg 10% Pd/C in 30 mL THF and 30 mL MeOH was hydrogenated at 3000 hPa hydrogen pressure and RT for 48 h. The catalyst was suction filtered, the filtrate was evaporated down and the residue was purified by HPLC; the fractions containing the product were combined and lyophilised.
Yield: 0.25 g (16% of theory)
ESI-MS: (M+H)$^+$=505
retention time (HPLC-MS): 2.6 min (method A)

20d) (R)-1-(4-hydroxy-3,5-dimethyl-benzyl)-2-oxo-2-[4-(tetrahydropyran-4-yl)-piperazin-1-yl]-ethyl 4-(2-oxo-1,2-dihydro-imidazo[4,5-c]quinolin-3-yl)-piperidine-1-carboxylate A solution of 100 mg (0.15 mmol) (R)-1-carboxy-2-(4-hydroxy-3,5-dimethyl-phenyl)-ethyl 4-(2-oxo-1,2-dihydro-imidazo[4,5-c]quinolin-3-yl)-piperidine-1-carboxylate, 53 mg (0.16 mmol) TBTU and 26 µL (0.19 mmol) triethylamine in 1 mL DMF was stirred for 15 min at RT. Then 28 mg (0.16 mmol) 1-(tetrahydropyran-4-yl)-piperazine was added and the reaction solution was stirred for 2 h. The reaction solution was purified by HPLC without any further working up; the fractions containing the product were combined and lyophilised.
Yield: 42 mg (43% of theory)
ESI-MS: (M+H)$^+$=657
retention time (HPLC-MS): 2.9 min (method C)

EXAMPLE 21

(R)-1-(4-hydroxy-3,5-dimethyl-benzyl)-2-oxo-2-[4-(tetrahydropyran-4-yl)-piperazin-1-yl]-ethyl 4-(2-oxo-1,2-dihydro-quinolin-3-yl)-piperidine-1-carboxylate

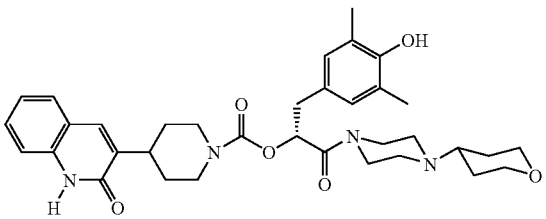

21a) (R)-2-(4-benzyloxy-3,5-dimethyl-phenyl)-1-methoxycarbonyl-ethyl 4-(2-oxo-1,2-dihydro-quinolin-3-yl)-piperidine-1-carboxylate Under a nitrogen atmosphere 0.91 g (4.38 mmol) 4-nitrophenyl chloroformate in 10 mL THF were metered into 20 mL pyridine within 10 min at a bath temperature of 60° C., the mixture was stirred for 10 min, then 1.38 g (4.38 mmol) methyl(R)-3-(4-benzyloxy-3,5-dimethyl-phenyl)-2-hydroxy-propionate in 40 mL pyridine were added and the reaction mixture was stirred for 2 h at 60° C. The reaction solution was combined with 1.00 g (4.38 mmol) 3-piperidin-4-yl-1H-quinoline-2-one and stirred for 4 h at 100° C. The reaction mixture was evaporated down i.vac. and the residue was purified by HPLC. The fractions containing the product were combined, evaporated down i.vac., the residue was made alkaline with 15% $K_2CO_3$ solution, the precipitate was suction filtered, washed with 20 mL water and dried at 50° C.

Yield: 0.62 g (25% of theory)
ESI-MS: $(M+H)^+=569$
retention time (HPLC-MS): 5.1 min (method A)

21 b) (R)-2-(4-benzyloxy-3,5-dimethyl-phenyl)-1-carboxy-ethyl 4-(2-oxo-1,2-dihydro-quinolin-3-yl)-piperidine-1-carboxylate A solution of 38 mg (1.60 mmol) LiOH in 50 mL water was added to a solution of 600 mg (1.06 mmol) (R)-2-(4-benzyloxy-3,5-dimethyl-phenyl)-1-methoxycarbonyl-ethyl 4-(2-oxo-1,2-dihydro-quinolin-3-yl)-piperidine-1-carboxylate in 30 mL THF and the reaction mixture was stirred for 1 h at RT. The organic solvent was eliminated i.vac., the aqueous residue was diluted with 50 mL water and acidified with 1 M HCL. The precipitate formed was filtered off, washed with 10 mL water and dried at 50° C.

Yield: 600 mg (100% of theory)
ESI-MS: $(M+H)^+=555$
retention time (HPLC-MS): 4.3 min (method A)

21c) (R)-2-(4-hydroxy-3,5-dimethyl-phenyl)-1-carboxy-ethyl 4-(2-oxo-1,2-dihydro-quinolin-3-yl)-piperidine-1-carboxylate A suspension of 600 mg (1.08 mmol) (R)-2-(4-benzyloxy-3,5-dimethyl-phenyl)-1-carboxy-ethyl 4-(2-oxo-1,2-dihydro-quinolin-3-yl)-piperidine-1-carboxylate and 250 mg of 10% Pd/C in 50 mL isopropanol was hydrogenated at 50° C. and 3447 hPa hydrogen pressure for 2 h. The catalyst was suction filtered, the filtrate was evaporated down i.vac., the residue was triturated with 50 mL diethyl ether, suction filtered, washed with 20 mL diethyl ether and dried at 50° C.

Yield: 430 mg (86% of theory)
ESI-MS: $(M+H)^+=465$
retention time (HPLC-MS): 3.4 min (method A)

21d) (R)-1-(4-hydroxy-3,5-dimethyl-benzyl)-2-oxo-2-[4-(tetrahydropyran-4-yl)-piperazin-1-yl]-ethyl 4-(2-oxo-1,2-dihydro-quinolin-3-yl)-piperidine-1-carboxylate Prepared analogously to Example 81 from 80.0 mg (0.17 mmol) (R)-2-(4-hydroxy-3,5-dimethyl-phenyl)-1-carboxy-ethyl 4-(2-oxo-1,2-dihydro-quinolin-3-yl)-piperidine-1-carboxylate and 29.2 mg (0.17 mmol) 1-(tetrahydropyran-4-yl)-piperazine, the reaction mixture being stirred overnight at RT.

Yield: 52 mg (49% of theory)
ESI-MS: $(M+H)^+=617$
retention time (HPLC-MS): 3.0 min (method A)

EXAMPLE 22

(R)-1-(4-hydroxy-3,5-dimethyl-benzyl)-2-oxo-2-[4-(tetrahydropyran-4-yl)-piperazin-1-yl]-ethyl 4-(7-methoxy-2-oxo-1,2,4,5-tetrahydro-1,3-benzodiazepin-3-yl)-piperidine-1-carboxylate

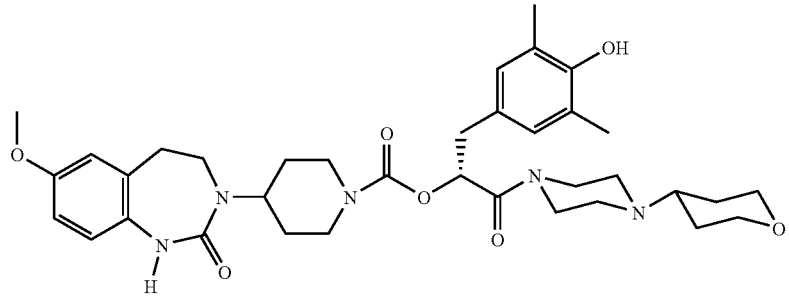

22a) (R)-2-(4-benzyloxy-3,5-dimethyl-phenyl)-1-methoxycarbonyl-ethyl 4-(7-methoxy-2-oxo-1,2,4,5-tetrahydro-1,3-benzodiazepin-3-yl)-piperidine-1-carboxylate Prepared analogously to Example 21a from 1.41 g (3.63 mmol) methyl(R)-3-(4-benzyloxy-3,5-dimethyl-phenyl)-2-hydroxy-propionate, 0.75 g (3.63 mmol) 4-nitrophenyl chloroformate and 1.00 g (3.63 mmol) 7-methoxy-3-piperidin-4-yl-1,3,4,5-tetrahydro-1,3-benzodiazepin-2-one.

Yield: 0.65 g (29% of theory)
ESI-MS: $(M+H)^+=616$
retention time (HPLC-MS): 5.1 min (method A)

22b) (R)-2-(4-benzyloxy-3,5-dimethyl-phenyl)-1-carboxy-ethyl 4-(7-methoxy-2-oxo-1,2,4,5-tetrahydro-1,3-benzodiazepin-3-yl)-piperidine-1-carboxylate Prepared analogously to Example 21b from 0.65 g (1.06 mmol) (R)-2-(4-benzyloxy-3,5-dimethyl-phenyl)-1-methoxycarbonyl-ethyl 4-(7-methoxy-2-oxo-1,2,4,5-tetrahydro-1,3-benzodiazepin-3-yl)-piperidine-1-carboxylate and 38.4 mg (1.60 mmol) LiOH.

Yield: 0.64 g (100% of theory)
ESI-MS: (M+H)$^+$=602
retention time (HPLC-MS): 4.5 min (method A)

22c) (R)-2-(4-hydroxy-3,5-dimethyl-phenyl)-1-carboxy-ethyl 4-(7-methoxy-2-oxo-1,2,4,5-tetrahydro-1,3-benzodiazepin-3-yl)-piperidine-1-carboxylate Prepared analogously to Example 21c from 0.64 g (1.06 mmol) (R)-2-(4-benzyloxy-3,5-dimethyl-phenyl)-1-carboxy-ethyl 4-(7-methoxy-2-oxo-1,2,4,5-tetra-hydro-1,3-benzodiazepin-3-yl)-piperidine-1-carboxylate and 100 mg 10% Pd/C.
Yield: 0.50 g (92% of theory)
ESI-MS: (M+H)$^+$=512
retention time (HPLC-MS): 3.5 min (method A)

22d) (R)-1-(4-hydroxy-3,5-dimethyl-benzyl)-2-oxo-2-[4-(tetrahydropyran-4-yl)-piperazin-1-yl]-ethyl 4-(7-methoxy-2-oxo-1,2,4,5-tetrahydro-1,3-benzodiazepin-3-yl)-piperidine-1-carboxylate Prepared analogously to Example 81 from 80.0 mg (0.17 mmol) (R)-2-(4-hydroxy-3,5-dimethyl-phenyl)-1-carboxy-ethyl 4-(2-oxo-1,2-dihydro-quinolin-3-yl)-piperidine-1-carboxylate and 29.0 mg (0.17 mmol) 1-(tetrahydropyran-4-yl)-piperazine, the reaction mixture being stirred overnight at RT.
Yield: 78 mg (75% of theory)
ESI-MS: (M+H)$^+$=664
retention time (HPLC-MS): 2.9 min (method A)

EXAMPLE 23

(S)-2-(4-hydroxy-3-methoxy-5-methyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione

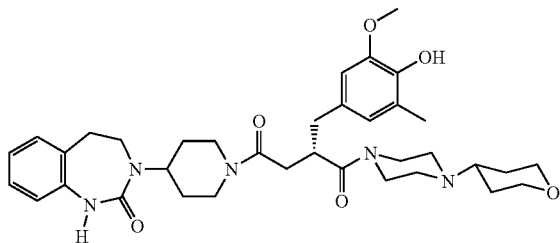

23a) 1-methyl 2-[1-(4-benzyloxy-3-methoxy-5-methyl-phenyl)-meth-(Z)-ylidene]-succinate Prepared analogously to Example 12b from 9.80 g (38.2 mmol) 4-benzyloxy-3-methoxy-5-methyl-benzaldehyde (Example 9c) and 45.0 g (115 mmol) 1-methyl 2-(triphenyl-λ$^5$-phosphanylidene)-succinate.
Yield: 13.6 g (96% of theory)
retention time (HPLC-MS): 12.5 min (method D)

23b) 1-methyl(S)-2-(4-benzyloxy-3-methoxy-5-methyl-benzyl)-succinate

Prepared analogously to Example 12c from 6.15 g (16.6 mmol) 1-methyl 2-[1-(4-benzyloxy-3-methoxy-5-methyl-phenyl)-meth-(Z)-ylidene]-succinate, using 82 mg (0.17 mmol) bis-(1,5-cyclooctadiene)dirhodium(I)dichloride as catalyst and 92 mg (0.17 mmol) tert-butyl(2S,4S)-4-diphenylphosphanyl-2-[(diphenylphosphanyl)-methyl]-pyrrolidine-1-carboxylate as ligand.
Yield: 5.8 g (94% of theory)
ESI-MS: (M+H)$^+$=373
retention time (HPLC-MS): 12.1 min (method D)

23c) methyl(S)-2-(4-benzyloxy-3-methoxy-5-methyl-benzyl)-4-oxo-4-[4-(2-oxo-1,2,4,5-tetrahydro-1,3-benzodiazepin-3-yl)-piperidin-1-yl]-butanoate Prepared analogously to Example 12d from 5.80 g (15.6 mmol) 1-methyl(S)-2-(4-benzyloxy-3-methoxy-5-methyl-benzyl)-succinate and 4.20 g (17.13 mmol) 3-piperidin-4-yl-1,3,4,5-tetrahydro-1,3-benzodiazepin-2-one, using 3.43 g (17.9 mmol) (3-dimethylamino-propyl)-ethyl-carbodiimide and 2.38 g (19.5 mmol) 4-dimethylamino-pyridine for the coupling and 130 mL acetonitrile and 50 mL THF as solvent.
Yield: 7.8 g (84% of theory)
ESI-MS: (M+H)$^+$=600
retention time (HPLC-MS): 13.2 min (method D)

23d) (S)-2-(4-benzyloxy-3-methoxy-5-methyl-benzyl)-4-oxo-4-[4-(2-oxo-1,2,4,5-tetrahydro-1,3-benzodiazepin-3-yl)-piperidin-1-yl]-butanoic acid Prepared analogously to Example 7g from 7.83 g (13.1 mmol) methyl(S)-2-(4-benzyloxy-3-methoxy-5-methyl-benzyl)-4-oxo-4-[4-(2-oxo-1,2,4,5-tetrahydro-1,3-benzodiazepin-3-yl)-piperidin-1-yl]-butanoate and 1.25 g (52.2 mmol) LiOH.
Yield: 7.6 g (99% of theory)
ESI-MS: (M+H)$^+$=586
retention time (HPLC-MS): 11.7 min (method D)

23e) (S)-2-(4-hydroxy-3-methoxy-5-methyl-benzyl)-4-oxo-4-[4-(2-oxo-1,2,4,5-tetrahydro-1,3-benzodiazepin-3-yl)-piperidin-1-yl]-butanoic acid A suspension of 7.60 g (12.98 mmol) (S)-2-(4-benzyloxy-3-methoxy-5-methyl-benzyl)-4-oxo-4-[4-(2-oxo-1,2,4,5-tetrahydro-1,3-benzodiazepin-3-yl)-piperidin-1-yl]-butanoic acid and 0.76 g 10% Pd/C in 2 mL triethylamine and 150 mL MeOH was hydrogenated at RT and 2620 hPa hydrogen pressure for 16 h. To complete the reaction a further 0.38 g 10% Pd/C were added and the mixture was again hydrogenated for 3 h at RT. The catalyst was filtered off through Celite and the filtrate was concentrated by evaporation i.vac. The product was further reacted without purification.
Yield: 7.2 g (81% of theory)
ESI-MS: (M+H)$^+$=496
retention time (HPLC-MS): 7.7 min (method D)

23f) (S)-2-(4-hydroxy-3-methoxy-5-methyl-benzyl)-4-[4-(2-oxo-1,2,4,5-tetrahydro-1,3-benzodiazepin-3-yl)-piperidin-1-yl]-1-[4-(tetrahydropyran-4-yl)-piperazin-1-yl]-butane-1,4-dione Prepared analogously to Example 7i from 100 mg (0.20 mmol) (S)-2-(4-hydroxy-3-methoxy-5-methyl-benzyl)-4-oxo-4-[4-(2-oxo-1,2,4,5-tetrahydro-1,3-benzodiazepin-3-yl)-piperidin-1-yl]-butanoic acid and 58.9 mg (0.24 mmol) 1-(tetrahydropyran-4-yl)-piperazine (used as the bis-hydrochloride salt), using 84.4 mg (0.22 mmol) HATU as the coupling reagent and 111 µL (0.65 mmol) ethyldiisopropylamine as the base.

Yield: 91 mg (56% of theory)
ESI-MS: (M+H)⁺=648
$R_f$=0.70 (silica gel, DCM/MeOH/NH$_3$ 80:20:2)

EXAMPLE 24

(R)-1-(3,5-dibromo-4-hydroxy-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

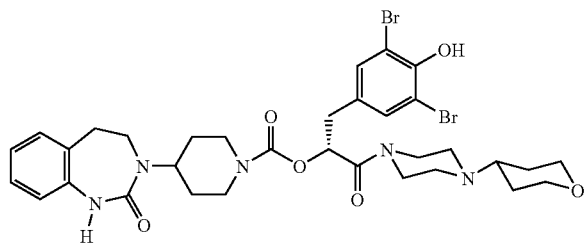

24a) (Z,E)-3-(4-acetoxy-3,5-dibromo-phenyl)-2-acetylamino-acrylic acid

Prepared analogously to Example 9d from 30.0 g (107 mmol) 3,5-dibromo-4-hydroxy-benzaldehyde and 18.8 g (161 mmol) N-acetylglycine. After the reaction mixture was cooled, the product precipitated out and was filtered, washed with water and dried.

Yield: 35.7 g (79% of theory)
ESI-MS: (M+H)⁺=420/422/424 (2 Br)
$R_f$=0.20 (silica gel, DCM/MeOH/AcOH 90:10:1)

24b) 3-(3,5-dibromo-4-hydroxyphenyl)-2-oxo-propionic acid

Prepared analogously to Example 7c from 35.7 g (84.8 mmol) (Z,E)-3-(4-acetoxy-3,5-dibromo-phenyl)-2-acetylamino-acrylic acid and 325 mL of 4 M HCl, using 290 mL NMP as solvent.

Yield: 20.5 g (72% of theory)
ESI-MS: (M–H)⁻=335/337/339 (2 Br)
$R_f$=0.35 (silica gel, DCM/MeOH/AcOH 80:20:2)

24c) (R)-3-(3,5-dibromo-4-hydroxy-phenyl)-2-hydroxy-propionic acid

Prepared analogously to Example 7d from 14.5 g (42.9 mmol) 3-(3,5-dibromo-4-hydroxy-phenyl)-2-oxo-propionic acid and 30.9 g (96.3 mmol) (1R)-B-chlorodiisopinocampheylborane.

Yield: 12.7 g (87% of theory)
ESI-MS: (M–H)⁻=337/339/341 (2 Br)
$R_f$=0.4 (silica gel, DCM/MeOH/AcOH 80:20:2)
retention time (HPLC-MS): 6.4 min (method G)

24d) methyl(R)-3-(3,5-dibromo-4-hydroxy-phenyl)-2-hydroxy-propionate

Prepared analogously to Example 7e from 14.0 g (34.8 mmol) (R)-3-(3,5-dibromo-4-hydroxy-phenyl)-2-hydroxy-propionic acid, using methanolic HCl (6 M).

Yield: 7.0 g (57% of theory)
ESI-MS: (M–H)⁻=351/353/355 (2 Br)
retention time (HPLC-MS): 9.8 min (method G)

24e) methyl(R)-3-[3,5-dibromo-4-(2-trimethylsilanyl-ethoxymethoxy)-phenyl]-2-hydroxy-propionate Under a nitrogen atmosphere 11.1 g (76.6 mmol) 40% KF/Al$_2$O$_3$ were added to a solution of 6.78 g (19.2 mmol) methyl(R)-3-(3,5-dibromo-4-hydroxy-phenyl)-2-hydroxy-propionate in 100 mL acetonitrile and the resulting suspension was stirred for a few min at RT. Then a solution of 4.07 mL (23.0 mmol) (2-chloromethoxyethyl)-trimethyl-silane in 20 mL acetonitrile was added and the reaction mixture was stirred for 20 h at RT. The mixture was filtered through Celite, the solvent was evaporated down i.vac. and the residue was purified by chromatography (silica gel, n-hexane/EtOAc 7:3).

Yield: 5.49 g (59% of theory)
$R_f$=0.45 (silica gel, n-hexane/EtOAc 1:1)

24f) (R)-2-[3,5-dibromo-4-(2-trimethylsilanyl-ethoxymethoxy)-phenyl]-1-methoxy-carbonyl-ethyl 4-(2-oxo-1,2,4,5-tetrahydro-1,3-benzodiazein-3-yl)-piperidine-1-carboxylate Prepared analogously to Example 7f from 4.63 g (9.56 mmol) methyl(R)-3-[3,5-dibromo-4-(2-trimethylsilanyl-ethoxymethoxy)-phenyl]-2-hydroxy-propionate and 2.35 g (9.56 mmol) 3-piperidin-4-yl-1,3,4,5-tetrahydro-1,3-benzodiazepin-2-one, using 1.23 g (10.04 mmol) 4-dimethylaminopyridine as base and acetonitrile as solvent.

Yield: 4.35 g (69% of theory)
ESI-MS: (M+H)⁺=754/756/758 (2 Br)
retention time (HPLC): 29.2 min (method G)

24g) (R)-2-(3,5-dibromo-4-hydroxy-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere 5.46 mL methanolic H$_2$SO$_4$ (0.5 M) was added to a solution of 4.30 g (5.69 mmol) (R)-2-[3,5-dibromo-4-(2-trimethylsilanyl-ethoxymethoxy)-phenyl]-1-methoxy-carbonyl-ethyl 4-(2-oxo-1,2,4,5-tetrahydro-1,3-benzodiazepin-3-yl)-piperidine-1-carboxylate in 40 mL THF and 40 mL MeOH and the reaction solution was stirred for 6 h at RT. The reaction mixture was evaporated down i.vac. and the residue was further reacted without purification.

Yield: quantitative
ESI-MS: (M+H)⁺=624/626/628 (2 Br)
retention time (HPLC): 17.3 min (method G)

24h) (R)-1-carboxy-2-(3,5-dibromo-4-hydroxy-phenyl)-ethyl 4-(2-oxo-1,2,4,5-tetrahydro-1,3-benzodiazepin-3-yl)-piperidine-1-carboxylate A solution of 0.51 g (21.3 mmol) LiOH was added to a solution of (R)-2-(3,5-dibromo-4-hydroxy-phenyl)-1-methoxycarbonyl-ethyl 4-(2-oxo-1,2,4,5-tetrahydro-1,3-benzodiazepin-3-yl)-piperidine-1-carboxylate (crude product from Example 24g) in 80 mL THF and the reaction mixture was stirred for 3 h at RT. The THF was eliminated i.vac., the aqueous phase was washed with EtOAc, acidified with 10% HCl and the aqueous phase was extracted exhaustively with EtOAc. The combined organic phases were evaporated down i.vac., suspended in diethyl ether, filtered, the residue was dried and then purified by chromatography (silica gel, DCM/MeOH/AcOH 90:10:1).

Yield: 3.5 g (100% of theory)
ESI-MS: (M+H)$^+$=610/612/614 (2 Br)
retention time (HPLC): 14.1 min (method G)

24i) (R)-1-(3,5-dibromo-4-hydroxy-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate Prepared analogously to Example 81 from 100 mg (0.16 mmol) (R)-1-carboxy-2-(3,5-dibromo-4-hydroxy-phenyl)-ethyl 4-(2-oxo-1,2,4,5-tetrahydro-1,3-benzodiazepin-3-yl)-piperidine-1-carboxylate and 30.6 mg (0.18 mmol) 1-(tetrahydropyran-4-yl)-piperazine, the reaction mixture being stirred overnight at RT.

Yield: 72 mg (58% of theory)
ESI-MS: (M+H)$^+$=762/764/766 (2 Br)
retention time (HPLC-MS): 3.0 min (method A)

EXAMPLE 25

(R)-1-(3-bromo-4-hydroxy-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate

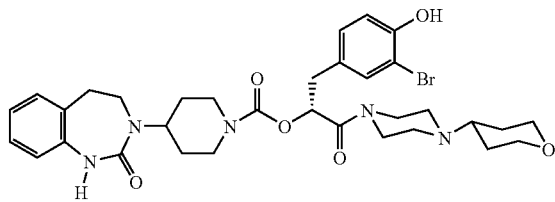

25a) (Z,E)-3-(4-acetoxy-3-bromo-phenyl)-2-acetylamino-acrylic acid

Prepared analogously to Example 9d from 75.0 g (366 mmol) 3-bromo-4-hydroxy-benzaldehyde and 64.2 g (548 mmol) N-acetylglycine. After the reaction mixture had cooled the product precipitated out and was then filtered, washed with water and dried.

Yield: 69.8 g (56% of theory)
retention time (HPLC): 7.6 min (method G)

25b) 3-(3-bromo-4-hydroxy-phenyl)-2-oxo-propionic acid

Prepared analogously to Example 24b from 69.7 g (204 mmol) (Z,E)-3-(4-acetoxy-3-bromo-phenyl)-2-acetylamino-acrylic acid and 750 mL 4 M HCl.

Yield: 45.8 g (87% of theory)
retention time (HPLC): 7.8 min (method G)

25c) (R)-3-(3-bromo-4-hydroxy-phenyl)-2-hydroxy-propionic acid

Prepared analogously to Example 7d from 45.0 g (174 mmol) 3-(3-bromo-4-hydroxy-phenyl)-2-oxo-propionic acid and 114.2 g (356 mmol) (1R)-B-chlorodiisopinocampheylborane.

Yield: 53.7 g (89% of theory) retention time (HPLC): 4.0 min (method G)

25d) methyl(R)-3-(3-bromo-4-hydroxy-phenyl)-2-hydroxy-propionate 2.5 mL concentrated sulphuric acid were added to a solution of 53.6 g (154 mmol) (R)-3-(3-bromo-4-hydroxy-phenyl)-2-hydroxy-propionic acid in 250 mL MeOH and the reaction mixture was stirred for 4 h at RT. The mixture was evaporated down i.vac., the residue was taken up in 250 mL EtOAc, the organic phase was washed twice with 100 mL saturated NaHCO$_3$ solution and saturated NaCl solution and dried over Na$_2$SO$_4$. After the desiccant and solvent had been eliminated the residue was further reacted without purification.

Yield: quantitative
retention time (HPLC): 6.8 min (method G)

25e) methyl(R)-3-[3-bromo-4-(2-trimethylsilanyl-ethoxymethoxy)-phenyl]-2-hydroxy-propionate 6.7 mL (39.1 mmol) ethyldiisopropylamine were added to a solution of 10.2 g (34.6 mmol) methyl(R)-3-(3-bromo-4-hydroxy-phenyl)-2-hydroxy-propionate in 100 mL DCM and the reaction mixture was cooled in the ice bath. Then a solution of 7.9 mL (44.6 mmol) (2-chloromethoxy-ethyl)-trimethyl-silane in 20 mL DCM was added. The reaction mixture was stirred for 3 h at RT and then combined with another 0.67 mL ethyldiisopropylamine and 0.8 mL (4.5 mmol) (2-chloromethoxy-ethyl)-trimethyl-silane to complete the reaction and stirred for 1.5 h at RT. The reaction mixture was washed with 5% Na$_2$CO$_3$ solution and saturated NaCl solution and dried over Na$_2$SO$_4$. After the desiccant and solvent had been eliminated the residue was purified by chromatography (silica gel, Cyc/EtOAc 75:25).

Yield: 9.6 g (68% of theory)
retention time (HPLC): 15.1 min (method D)

25f) (R)-2-[3-bromo-4-(2-trimethylsilanyl-ethoxymethoxy)-phenyl]-1-methoxycarbonyl-ethyl 4-(2-oxo-1,2,4,5-tetrahydro-1,3-benzodiazepin-3-yl)-piperidine-1-carboxylate Prepared analogously to Example 24f from 4.55 g (11.2 mmol) methyl(R)-3-[3-bromo-4-(2-trimethylsilanyl-ethoxymethoxy)-phenyl]-2-hydroxy-propionate and 2.75 g (11.2 mmol) 3-piperidin-4-yl-1,3,4,5-tetrahydro-1,3-benzodiazepin-2-one.

Yield: 5.46 g (72% of theory)
retention time (HPLC): 16.5 min (method D)

25g) (R)-2-(3-bromo-4-hydroxy-phenyl)-1-methoxycarbonyl-ethyl 4-(2-oxo-1,2,4,5-tetrahydro-1,3-benzodiazepin-3-yl)-piperidine-1-carboxylate Prepared analogously to Example 24g from 5.40 g (7.98 mmol) (R)-2-[3-bromo-4-(2-trimethylsilanyl-ethoxy-methoxy)-phenyl]-1-methoxycarbonyl-ethyl 4-(2-oxo-1,2,4,5-tetrahydro-1,3-benzodiazepin-3-yl)-piperidine-1-carboxylate and 7.7 mL (4.2 mmol) methanolic sulphuric acid (0.5 M). The crude product (5.44 g) was further reacted without purification.

Yield: quantitative
retention time (HPLC): 9.9 min (method D)

25h) (R)-2-(3-bromo-4-hydroxy-phenyl)-1-carboxy-ethyl 4-(2-oxo-1,2,4,5-tetrahydro-1,3-benzodiazepin-3-yl)-piperidine-1-carboxylate A solution of 0.84 g (34.1 mmol) LiOH in 20 mL water was added to a solution of 5.44 g of the crude product from Example 25g in 80 mL THF and the reaction mixture was stirred for 1 h at RT. The organic solvent was eliminated i.vac., the aqueous phase was washed with EtOAc, acidified with 10% HCl and exhaustively extracted with EtOAc. The combined organic phases were washed with saturated NaCl solution and dried over $Na_2SO_4$. After the desiccant and solvent had been eliminated the residue was triturated with 90 mL diethyl ether, filtered, the solid was washed with diethyl ether and dried at 45° C.

Yield: 4.10 g (89% of theory)
retention time (HPLC): 8.2 min (method D)

25i) (R)-1-(3-bromo-4-hydroxy-benzyl)-2-oxo-2-[4-(tetrahydropyran-4-yl)-piperazin-1-yl]-ethyl 4-(2-oxo-1,2,4,5-tetrahydro-1,3-benzodiazepin-3-yl)-piperidine-1-carboxylate Prepared analogously to Example 7i from 100 mg (0.19 mmol) (R)-2-(3-bromo-4-hydroxy-phenyl)-1-carboxy-ethyl 4-(2-oxo-1,2,4,5-tetrahydro-1,3-benzodiazepin-3-yl)-piperidine-1-carboxylate and 35.1 mg (0.21 mmol) 1-(tetrahydropyran-4-yl)-piperazine.

Yield: 58 mg (45% of theory)
ESI-MS: $(M+H)^+=684/686$ (Br)
retention time (HPLC-MS): 2.4 min (method A)

EXAMPLE 26

(R)-1'-(4-hydroxy-3,5-dimethyl-benzyl)-2-[4-(tetrahydropyran-4-yl)-piperazin-1-yl]-2-oxo-ethyl 1',2'-dihydro-2'-oxospiro-4H-3',1-benzoxazine-4,4'-piperidine-1-carboxylate

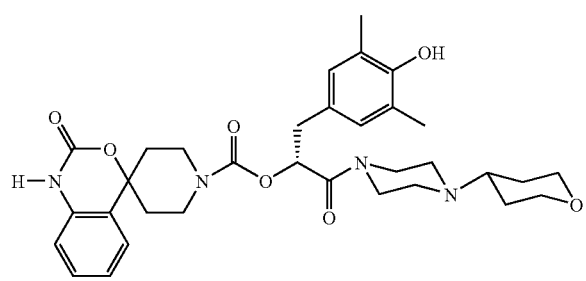

26a) (R)-2-(4-benzyloxy-3,5-dimethyl-phenyl)-1-carboxy-ethyl 1',2'-dihydro-2'-oxospiro-4H-3' 1-benzoxazine-4,4'-piperidine-1-carboxylate Prepared analogously to Example 2g from 2.00 g (6.36 mmol) methyl(R)-3-(4-benzyloxy-3,5-dimethyl-phenyl)-2-hydroxy-propionate and 1.63 g (6.40 mmol) 3-piperidin-4-yl-1,3,4,5-tetrahydro-1,3-benzodiazepin-2-one. The hydrolysis of the methyl ester was carried out with 310 mg (12.95 mmol) LiOH.

Yield: 1.00 g (29% of theory)
ESI-MS: $(M+NH_4)^+=562$
$R_f=0.12$ (silica gel, DCM/Cyc/MeOH/$NH_3$ 70:15:15:2)

26b) (R)-1-(4-benzyloxy-3,5-dimethyl-benzyl)-2-[4-(tetrahydropyran-4-yl)-piperazin-1-yl]-2-oxo-ethyl 1',2'-dihydro-2'-oxospiro-4H-3',1-benzoxazine-4,4'-piperidine-1-carboxylate Prepared analogously to Example 81 from 200 mg (0.37 mmol) (R)-2-(4-benzyloxy-3,5-dimethyl-phenyl)-1-carboxy-ethyl 1',2'-dihydro-2'-oxospiro-4H-3',1-benzoxazine-4,4'-piperidine-1-carboxylate and 70.0 mg (0.41 mmol) 1-(tetrahydropyran-4-yl)-piperazine.

Yield: 130 mg (51% of theory)
ESI-MS: $(M+H)^+=697$
$R_f=0.42$ (silica gel, DCM/Cyc/MeOH/$NH_3$ 70:15:15:2)

26c) (R)-1-(4-hydroxy-3,5-dimethyl-benzyl)-2-[4-(tetrahydropyran-4-yl)-piperazin-1-yl]-2-oxo-ethyl 1',2'-dihydro-2'-oxospiro-4H-3',1-benzoxazine-4,4'-piperidine-1-carboxylate A suspension of 120 mg (0.17 mmol) (R)-1-(4-benzyloxy-3,5-dimethyl-benzyl)-2-[4-(tetrahydropyran-4-yl)-piperazin-1-yl]-2-oxo-ethyl 1',2'-dihydro-2'-oxospiro-4H-3',1-benzoxazine-4,4'-piperidine-1-carboxylate and 20 mg 10% Pd/C in 20 mL MeOH was hydrogenated at RT and 3000 hPa hydrogen pressure for 7.5 h. The catalyst was suction filtered and the filtrate was concentrated by evaporation. The residue was triturated with DIPE, suction filtered and dried at 50° C.

Yield: 95 mg (91% of theory)
ESI-MS: $(M+H)^+=607$
$R_f=0.41$ (silica gel, DCM/Cyc/MeOH/$NH_3$ 70:15:15:2)

The following Examples describe the preparation of pharmaceutical formulations which contain as active substance any desired compound of general formula I:

EXAMPLE I

Capsules for Powder Inhalation Containing 1 mg of Active Ingredient

Composition:

1 capsule for powder inhalation contains:

| | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

EXAMPLE II

Inhalable Solution for Respimat® Containing 1 mg of Active Ingredient

Composition:
1 spray contains:

| | |
|---|---|
| active ingredient | 1.0 mg |
| benzalkonium chloride | 0.002 mg |
| disodium edetate | 0.0075 mg |
| purified water ad | 15.0 μl |

Method of Preparation:
The active ingredient and benzalkonium chloride are dissolved in water and transferred into Respimat® cartridges.

EXAMPLE III

Inhalable Solution for Nebulisers Containing 1 mg of Active Ingredient

Composition:
1 vial contains:

| | |
|---|---|
| active ingredient | 0.1 g |
| sodium chloride | 0.18 g |
| benzalkonium chloride | 0.002 g |
| purified water ad | 20.0 ml |

Method of Preparation:
The active ingredient, sodium chloride and benzalkonium chloride are dissolved in water.

EXAMPLE IV

Propellant Gas-Operated Metering Aerosol Containing 1 mg of Active Ingredient

Composition:
1 puff contains:

| | |
|---|---|
| active ingredient | 1.0 mg |
| lecithin | 0.1% |
| propellant gas ad | 50.0 μl |

Method of Preparation:
The micronised active ingredient is homogeneously suspended in the mixture of lecithin and propellant gas. The suspension is transferred into a pressurised container with a metering valve.

EXAMPLE V

Nasal Spray Containing 1 mg of Active Ingredient

Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:
The active ingredient and the excipients are dissolved in water and transferred into a suitable container.

EXAMPLE VI

Injectable Solution Containing 5 mg of Active Substance Per 5 ml

Composition:

| | |
|---|---|
| active substance | 5 mg |
| glucose | 250 mg |
| human serum albumin | 10 mg |
| glycofurol | 250 mg |
| water for injections ad | 5 ml |

Preparation:
Glycofurol and glucose are dissolved in water for injections (Wfl); human serum albumin is added; active ingredient is dissolved with heating; made up to specified volume with Wfl; transferred into ampoules under nitrogen gas.

EXAMPLE VII

Injectable Solution Containing 100 mg of Active Substance Per 20 ml

Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:
Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

EXAMPLE VIII

Lyophilisate Containing 10 mg of Active Substance

Composition:

| | |
|---|---|
| Active substance | 10 mg |
| Mannitol | 300 mg |
| human serum albumin | 20 mg |
| water for injections ad | 2 ml |

Preparation:

Mannitol is dissolved in water for injections (Wfl); human serum albumin is added; active ingredient is dissolved with heating; made up to specified volume with Wfl; transferred into vials; freeze-dried.

Solvent for Lyophilisate:

| | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (Wfl); transferred into ampoules.

EXAMPLE IX

Tablets Containing 20 mg of Active Substance

Composition:

| | |
|---|---|
| active substance | 20 mg |
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

EXAMPLE X

Capsules Containing 20 mg Active Substance

Composition:

| | |
|---|---|
| active substance | 20 mg |
| corn starch | 80 mg |
| highly dispersed silica | 5 mg |
| magnesium stearate | 2.5 mg |

Preparation:

Active substance, corn starch and silica are homogeneously mixed; mixed with magnesium stearate; the mixture is packed into size for 3 hard gelatine capsules in a capsule filling machine.

EXAMPLE XI

Suppositories Containing 50 mg of Active Substance

Composition:

| | |
|---|---|
| active substance | 50 mg |
| hard fat (Adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

EXAMPLE XII

Injectable Solution Containing 10 mg of Active Substance Per 1 ml

Composition:

| | |
|---|---|
| active substance | 10 mg |
| mannitol | 50 mg |
| human serum albumin | 10 mg |
| water for injections ad | 1 ml |

Preparation:

Mannitol is dissolved in water for injections (Wfl); human serum albumin is added; active ingredient is dissolved with heating; made up to specified volume with Wfl; transferred into ampoules under nitrogen gas.

The invention claimed is:

1. A compound of the formula I $$R^1 \underset{O}{\overset{O}{\|}} C - X - \underset{\underset{O}{\overset{\|}{C}} - R^3 - R^4}{\overset{CH_2 - R^2}{|}}$$
(I)

wherein:
 X denotes $CH_2$, NH or O,
 $R^1$ denotes a moiety of the formula

[structure showing benzazepine with $R^{1.1}$ substituent, connected to piperidine with N—*]

wherein
 $R^{1.1}$ denotes H or $H_3C$—O,
 $R^2$ denotes a moiety selected from the group consisting of

[pyridine with CH_3 and NH_2 substituents]

[benzene with $R^{2.1}$, $R^{2.2}$, Cl substituents]

[benzene with $R^{2.1}$, $R^{2.2}$, Br substituents]

[benzene with $R^{2.1}$, $R^{2.2}$ substituents]

-continued
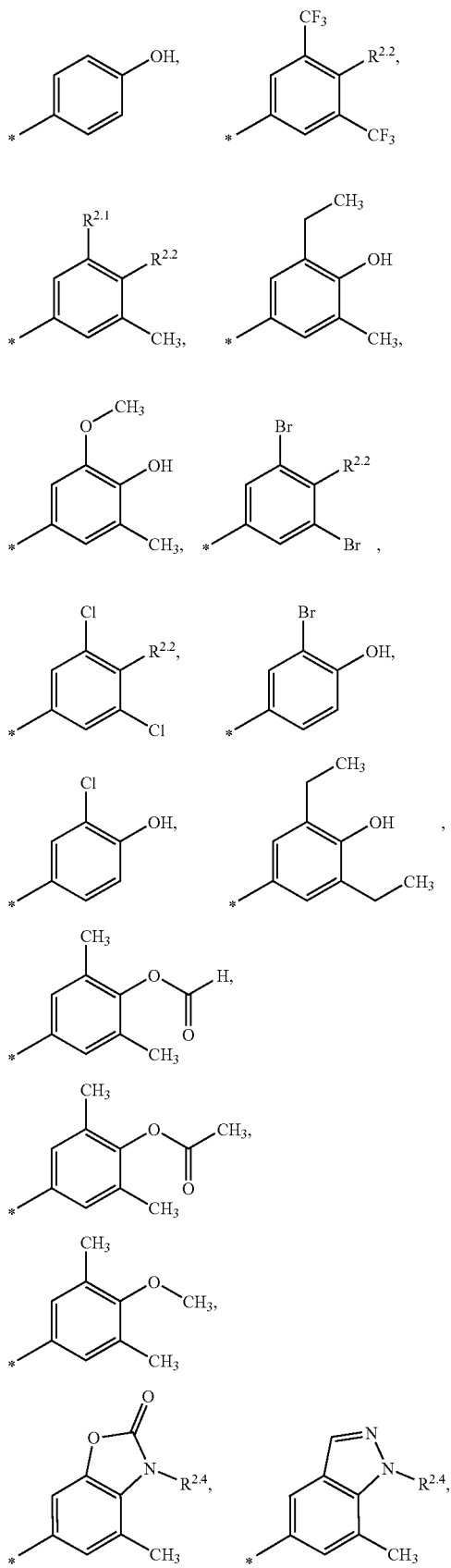
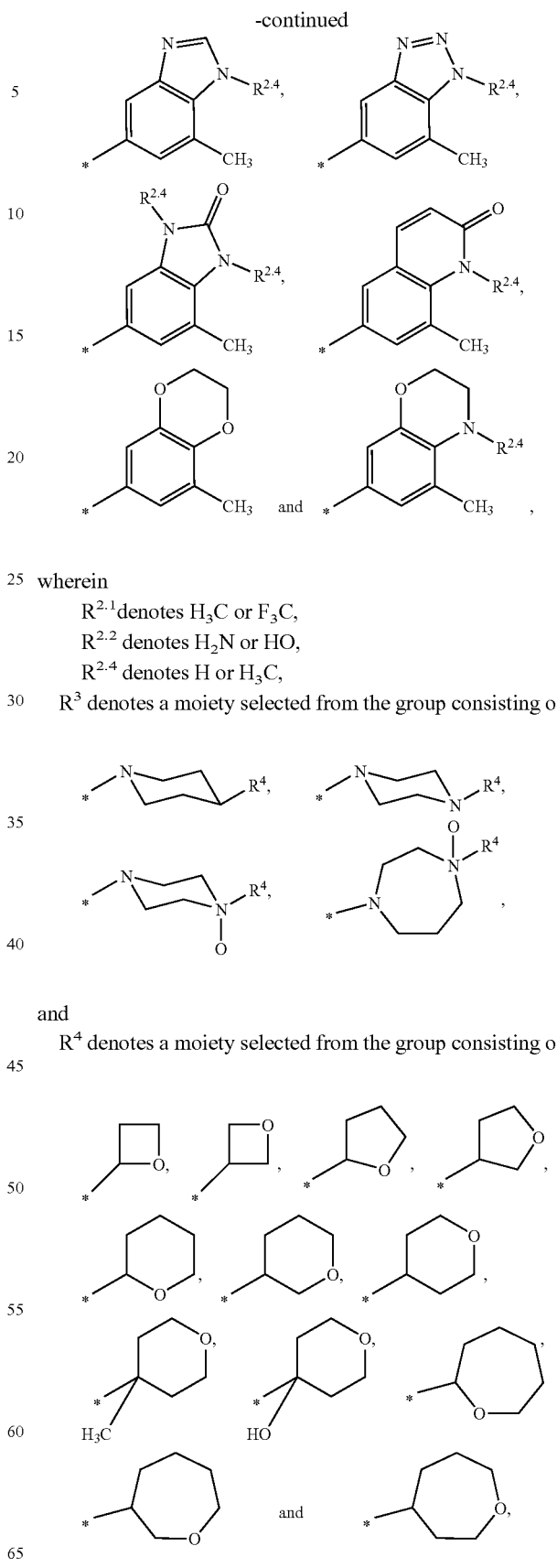
wherein
  $R^{2.1}$ denotes $H_3C$ or $F_3C$,
  $R^{2.2}$ denotes $H_2N$ or HO,
  $R^{2.4}$ denotes H or $H_3C$,
  $R^3$ denotes a moiety selected from the group consisting of
and
  $R^4$ denotes a moiety selected from the group consisting of
or a tautomor or salt thereof.

2. A compound of the formula I according to claim 1, wherein
R² denotes a moiety selected from the group consisting of
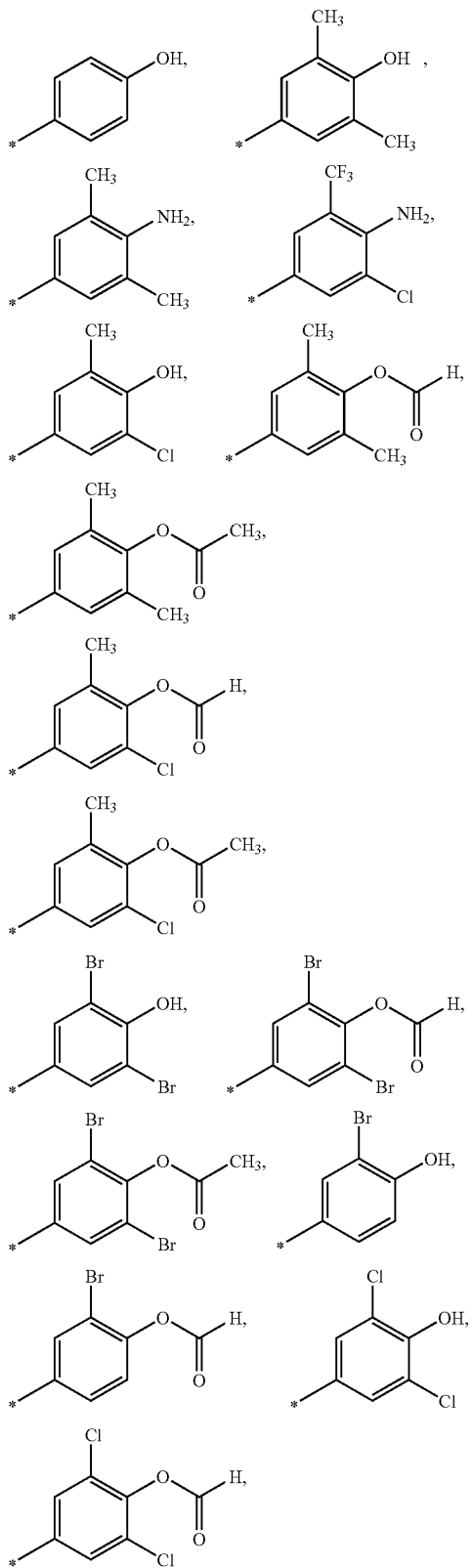
-continued
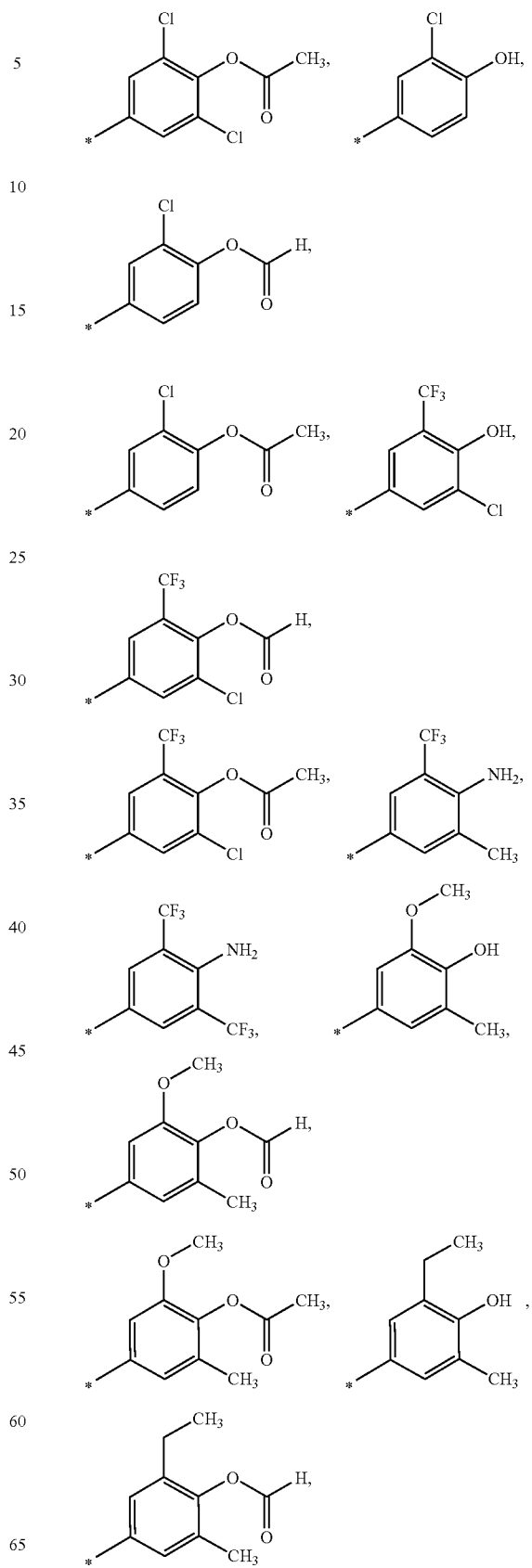

-continued
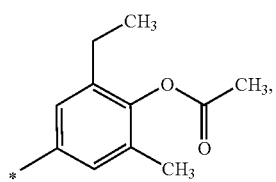
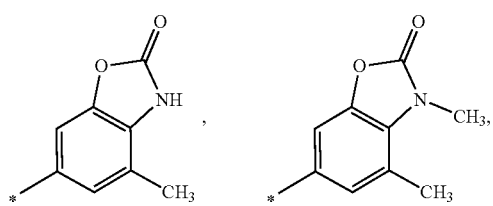
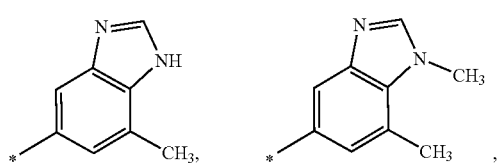
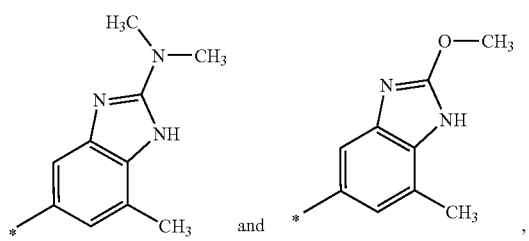
R³ denotes a moiety selected from to group consisting of
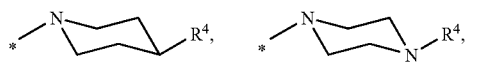
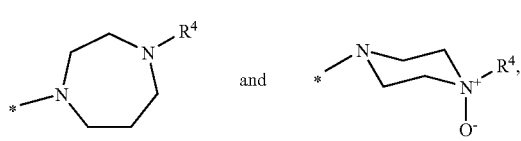
R⁴ denotes a moiety selected from to group consisting of
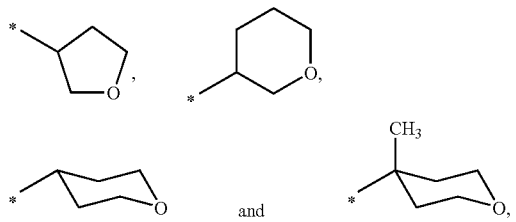
or a tautomer or salt tereof.
3. A compound of the formula I according to claim 1, wherein
R² denotes a moiety selected from to group consisting of
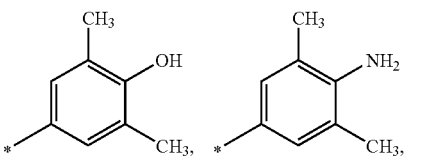
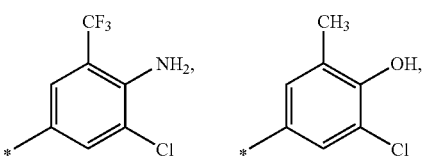
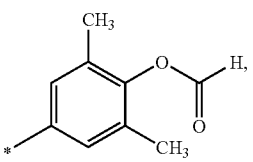
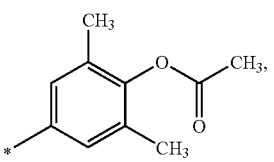
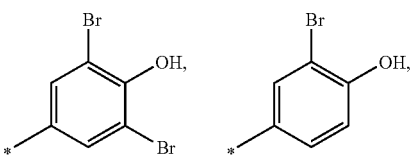
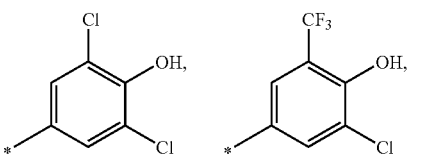
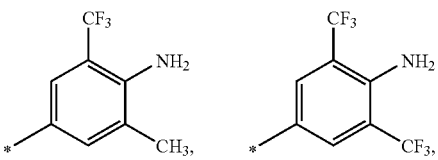
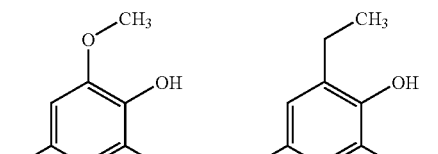
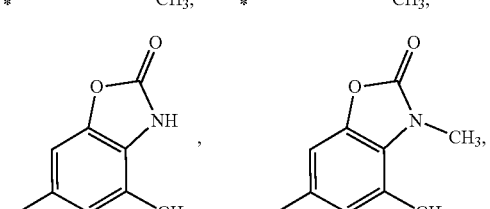

-continued
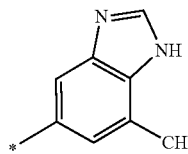 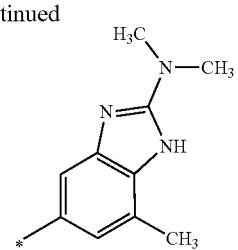 and
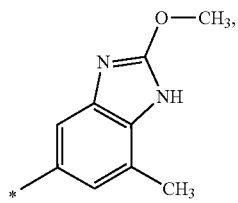
$R^3$-$R^4$ together represent a moiety selected from the group consisting of
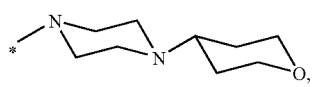
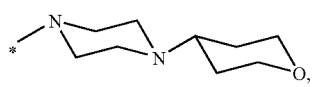
-continued
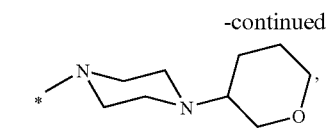
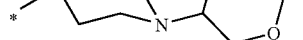
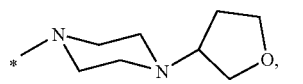
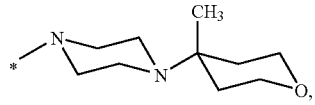 and
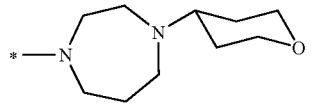
or a tautomer or salt thereof.
4. A compound according to claim 1 selected from the group consisting of:
| No. | Structure |
|---|---|
| (28) | 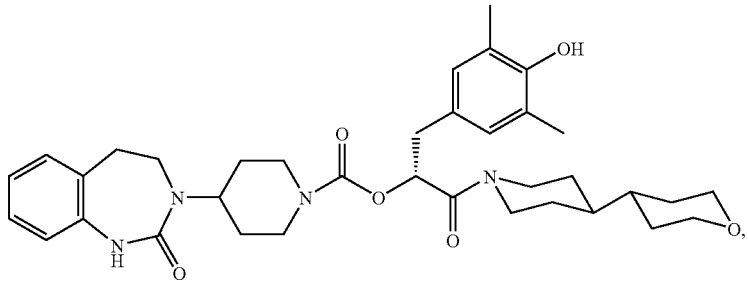 |
| (29) | 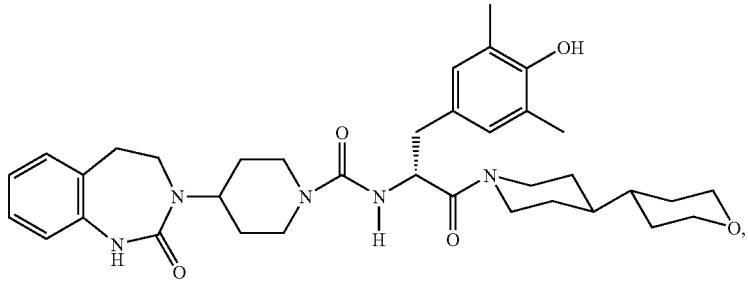 |

-continued
| No. | Structure |
|---|---|
| (30) | 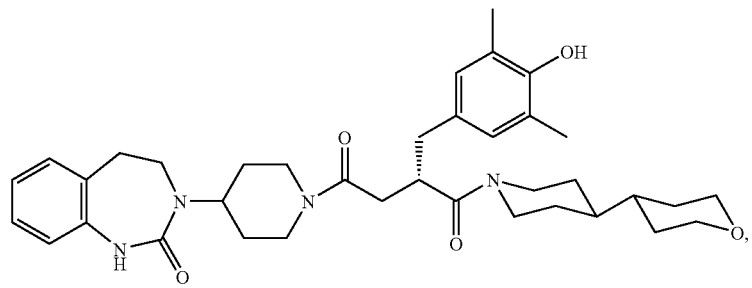 |
| (31) | 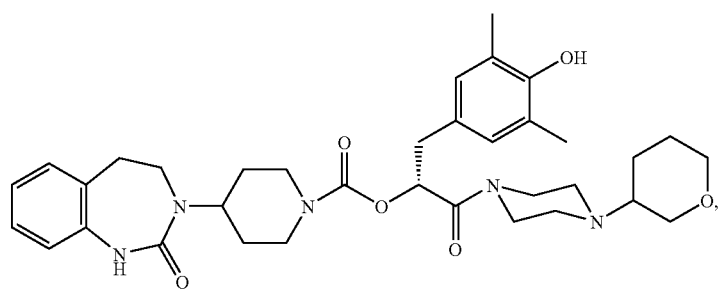 |
| (32) | 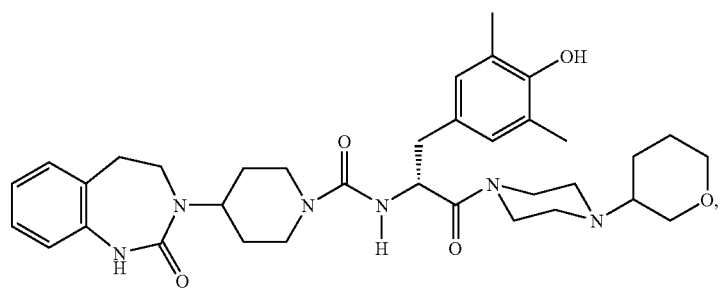 |
| (33) | 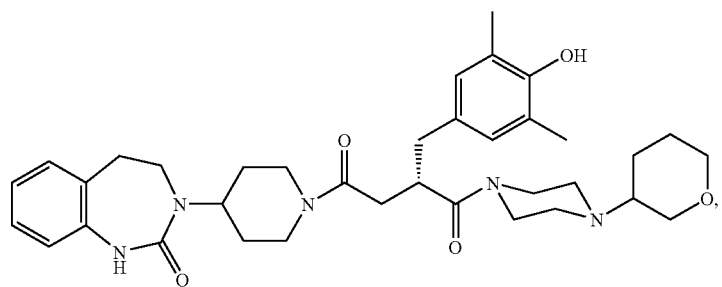 |
| (34) | 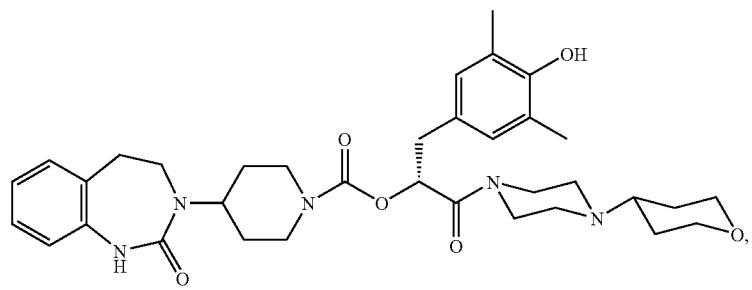 |

| No. | Structure |
|---|---|
| (35) | 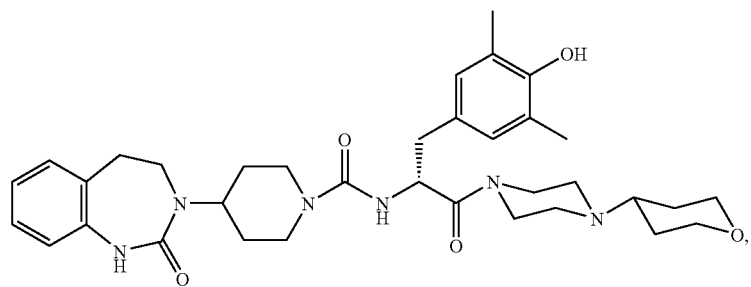 |
| (36) | 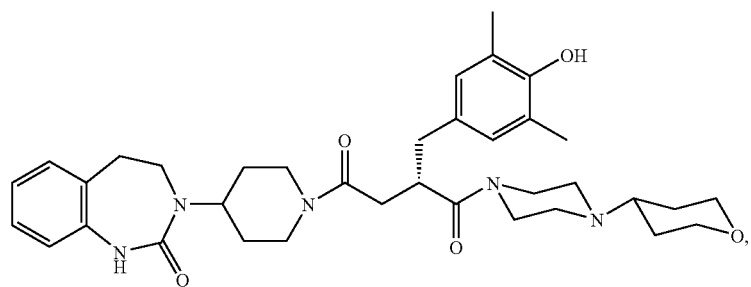 |
| (37) | 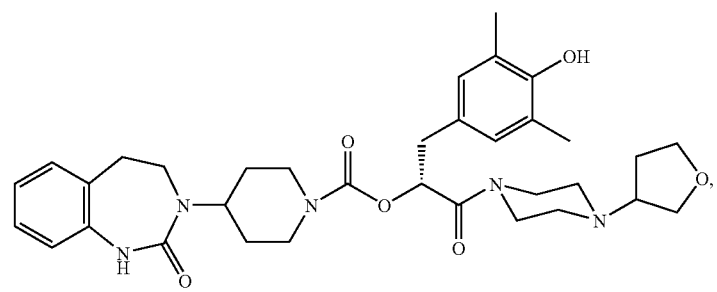 |
| (38) | 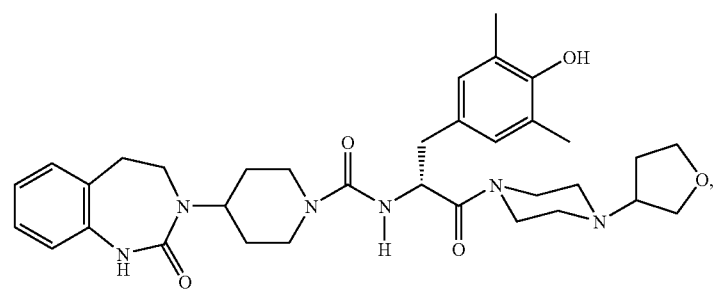 |
| (39) | 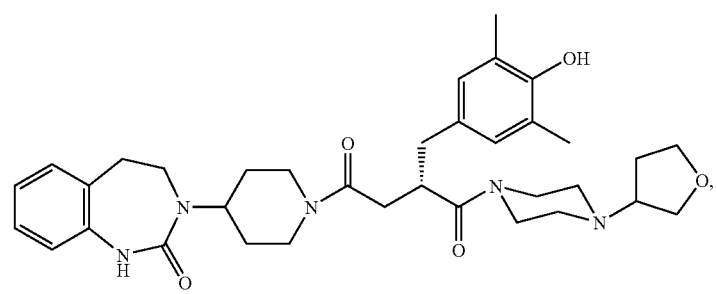 |

| No. | Structure |
|---|---|
| (40) | 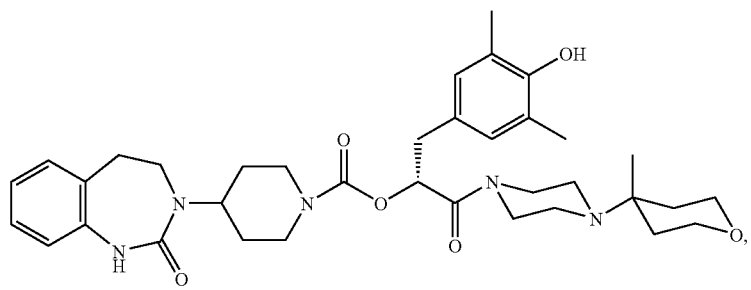 |
| (41) | 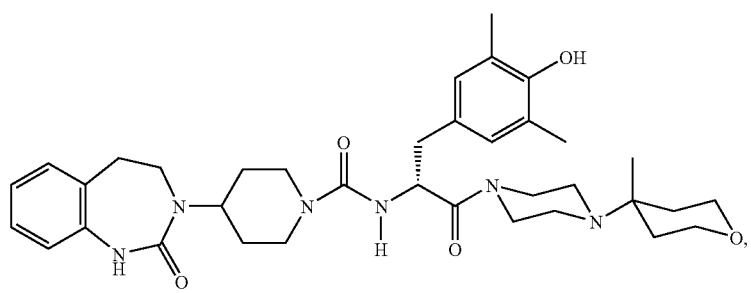 |
| (42) | 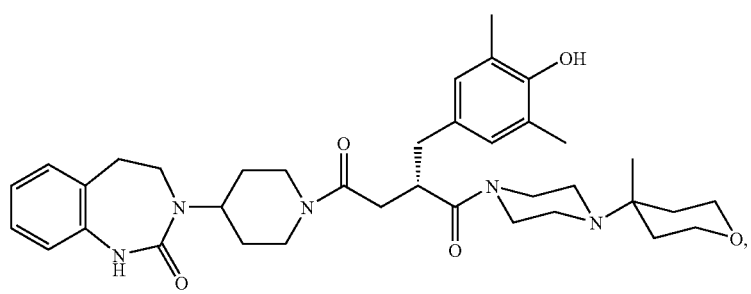 |
| (43) | 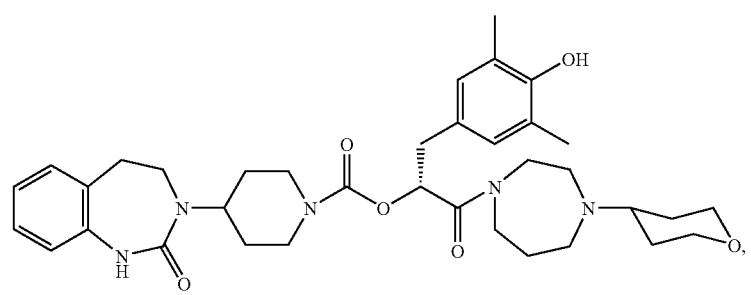 |
| (44) | 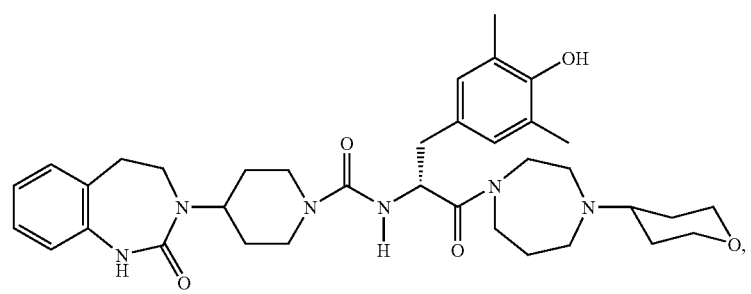 |

| No. | Structure |
|---|---|
| (45) | 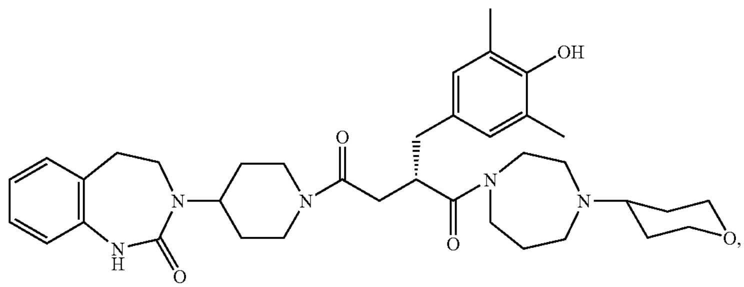 |
| (46) | 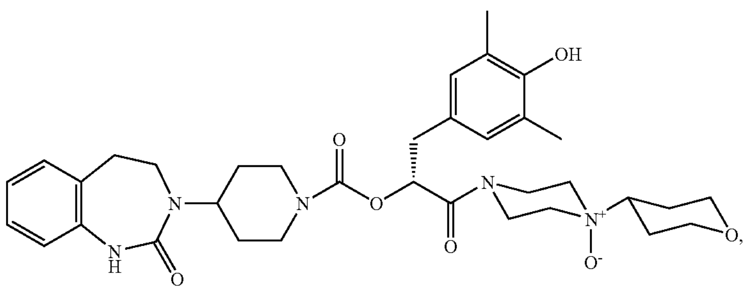 |
| (47) | 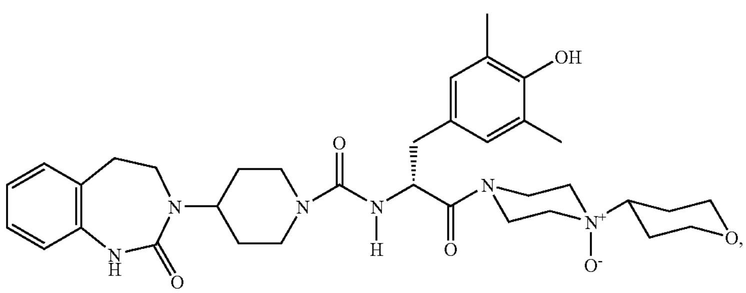 |
| (48) | 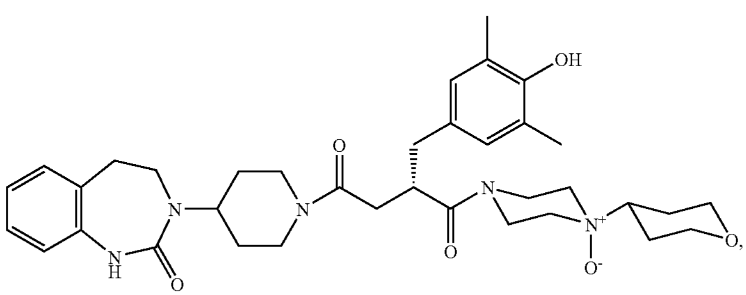 |
| (49) | 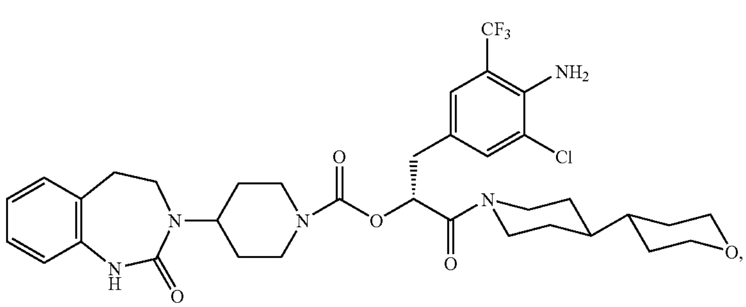 |

-continued
| No. | Structure |
|---|---|
| (50) | 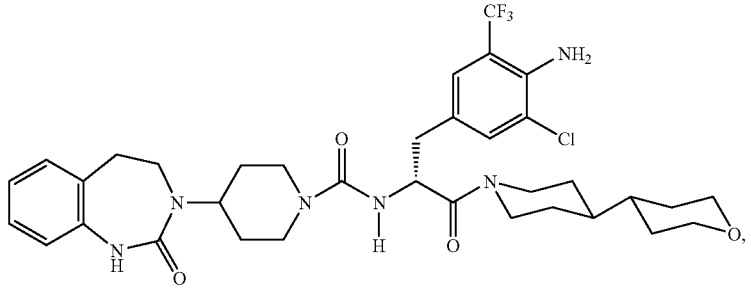 |
| (51) | 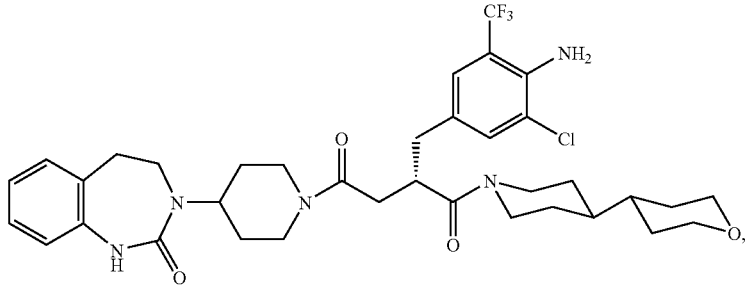 |
| (52) | 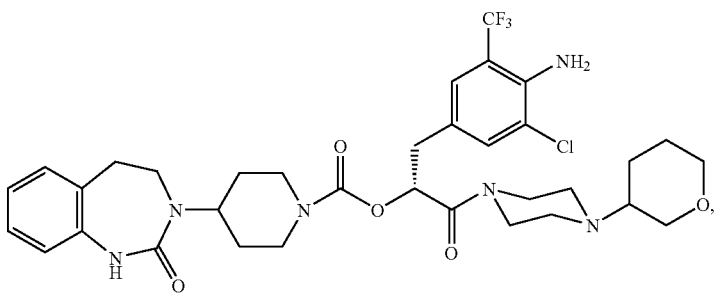 |
| (53) | 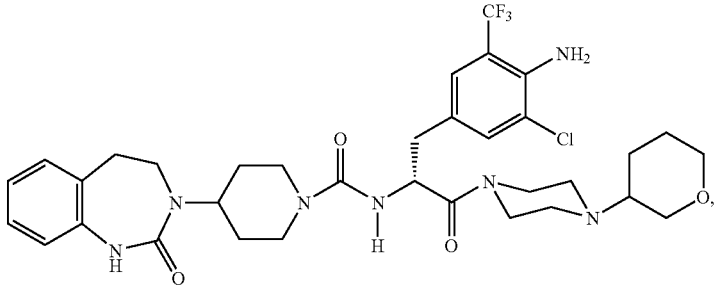 |
| (54) | 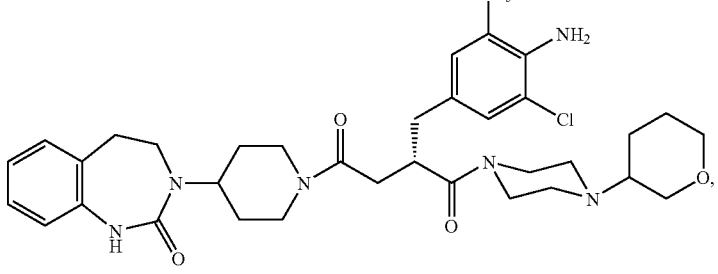 |

| No. | Structure |
|---|---|
| (55) | 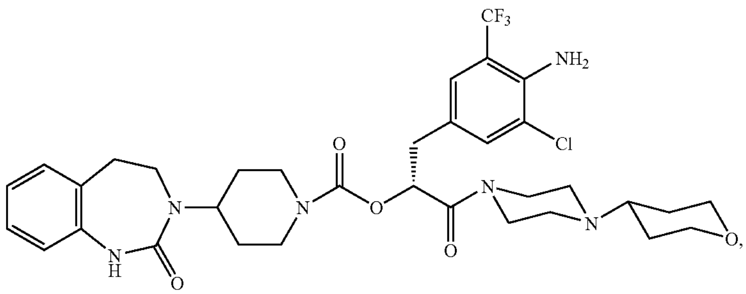 |
| (56) | 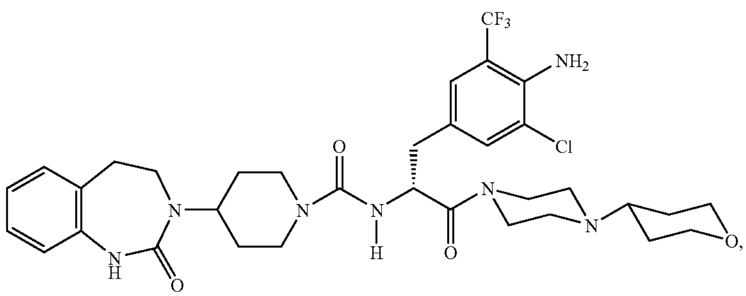 |
| (57) | 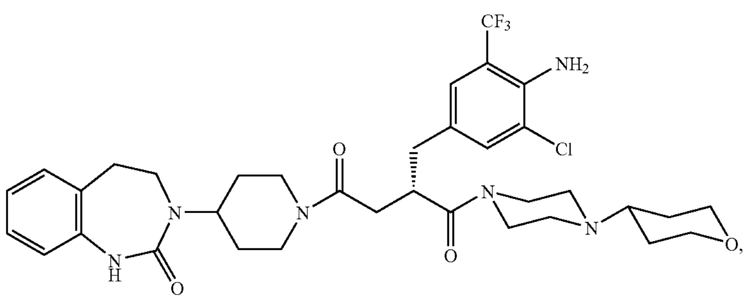 |
| (58) | 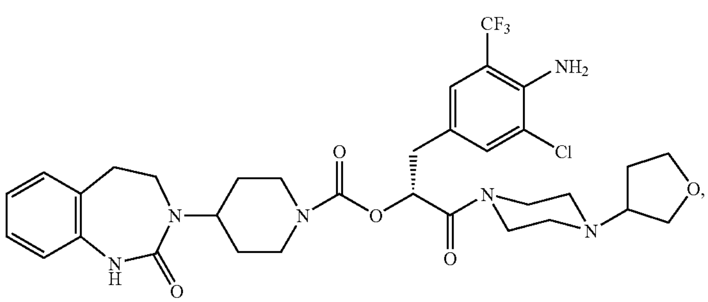 |
| (59) | 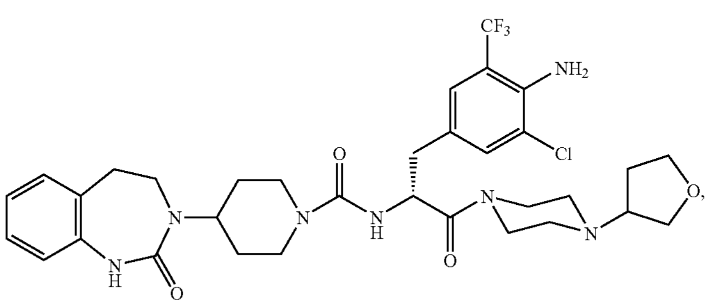 |

-continued
| No. | Structure |
|---|---|
| (60) | 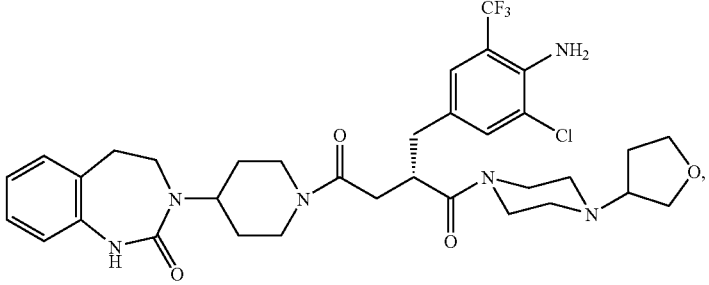 |
| (61) | 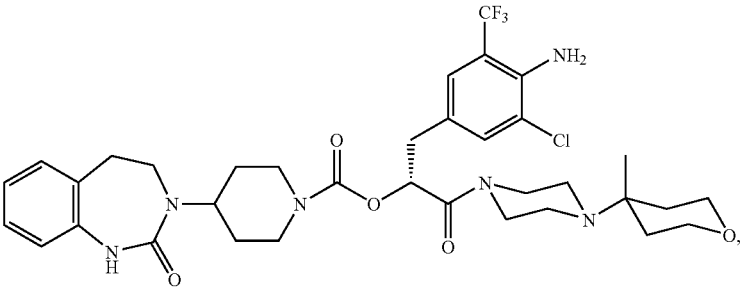 |
| (62) | 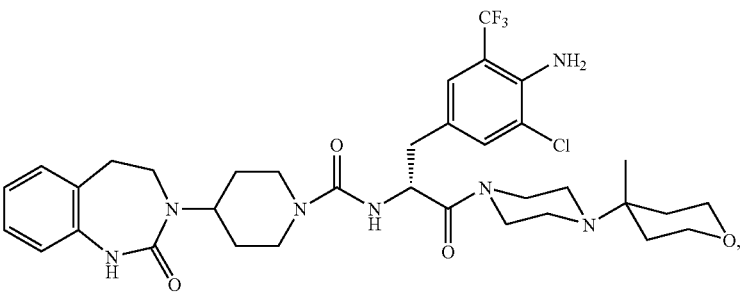 |
| (63) | 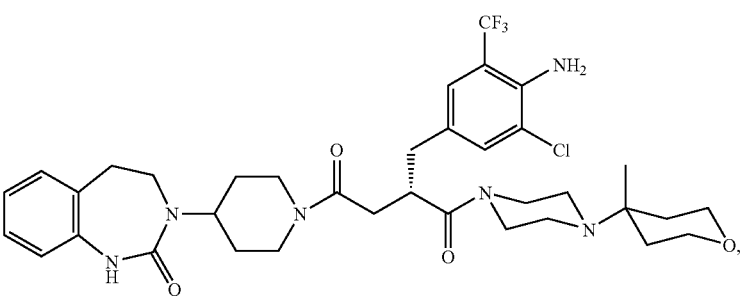 |
| (64) | 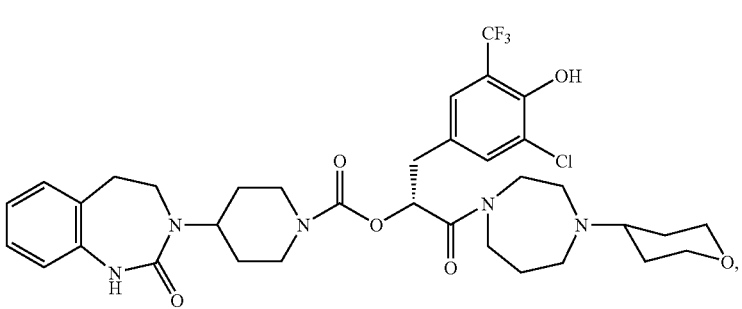 |

| No. | Structure |
|---|---|
| (65) | 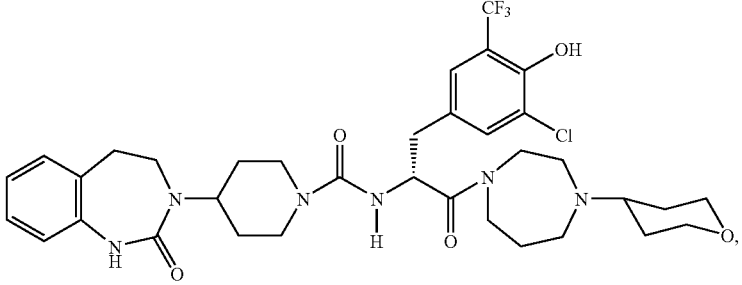 |
| (66) | 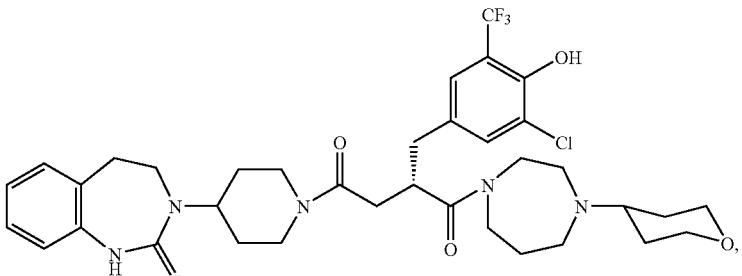 |
| (67) | 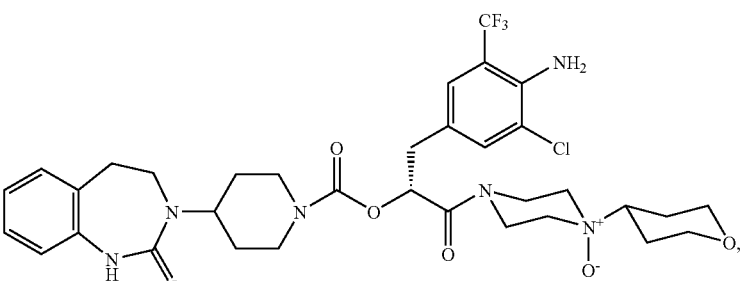 |
| (68) | 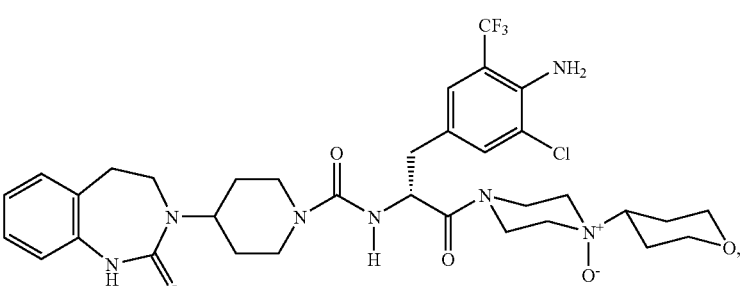 |
| (69) | 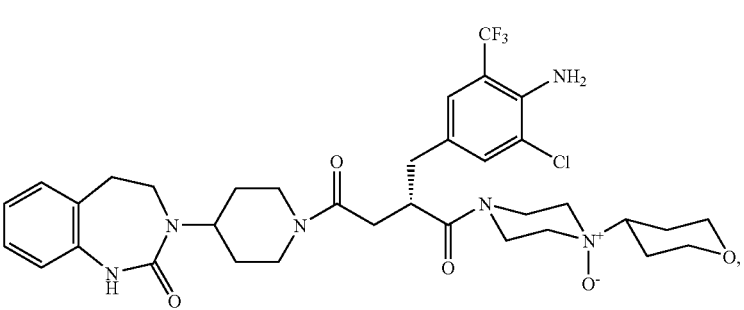 |

| No. | Structure |
|---|---|
| (70) | 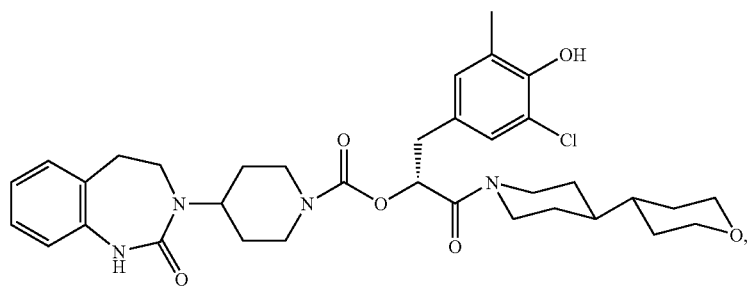 |
| (71) | 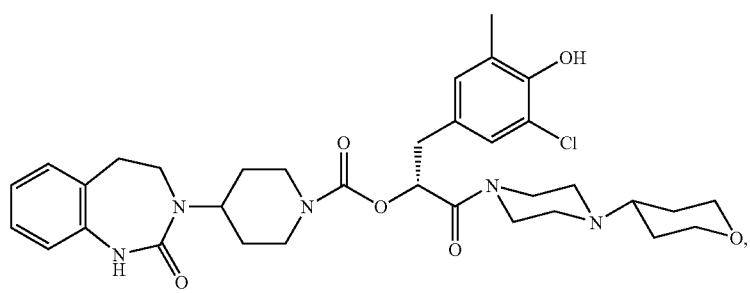 |
| (72) | 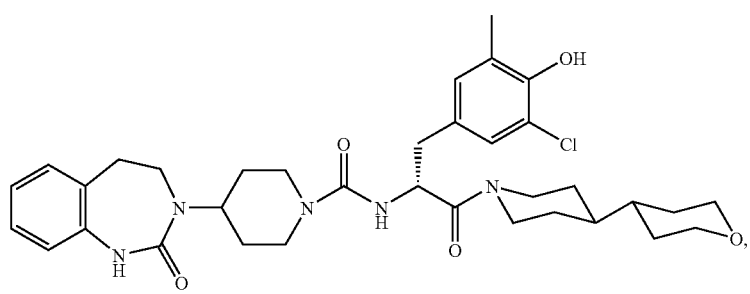 |
| (73) | 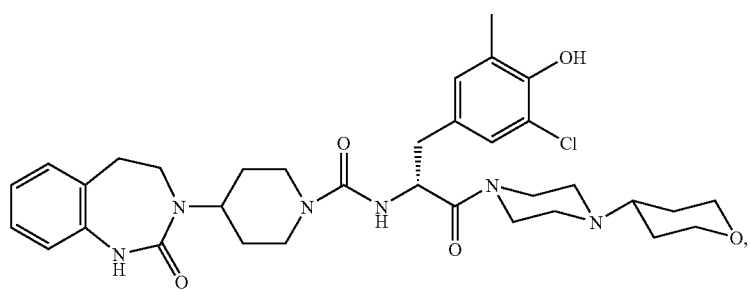 |
| (74) | 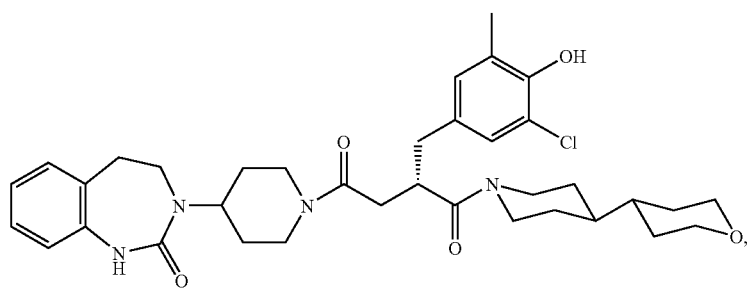 |

-continued
| No. | Structure |
|---|---|
| (75) | 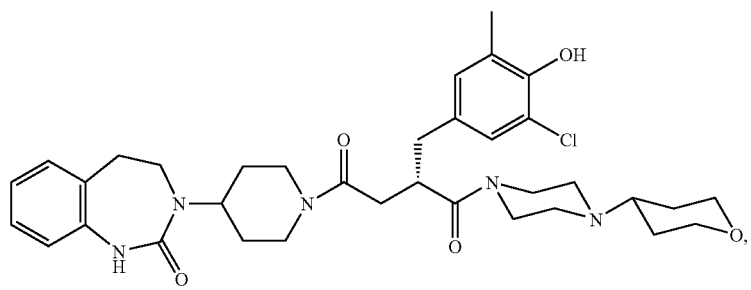 |
| (76) | 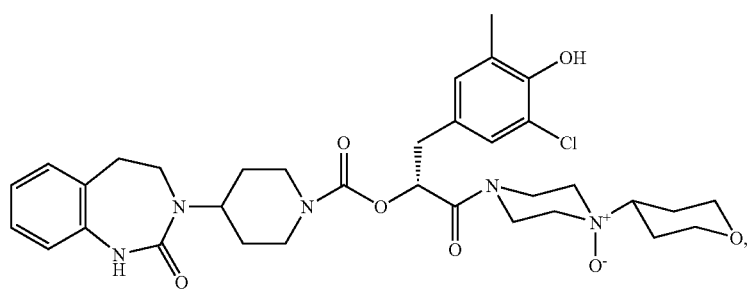 |
| (77) | 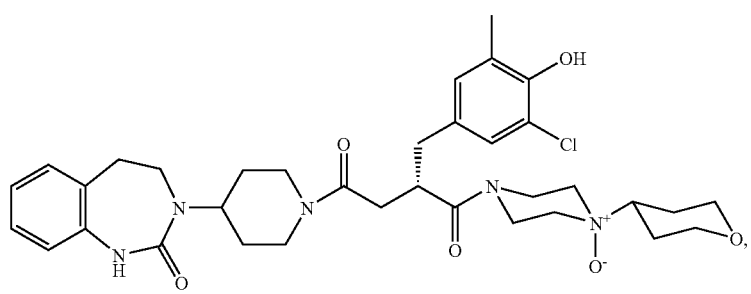 |
| (78) | 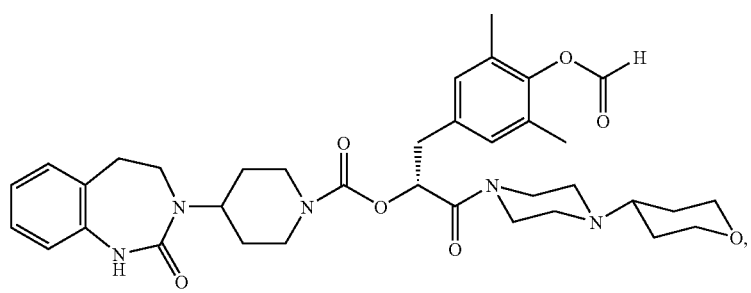 |
| (79) | 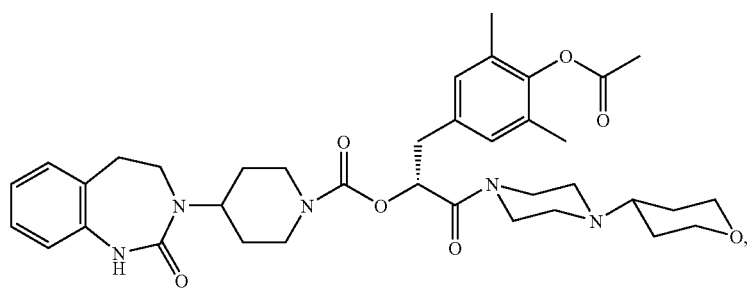 |

| No. | Structure |
|---|---|
| (80) | 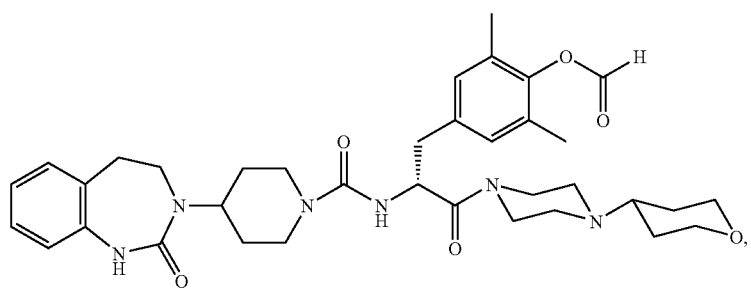 |
| (81) | 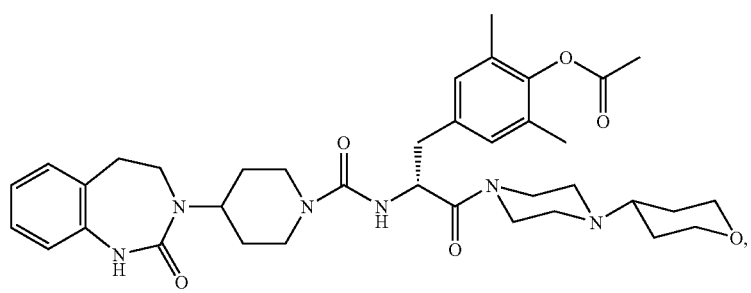 |
| (82) | 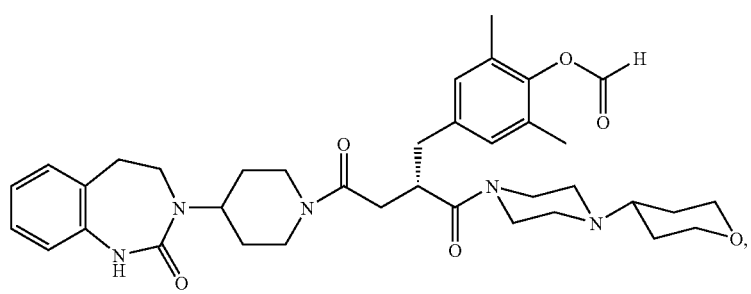 |
| (83) | 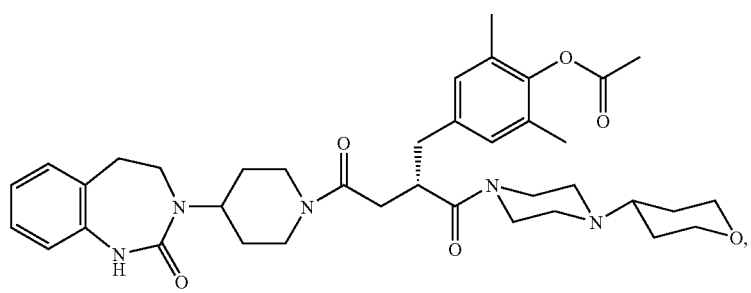 |
| (84) | 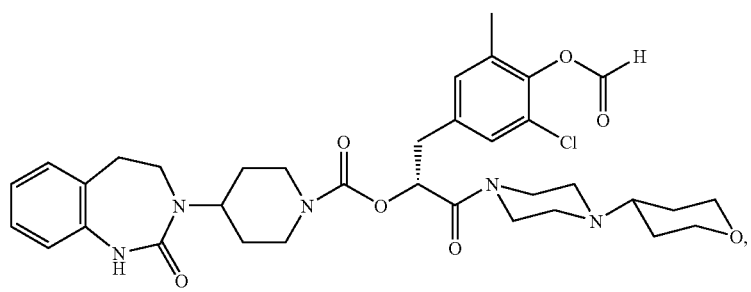 |

| No. | Structure |
|---|---|
| (85) | 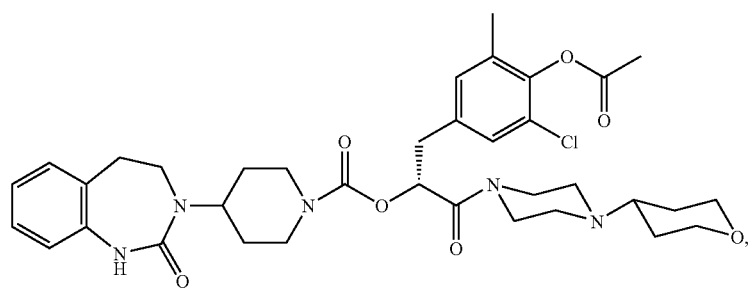 |
| (84a) | 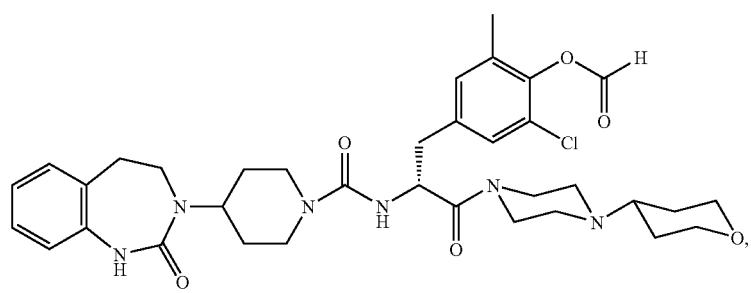 |
| (85a) | 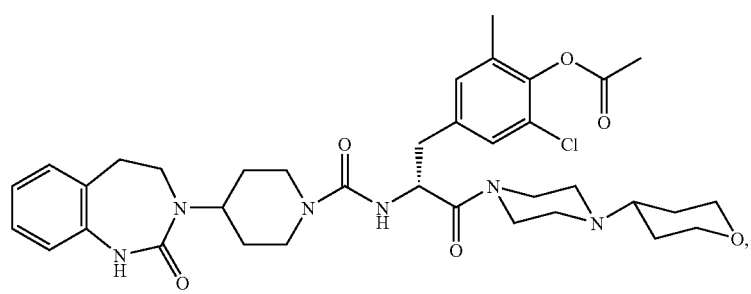 |
| (86) | 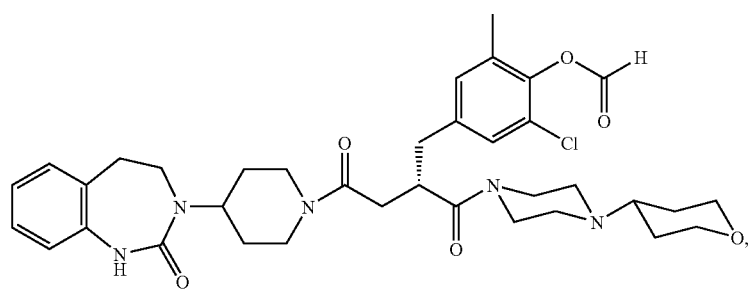 |
| (87) | 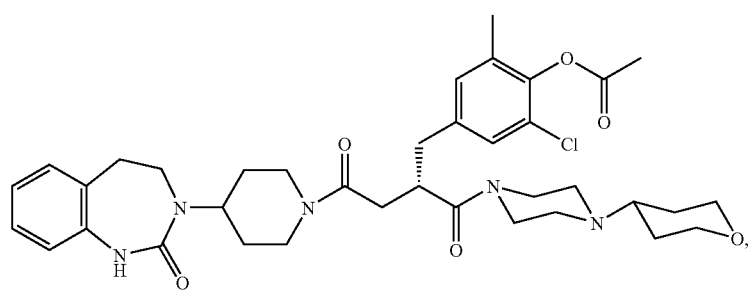 |

| No. | Structure |
|---|---|
| (88) | 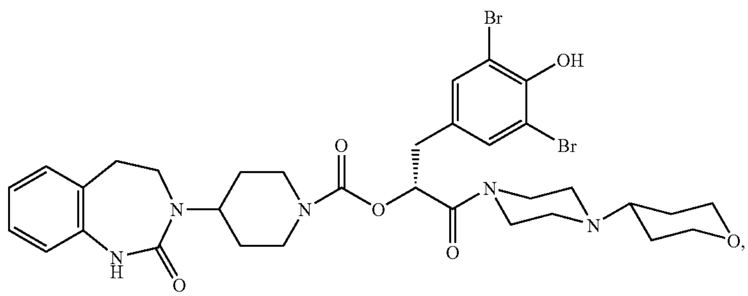 |
| (89) | 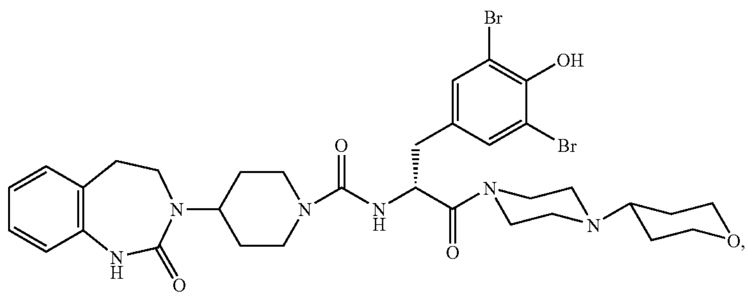 |
| (90) | 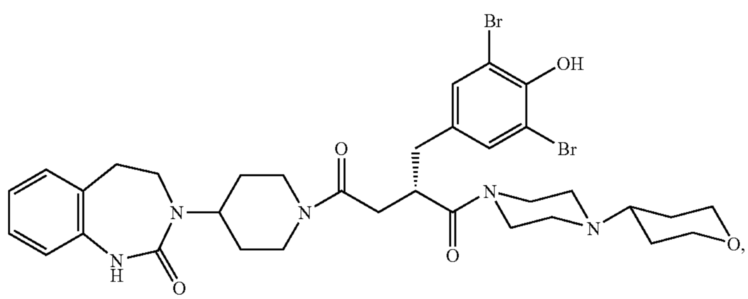 |
| (91) | 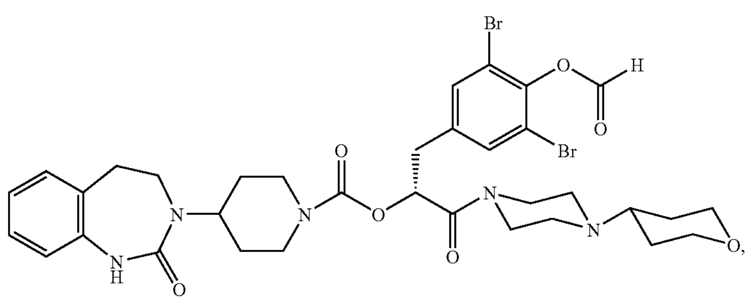 |
| (92) | 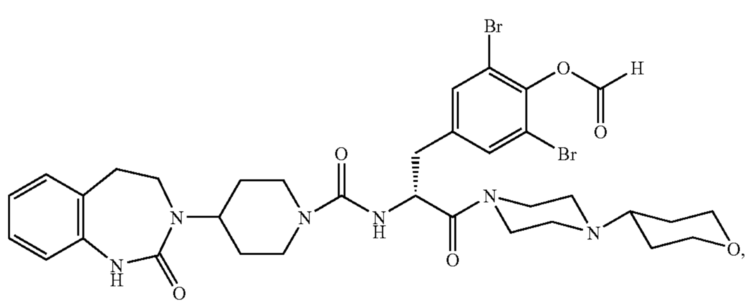 |

| No. | Structure |
|---|---|
| (93) | 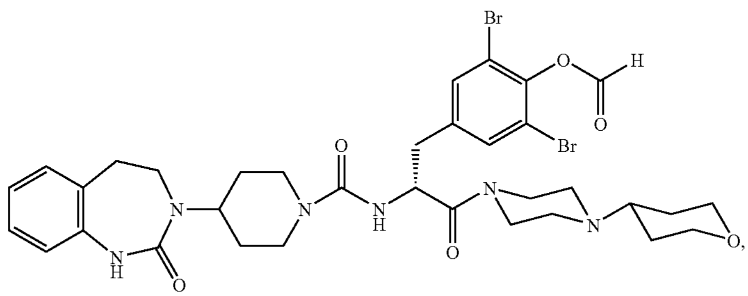 |
| (94) | 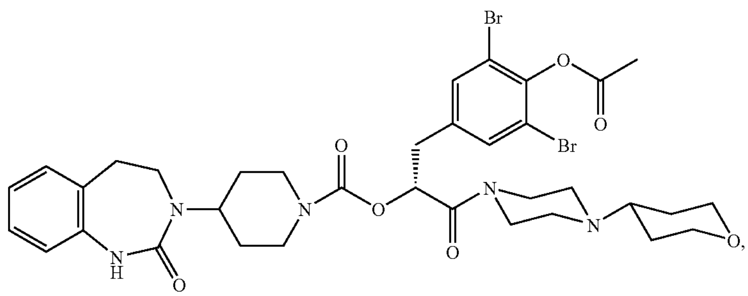 |
| (95) | 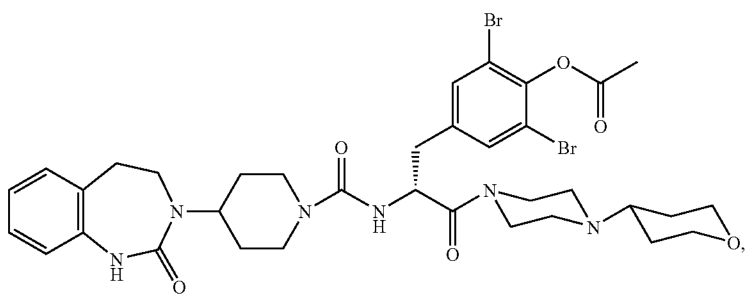 |
| (96) | 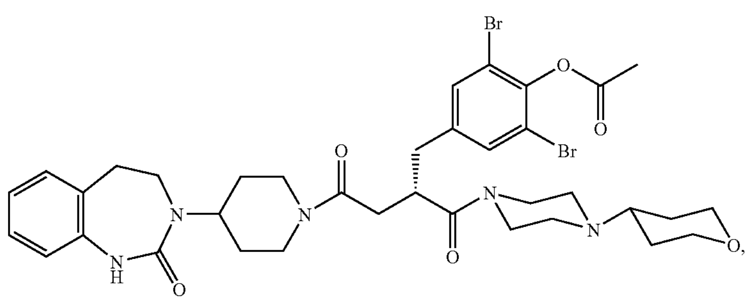 |
| (97) | 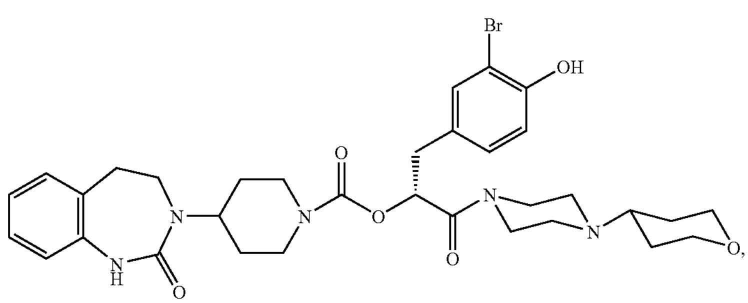 |

-continued

| No. | Structure |
|---|---|
| (98) | 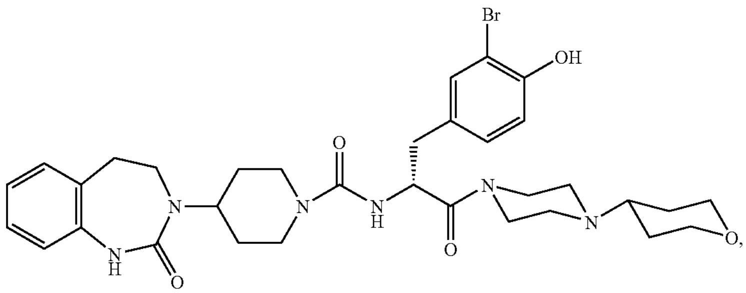 |
| (99) | 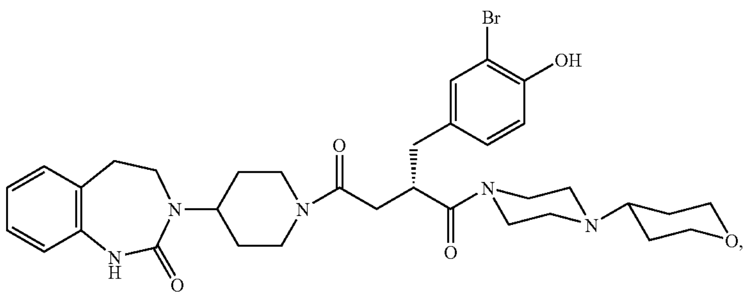 |
| (100) | 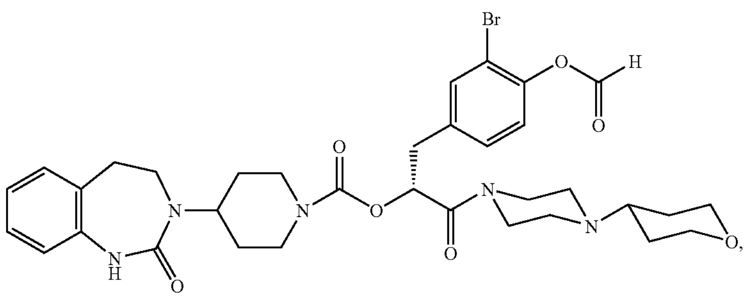 |
| (101) | 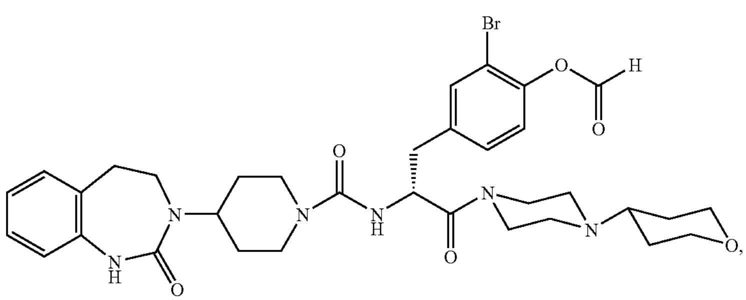 |
| (102) | 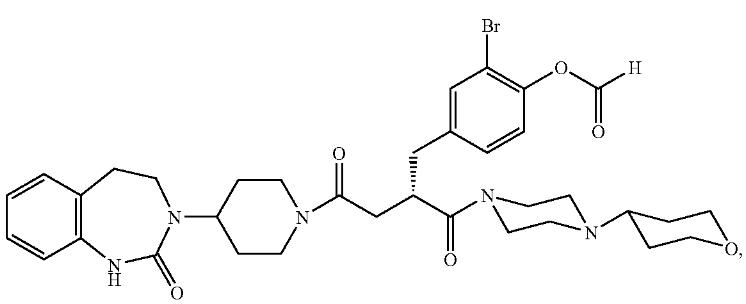 |

-continued

| No. | Structure |
|---|---|
| (103) | 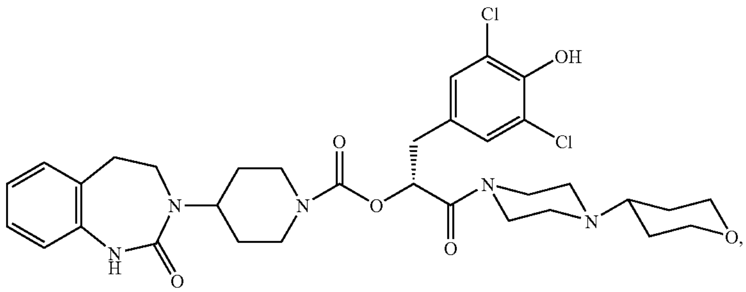 |
| (104) | 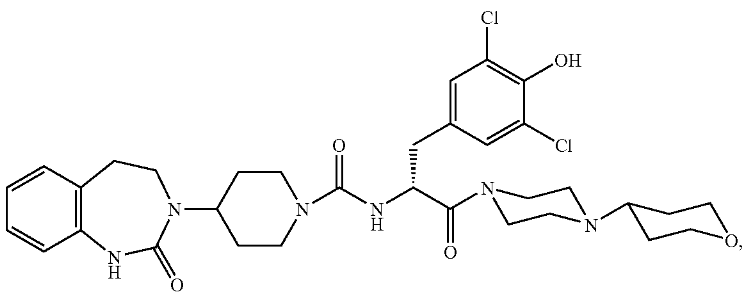 |
| (105) | 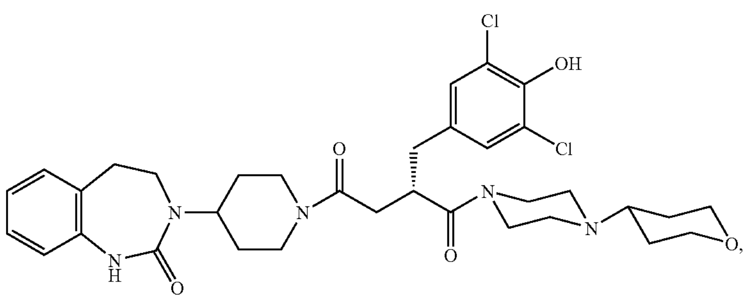 |
| (106) | 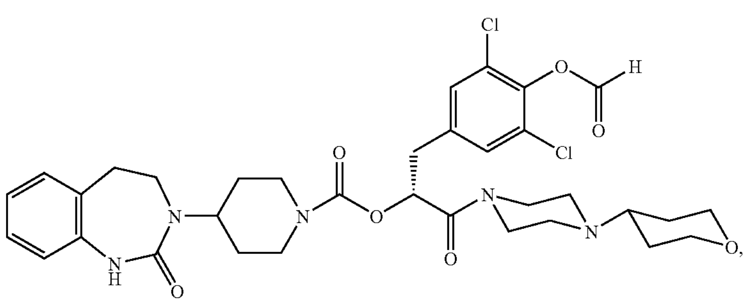 |
| (107) | 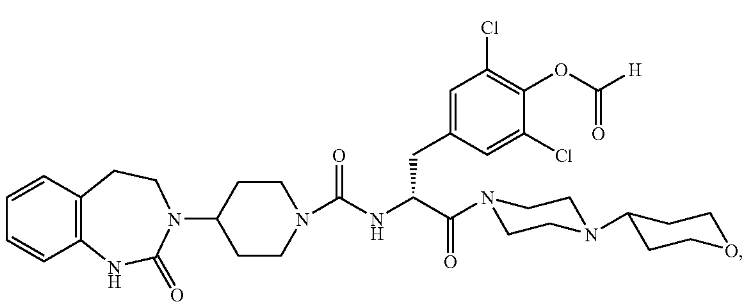 |

| No. | Structure |
|---|---|
| (108) | 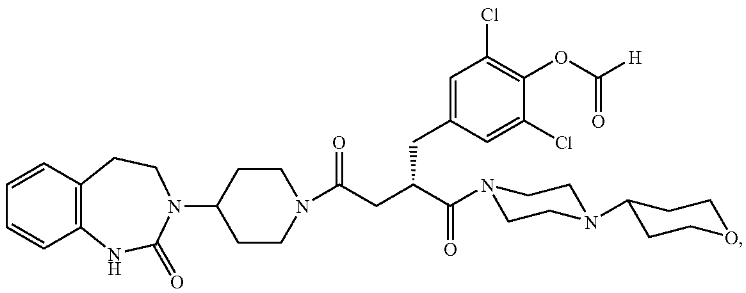 |
| (109) | 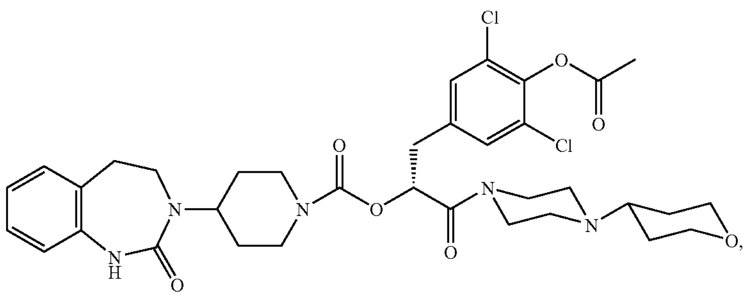 |
| (110) | 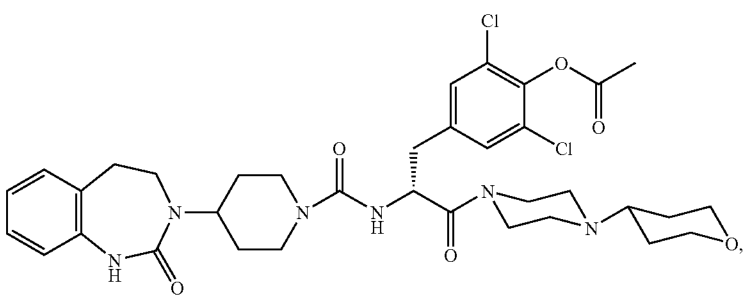 |
| (111) | 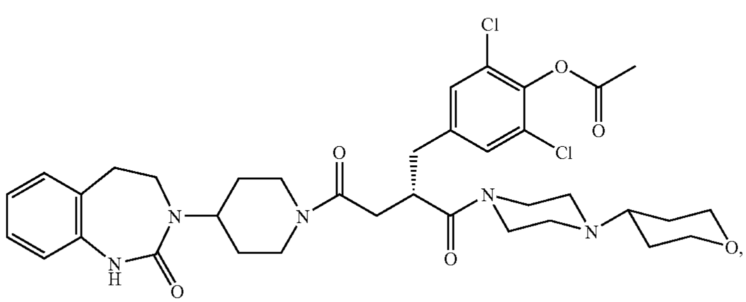 |
| (112) | 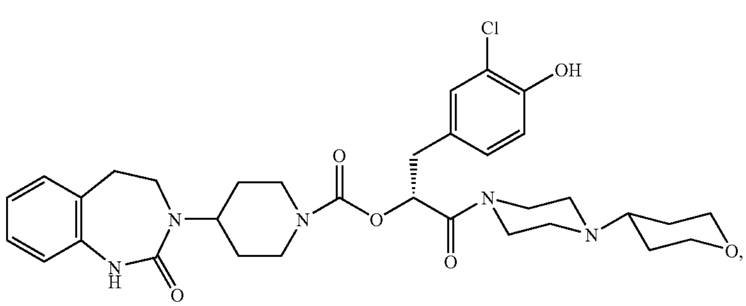 |

-continued
| No. | Structure |
|---|---|
| (113) | 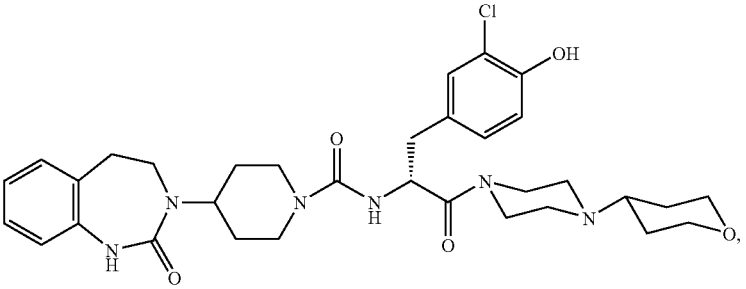 |
| (114) | 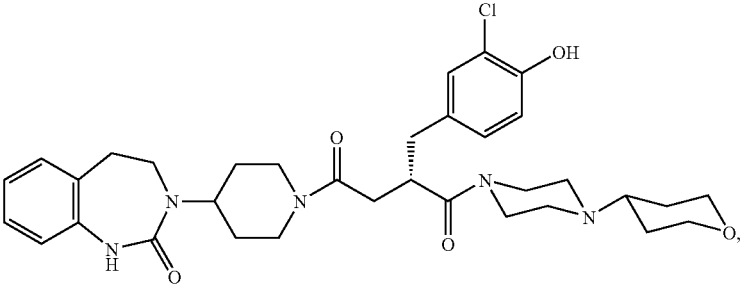 |
| (115) | 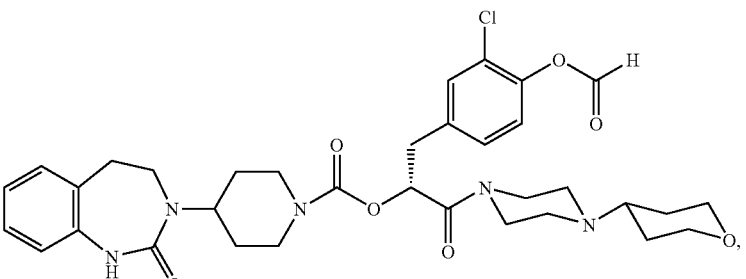 |
| (116) | 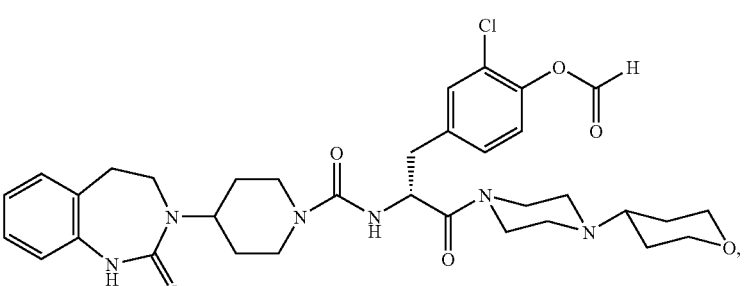 |
| (117) | 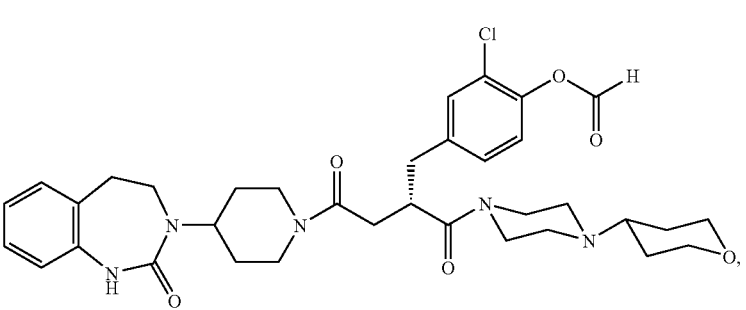 |

-continued
| No. | Structure |
|---|---|
| (118) | 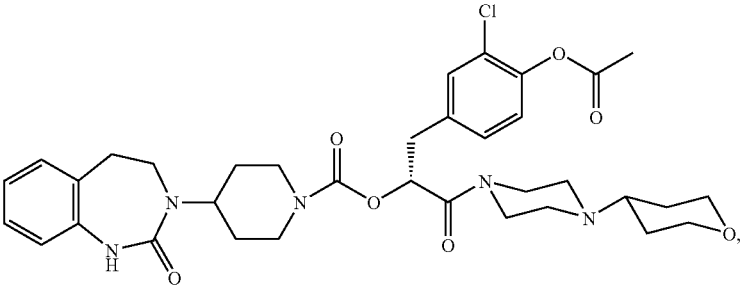 |
| (119) | 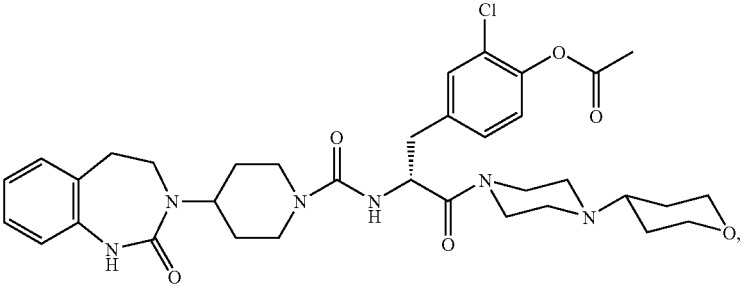 |
| (120) | 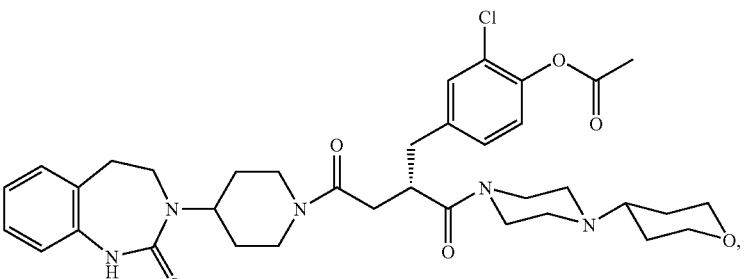 |
| (121) | 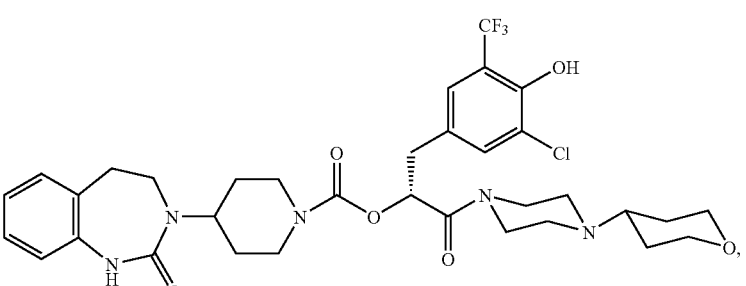 |
| (122) | 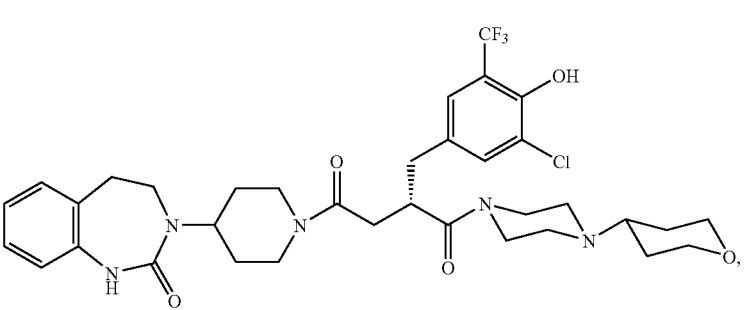 |

-continued
| No. | Structure |
|---|---|
| (123) | 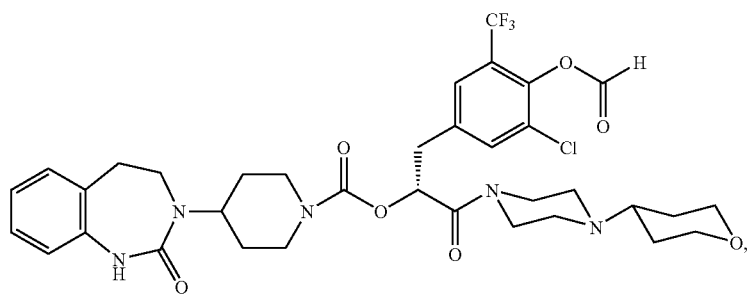 |
| (124) | 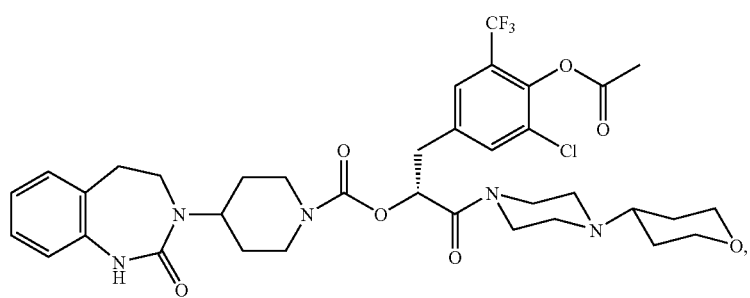 |
| (125) | 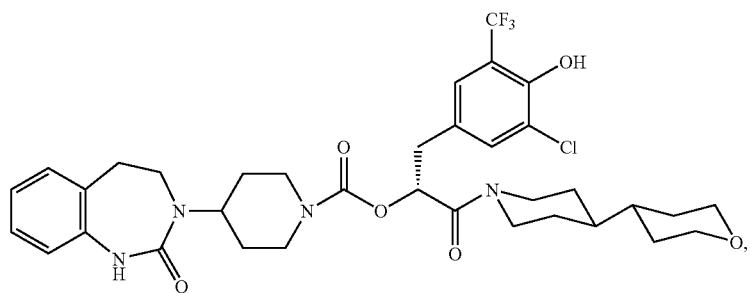 |
| (126) | 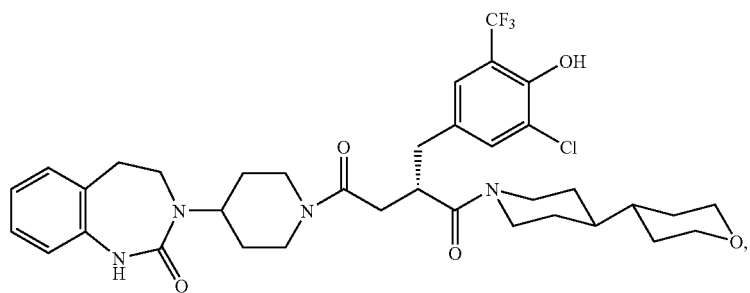 |
| (127) | 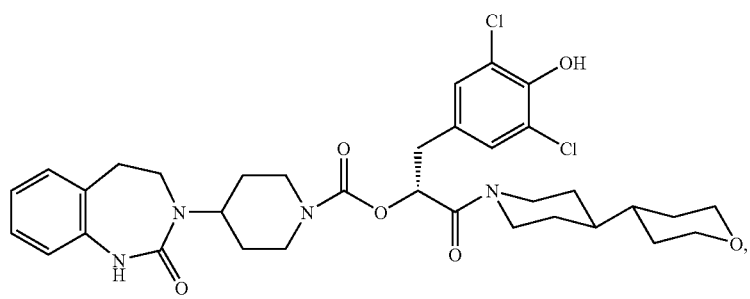 |

-continued

| No. | Structure |
|---|---|
| (128) | 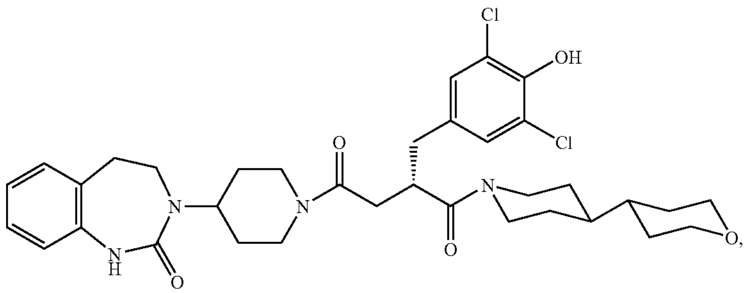 |
| (129) | 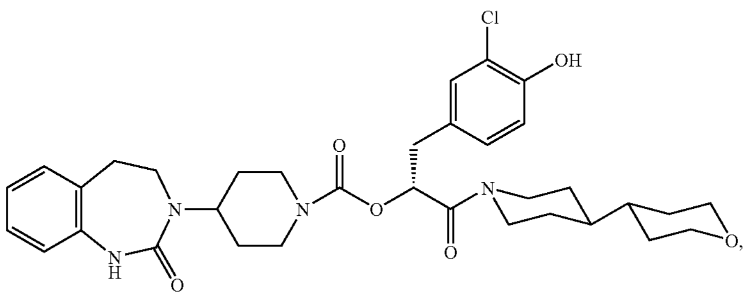 |
| (130) | 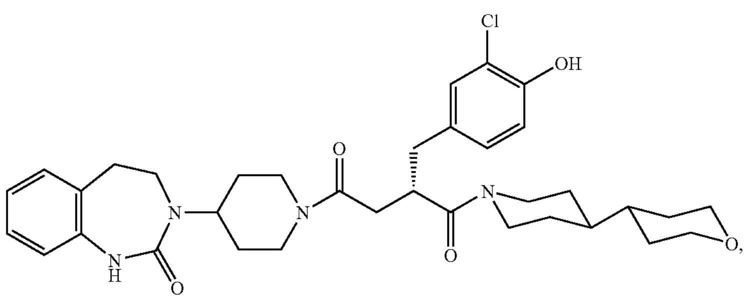 |
| (131) | 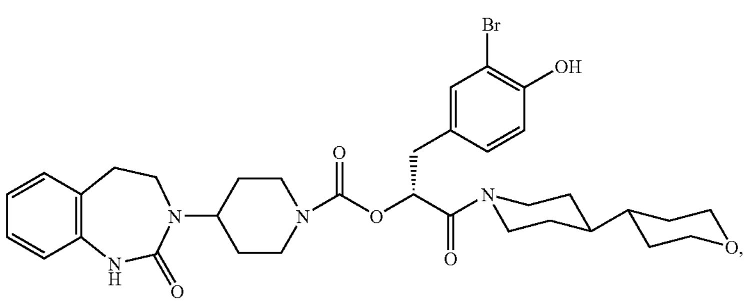 |
| (132) | 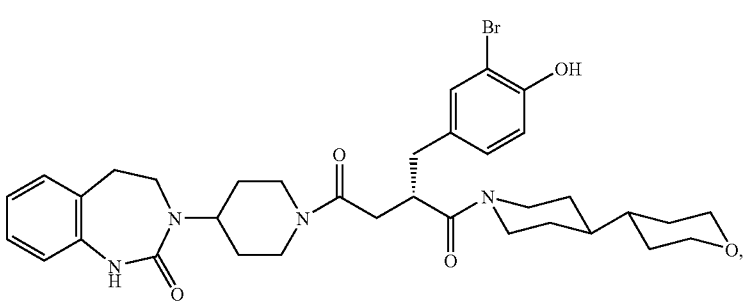 |

-continued

| No. | Structure |
|---|---|
| (133) | 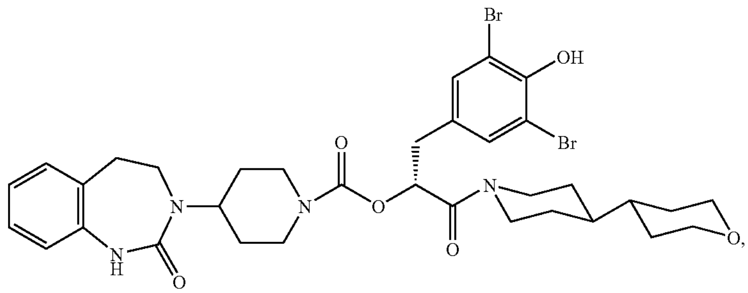 |
| (134) | 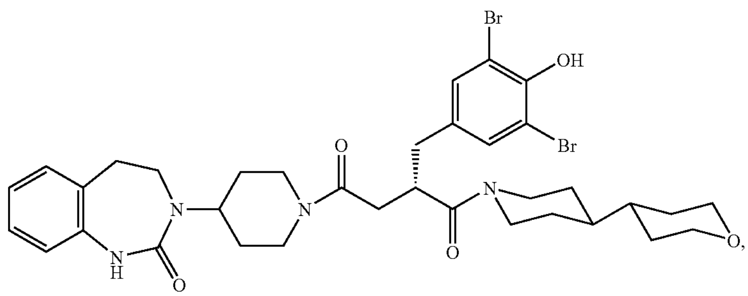 |
| (135) | 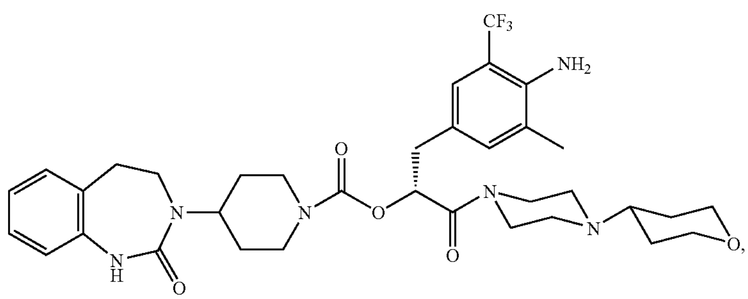 |
| (136) | 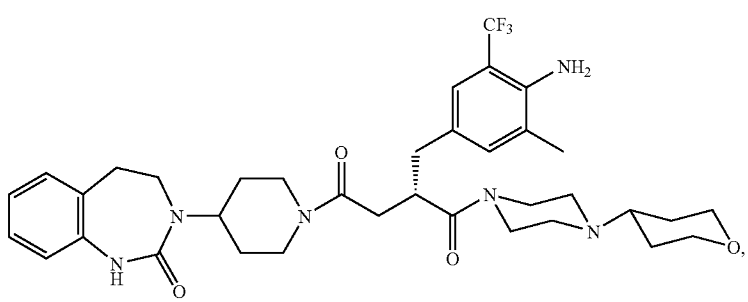 |
| (137) | 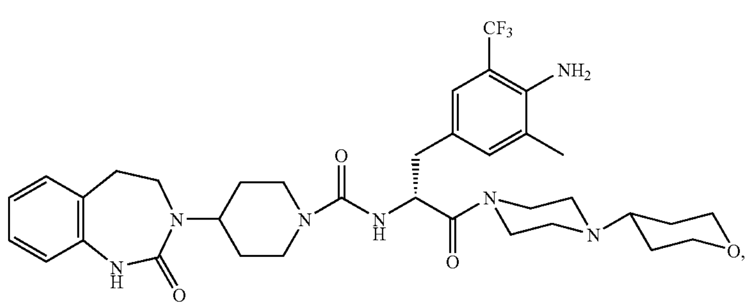 |

-continued
| No. | Structure |
|---|---|
| (138) | 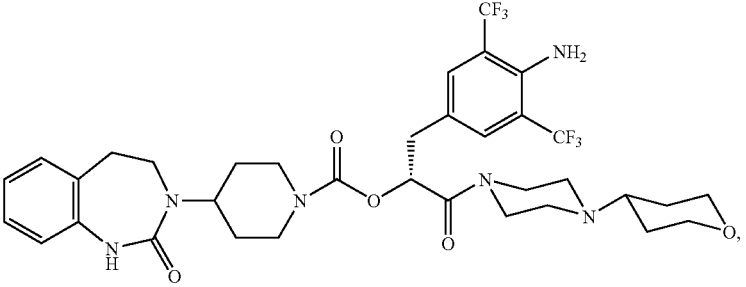 |
| (139) | 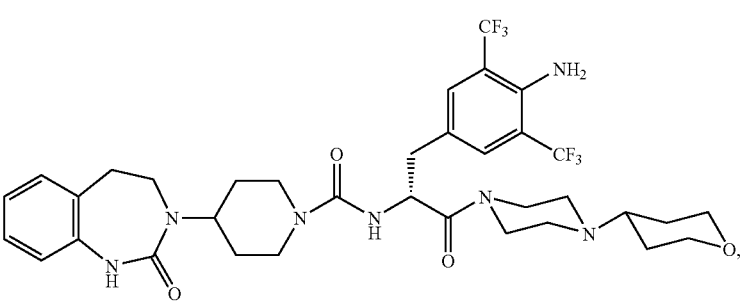 |
| (140) | 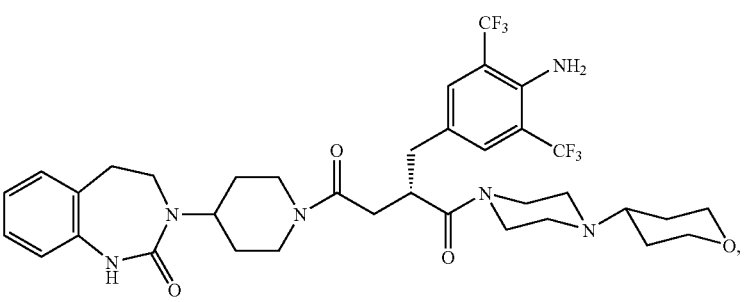 |
| (141) | 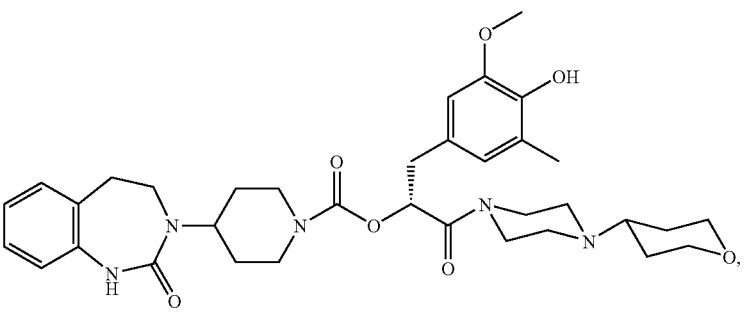 |
| (142) | 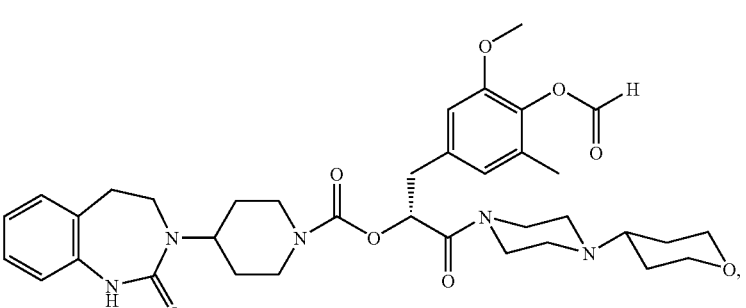 |

-continued
| No. | Structure |
|---|---|
| (143) | 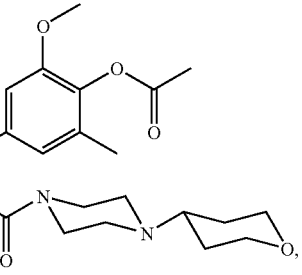 |
| (144) | 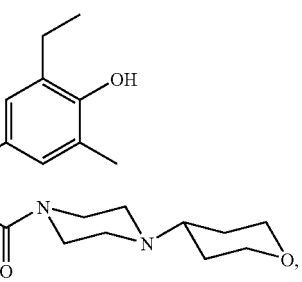 |
| (145) | 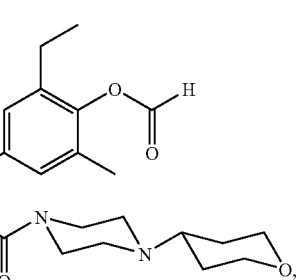 |
| (146) | 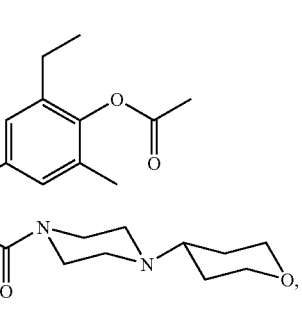 |
| (171) | 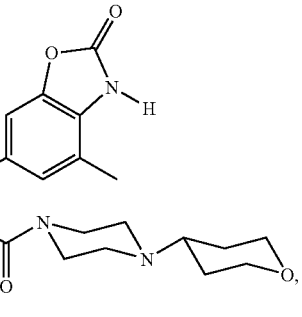 |

-continued
| No. | Structure |
|---|---|
| (172) | 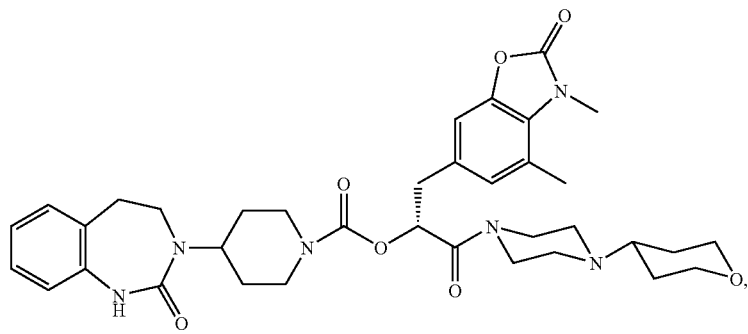 |
| (173) | 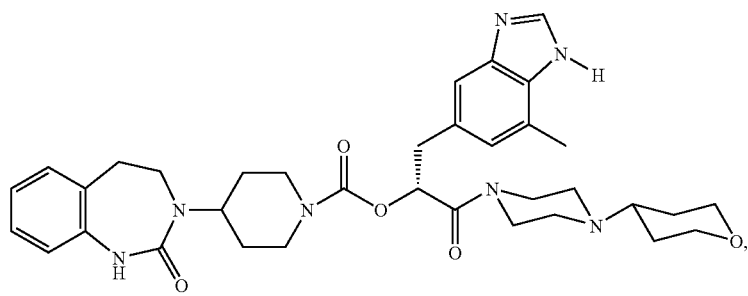 |
| (174) | 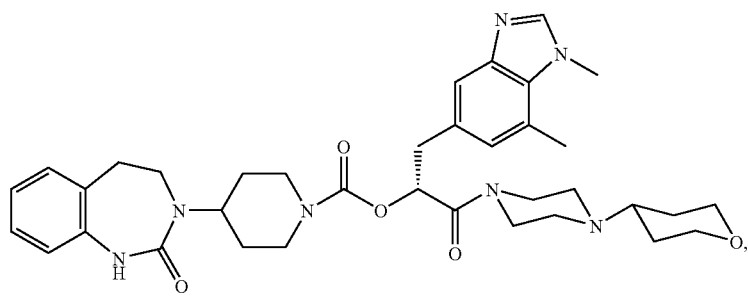 |
| (175) | 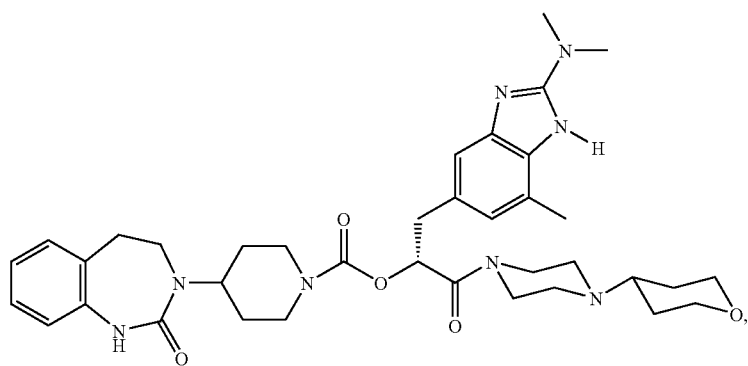 |

-continued
| No. | Structure |
|---|---|
| (176) | 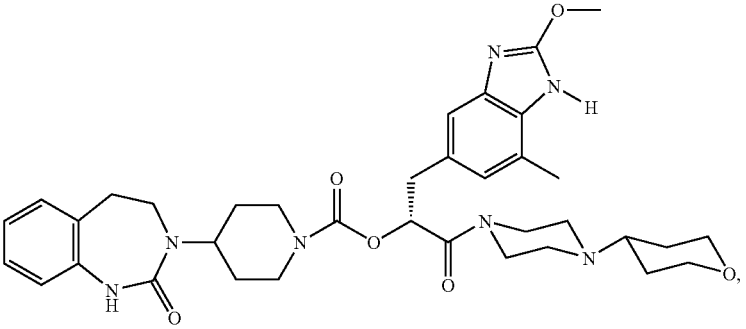 |
| (177) | 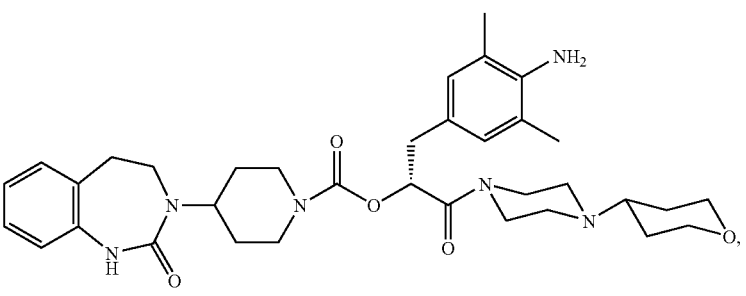 |
| (178) | 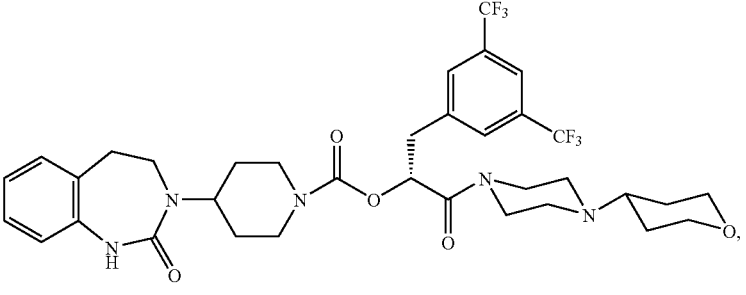 |
| (179) | 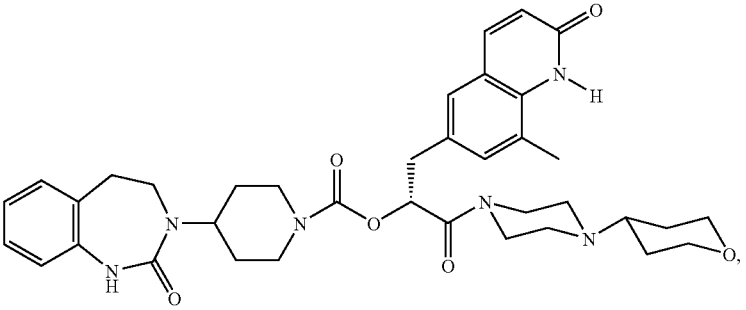 |
| (180) | 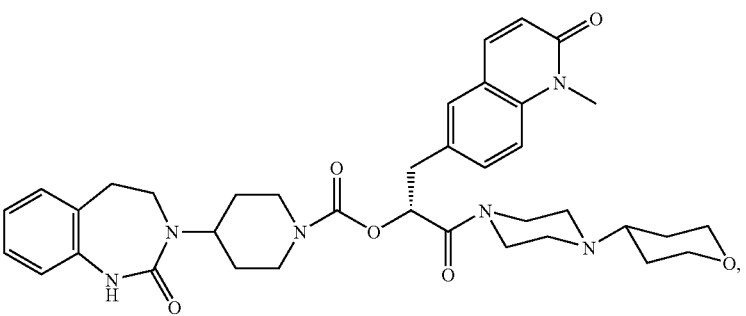 |

-continued
| No. | Structure |
|---|---|
| (181) | 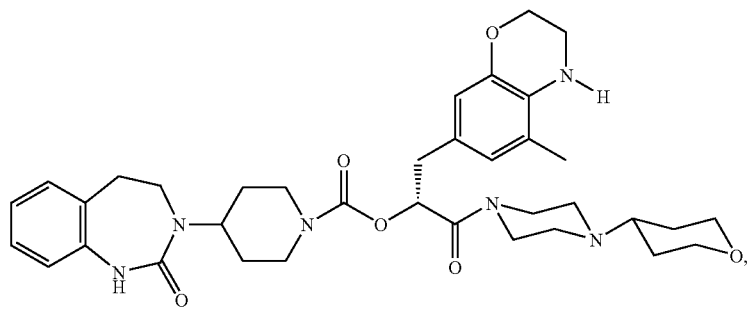 |
| (182) | 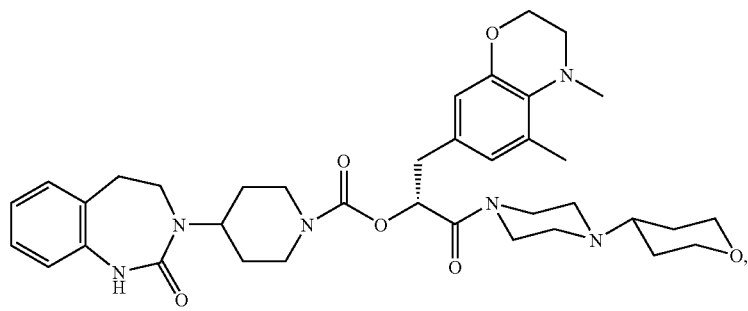 |
| (183) | 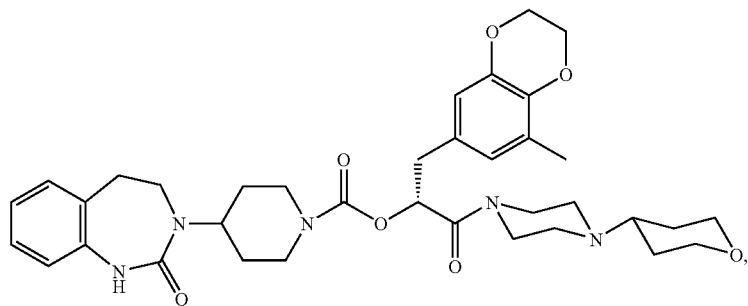 |
| (184) | 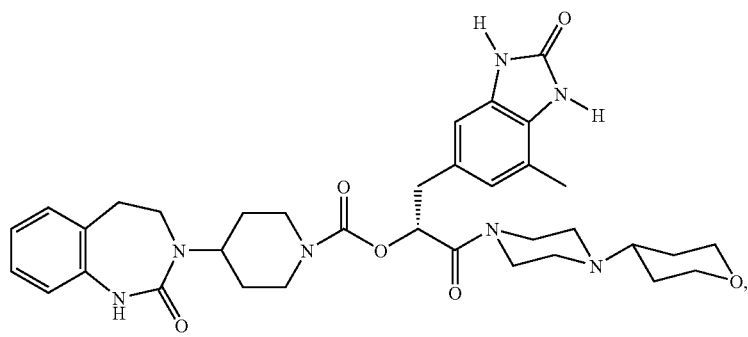 |

-continued
| No. | Structure |
|---|---|
| (185) | 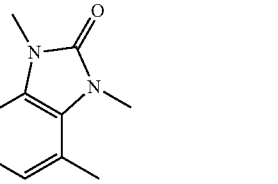 |
| (186) | 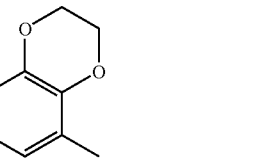 |
| (187) | 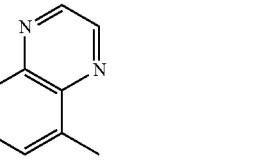 |
| (188) | 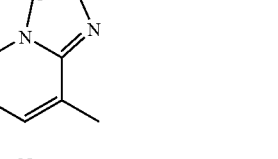 |
| (189) | 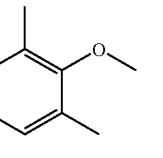 |

| No. | Structure |
|---|---|
| (190) | 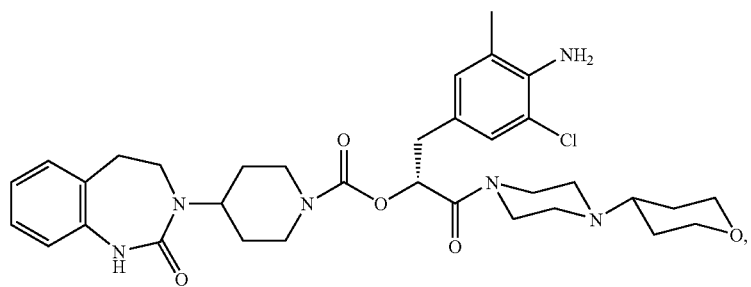 |
| (191) | 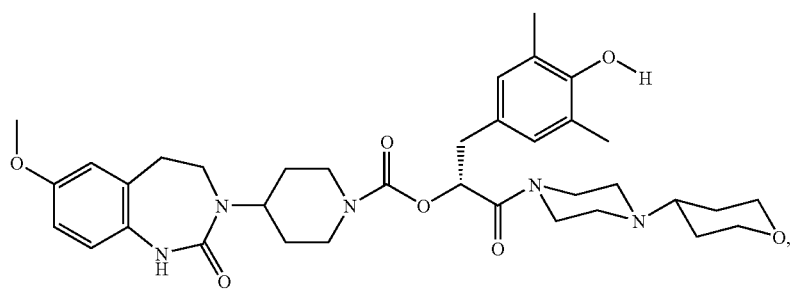 |
| (192) | 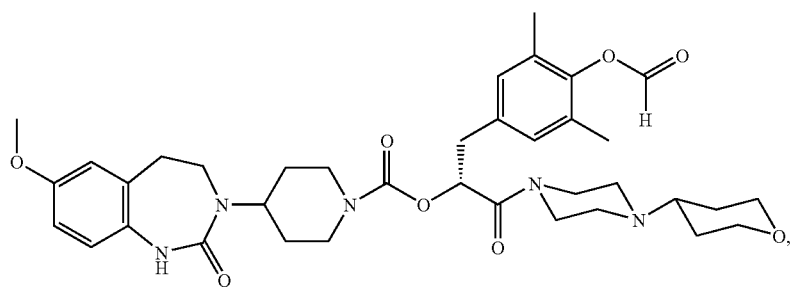 |
| (193) | 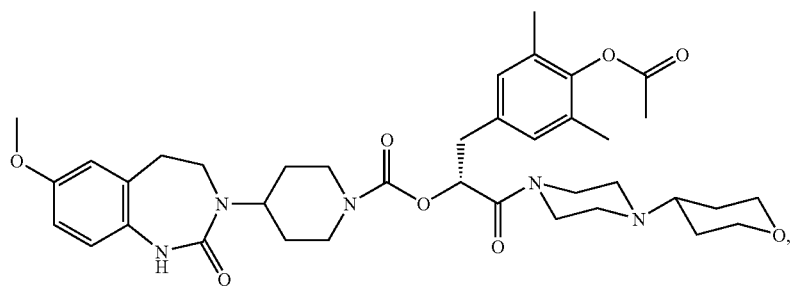 |
| (194) | 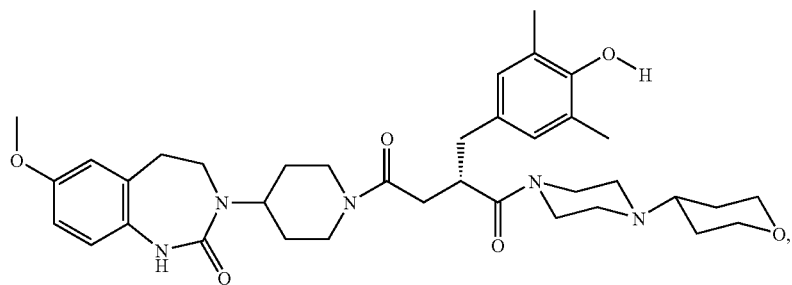 |

-continued

| No. | Structure |
|---|---|
| (195) | 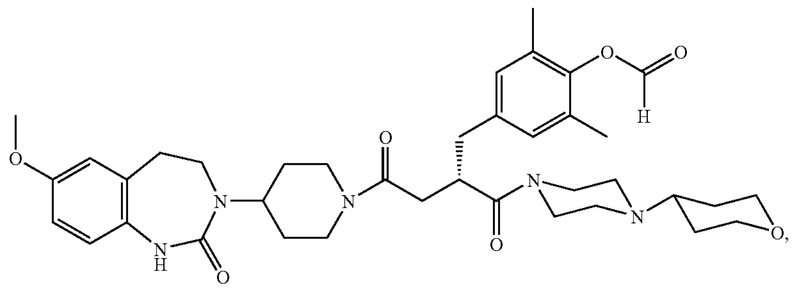 |
| (196) | 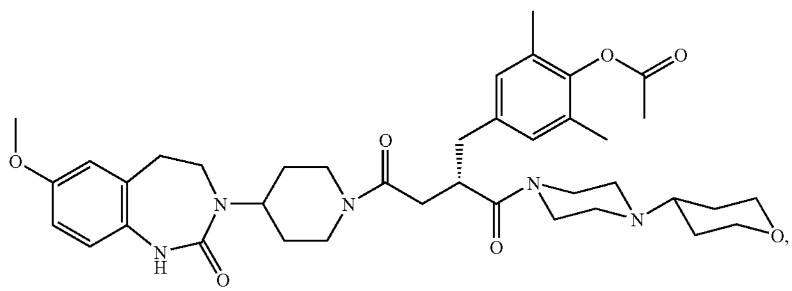 |
| (197) | 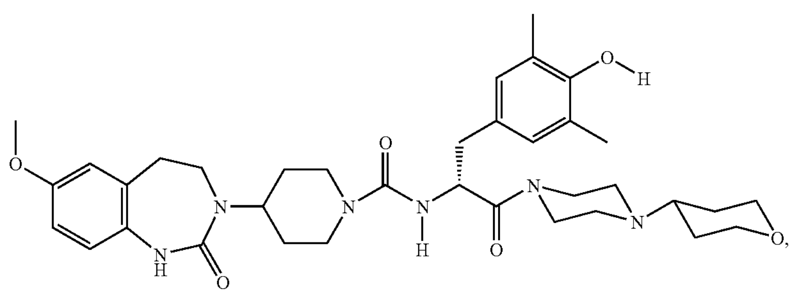 |
| (198) | 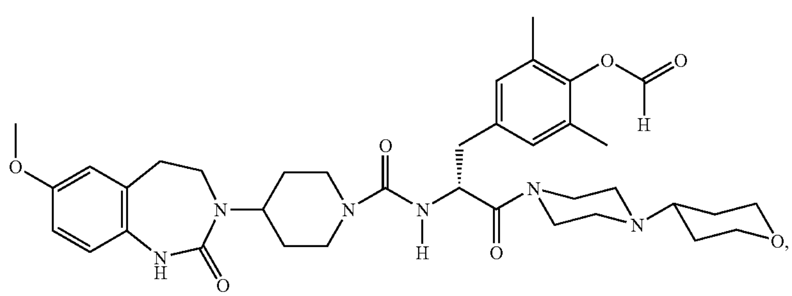 |
| (199) | 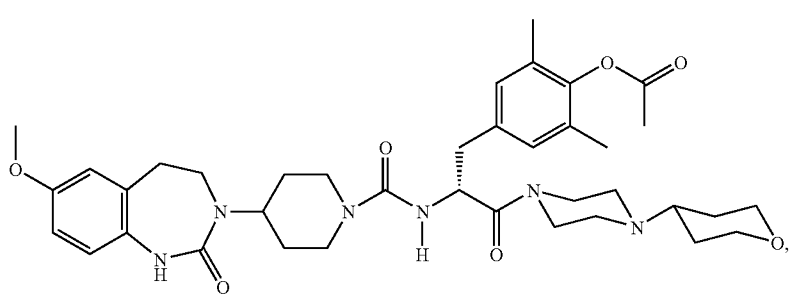 |

-continued

| No. | Structure |
|---|---|
| (200) | 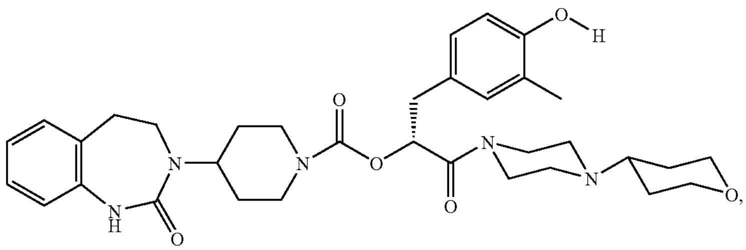 |
| (201) | 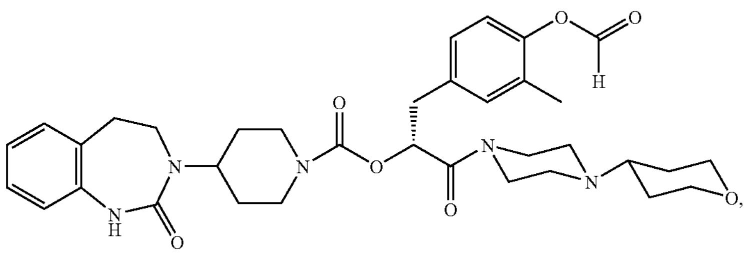 |
| (202) | 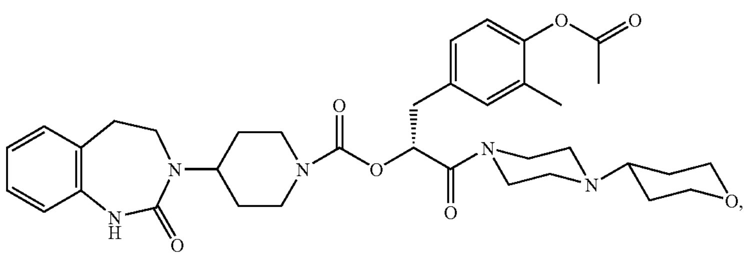 |
| (203) | 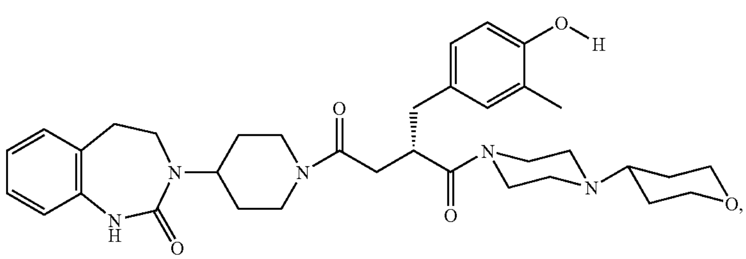 |
| (204) | 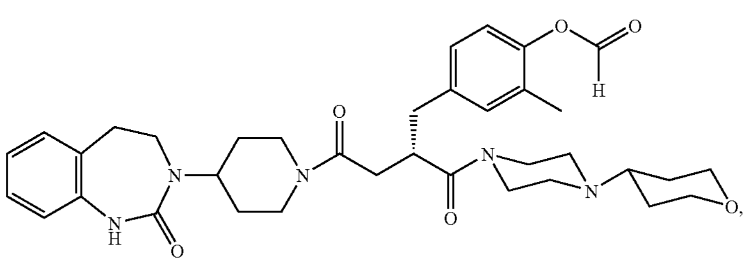 |
| (205) | 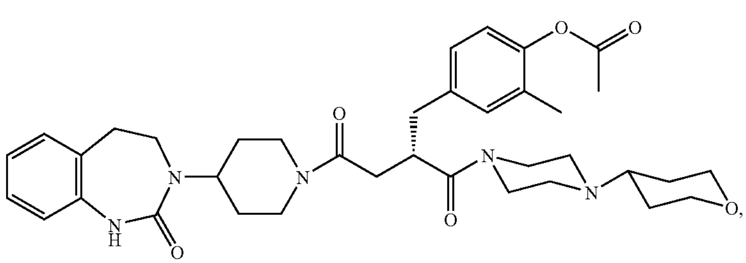 |

| No. | Structure |
|---|---|
| (206) | 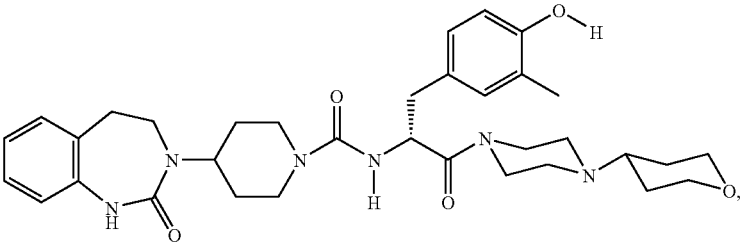 |
| (207) | 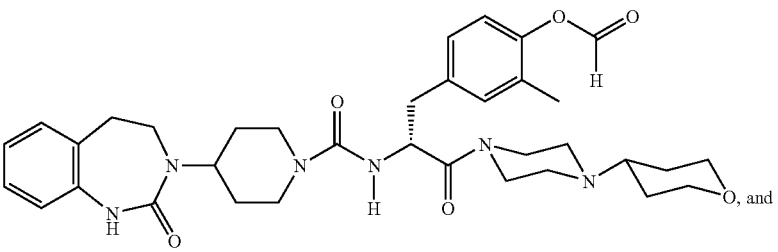 |
| (208) | 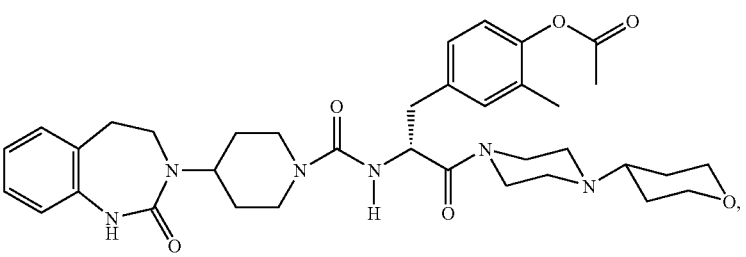 | or a tautomer or salt thereof.

5. A physiologically acceptable salt of a compound according to claim 1, 2, 3 or 4.

6. A pharmaceutical composition containing a compound according to claim 1, 2, 3 or 4 or a physiologically acceptable salt thereof together with one or more inert carriers and/or diluents.

7. A method for the treatment of migraine, cluster headache and tension headache, which comprises the administration to a person suffering from the same a therapeutic amount of a compound according to claim 1, 2, 3 or 4 or a physiologically acceptable salt thereof together.

8. A method for the treatment of non-insulin-dependent diabetes mellitus (NIDDM), which comprises the administration to a person suffering from the same a therapeutic amount of a compound according to claim 1, 2, 3 or 4 or a physiologically acceptable salt thereof together.

9. A compound according to claim 1, selected from the group consisting of:

| No. | Structure |
|---|---|
| (34) | 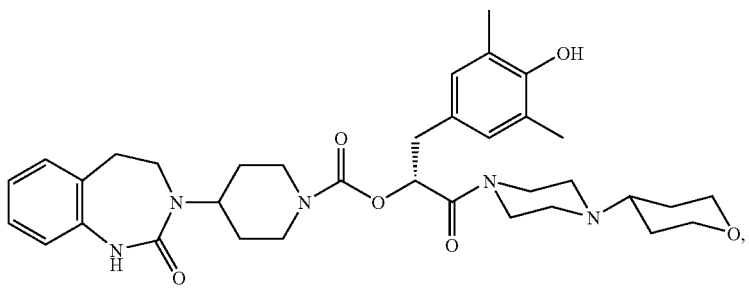 |

| No. | Structure |
|---|---|
| (35) | 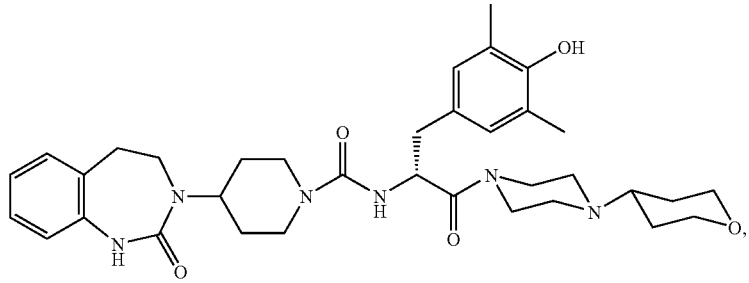 |
| (36) | 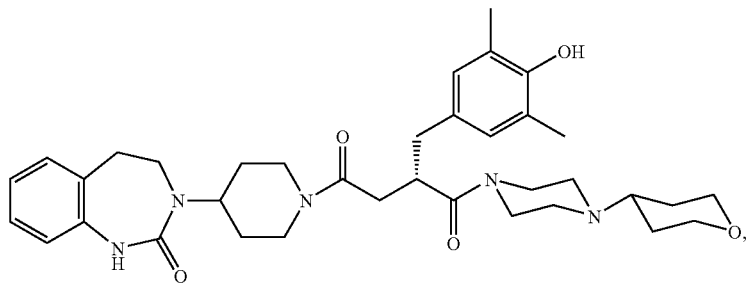 |
| (40) | 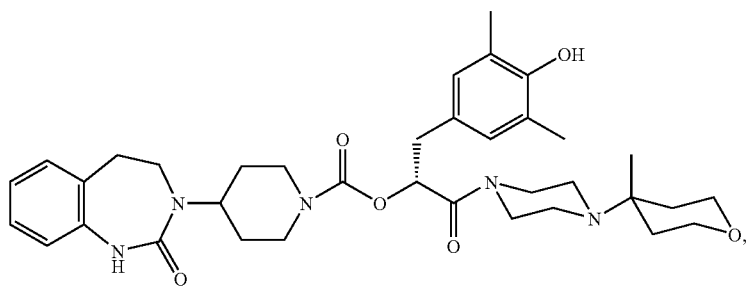 |
| (71) | 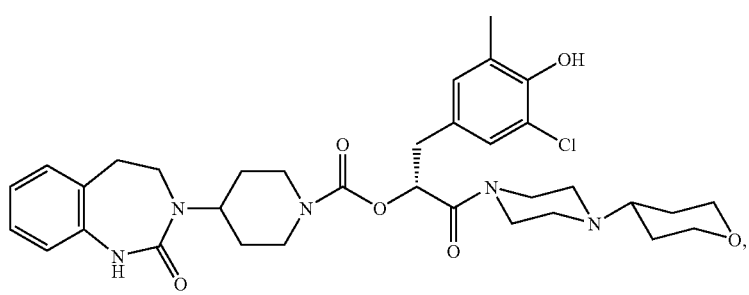 |
| (73) | 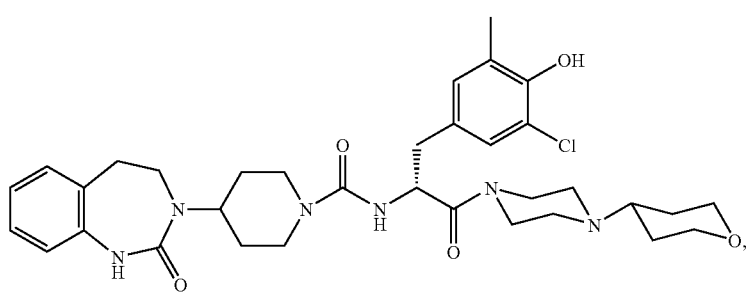 |

-continued
| No. | Structure |
|---|---|
| (75) | 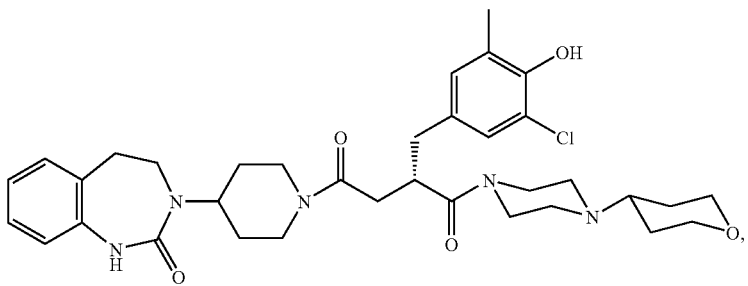 |
| (122) | 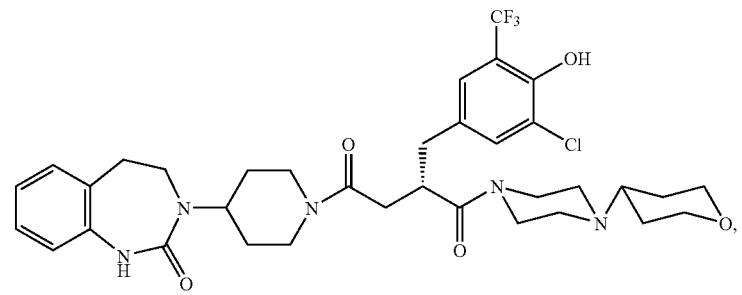 |
| (135) | 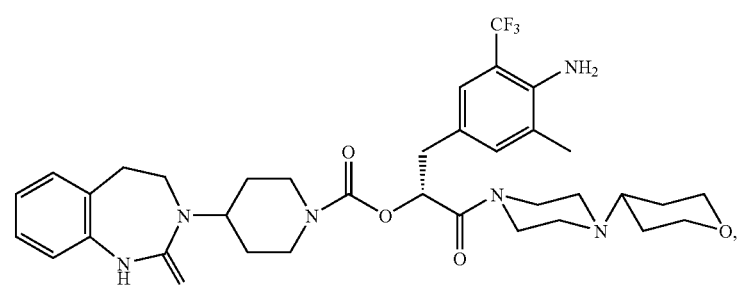 |
| (141) | 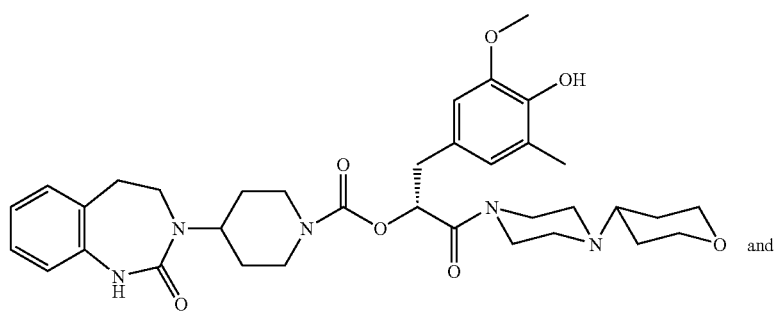 and |
| (144) | 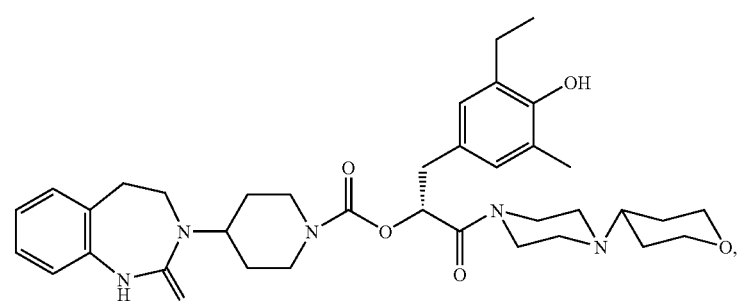 |
or a tautomer or salt thereof.

10. The compound according to claim 1 which is
(34)
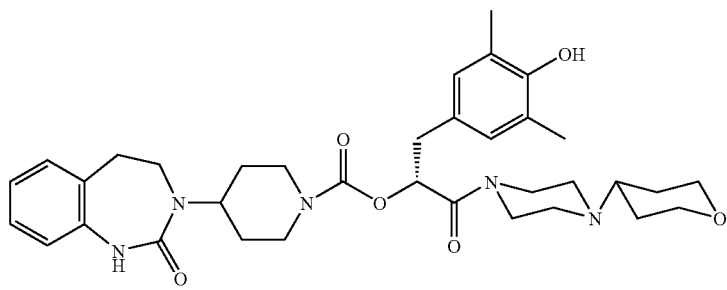
or a tautomer or salt thereof.
11. The compound according to claim 1 which is
(35)
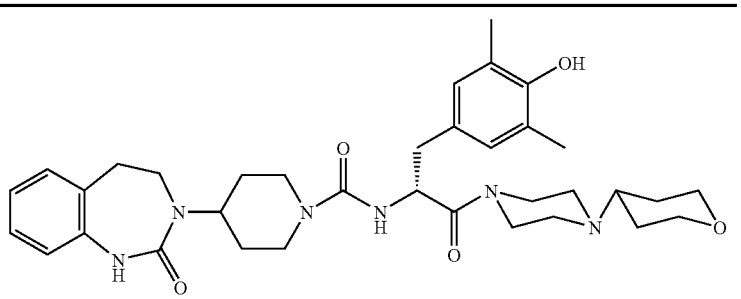
or a tautomer or salt thereof.
12. The compound according to claim 1 which is
(36)
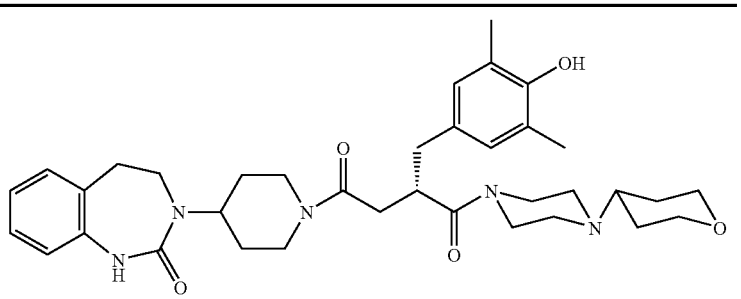
or a tautomer or salt thereof.
13. The compound according to claim 1 which is
(40)
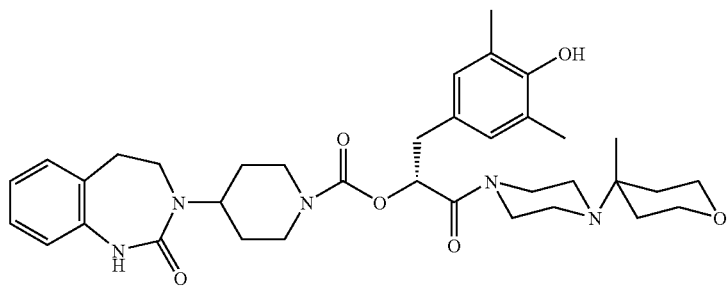
or a tautomer or salt thereof.

14. The compound according to claim 1 which is
(71)
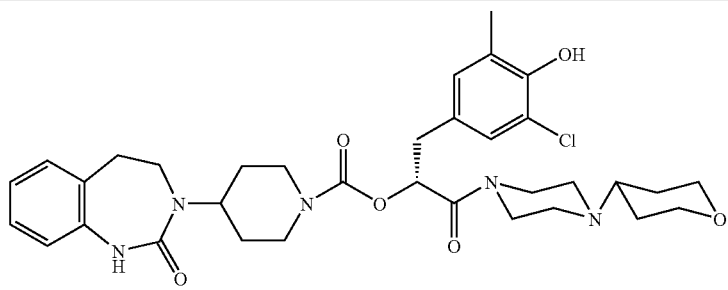
or a tautomer or salt thereof.
15. The compound according to claim 1 which is
(73)
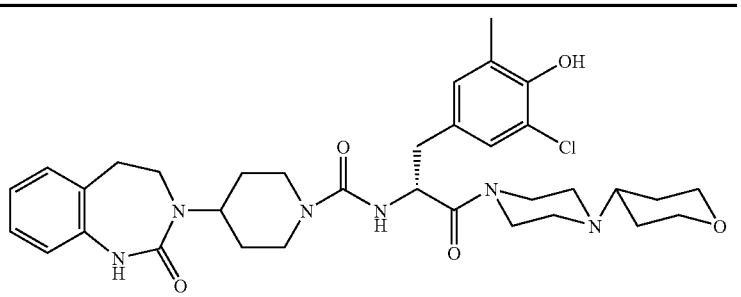
or a tautomer or salt thereof.
16. The compound according to claim 1 which is
(75)
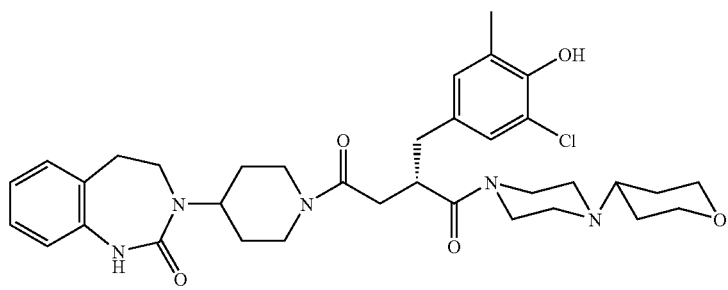
or a tautomer or salt thereof.
17. The compound according to claim 1 which is
(122)
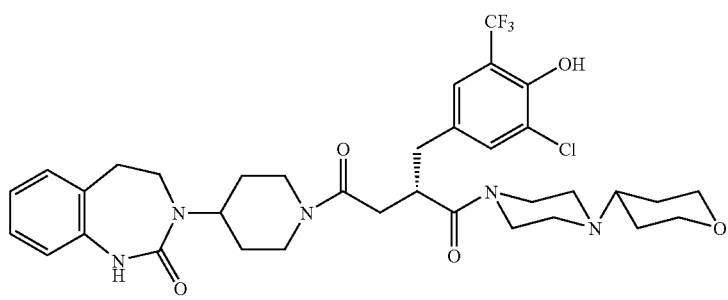
or a tautomer or salt thereof.

18. The compound according to claim 1 which is:
(135)
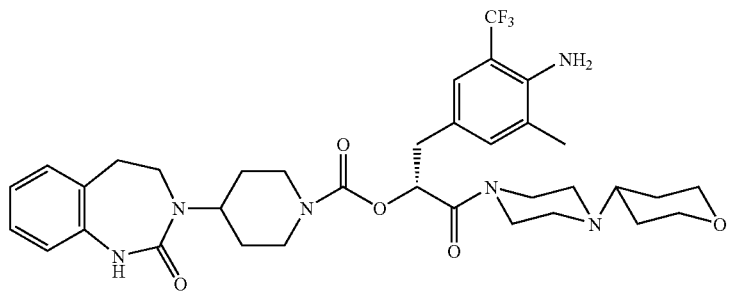
or a tautomer or salt thereof.
19. The compound according to claim 1 which is
(141)
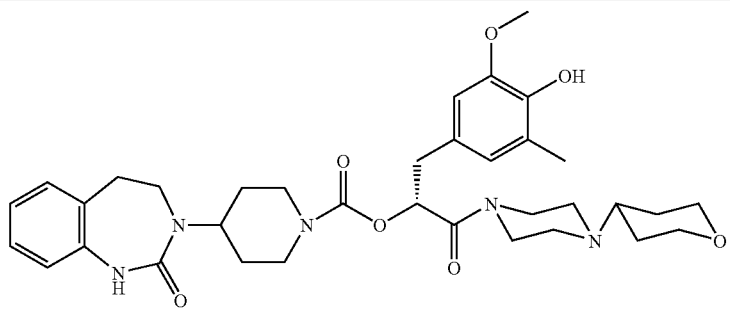
or a tautomer or salt thereof.
20. The compound according to claim 1 which is
(144)
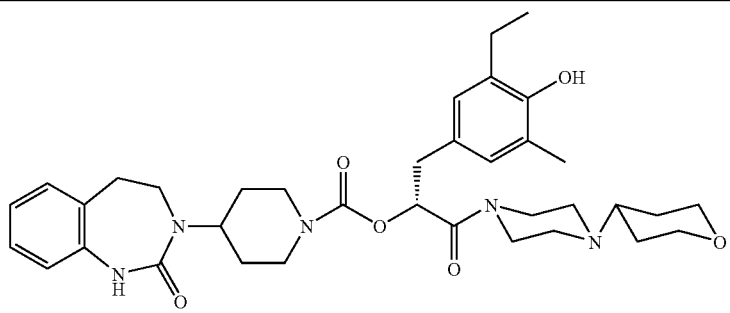
or a tautomer or salt thereof.
* * * * *